United States Patent
McCormick et al.

(10) Patent No.: US 8,324,213 B2
(45) Date of Patent: Dec. 4, 2012

(54) BIARYL-SPIROAMINOOXAZOLINE ANALOGUES AS ALPHA 2C ADRENERGIC RECEPTOR MODULATORS

(75) Inventors: Kevin D. McCormick, Basking Ridge, NJ (US); Li Dong, Lawrenceville, NJ (US); Christopher W. Boyce, Flemington, NJ (US); Manuel de Lera Ruiz, Branchburg, NJ (US); Salem Fevrier, Cranford, NJ (US); Jie Wu, Scotch Plains, NJ (US); Junying Zheng, New Providence, NJ (US); Youngong Yu, East Brunswick, NJ (US); Jianhua Chao, San Diego, CA (US); Walter S. Won, Alpine, NJ (US); Ashwin U. Rao, Avenel, NJ (US); Rongze Kuang, Green Brook, NJ (US); Pauline C. Ting, New Providence, NJ (US); Xianhai Huang, Warren, NJ (US); Ning Shao, Clark, NJ (US); Anandan Palani, Bridgewater, NJ (US); Michael Y. Berlin, Flemington, NJ (US); Robert G. Aslanian, Rockaway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/122,679

(22) PCT Filed: Oct. 6, 2009

(86) PCT No.: PCT/US2009/059636
§ 371 (c)(1),
(2), (4) Date: Jun. 22, 2011

(87) PCT Pub. No.: WO2010/042473
PCT Pub. Date: Apr. 15, 2010

(65) Prior Publication Data
US 2011/0251207 A1   Oct. 13, 2011

Related U.S. Application Data

(60) Provisional application No. 61/103,409, filed on Oct. 7, 2008.

(51) Int. Cl.
| | |
|---|---|
| *A61K 31/501* | (2006.01) |
| *A61K 31/497* | (2006.01) |
| *A61K 31/506* | (2006.01) |
| *A61K 31/4439* | (2006.01) |
| *A61K 31/427* | (2006.01) |
| *A61K 31/423* | (2006.01) |
| *C07D 235/02* | (2006.01) |
| *C07D 405/02* | (2006.01) |
| *C07D 409/02* | (2006.01) |
| *C07D 413/02* | (2006.01) |
| *C07D 263/52* | (2006.01) |

(52) U.S. Cl. ............. 514/252.06; 514/255.05; 514/256; 514/278; 514/365; 514/375; 544/230; 546/15; 548/147; 548/216; 548/247

(58) Field of Classification Search ............. 514/252.06, 514/256, 278, 365, 255.05, 375, 393, 378; 544/230; 546/15; 548/147, 216, 301.1, 247, 548/300.7

See application file for complete search history.

(56) References Cited

U.S. PATENT DOCUMENTS

| | | | |
|---|---|---|---|
| 5,436,261 | A | 7/1995 | Cordi et al. |
| 5,486,532 | A | 1/1996 | Cordi et al. |
| 5,648,374 | A | 7/1997 | Cordi et al. |
| 5,658,938 | A | 8/1997 | Geerts et al. |
| 6,673,337 | B2 | 1/2004 | Olejnik et al. |
| 6,841,684 | B2 | 1/2005 | Chow et al. |
| 7,700,592 | B2 | 4/2010 | McCormick et al. |
| 7,803,828 | B2 | 9/2010 | McCormick et al. |
| 2003/0023098 | A1 | 1/2003 | Chow et al. |
| 2008/0027100 | A1 | 1/2008 | McCormick et al. |
| 2010/0173823 | A1 | 7/2010 | McCormick et al. |

FOREIGN PATENT DOCUMENTS

| | | |
|---|---|---|
| EP | 0635495 | 6/1994 |
| WO | 9712874 | 4/1997 |
| WO | 9928300 | 6/1999 |
| WO | 0100586 | 1/2001 |
| WO | 0164645 | 9/2001 |
| WO | 02076950 | 10/2002 |
| WO | 03082825 | 10/2003 |
| WO | 2006080890 | 8/2006 |
| WO | 2008100456 | 8/2008 |
| WO | 2008100459 | 8/2008 |
| WO | 2008100480 | 8/2008 |

OTHER PUBLICATIONS

Bagley et al., Med. Chem. Res 1994, 4:346-364.
Miller et al., J. Med. Chem., 1994, 37:2328-2333.
J Med Chem, 1996, 39:3001-3013.
J Med Chem, 1997, 40:3014-3024.
Hoeglund et al., J. Med Chem. 49:6351-6363, 2006.
Sallinen et al., British J. Pharmacol. 150:391-402, 2007.
J. Med chem., 1994, 38:4056-4069.
Millan, Mark J., et al. J. of Pharmacology and Experimental Ther., 295(3), 1192-1205, 2000.

*Primary Examiner* — Kristin Bianchi
(74) *Attorney, Agent, or Firm* — H. Eric Fischer; Gerard M. Devlin

(57) ABSTRACT

In its many embodiments, the present invention provides a novel class of biaryl spiroaminooxazoline analogues as modulators of α2C adrenergic receptor agonists, methods of preparing such compounds, pharmaceutical compositions containing one or more such compounds, methods of preparing pharmaceutical formulations comprising one or more such compounds, and methods of treatment, prevention, inhibition, or amelioration of one or more conditions associated with the α2C adrenergic receptors using such compounds or pharmaceutical compositions.

11 Claims, No Drawings

BIARYL-SPIROAMINOOXAZOLINE ANALOGUES AS ALPHA 2C ADRENERGIC RECEPTOR MODULATORS

CROSS-REFERENCE TO RELATED APPLICATIONS

This application is the National Stage of International Application No. PCT/US2009/059636 filed on Oct. 6, 2009, which claims the benefit under 35 U.S.C. 119(e) of U.S. Provisional Application No. 61/103,409 filed Oct. 7, 2008, each of which applications are incorporated by reference as if fully set forth herein.

FIELD OF THE INVENTION

The present invention relates to biaryl spiroaminooxazoline analogues useful as alpha-2C (or "α2C") adrenergic receptor modulators, methods for making these compounds, pharmaceutical compositions containing the compounds, and methods of treatment and prevention using the compounds and compositions to treat disease states associated with the modulation of the alpha-2C receptor, such as congestion (including nasal), migraine, congestive heart failure, cardiac ischemia, glaucoma, stress-induced urinary incontinence, Alzheimer's disease, Parkinson's disease, attention deficit hyperactivity disorder, pain and psychotic disorders (e.g., depression and schizophrenia).

BACKGROUND OF THE INVENTION

The initial classification of adrenergic receptors into α- and β-families was first described by Ahlquist in 1948 (Ahlquist R P, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation). β-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into α1- and α2-adrenergic receptors. Cloning and expression of α-adrenergic receptors have confirmed the presence of multiple subtypes of both α1-(α1A, α1B, α1D) and α2-(α2A, α2B, α2C) adrenergic receptors (Michel et al., "Classification of $α_1$-Adrenoceptor Subtypes," Naunyn-Schmiedeberg's Arch. Pharmacol, 352:1-10 (1995); Macdonald et al., "Gene Targeting—Homing in on $α_2$-Adrenoceptor-Subtype Function," TIPS, 18:211-219 (1997)).

Current therapeutic uses of α-2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds having adrenergic activity are well-known in the art and are described in numerous patents and scientific publications. It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, and psychotic disorders (e.g., schizophrenia).

For example, published PCT application WO 02/076950 discloses compounds having α2 agonist activity of the following general formula:

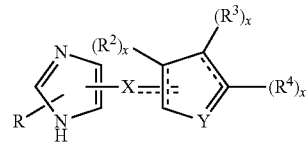

Other publications disclosing similar compounds includes WO 01/00586, WO 99/28300, U.S. Pat. No. 6,841,684 B2 and US 2003/0023098 A1.

Another class of compounds having α2-agonist properties is disclosed in U.S. Pat. No. 5,658,938, and has the following general formula:

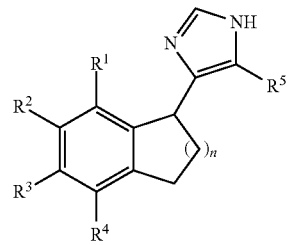

wherein n=1-2, $R^1$-$R^3$ represent hydrogen, halogen hydroxy, alkyl or alkoxy, and $R^5$ is hydrogen or alkyl.

Another class of compounds reported to have affinity for α2 receptors includes the following two compounds (Bagley et. al., Med. Chem. Res. 1994, 4:346-364):

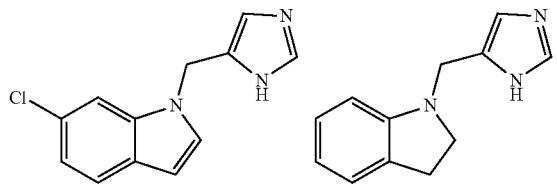

It is also known that compounds having adrenergic activity, such as α2A agonists, may be associated with undesirable side effects. Examples of such side effects include hyper- and hypotension, sedation, locomotor activity, psychotic disorders (e.g., schizophrenia).

Another class of compounds reported to have affinity for α2 receptors includes the following two compounds (Miller et. al., *J. Med. Chem.* 1994, 37:2328-2333; *J. Med. Chem.* 1996, 39:3001-3013; *J. Med. Chem.* 1997, 37:3014-3024):

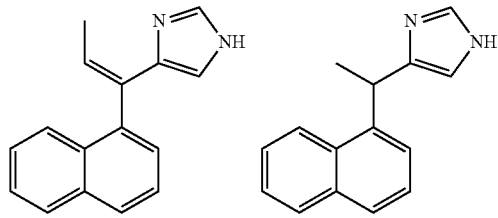

Another class of indane and tetrahyrdonaphthalene type compounds having α2-agonist properties is disclosed in PCT application WO 97/12874 and WO20040506356. This class has the following general formula:

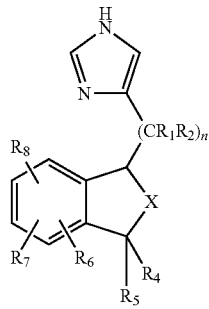

wherein n=0-1, X is 1 or 2 carbon units, $R_4$ is H, OH, alkyl, or alkoxy, $R_5$ may be taken together with $R^4$ to form a carbonyl, and $R^6$-$R^8$=H, OH, SH, alkyl, alkenyl, cycloalkyl, alkoxy, hydroxyalkyl, alkylthio, alkylthiol, halo, $CF_3$, $NO_2$, or alkylamino. This class specifically includes MPV-2426 (fadolmidine) and its prodrug esters:

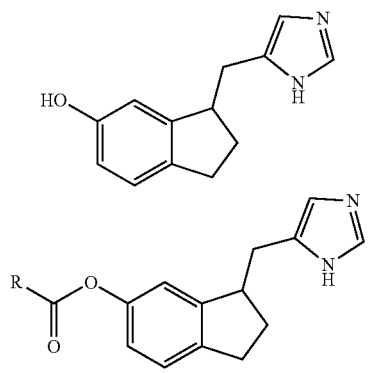

wherein R is optionally substituted lower alkyl, aryl, cycloalkyl, heteroaryl, lower alkylamino, and saturated 5- or 6-membered heterocyclic groups containing 1 or 2 N atoms.

Further, other classes of compounds that exhibit functional selectivity for the alpha 2C receptor have been discovered. Application U.S. Ser. No. 11/508,458, filed Aug. 23, 2006, discloses indoline compounds that possess this activity and application U.S. Ser. No. 11/508,467, filed on the same date, describes morpholine compounds that are functionally selective of the alpha 2C receptor. CIP applications of these applications have been filed; the Ser. Nos. 11/705,673 and 11/705,683, both filed on Feb. 13, 2009.

Additional applications that have been filed by Schering-Plough and disclose alpha2C receptor agonists include applications WO 2008/100480 (PCT/US2008/001808); WO 2008/100459 (PCT/US2008/001770) and WO 2008/100456 (PCT/US2008/001765.

Compounds that act as antagonists of the alpha-2C receptor are also known in the art. Hoeglund et al. describe quinoline derivatives that are said to be potent and selective alpha 2C antagonists and said to be useful in treating "certain psychiatric disorders such as depression and schizophrenia" (Hoeglund et al., J. Med. Chem. 49:6351-6363 (2006)). WO 2001/64645 to Orion Corp. also describes quinoline derivatives that are alpha-2C receptor antagonists and indicates that these compounds are useful for the treatment of conditions of the pheripheric or CNS system, including treating depression, anxiety, post traumatic stress disorder, schizophrenia, Parkinson's disease and other movement disorders, and dementias (e.g., Alzheimer's disease). WO 2003/082825, also to Orion Corp., indicates alpha-2C receptor antagonists have utility in treating symptoms of disorders and conditions with sensorimotor-gating deficits. Selliner et al., indicate that acridin-9-yl-[4-(4-methylpiperazinal-1-yl)-phenyl]amine is a highly selective alpha-2C adrenergic receptor antagonist and may be useful intreating neuropsychiatric disorders (Salliner et al., British J. Pharmacol. 150:391-402 (2007)).

It is also known that compounds having adrenergic activity, such as α2A agonists, may be associated with undesirable side effects. Examples of such side effects include hyper- and hypotension, sedation, locomotor activity, and body temperature variations.

Cordi et al. in U.S. Pat. Nos. 5,436,261, 5,486,532 and 5,648,374 describe benzospiroalkene heterocyclic compounds of the general formula

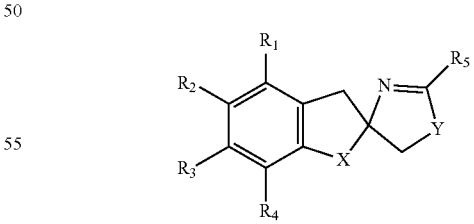

that are said to be useful as α2-adrenergic agonists; in the compounds described therein the definition of X includes —$(CH_2)_2$—, —O—, —O—$CH_2$—, and —S—$CH_2$—; of Y includes —O—, —S—, and —N($R_6$)—; and of $R_5$ includes hydrogen or an amino group. Cordi et al. also disclose spiro [1,3-diazacyclopent-1-ene)5,2'-(1',2',3',4'-tetrahydronaphthylene)] or spiro-imidazolines compounds such as

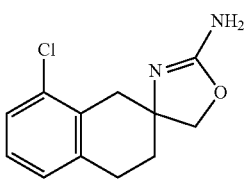

in *J. Med. Chem.* 1994, 38:4056-4069 as α-adrenergic agonists. WO 2006/080890 discloses that this compound may be used in combinations with other agents to prevent biofouling organisms.

U.S. Pat. No. 6,673,337 describes and claims an ophthalmic composition comprising an alpha-2C agonist component and a solubility enhancing component other than cyclodextrin. The patent does not specifically describe alpha-2C receptor agonists.

It has been discovered in accordance with the present invention that the inventive compounds act as modulators of the alpha-2C receptor (i.e., they can act as alpha-2C receptor agonists or as alpha-2C receptor antagonists) and are useful in treating disorders modulated by the alpha-2C receptor.

There is a need for new compounds, formulations, treatments and therapies to treat diseases and disorders associated with α2C adrenergic receptors. Further, there is a need for alpha-2C receptor modulators that minimize adverse side effects, such as those associated with the alpha-2A receptor subtype (viz., blood pressure or sedation). It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds that are modulators of the α2C adrenergic receptor, or metabolites, stereoisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts or metabolites, solvates, prodrugs or polymorphs of said compound, said compound having the general structure shown in Formula I

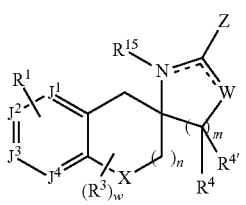

I wherein:
$J^1$, $J^2$, $J^3$ and $J^4$ are independently —N—, —N(O)—, or —C($R^2$)—;
X is —C($R^6$)($R^{6'}$)—, —N($R^6$)—, —O— or —S—;
W is —N($R^{15}$)—, —O— or —S—;

Z is independently selected from the group consisting of H, —OH, halo, —CN, —NO$_2$, —S(O)$_p$R$^7$, —NR$^7$R$^{7'}$, —[C(R$^a$)(R$^b$)]$_q$YR$^7$, —[C(R$^a$)(R$^b$)]$_q$N(R$^7$)YR$^{7'}$, —[C(R$^a$)(R$^b$)]$_q$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

wherein ≈ is a single or double bond provided that when W is —O— or —S—, the double bond is present between N and the 2-position, and when W is —N(R$^{15}$)—, the double bond is present between the N and the 2-position or W and the 2-position, but cannot form 2 contiguous double bonds;

R$^1$ is a ring selected from the group consisting of cycloalkyl, cycloalkenyl, aryl, heterocyclyl, heterocyclenyl, and heteroaryl, each of which is optionally substituted with at least one (preferably 1 to 5, more preferably 1 to 3) R$^{12}$;

R$^2$ is absent or independently selected from the group consisting of H, halo, —CN, —NO$_2$, —OH, —S(O)$_p$R$^7$, —NR$^7$R$^{7'}$, —[C(R$^a$)(R$^b$)]$_q$YR$^7$, —[C(R$^a$)(R$^b$)]$_q$N(R$^7$)YR$^{7'}$, —[C(R$^a$)(R$^b$)]$_q$N(R$^7$)CN, —[C(R$^a$)(R$^b$)]$_q$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

Y is selected from the group consisting of a bond, —C(═O)—, —C(═O)NR$^7$—, —C(═O)O—, —C(═O)N(R$^c$)—O—, —C(═NR$^7$)—, —C(═NOR$^7$)—, —C(═NR$^7$)NR$^7$—, —C(═NR$^7$)NR$^7$O—, —C(═N—CN)—, —S(O)$_p$—, —SO$_2$NR$^7$—, and —C(═S)NR$^7$—;

wherein R$^a$ and R$^b$ are independently selected from the group consisting of H, alkyl, alkoxy, and halo, and R$^c$ is H or alkyl;

R$^3$ is independently selected from the group consisting of H, —OH, halo, —CN, —NO$_2$, —S(O)$_p$R$^7$, —NR$^7$R$^{7'}$, —S(O)$_p$NR$^7$R$^{7'}$, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$, provided that when w is 3, no more than 2 of the R$^3$ groups may be (═O);

R$^4$ is independently selected from the group consisting of H, D, —OH, halo, —CN, —S(O)$_p$R$^7$, —NR$^7$R$^{7'}$ and —S(O)$_p$NR$^7$R$^{7'}$, and alkyl, deuterated alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R$^5$;

R$^{4'}$ is independently selected from the group consisting of H, D, halo, —OH, and alkyl, deuterated alkyl and alkoxy; or R$^4$ and R$^{4'}$ may be taken together to form (═O), provided that when m>1, there is no more than 1 (═O) group;

R$^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (═O) groups, R$^6$ is selected from the group consisting of H, —OH, halo, —CN, —NO$_2$, —S(O)$_p$R$^7$, —NR$^7$R$^{7'}$, —S(O)$_p$NR$^7$R$^{7'}$, —C(O)R$^{10}$, —C(O)—OR$^{10}$, and —C(O)—N(R$^7$)R$^{10}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (═O) groups, and —C(═O)R$^7$, —C(═O)OR$^7$, —C(═O)NR$^7$R$^{7'}$, —SO$_2$R$^7$ and —SO$_2$NR$^7$R$^{7'}$;

R$^{6'}$ is selected from the group consisting of H, —S(O)$_p$R$^7$, —S(O)$_p$NR$^7$R$^{7'}$, —C(O)—R$^{10}$, —C(O)—OR$^{10}$, —C(O)—N(R$^7$)R$^{10}$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ and/or 1 or 2 (═O) groups substituents, and —C(═O)R$^7$, —C(═O)OR$^7$, —C(═O)NR$^7$R$^{7'}$, —SO$_2$R$^7$ and —SO$_2$NR$^7$R$^{7'}$; or R$^6$ and R$^{6'}$ may be taken together to form (═O);

R$^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by R$^{12}$;

R$^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by R$^{12}$; or a) when a variable is —NR$^7$R$^{7'}$, —C(O)NR$^7$R$^{7'}$ or —SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected R$^{12}$ moieties and/or 1 or 2 (═O) groups, or b) when a variable is —(CH$_2$)$_q$ON═CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said heterocyclyl, heterocyclenyl or heteroaryl rings have 1-3 heteroatoms which are independently selected from the group consisting of O, N, —N(R$^9$)— and S, wherein said rings are optionally substituted by 1 to 5 independently selected R$^{12}$ moieties and/or 1 or 2 (═O) groups, R$^9$ is independently selected from the group consisting of H, —C(O)—R$^{10}$, —C(O)—OR$^{10}$, and —S(O)$_p$—R$^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (═O) groups; and R$^{10}$ is independently selected from the group consisting of H, and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N(R$^{11}$)$_2$, and —S(O)$_p$R$^{11}$ substituents and/or 1 or 2 (═O);

R$^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11'}$ and/or 1 or 2 (═O) groups;

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, —C(O)—N(R$^{11}$)$_2$, —N(R$^{14}$)—S(O)$_2$—R$^{11}$, —S(O)$_2$—N(R$^{11}$)$_2$ and —S(O)$_p$R$^{11}$ and/or 1 or 2 (═O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (═O) groups, wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

R$^{14}$ is independently H, alkyl, or aryl;

R$^{15}$ is absent (i.e., the nitrogen and the 2-position carbon atom form a —N═C(Z)-bond) independently selected from the group consisting of H, —C(O)—R$^{10}$, —C(O)—OR$^{10}$, —C(O)—N(R$^7$)(R$^{7'}$), and —S(O)$_p$—R$^{10}$, SO$_2$—NR$^7$R$^{7'}$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (═O) groups substituents, and —C(═O)R$^7$, —C(═O)OR$^7$, —C(═O)NR$^7$R$^{7'}$, —SO$_2$R$^7$ and —SO$_2$NR$^7$R$^{7'}$;

q is independently an integer from 0-10;

n is independently an integer from 0-2;

m is independently an integer from 1-3;

p is independently an integer from 0-2; and w is an integer from 0-3.

In another aspect, the present application discloses a compound, or pharmaceutically acceptable salts or metabolites, solvates, prodrugs or polymorphs of said compound, said compound having the general structure shown in Formula II

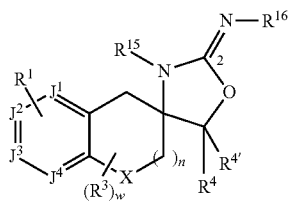

II wherein:
J¹, J², J³ and J⁴ are independently —N—, —N(O)—, or —C(R²)—;
X is —C(R⁶)(R⁶')—, —N(R⁶')—, —O— or —S—;
R¹ is a ring selected from the group consisting of cycloalkyl, cycloalkenyl, aryl, heterocyclyl, heterocyclenyl, and heteroaryl, each of which is optionally substituted with at least one (preferably 1 to 5, more preferably 1 to 3) R¹²;
R² is absent or independently selected from the group consisting of H, halo, —CN, —NO₂, —OH, —S(O)$_p$R⁷, —NR⁷R⁷', —[C(R$^a$)(R$^b$)]$_q$YR⁷', —[C(R$^a$)(R$^b$)]$_q$N(R⁷')YR⁷', —[C(R$^a$)(R$^b$)]$_q$N(R⁷')CN, —[C(R$^a$)(R$^b$)]$_q$OYR⁷', and —(CH₂)$_q$ON═CR⁷R⁷', and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R⁵;
Y is selected from the group consisting of a bond, —C(═O)—, —C(═O)NR⁷—, —C(═O)O—, —C(═O)N(R$^c$)—O—, —C(═NR⁷)—, —C(═NOR⁷)—, —C(═NR⁷)NR⁷—, —C(═NR⁷)NR⁷O—, —C(═N—CN)—, —S(O)$_p$—, —SO₂NR⁷—, and —C(═S)NR⁷—;
  wherein R$^a$ and R$^b$ are independently selected from the group consisting of H, alkyl, alkoxy, and halo, and R$^c$ is H or alkyl;
R³ is independently selected from the group consisting of H, —OH, halo, —CN, —NO₂, —S(O)$_p$R⁷, —NR⁷R⁷', —S(O)$_p$NR⁷R⁷', and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R⁵, provided that when w is 3, no more than 2 of the R³ groups may be (═O);
R⁴ is independently selected from the group consisting of H, D, —OH, halo, —CN, —S(O)$_p$R⁷, —NR⁷R⁷' and —S(O)$_p$NR⁷R⁷', and alkyl, deuterated alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) R⁵;
R⁴' is independently selected from the group consisting of H, D, halo, —OH, and alkyl, deuterated alkyl and alkoxy; or
R⁴ and R⁴' may be taken together to form (═O);
R⁵ is independently selected from the group consisting of H, halo, —OH, —CN, —NO₂, —NR⁷R⁷', and —S(O)$_p$R⁷, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO₂, —NR⁷R⁷', and —S(O)$_p$R⁷ substituents and/or 1 or 2 (═O) groups;
R⁶ is selected from the group consisting of H, —OH, halo, —CN, —NO₂, —S(O)$_p$R⁷, —NR⁷R⁷', —S(O)$_p$NR⁷R⁷', —C(O)—R¹⁰, —C(O)—OR¹⁰, and —C(O)—N(R⁷)R¹⁰, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO₂, —NR⁷R⁷', and —S(O)$_p$R⁷ substituents and/or 1 or 2 (═O) groups, and —C(═O)R⁷, —C(═O)OR⁷, —C(═O)NR⁷R⁷', —SO₂R⁷ and —SO₂NR⁷R⁷';
R⁶' is selected from the group consisting of H, —S(O)$_p$R⁷, —S(O)$_p$NR⁷R⁷', —C(O)—R¹⁰, —C(O)—OR¹⁰, —C(O)—N(R⁷)R¹⁰ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO₂, —NR⁷R⁷', and —S(O)$_p$R⁷ and/or 1 or 2 (═O) groups substituents, and —C(═O)R⁷, —C(═O)OR⁷, —C(═O)NR⁷R⁷', —SO₂R⁷ and —SO₂NR⁷R⁷'; or
R⁶ and R⁶' may be taken together to form (═O);
R⁷ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by R¹²;
R⁷' is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times (preferably 1 to 5, more preferably 1 to 3) by R¹²; or
  a) when a variable is —NR⁷R⁷', —C(O)NR⁷R⁷' or —SO₂NR⁷R⁷', R⁷ and R⁷' together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R⁹)— and S, wherein said rings are optionally substituted by 1 to 5 independently selected R¹² moieties and/or 1 or 2 (═O) groups, or
  b) when a variable is —(CH₂)$_q$ON═CR⁷R⁷', R⁷ and R⁷' together with the carbon atom to which they are attached independently form a 3- to 8-membered cycloalkyl, cycloalkenyl, aryl, heterocyclyl, heterocyclenyl or heteroaryl ring, wherein said heterocyclyl, heterocyclenyl or heteroaryl rings have 1-3 heteroatoms which are independently selected from the group consisting of O, N, —N(R⁹)— and S, wherein said rings are optionally substituted by 1 to 5 independently selected R¹² moieties and/or 1 or 2 (═O) groups,
R⁹ is independently selected from the group consisting of H, —C(O)—R¹⁰, —C(O)—OR¹⁰, and —S(O)$_p$—R¹⁰ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO₂, —N(R¹¹)₂, and —S(O)$_p$R¹¹ substituents and/or 1 or 2 (═O) groups; and
R¹⁰ is independently selected from the group consisting of H, and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO₂, —N(R¹¹)₂, and —S(O)$_p$R¹¹ substituents and/or 1 or 2 (═O);
R¹¹ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N(R$^{11'}$)$_2$, and —S(O)$_p$R$^{11'}$ and/or 1 or 2 (═O) groups;

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, —C(O)—N(R$^{11}$)$_2$, —N(R$^{14}$)—S(O)$_2$—R$^{11}$, —S(O)$_2$—N(R$^{11}$)$_2$ and —S(O)$_p$R$^{11}$ and/or 1 or 2 (═O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (═O) groups, wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by R$^{11}$;

R$^{14}$ is independently H, alkyl, or aryl;

R$^{15}$ is independently selected from the group consisting of H, —C(O)—R$^{10}$, —C(O)—OR$^{10}$, —C(O)—N(R$^7$)(R$^{7'}$), and —S(O)$_p$—R$^{10}$, SO$_2$—NR$^7$R$^{7'}$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (═O) groups substituents, and —C(═O)R$^7$, —C(═O)OR$^7$, —C(═O)NR$^7$R$^{7'}$, —SO$_2$R$^7$ and —SO$_2$NR$^7$R$^{7'}$;

R$^{16}$ is H, alkyl or cycloalkyl;

q is independently an integer from 0-10;

n is independently an integer from 0-2;

p is independently an integer from 0-2; and w is an integer from 0-3.

The compounds of Formulae I and II can be useful as α2C adrenergic receptor modulators and can be useful in the treatment or prevention of one or more conditions associated with the α2C receptor by administering at least one compound of Formula I or Formula II to a mammal in need of such treatment. Conditions that my be treated by modulating the α2C receptor include allergic rhinitis, congestion (including congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis, congestion caused by polyps, or caused by the common cold), pain (e.g., neuropathy, inflammation, arthritis, or diabetes), diarrhea, glaucoma, congestive heart failure, chronic heart failure, cardiac ischemia, manic disorders, depression, anxiety, migraine, stress-induced urinary incontinence, neuronal damage from ischemia, schizophrenia, attention deficit hyperactivity disorder, symptoms of diabetes, post traumatic stress disorder, Parkinson's disease or a dementia (e.g., Alzheimer's disease).

Another embodiment of this invention is the treatment or prevention of one or more conditions associated with the α2C receptor by administering at least one compound of Formula I or Formula II to a mammal in need of such treatment by selectively modulating α2C adrenergic receptors in the mammal.

Another embodiment of this invention is the treatment or prevention of one or more conditions associated with the α2C receptor by administering an effective amount at least one compound of Formula I or Formula II to a mammal in need of such treatment without modifying blood pressure at the therapeutic dose.

Another embodiment of the present invention is a method for selectively modulating α2C adrenergic receptors in a cell in a mammal in need thereof, comprising contacting said cell with a therapeutically effective amount of at least one compound of Formula I or Formula II or a pharmaceutically acceptable salt, ester, prodrug or salt thereof.

Another embodiment of the present invention is a method for the treatment of congestion in a mammal in need thereof without modifying the blood pressure at therapeutic doses which comprises administering to the mammal an effective dose of at least one compound having adrenergic activity wherein said compound is a selective agonist of the α2C receptor.

DETAILED DESCRIPTION

In an embodiment, the present invention discloses certain spiroaminooxazoline derivatives, which are represented by structural Formula I, or a pharmaceutically acceptable salt thereof, wherein the various moieties are as described above.

In another embodiment, J$^1$, J$^2$ and J$^3$ are each —C(R$^2$)—.

In another embodiment, J$^2$, J$^3$ and J$^4$ are each —CH—.

In another embodiment, J$^1$ and J$^3$ are —CH— and J$^1$ is —N—.

In another embodiment, J$^2$ and J$^3$ are —CH— and J$^2$ is —N—.

In another embodiment, J$^1$, J$^2$ and J$^3$ are independently —CR$^2$— or —N—.

In another embodiment, J$^1$ and J$^2$ are —CH— and J$^3$ is —N—.

In another embodiment, J$^1$ and J$^2$ are —CH— and J$^3$ is —N—.

In another embodiment, n is 1.

In another embodiment, n is 2.

In another embodiment, n is 0.

In another embodiment, q is 0 or 1

In another embodiment, p is 1 or 2.

In another embodiment, X is —CH$_2$—.

In another embodiment, X is —NH—.

In another embodiment, X is —O—.

In another embodiment, X is —S—.

In another embodiment, X is —N(R$^{6'}$).

In one embodiment R$^1$ is optionally substituted (preferably 1 to 5 times) aryl (preferably optionally substituted phenyl) or optionally substituted (preferably 1 to 5 times) heteroaryl, wherein the optional substituents are, for example, any of the "ring system substituents" identified below. Examples of heteroaryl rings include pyridine, pyrimidine, furan, pyrrole, thiophene, pyridazine, pyrazine, indolizine, oxazole, pyrazole, isoxazole, indole, isoindole, imidazole, indoline, benzofuran, benzothiophene, indazole, benzimidazole, benzthiazole, quinoline, isoquinoline, cinnoline, phthalazine, quinazoline, quinoxaline, and naphthyridine. Preferred heteroaryl rings include pyridine, pyrimidine, furan, pyrrole, thiophene, pyridazine, pyrazine, indole, indoline, benzofuran, benzothiophene, benzimidazole, and benzthiazole. More preferred heteroaryl rings include pyridine, pyrimidine, pyrazole, isoxazole, and oxazole. Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment $R^1$ is an optionally substituted (preferably 1 to 5 times) cycloalkyl or cycloalkenyl ring. Examples of rings include cyclopentane, cyclohexane and cyclohexene. Examples of substituents include any of the "ring system substituents" identified below. Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment $R^1$ is an optionally substituted (preferably 1 to 5 times) heterocyclyl or heterocyclenyl ring or cycloalkenyl ring. Examples of rings include morpholine, piperazine, 2-pyrrolidine and tetrahydrofurane. Examples of substituents include any of the "ring system substituents" identified below. Preferred optional substituents include Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment, $R^1$ is an optionally substituted pyridine ring.

In another embodiment, $R^1$ is an optionally substituted pyrimidine ring.

In another embodiment, $R^1$ is an optionally substituted oxazole ring.

In another embodiment, $R^1$ is an optionally substituted phenyl ring.

In another embodiment, $R^1$ is an optionally substituted napthylene ring.

In another embodiment, $R^1$ is an optionally substituted isoxazole ring.

In another embodiment, $R^1$ is an optionally substituted pyrazole ring.

In another embodiment, $R^1$ is bonded to $J^1$; $J^2$, $J^3$ and $J^4$ are —CH—; and X is —CH$_2$—.

In another embodiment, $R^1$ is bonded to $J^1$; $J^2$, $J^3$ and $J^4$ are —CH—; and X is —NH—.

In another embodiment, $R^1$ is bonded to $J^1$; $J^2$, $J^3$ and $J^4$ are —CH—; and X is —O—.

In another embodiment, $R^1$ is bonded to $J^1$; $J^2$, $J^3$ and $J^4$ are —CH—; and X is —S—.

In another embodiment, $R^1$ is bonded to $J^4$; $J^1$, $J^2$ and $J^3$ are —CH—; and X is —CH$_2$—.

In another embodiment, $R^1$ is bonded to $J^4$; $J^1$, $J^2$ and $J^3$ are —CH—; and X is —NH—.

In another embodiment, $R^1$ is bonded to $J^4$; $J^1$, $J^2$ and $J^3$ are —CH—; and X is —O—.

In another embodiment, $R^1$ is bonded to $J^4$; $J^1$, $J^2$ and $J^3$ are —CH—; and X is —S—.

In another embodiment, $R^1$ is bonded to $J^2$; $J^1$, $J^3$ and $J^4$ are —CH—; and X is —CH$_2$—.

In another embodiment, $R^1$ is bonded to $J^2$; $J^1$, $J^3$ and $J^4$ are —CH—; and X is —NH—.

In another embodiment, $R^1$ is bonded to $J^2$; $J^1$, $J^3$ and $J^4$ are —CH—; and X is —O—.

In another embodiment, $R^1$ is bonded to $J^2$; $J^1$, $J^3$ and $J^4$ are —CH—; and X is —S—.

In another embodiment, $R^1$ is bonded to $J^3$; $J^1$, $J^2$ and $J^4$ are —CH—; and X is —CH$_2$—.

In another embodiment, $R^1$ is bonded to $J^3$; $J^1$, $J^2$ and $J^4$ are —CH—; and X is —NH—.

In another embodiment, $R^1$ is bonded to $J^3$; $J^1$, $J^2$ and $J^4$ are —CH—; and X is —O—.

In another embodiment, $R^1$ is bonded to $J^3$; $J^1$, $J^2$ and $J^4$ are —CH—; and X is —S—.

In another embodiment, Z is —NR$^7$R$^{7'}$, wherein R$^7$ and R$^{7'}$ are independently H, alkyl, R$^{12}$-aryl, and R$^{12}$-cycloalkyl.

In another embodiment $R^4$ is H, —OH, halo, —CN, —NO$_2$, —NR$^7$R$^{7'}$, wherein R$^7$ and R$^{7'}$ are independently H, alkyl, R$^{12}$-aryl, and R$^{12}$-cycloalkyl, alkyl, or haloalkyl In another embodiment, m is 1 and W is —O—.

In another embodiment, m is 1 and W is —S—.

In another embodiment, the spiro ring is:

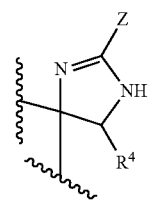

In another embodiment, the spiro ring is:

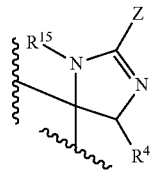

In another embodiment $R^{15}$ is H, optionally substituted alkyl, optionally substituted cycloalkyl (e.g., cyclopropyl, cyclopentyl, or cyclohexyl) or, optionally substituted aryl (e.g., phenyl), wherein the optional substituents are halo, hydroxyl, amino, alkyl amino, dialkyl amino, nitro, or cyano.

In another embodiment Z is amino, alkyl amino or dialkyl amino.

In another embodiment $R^{15}$ is H or alkyl.

In another embodiment, the present invention discloses compounds which are represented by structural formulae III-VI or a pharmaceutically acceptable salt, solvate or ester thereof, wherein the various definitions are those described above for Formula I:

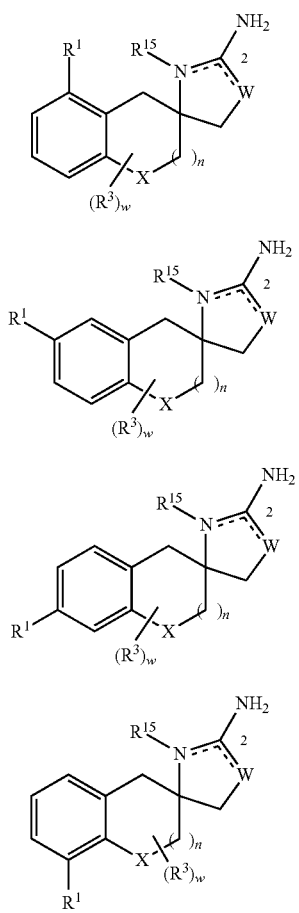

Formula III

Formula IV

Formula V

Formula VI

An embodiment of Formulae II-VI is those compounds wherein:

$R^1$ is optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy; and $R^{15}$ is absent or is H or alkyl (e.g., methyl or ethyl) or a pharmaceutically acceptable salt thereof.

Another embodiment of the compounds of Formula I is compounds of the formula

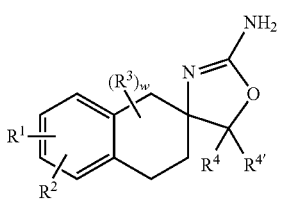

VII or a pharmaceutically acceptable salt thereof, wherein the definitions are the same as those for Formula I.

An embodiment of compounds of Formula VII is those compounds wherein:

$R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^2$ is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^3$ is independently H, alkyl, —OH, halo, or (=O);

$R^4$ is H, D, alkyl or deuterated alkyl (e.g., —CH$_2$D, CHD$_2$ or CD$_3$);

$R^{4'}$ is H, D, alkyl or deuterated alkyl (e.g., —CH$_2$D, CHD$_2$ or CD$_3$); and w is 0, 1 or 2, or a pharmaceutically acceptable salt thereof.

Another embodiment of the compounds of Formula I is the compounds of the formula

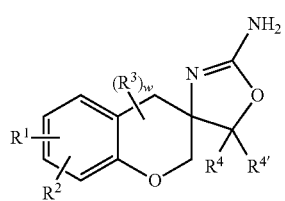

VIII or a pharmaceutically acceptable salt thereof, wherein the definitions are the same as those for Formula I.

An embodiment of compounds of Formula VIII is those compounds wherein:

$R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^2$ is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^3$ is independently H, alkyl, —OH, halo, or (=O);

$R^4$ is H, D, alkyl or deuterated alkyl (e.g., —CH$_2$D, CHD$_2$ or CD$_3$);

$R^{4'}$ is H, D, alkyl or deuterated alkyl (e.g., —CH$_2$D, CHD$_2$ or CD$_3$); and w is 0, 1 or 2, or a pharmaceutically acceptable salt thereof.

Another embodiment of the compounds of Formula I is compounds of the formula

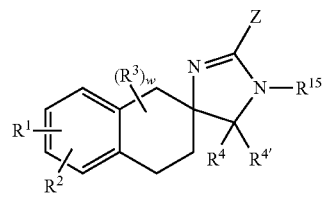

IX or a pharmaceutically acceptable salt thereof, wherein the definitions are the same as those for Formula I.

Another embodiment of the compounds of Formula IX is the compounds wherein $R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^2$ is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^3$ is independently H, alkyl, —OH, halo, or (=O);

$R^4$ is H, D, alkyl or deuterated alkyl (e.g., —CH$_2$D, CHD$_2$ or CD$_3$);

$R^{4'}$ is H, D, alkyl or deuterated alkyl (e.g., —CH$_2$D, CHD$_2$ or CD$_3$);

Z is H, alkyl or NH$_2$;

$R^{15}$ is H or alkyl (e.g., methyl, ethyl, propyl etc.); and w is 0, 1 or 2, or a pharmaceutically acceptable salt thereof.

Another embodiment of the compounds of Formula I is the compounds of the formula

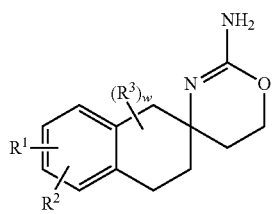

X or a pharmaceutically acceptable salt thereof, wherein the definitions are the same as those for Formula I.

An embodiment of the compounds of Formula X is those compounds wherein $R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^2$ is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^3$ is independently H, alkyl, —OH, halo, or (=O); and w is 0, 1 or 2, or a pharmaceutically acceptable salt thereof.

Another embodiment of the compounds of Formula I is the compounds of the formula

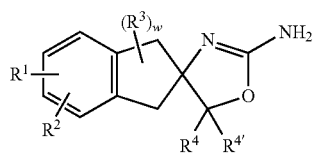

XI or a pharmaceutically acceptable salt thereof, wherein the definitions are the same as those for Formula I.

Another embodiment of compounds of Formula XI is the compounds wherein:

$R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substituents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)₂-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

R² is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)₂-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

R³ is independently H, alkyl, —OH, halo, or (=O);

R⁴ and R⁴' are independently H or alkyl; and w is 0, 1 or 2, or a pharmaceutically acceptable salt thereof.

A group of compounds falling within Formula I are those shown below:

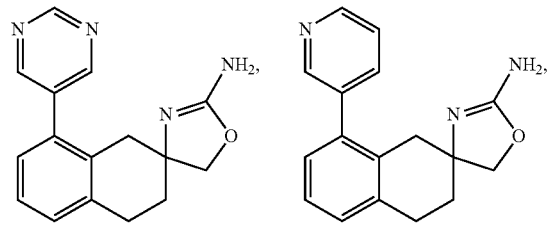
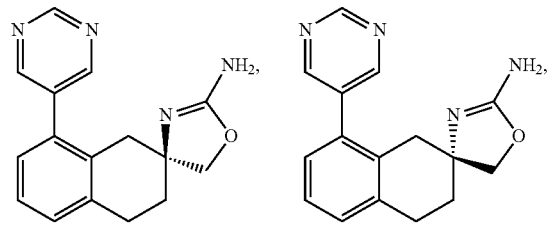
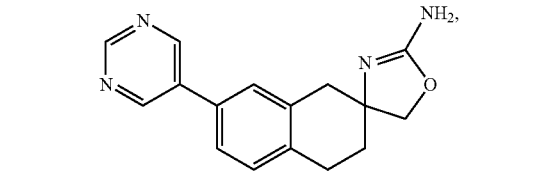

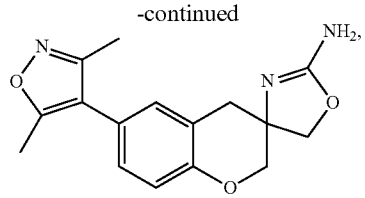
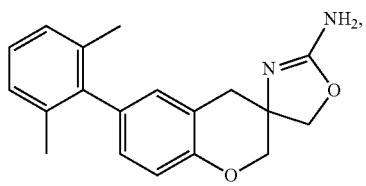
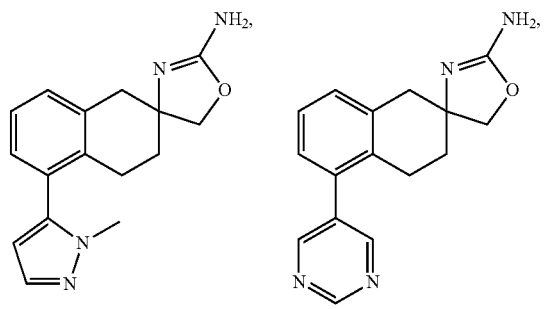
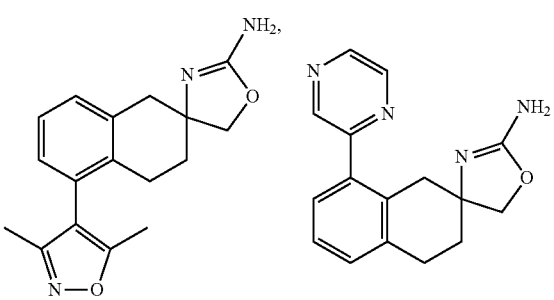
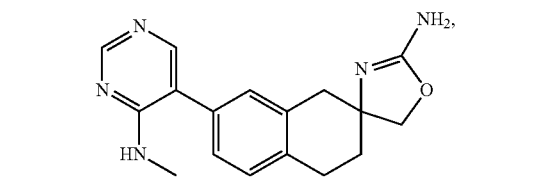
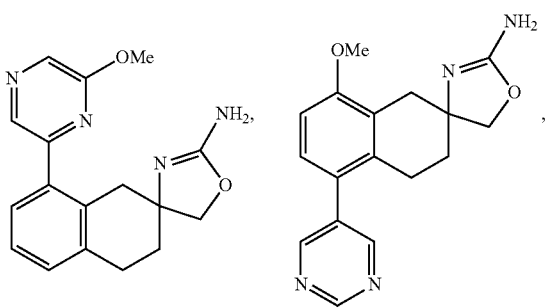

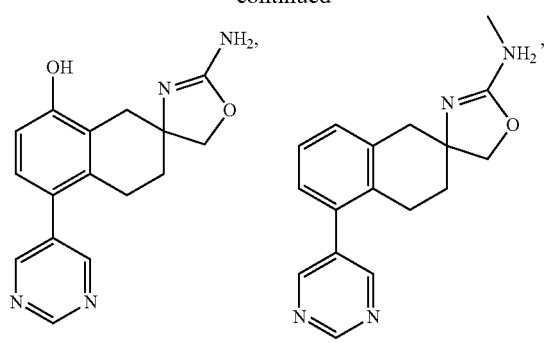
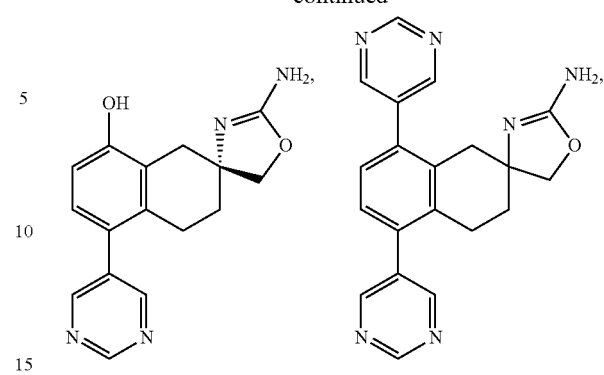
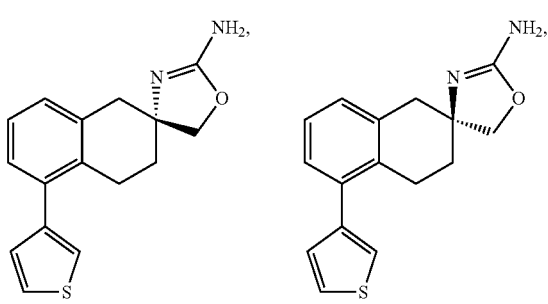
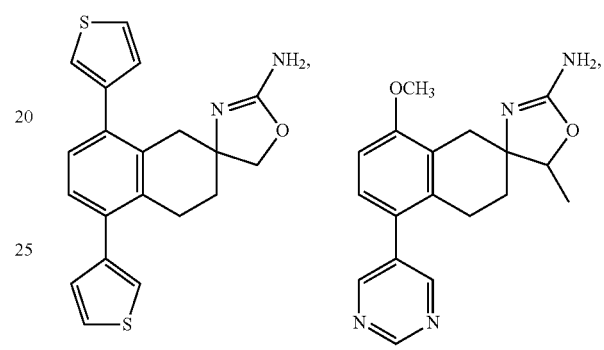
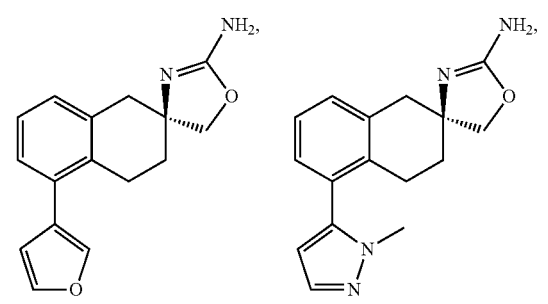
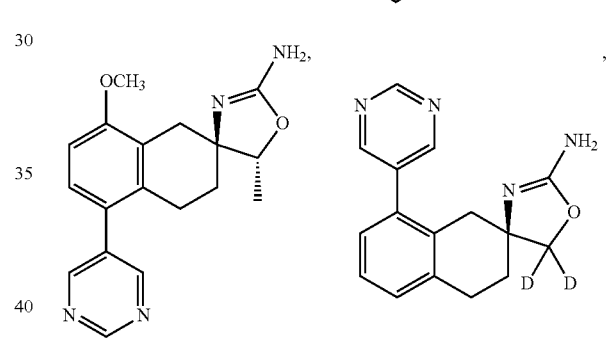
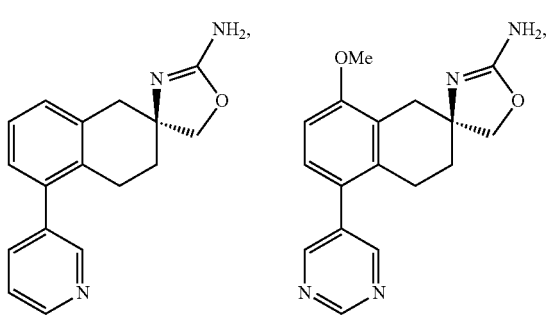
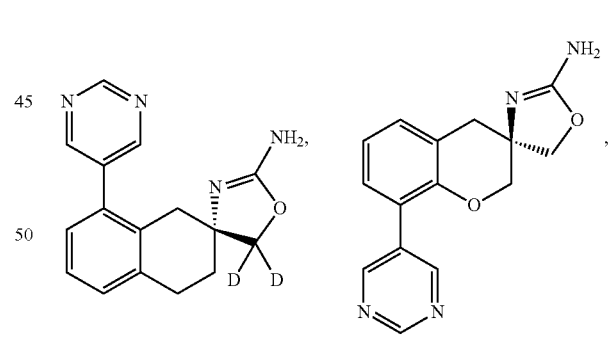
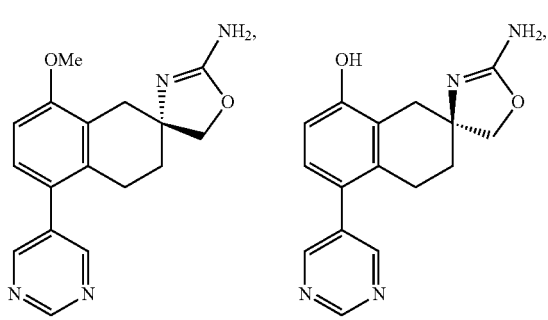
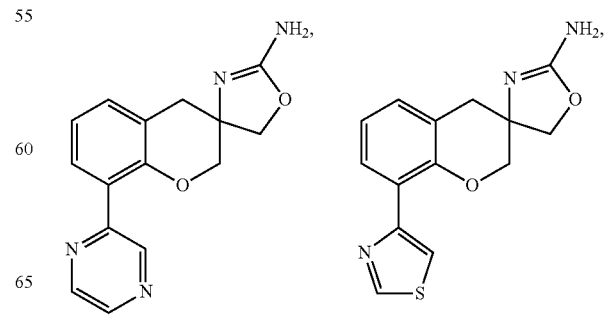

-continued
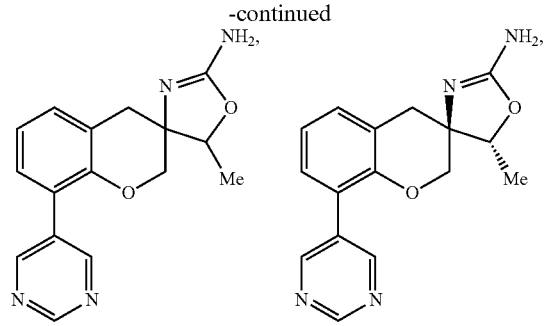
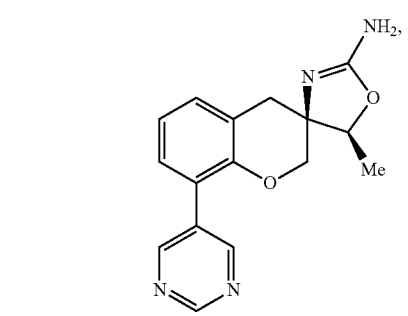
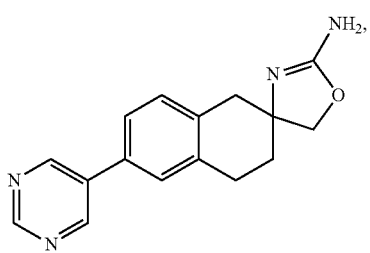
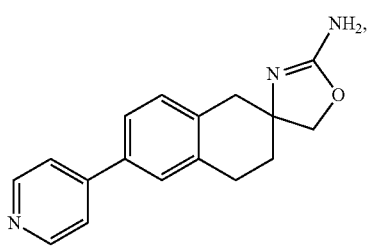
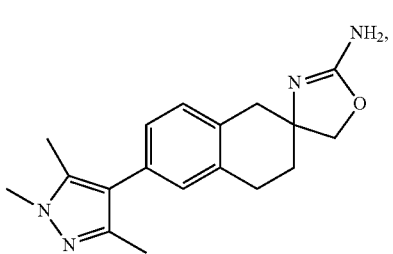
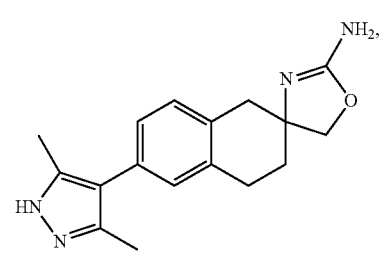
-continued
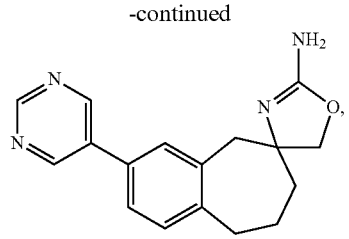
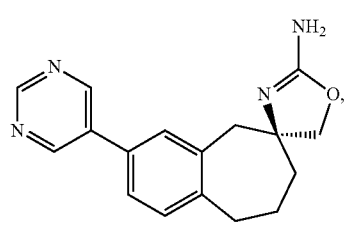
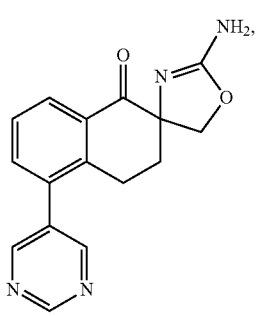
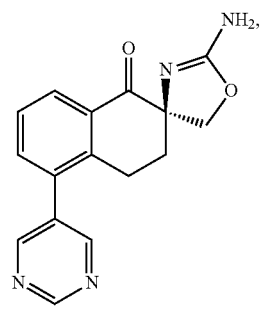
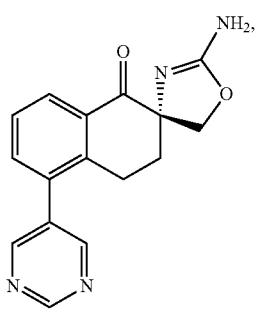
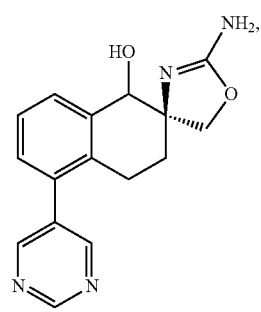
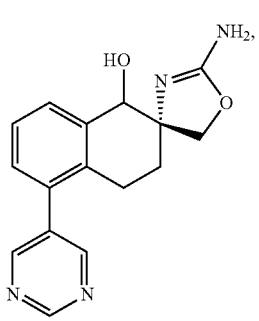
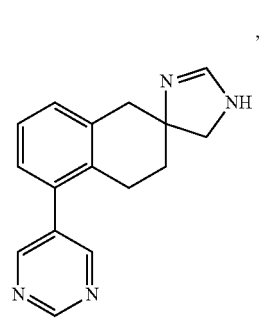
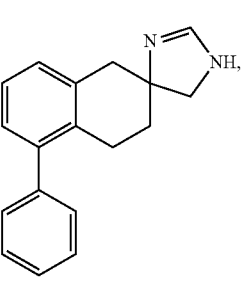
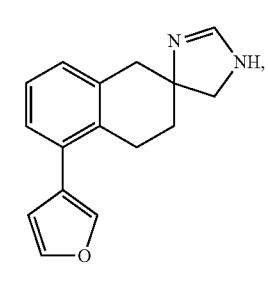

27
-continued
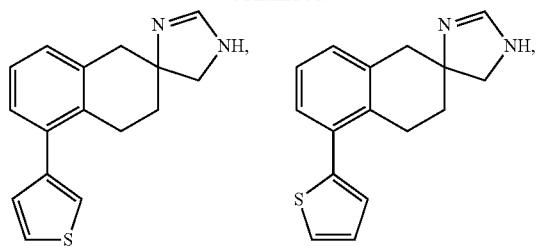
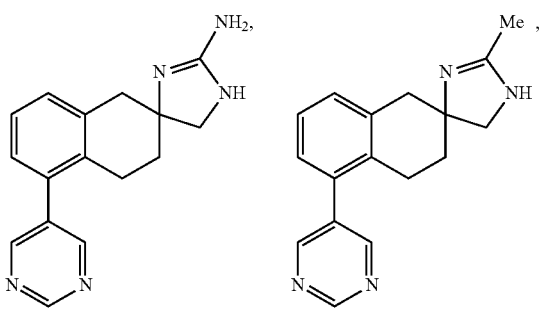
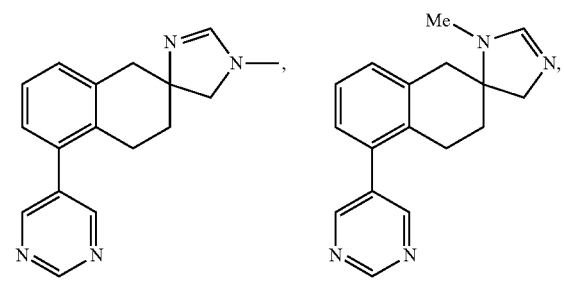
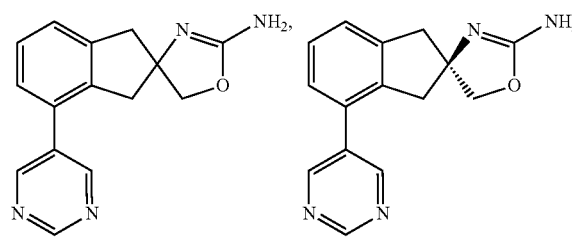
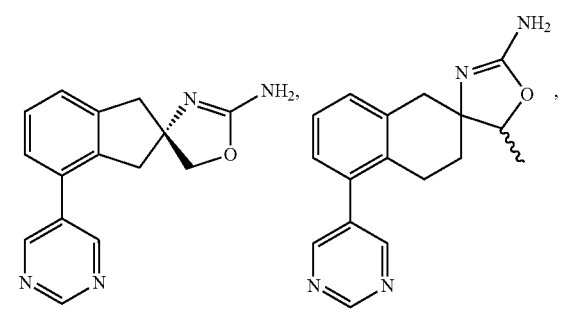
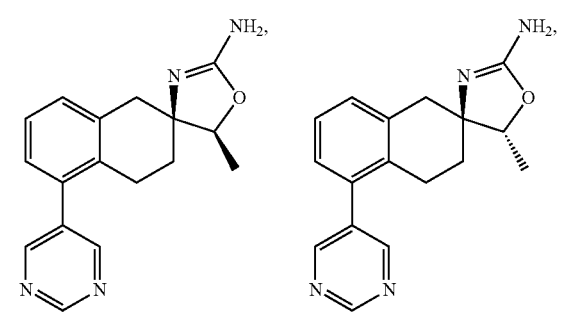
28
-continued
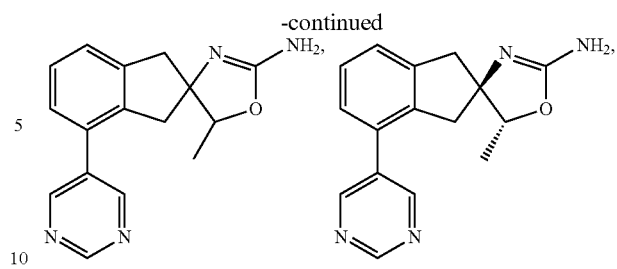
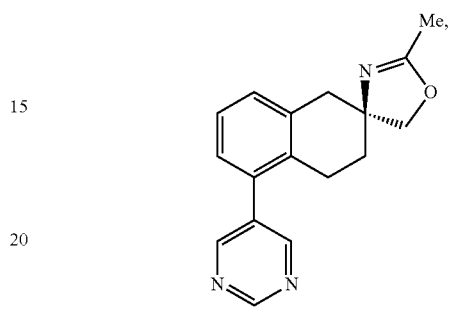
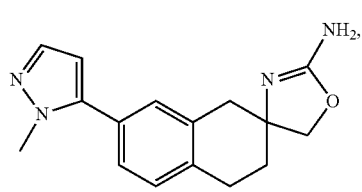
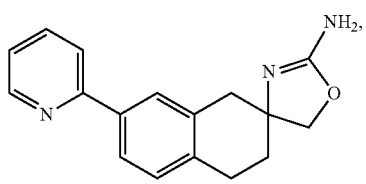
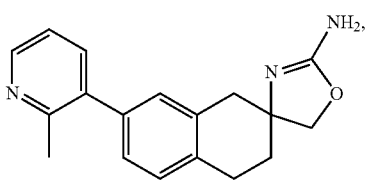
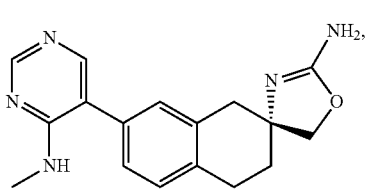
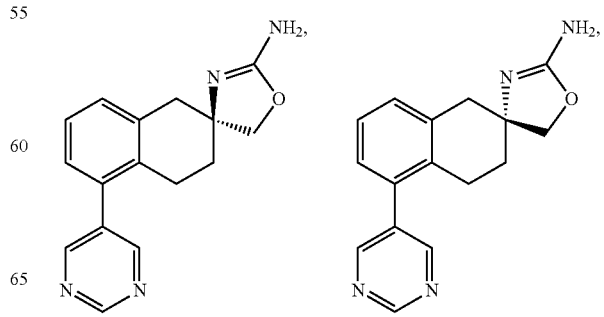

-continued
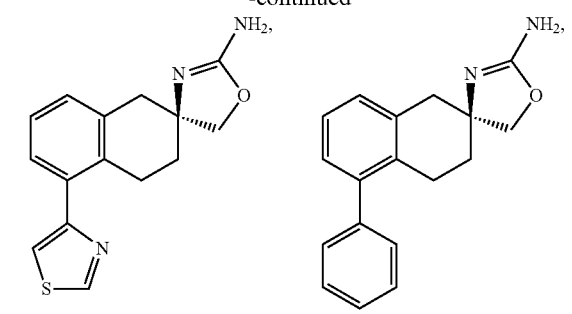
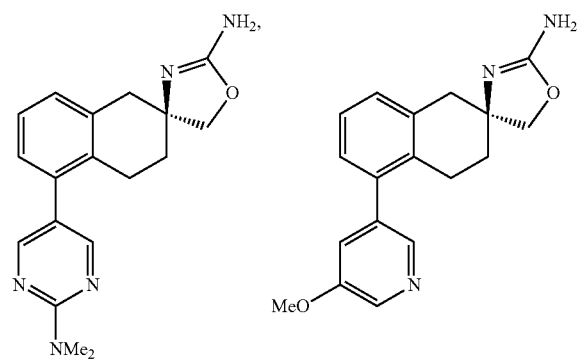
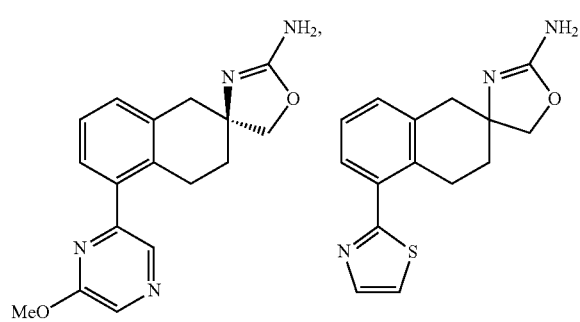
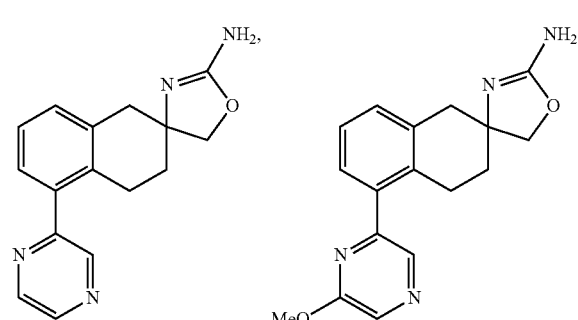
-continued
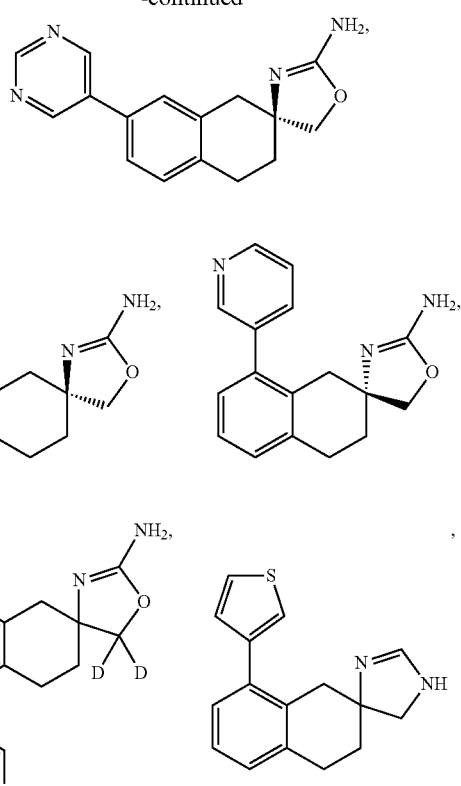
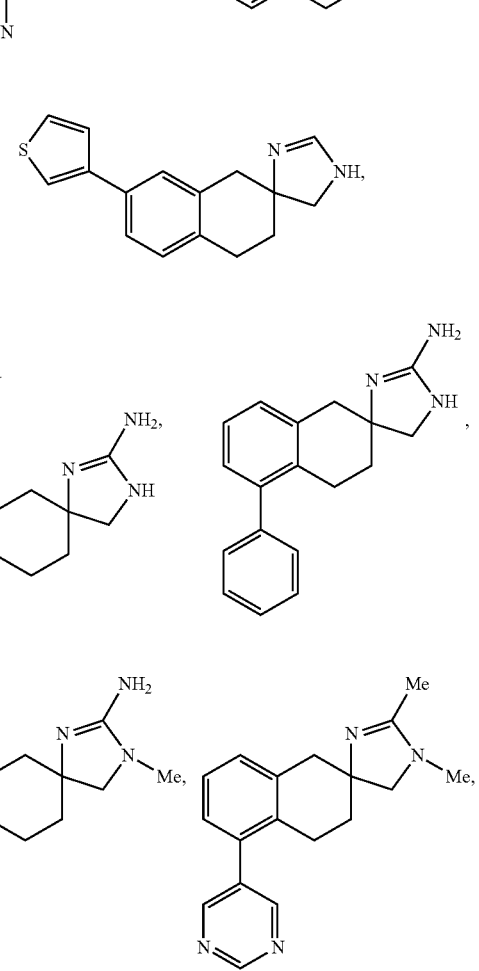
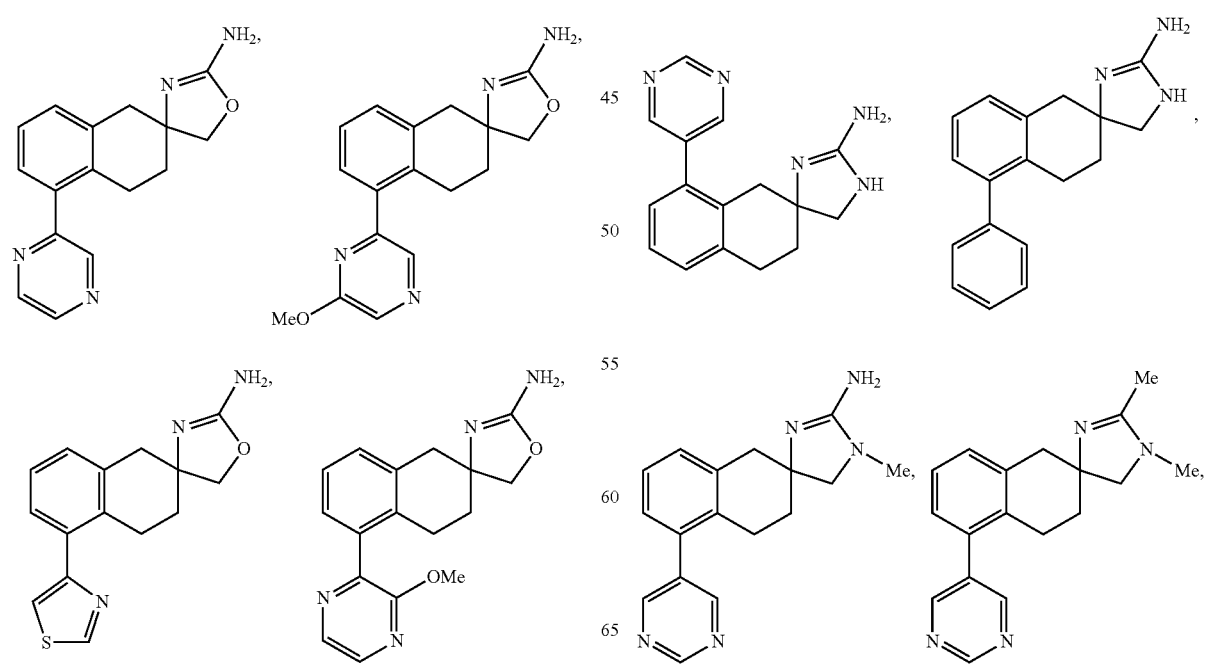

-continued
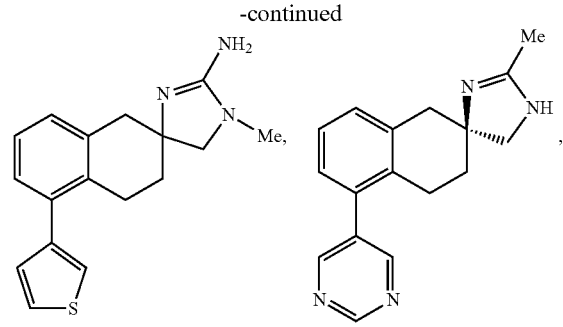
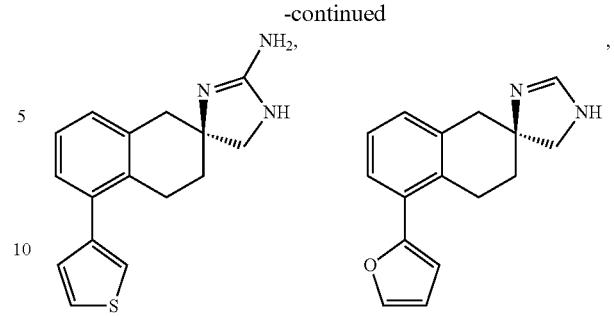
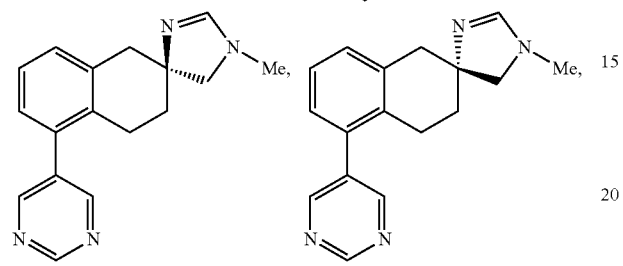
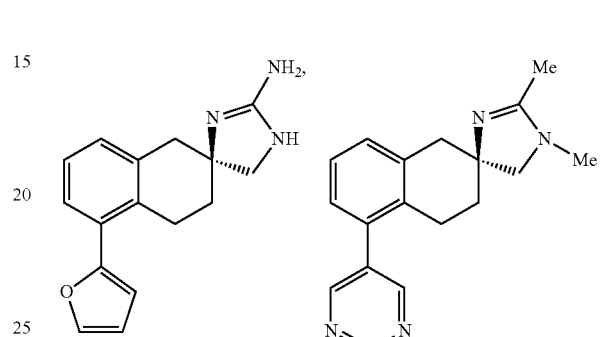
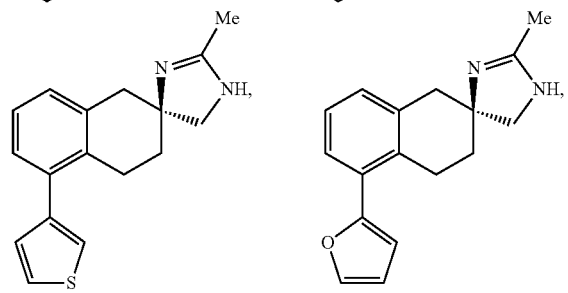
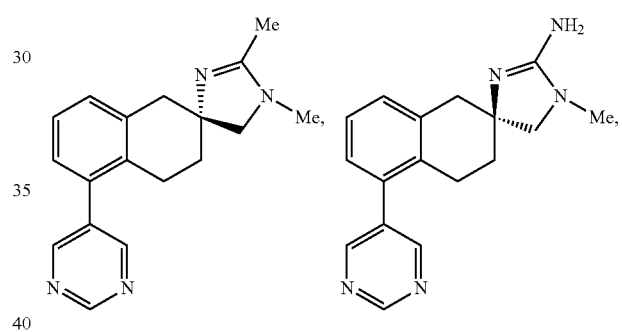
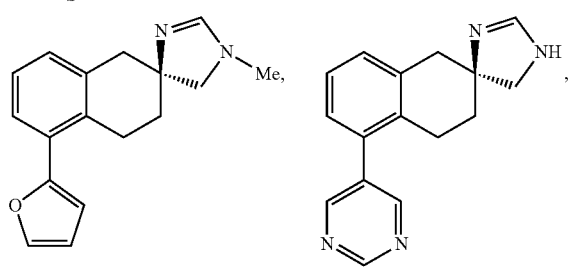
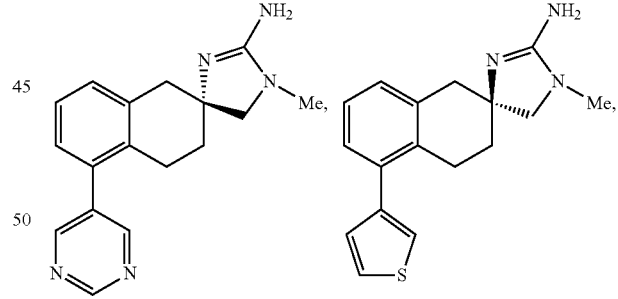
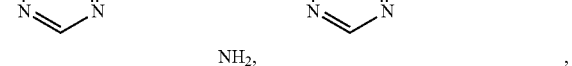
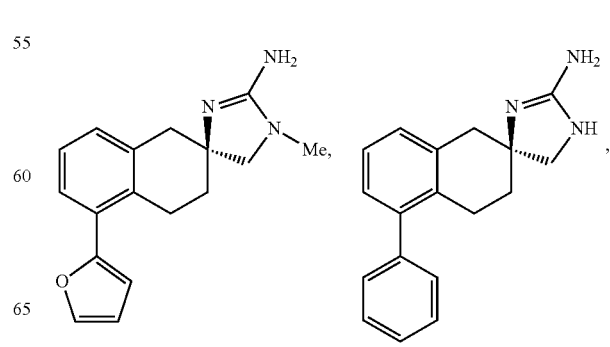

-continued
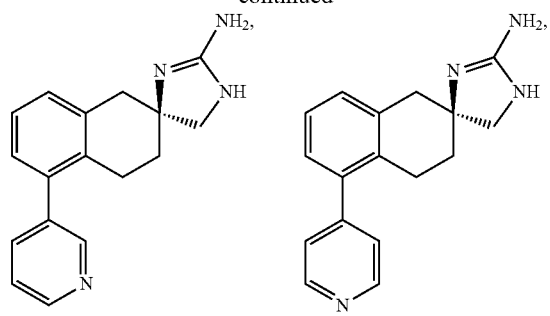
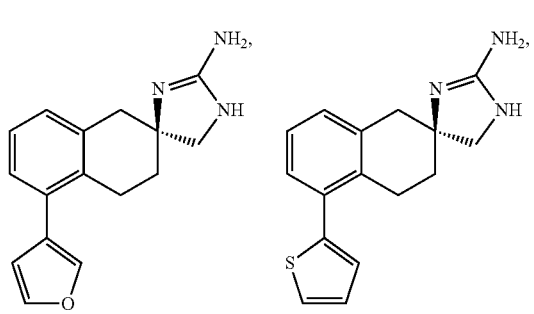
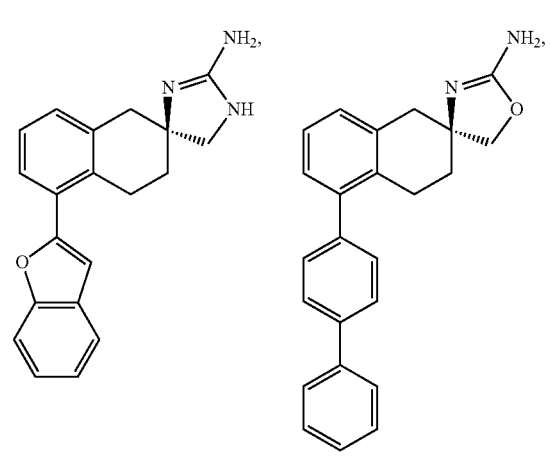
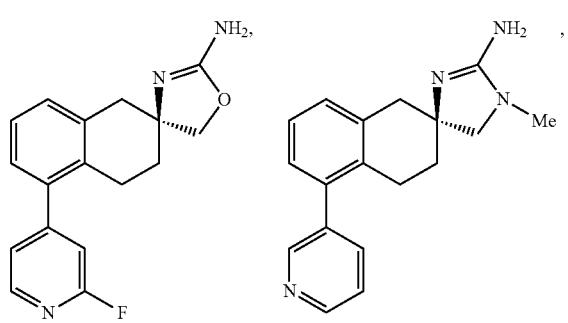
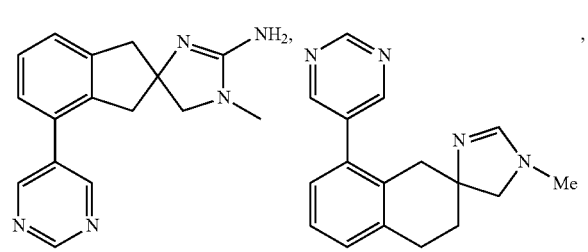
-continued
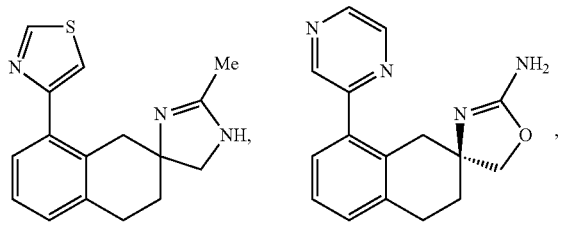
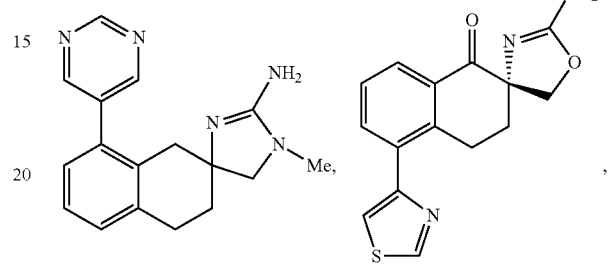
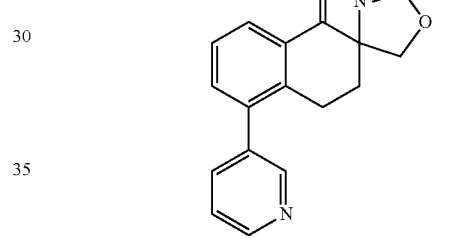
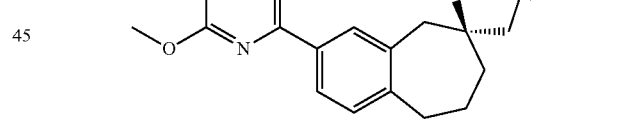
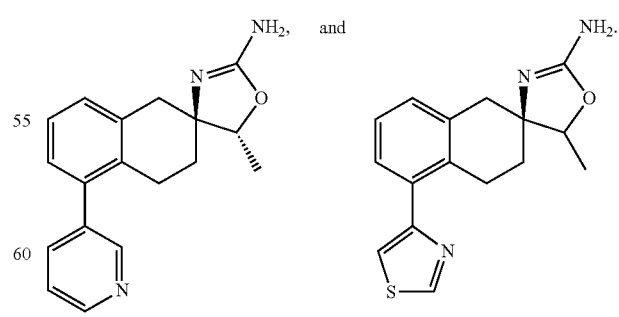
Another group of compounds falling within Formula I are those shown below:

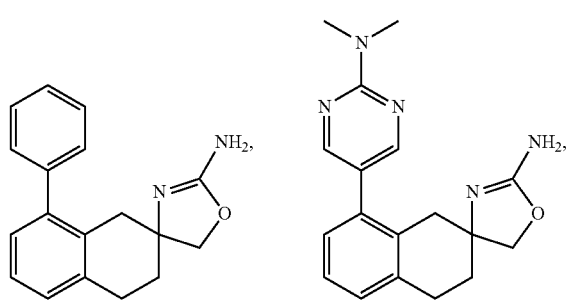
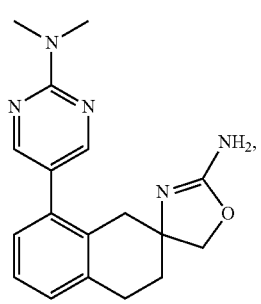
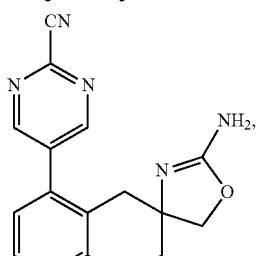
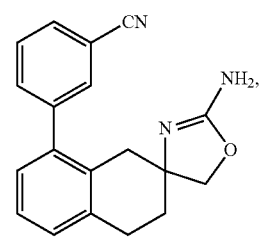
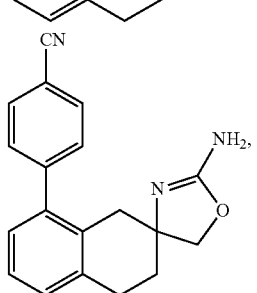
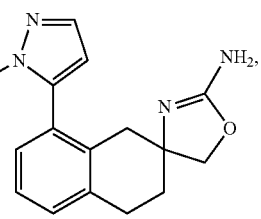
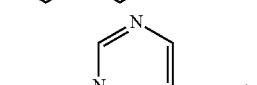
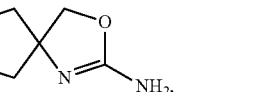
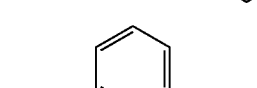
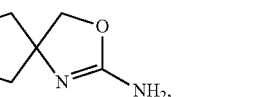
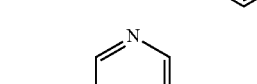
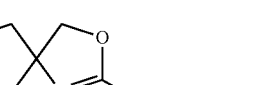
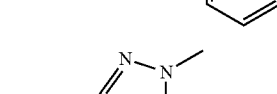
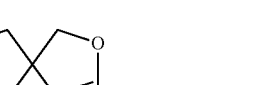
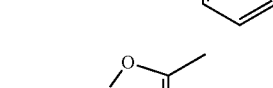
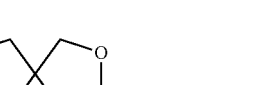
-continued
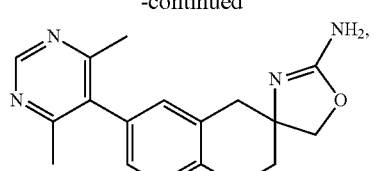
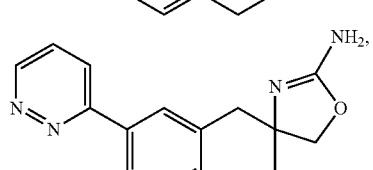
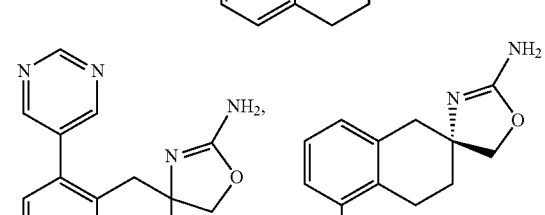
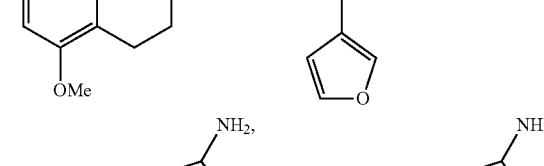
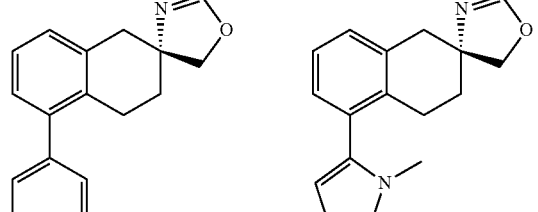
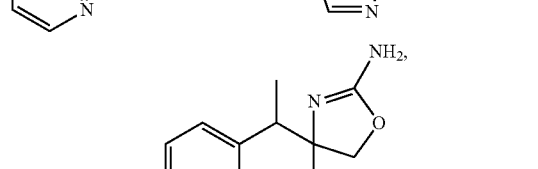
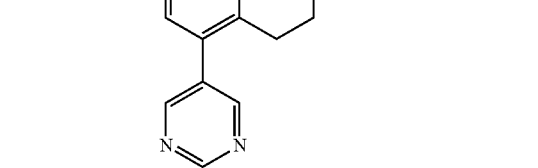
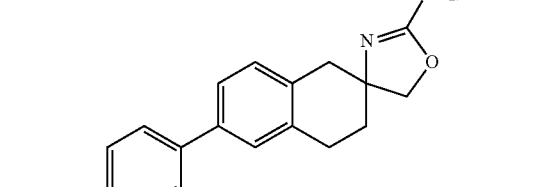
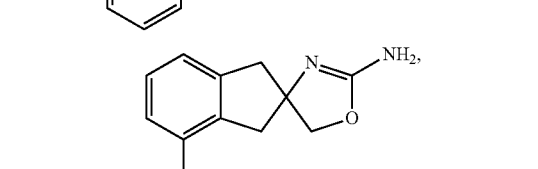

-continued
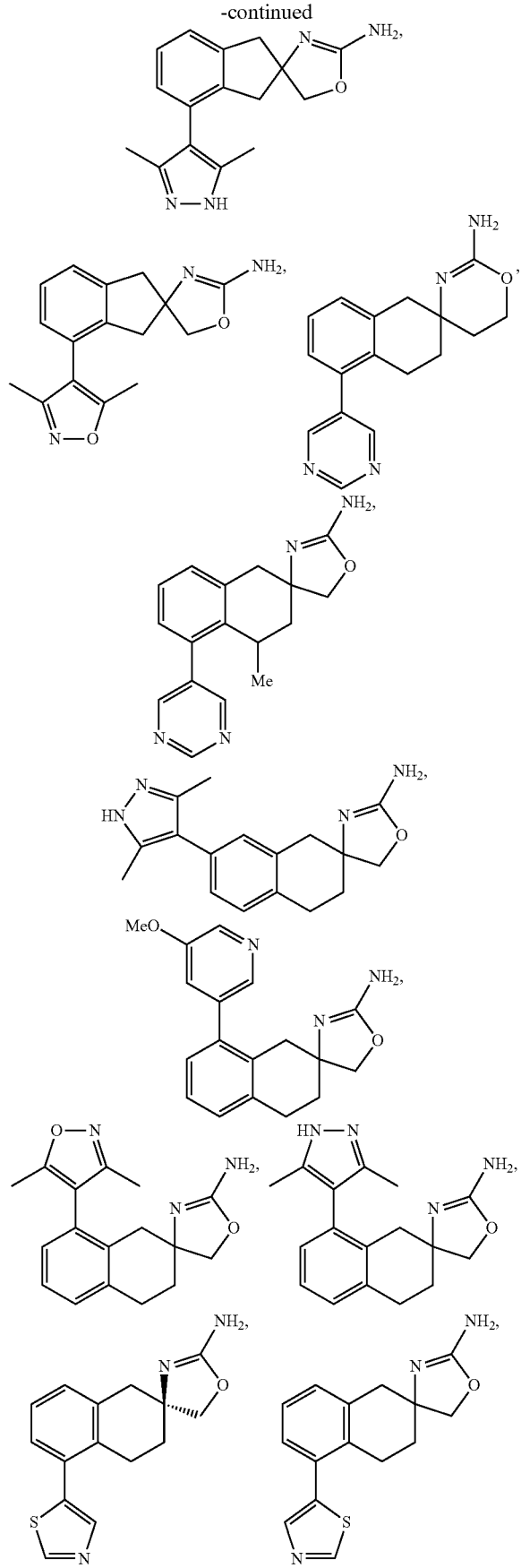
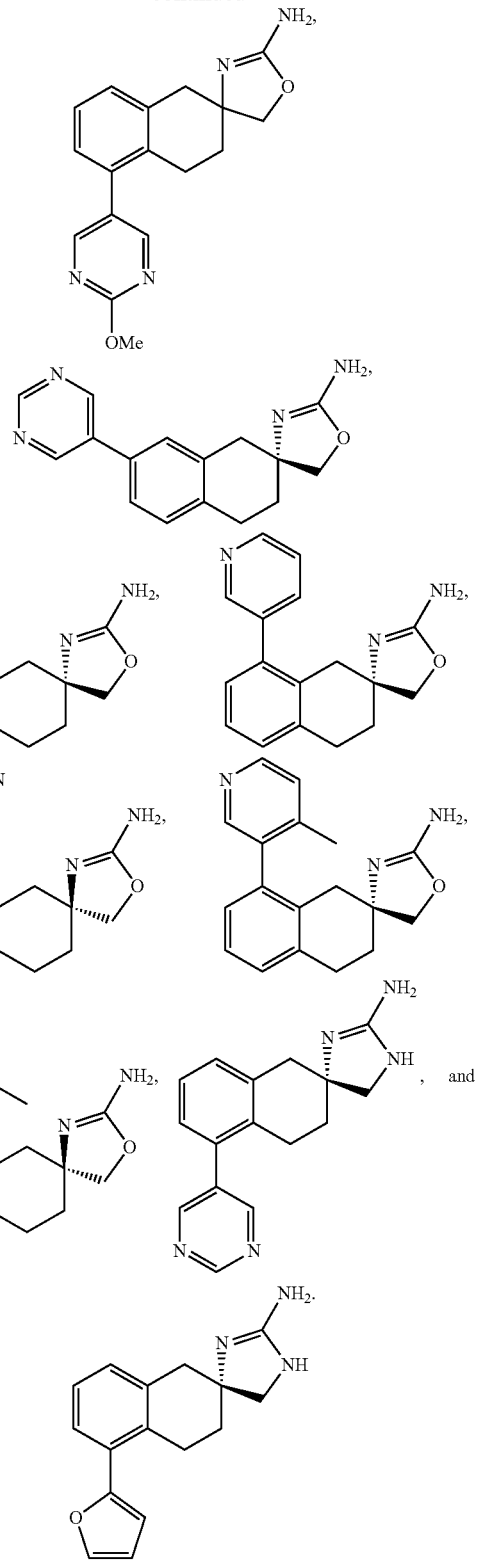
Another embodiment the compound of Formula I or a pharmaceutically acceptable salt thereof is present in its isolated and purified form.
In an another embodiment, the present invention discloses certain spiroaminooxazoline derivatives, which are represented by structural Formula II, or a pharmaceutically acceptable salt thereof, wherein the various moieties are as described above.

In another embodiment of Formula II, $J^1$, $J^2$ and $J^3$ are each —C($R^2$)—.

In another embodiment of Formula II, $J^2$, $J^3$ and $J^4$ are each —CH—.

In another embodiment of Formula II, $J^1$ and $J^3$ are —CH— and $J^1$ is —N—.

In another embodiment of Formula II, $J^2$ and $J^3$ are —CH— and $J^2$ is —N—.

In another embodiment, $J^1$, $J^2$ and $J^3$ are independently —$CR^2$— or —N—.

In another embodiment of Formula II, $J^1$ and $J^2$ are —CH— and $J^3$ is —N—.

In another embodiment of Formula II, $J^1$ and $J^2$ are —CH— and $J^3$ is —N—.

In another embodiment of Formula II, n is 1.
In another embodiment of Formula II, n is 2.
In another embodiment of Formula II, n is 0.
In another embodiment of Formula II, q is 0 or 1
In another embodiment of Formula II, p is 1 or 2.
In another embodiment of Formula II, X is —$CH_2$—.
In another embodiment of Formula II, X is —NH—.
In another embodiment of Formula II, X is —O—.
In another embodiment of Formula II, X is —S—.
In another embodiment of Formula II, X is —N($R^{6'}$).

In one embodiment of Formula II, $R^1$ is optionally substituted (preferably 1 to 5 times) aryl (preferably optionally substituted phenyl) or optionally substituted (preferably 1 to 5 times) heteroaryl, wherein the optional substituents are, for example, any of the "ring system substituents" identified below. Examples of heteroaryl rings include pyridine, pyrimidine, furan, pyrrole, thiophene, pyridazine, pyrazine, indolizine, oxazole, pyrazole, isoxazole, indole, isoindole, imidazole, indoline, benzofuran, benzothiophene, indazole, benzimidazole, benzthiazole, quinoline, isoquinoline, cinnoline, phthalazine, quinazoline, quinoxaline, and naphthyridine. Preferred heteroaryl rings include pyridine, pyrimidine, furan, pyrrole, thiophene, pyridazine, pyrazine, indole, indoline, benzofuran, benzothiophene, benzimidazole, and benzthiazole. More preferred heteroaryl rings include pyridine, pyrimidine, pyrazole, isoxazole, and oxazole. Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment of Formula II, $R^1$ is an optionally substituted (preferably 1 to 5 times) cycloalkyl or cycloalkenyl ring. Examples of rings include cyclopentane, cyclohexane and cyclohexene. Examples of substituents include any of the "ring system substituents" identified below. Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment of Formula II, $R^1$ is an optionally substituted (preferably 1 to 5 times) heterocyclyl or heterocyclenyl ring or cycloalkenyl ring. Examples of rings include morpholine, piperazine, 2-pyrrolidine and tetrahydrofurane. Examples of substituents include any of the "ring system substituents" identified below. Preferred optional substituents include Preferred optional substituents include alkyl, haloalkyl, nitro, cyano, halo, hydroxyl, alkoxy, amino, alkylamino, dialkylamino, haloalkoxy, aryl, and heteroaryl, wherein said aryl and heteroaryl are optionally substituted 1 to 5, preferably 1 to 3, times by alkyl, haloalkyl, nitro, cyano, halo, hydroxyl, alkoxy, amino, alkylamino, dialkylamino and haloalkoxy.

In another embodiment of Formula II, $R^1$ is an optionally substituted pyridine ring.

In another embodiment of Formula II, $R^1$ is an optionally substituted pyrimidine ring.

In another embodiment of Formula II, $R^1$ is an optionally substituted oxazole ring.

In another embodiment of Formula II, $R^1$ is an optionally substituted phenyl ring.

In another embodiment of Formula II, $R^1$ is an optionally substituted napthylene ring.

In another embodiment of Formula II, $R^1$ is an optionally substituted isoxazole ring.

In another embodiment of Formula II, $R^1$ is an optionally substituted pyrazole ring.

In another embodiment of Formula II, $R^1$ is bonded to $J^1$; $J^2$, $J^3$ and $J^4$ are —CH—; and X is —$CH_2$—.

In another embodiment of Formula II, $R^1$ is bonded to $J^1$; $J^2$, $J^3$ and $J^4$ are —CH—; and X is —NH—.

In another embodiment of Formula II, $R^1$ is bonded to $J^1$; $J^2$, $J^3$ and $J^4$ are —CH—; and X is —O—.

In another embodiment of Formula II, $R^1$ is bonded to $J^1$; $J^2$, $J^3$ and $J^4$ are —CH—; and X is —S—.

In another embodiment of Formula II, $R^1$ is bonded to $J^4$; $J^1$, $J^2$ and $J^3$ are —CH—; and X is —$CH_2$—.

In another embodiment of Formula II, $R^1$ is bonded to $J^4$; $J^1$, $J^2$ and $J^3$ are —CH—; and X is —NH—.

In another embodiment of Formula II, $R^1$ is bonded to $J^4$; $J^1$, $J^2$ and $J^3$ are —CH—; and X is —O—.

In another embodiment of Formula II, $R^1$ is bonded to $J^4$; $J^1$, $J^2$ and $J^3$ are —CH—; and X is —S—.

In another embodiment of Formula II, $R^1$ is bonded to $J^2$; $J^1$, $J^3$ and $J^4$ are —CH—; and X is —$CH_2$—.

In another embodiment of Formula II, $R^1$ is bonded to $J^2$; $J^1$, $J^3$ and $J^4$ are —CH—; and X is —NH—.

In another embodiment of Formula II, $R^1$ is bonded to $J^2$; $J^1$, $J^3$ and $J^4$ are —CH—; and X is —O—.

In another embodiment of Formula II, $R^1$ is bonded to $J^2$; $J^1$, $J^3$ and $J^4$ are —CH—; and X is —S—.

In another embodiment of Formula II, $R^1$ is bonded to $J^3$; $J^1$, $J^2$ and $J^4$ are —CH—; and X is —$CH_2$—.

In another embodiment of Formula II, $R^1$ is bonded to $J^3$; $J^1$, $J^2$ and $J^4$ are —CH—; and X is —NH—.

In another embodiment of Formula II, $R^1$ is bonded to $J^3$; $J^1$, $J^2$ and $J^4$ are —CH—; and X is —O—.

In another embodiment of Formula II, $R^1$ is bonded to $J^3$; $J^1$, $J^2$ and $J^4$ are —CH—; and X is —S—.

In another embodiment $R^4$ is H, D, —OH, halo, —CN, —$NO_2$, alkyl, deuterated alkyl (e.g., $CD_3$) or —$NR^7R^{7'}$, wherein $R^7$ and $R^{7'}$ are independently H, alkyl, $R^{12}$-aryl, and $R^{12}$-cycloalkyl, alkyl, or haloalkyl.

In another embodiment of Formula II, $R^{16}$ is H or alkyl.

In another embodiment of Formula II, $R^{4'}$ is H or D.

Another embodiment of the compounds of Formula II is compounds of the formula

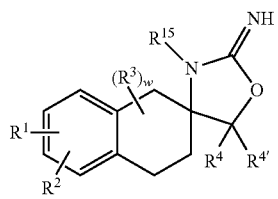

XII or a pharmaceutically acceptable salt thereof, wherein the definitions are the same as those for Formula II.

Another embodiment of the compounds of Formula XII is the compounds wherein $R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^2$ is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^3$ is independently H, alkyl, —OH, halo, or (═O);

$R^4$ is H, D, alkyl or deuterated alkyl (e.g., —CH$_2$D, CHD$_2$ or CD$_3$);

$R^{4'}$ is H, D, alkyl or deuterated alkyl (e.g., —CH2D, CHD2 or CD3); and $R^{15}$ is H or alkyl (e.g., methyl, ethyl, propyl etc.); and w is 0, 1 or 2, or a pharmaceutically acceptable salt thereof.

Another embodiment of the compounds of Formula II is compounds of the formula

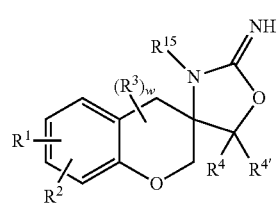

XIII or a pharmaceutically acceptable salt thereof, wherein the definitions are the same as those for Formula II.

Another embodiment of the compounds of Formula XIII is the compounds wherein $R^1$ is optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^2$ is H, alkyl, alkenyl, halo, alkoxy, optionally substituted aryl, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy;

$R^3$ is independently H, alkyl, —OH, halo, or (═O);
$R^4$ is H, D, alkyl or deuterated alkyl (e.g., —CH$_2$D, CHD$_2$ or CD$_3$);
$R^{4'}$ is H, D, alkyl or deuterated alkyl (e.g., —CH$_2$D, CHD2 or CD3); and
$R^{15}$ is H or alkyl (e.g., methyl, ethyl, propyl etc.); and
w is 0, 1 or 2, or a pharmaceutically acceptable salt thereof.

Two compound falling within Formula II is a compound of the formula

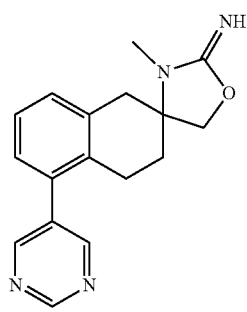

and its stereoisomer:

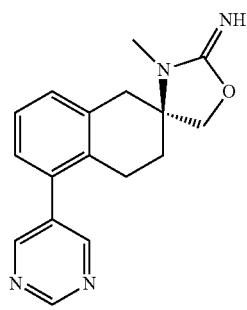

In another embodiment the compound of Formula II or a pharmaceutically accept salt thereof is present in its isolated and purified form.

One embodiment of the present invention is compounds that act as agonists of the α2C receptor. Alpha-2C receptor agonists can by used in the treatment or prevention of allergic rhinitis, congestion (including, but not limited to nasal congestion), migraine, congestive heart failure, chronic heart failure, cardiac ischemia, glaucoma, stress-induced urinary incontinence, attention deficit hyperactivity disorder, neuronal damage from ischemia and psychotic disorders. Further, alpha-2C receptor agonists can be useful in the treatment of pain (both chronic and acute), such as pain that is caused by inflammation, neuropathy, arthritis (including osteo and rheumatoid arthritis), diabetes (e.g., diabetes mellitus or diabetes insipidus) or pain of an unknown origin. Examples of neuropathic pain may include but not limited to; diabetic neuropathy, neuralgia of any etiology (e.g. post-herpetic, trigeminal), chemotherapy-induced neuropathy, HIV, lower back pain of neuropathic origin (e.g. sciatica), traumatic peripheral nerve injury of any etiology, central pain (e.g. post-stroke, thalamic, spinal nerve injury). Other pain that can be treated is nociceptive pain and pain that is visceral in origin or pain that is secondary to inflammation or nerve damage in other diseases or diseases of unknown origin. Further, alpha-2C receptor agonists can be useful in the treatment of symptoms of diabetes. Examples of symptoms of diabetes may include but are not limited to: hyperglycemia, hypertriglyceridemia, increased levels of blood insulin and hyperlipidemia.

A compound is defined to be an agonist of the alpha-2c receptor if the compound's efficacy at the α2C receptor is ≧30% $E_{max}$ (GTPγS assay).

A further embodiment of the present invention are that act selectively, and preferably even specifically, as agonists of the α2C or the α2B/α2C (hereinafter referred to as α2C or α2B/2C) receptor subtypes in preference over the α2A receptor subtype and that act functionally selectively as agonists of the α2C or the α2B/2C receptor subtype in preference over the α2A receptor subtype possess desirable therapeutic properties associated with adrenergic receptors but without having one or more undesirable side effects such as changes in blood pressure or sedation. For the purposes of the present invention, a compound is defined to be a specific or at least functionally selective agonist of the α2C receptor subtype over the α2A receptor subtype if the compound's efficacy at the α2C receptor is ≧30% $E_{max}$ (GTPγS assay) and its efficacy at the α2A receptor is ≦35% $E_{max}$, (GTPγS assay).

In another embodiment of the present invention the compound acts as an antagonist of the alpha-2C receptor. Alpha-2C receptor antagonists can be used in the treatment or prevention of disease states such as depression, schizophrenia, post traumatic stress disorder, Parkinson's disease, dementias (e.g., Alzheimer's disease and neuropathic disorders.

A compound is defined to be an antagonist of the alpha-2C receptor if the compounds's efficacy at the α2C receptor is <30% $E_{max}$ (GTPγS assay) and the binding inhibition of at the α2C receptor ($K_i$) is <500 nM, preferably <200 nM, and most preferably <20 nM. In a further embodiment of the present invention, the α2C receptor subtype antagonists possess desirable therapeutic properties associated with the α2C adrenergic receptor but without having one or more undesirable side effects associated with α2A agonism. For the purposes of this invention, compounds that act as antagonists at the α2C receptor subtype preferably do not possess an efficacy at the α2A receptor of 35% $E_{max}$ or more (GTPγS assay).

Alternatively, the present invention provides for a method for the treatment of congestion in a mammal in need thereof which comprises administering to a mammal an effective dose of at least one compound having adrenergic activity wherein said compound is a functionally selective agonist of the α2c receptor or the α2C/αB adrenergic receptor.

A further embodiment of the present invention is a method for the treatment of congestion in a mammal in need thereof which comprises administering to a mammal an effective dose of at least one compound having adrenergic activity wherein said compound is a functionally selective agonist of the α2C receptor or the α2C/αB adrenergic receptor, wherein the selective agonist of the α2c receptor or the α2C/αB adrenergic receptor has an efficacy that is greater than or equal to 30% $E_{max}$ when assayed in the GTPγS assay and its efficacy at the α2A receptor is ≦35% $E_{max}$ (GTPγS assay).

A further embodiment of the present invention is a method for treating one or more conditions associated with α2C adrenergic receptors, comprising administering to a mammal in need of such treatment a compound of Formulae I or II or a pharmaceutically acceptable salt thereof.

Another embodiment of the present invention is a method for treating one or more conditions associated with α2C adrenergic receptors, comprising administering to a mammal in need of such treatment a compound of Formulae I or II or a pharmaceutically acceptable salt thereof wherein the conditions are selected from the group consisting of allergic rhinitis, congestion, pain, diarrhea, glaucoma, congestive heart failure, chronic heart failure, cardiac ischemia, manic disorders, depression, anxiety, migraine, stress-induced urinary incontinence, neuronal damage from ischemia, schizophrenia, attention deficit hyperactivity disorder, and symptoms of diabetes.

Another embodiment of the present invention is a method for treating one or more conditions associated with α2C adrenergic receptors, comprising administering to a mammal in need of such treatment a compound of Formulae I or II or a pharmaceutically acceptable salt thereof wherein the condition is congestion.

Another embodiment of the present invention is a method for treating one or more conditions associated with α2C adrenergic receptors, comprising administering to a mammal in need of such treatment a compound of Formulae I or II or a pharmaceutically acceptable salt thereof wherein the condition is congestion and the congestion is associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or the congestion is caused by polyps or is associated with the common cold.

Another embodiment of the present invention is a method for treating one or more conditions associated with α2C adrenergic receptors, comprising administering to a mammal in need of such treatment a compound of Formulae I or II or a pharmaceutically acceptable salt thereof wherein the condition is pain.

Another embodiment of the present invention is a method for treating one or more conditions associated with α2C adrenergic receptors, comprising administering to a mammal in need of such treatment a compound of Formulae I or II or a pharmaceutically acceptable salt thereof wherein the condition is pain wherein the pain is associated with neuropathy, inflammation, arthritis, or diabetis.

Another embodiment of the present invention is a method for treating one or more conditions associated with α2C adrenergic receptors, comprising administering to a mammal in need of such treatment a compound of Formulae I or II or a pharmaceutically acceptable salt thereof wherein the condition is Alzheimer's disease, depression, anxiety or Parkinson's disease.

As used above, and throughout this disclosure, the following terms, unless otherwise indicated, shall be understood to have the following meanings:

"Patient" includes both human and animals.

"Mammal" means humans and other mammalian animals.

"alpha-2C modulator" or "α2C modulator" means that a compound has affinity for (or binds to) the α2C receptor which provokes a biological response (i.e., either an agonistic or antagonistic response).

"alpha-2C receptor agonist" or "a2C receptor agonist" is a compound that has affinity for the α2C receptor and elicits a biological response that mimics the response observed by the endogenous ligand (e.g., neurotransmitter) that binds to the same receptor.

"alpha-2C receptor antagonist or "a2C receptor antagonist" is a compound that has affinity for the α2C receptor and elicits a biological response that blocks or dampens the response observed by the endogenous ligand (e.g., neurotransmitter) that binds to the same receptor.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Deuterated alkyl" means an alkyl group wherein at least on of the hydrogens in the aliphatic hydrocarbon group is replaced by a deuterium atom. Examples of deuterated alkyl groups include, for example, —CDH$_2$, —CD$_2$H, —CD$_3$, —CH$_2$CD$_3$ etc. This term covers deuterated alkyl groups wherein the amount of deuterium is enriched so that a group containing a naturally occurring amount of deuterium is not contemplated.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system, in which at least one of the multicyclic rings is an aryl ring, comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Non-limiting examples of aryl multicyclic ring systems include:

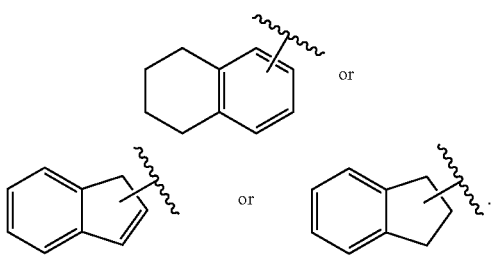

"Heteroaryl" means an aromatic monocyclic or multicyclic ring system, in which at least one of the multicyclic rings is aromatic, comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

Non-limiting examples of heteroaryl multicyclic ring systems include:

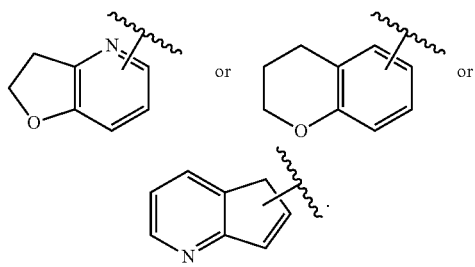

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, imidazolidinyl, pyrazolidinyl, piperazinyl, morpholinyl, thiomorpholinyl, thiazolidinyl, 1,4-dioxanyl, tetrahydrofuranyl, tetrahydrothiophenyl, and the like.

Compounds of Formulae I and II and salts, esters, solvates and prodrugs thereof, may exist in their tautomeric form (for example, as an amide or imino ether). All such tautomeric forms are contemplated herein as part of the present invention. Non-limiting examples of tautomeric forms that are part of this invention are as follows:

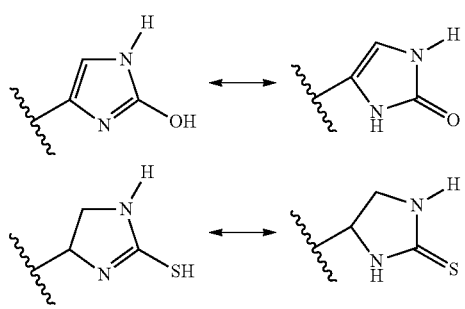

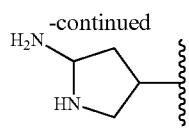

It should be noted that in saturated heterocyclyl containing systems of this invention, there are no hydroxyl, amino, or thiol groups on carbon atoms adjacent to a N, O or S atom. Thus, for example, in the ring:

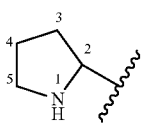

there is no —OH attached directly to carbons marked 2 and 5. It should also be noted that this definition does not preclude (=O), (=S), or (=N) substitutions, or their tautomeric forms, on C atoms adjacent to a N, O or S. Thus, for example, in the above ring, (=O) substitution on carbon 5, or its imino ether tautomer is allowed.

Non-limiting examples which illustrate the present invention are as follows:

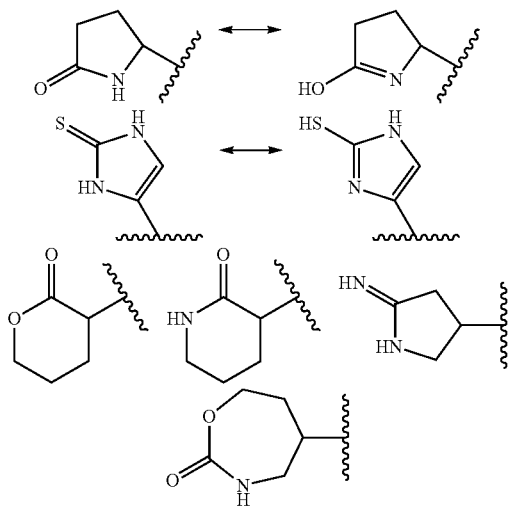

The following non-limiting examples serve to illustrate radicals not contemplated by the present invention:

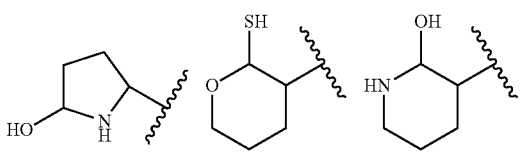

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, 2-oxazolinyl, 2-thiazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclenylalkyl" means a heterocyclenyl-alkyl group in which the heterocyclenyl and the alkyl are as previously described.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C (O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" or "arylalkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Heteroarylalkoxy" means a heteroarylalkyl-O— group in which the heteroarylalkyl group is as previously described.

"Heterocyclylalkoxy" means a heterocyclylalkyl-O group in which the hetorcyclylalkyl group is as previously described.

"Heterocyclenylalkoxy" means a heterocyclenylalkyl-O group in which the heterocyclenylalkyl group is as previously described.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

It is noted that carbons of Formulae I and II can be replaced with 1-3 silicon atoms, provided all valency requirements are satisfied.

The term "optionally substituted" means optional substitution with the specified groups, radicals or moieties.

The straight line —— as a bond generally indicates a mixture of, or either of, the possible isomers, non-limiting example(s) include, containing (R)- and (S)-stereochemistry. For example,

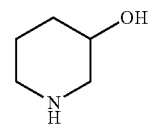

means containing both

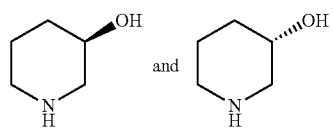

A dashed line ( _ _ _ _ _ ) represents an optional bond.
Lines drawn into the ring systems, such as, for example:

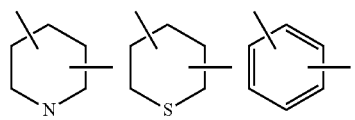

indicate that the indicated line (bond) may be attached to any of the substitutable ring atoms, non-limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

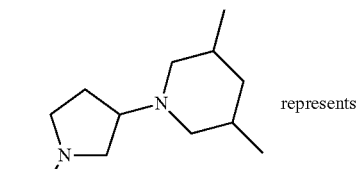

represents

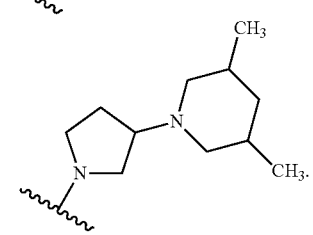

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or formula, its definition on each occurrence is independent of its definition at every other occurrence.

Unless defined otherwise, all definitions for the variables follow the convention that the group to the right forms the point of attachment to the molecule; i.e., if a definition is arylalkyl, this means that the alkyl portion of the definition is attached to the molecule.

Further, all divalent variable are attached from left to right. For example when $R^2$ is $—[C(R^a)(R^b)]_qN(R^7)YR^{7'}$ and Y is $—C(=O)—$, $—C(=O)O—$ or $—C(=O)NR^7$, then $R^2$ forms the group $—[C(R^a)(R^b)]_qN(R^7)—C(=O)—R^{7'}$, $—[C(R^a)(R^b)]_qN(R^7)—C(=O)O—R^{7'}$, or $—[C(R^a)(R^b)]_qN(R^7)—C(=O)N(R^7)(R^{7'})$.

In this application, unless otherwise indicated, whenever there is a structural formula provided, such as those of Formulae I to XIII, this formula is intended to encompass all forms of a compound such as, for example, any solvates, hydrates, stereoisomers, tautomers, etc.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formulae I and II or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formulae I and II or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$alkyl, and the like.

Similarly, if a compound of Formulae I and II contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formulae I and II incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Metabolic conjugates, such as glucuronides and sulfates which can undergo reversible conversion to the compounds of Formulae I and II are contemplated in the present invention.

"Effective amount" or "therapeutically effective amount" is meant to describe an amount of compound or a composition of the present invention effective in producing the desired therapeutic, ameliorative, inhibitory or preventative effect.

The terms "purified", "in purified form" or "in isolated and purified form," as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formulae I and II can form salts which are also within the scope of this invention. Reference to a compound of Formulae I and II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulae I and II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formula I or may be formed, for example, by reacting a compound of Formulae I and II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formulae I and II incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

Polymorphic forms of the compounds of Formulae I and II, and of the salts, solvates and prodrugs of the compounds of Formulae I and II, are intended to be included in the present invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formulae I and II (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formulae I and II can be useful as α2C adrenoreceptor agonists.

A preferred dosage is about 0.001 to 500 mg/kg of body weight/day of the compound of Formula I or Formula II. An especially preferred dosage is about 0.01 to 25 mg/kg of body weight/day of a compound of Formula I or Formula II, or a pharmaceutically acceptable salt or solvate of said compound.

The compounds of this invention may also be useful in combination (administered together or sequentially) with one or more therapeutic agents such as, for example, glucocorticosteroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, and therapeutic agents suitable for treating heart conditions, psychotic disorders, and glaucoma.

Suitable steroids include prednisolone, fluticasone (including all ester such as the propionate or furoate esters), triamcinolone, beclomethasone, mometasone (including any ester form such as mometasone furoate), budasamine, ciclesonide betamethasone, dexamethasone, prednisone, flunisolide, and cortisone.

Suitable PDE-4 inhibitors include roflumilast, theophylline, rolipram, piclamilast, cilomilast and CDP-840.

Suitable antimuscarinic agents include ipratropium bromide and tiatropium bromide.

Suitable $H_1$ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, and tolmetin.

Suitable aldosterone antagonists include spironolactone.

Suitable ionotropic agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlorthalidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, amitriptyline, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, percocet, morphine sulfate, dilaudid, stadol, stadol NS, acetaminophen with codeine, acetaminophen with codeine #4, Lidoderm® patches, ziconotide, duloxetine, roboxetine, gabapentin and pregabalin.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leucotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Fiorninal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, and trimipramine maleate.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I or Formula II, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. When preparing a liquid preparation, the inclusion of one or more solubility enhancing components is excluded. Solubility enhancing components are described, for example, in U.S. Pat. No. 6,673,337 in column 2, line 50 to column 3, line 17 and in column 6, line 49 to line 31; U.S. Pat. No. 6,673,337 is expressly incorporated by reference. Specific solubility enhancing agents that are excluded in the liquid form preparations include metal carboxymethylcelluloses, metal carboxymethylhydroxyethylcelloses, hydroxypropylmethyl celluloses derivative of these compounds, and cyclodextrins. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

An aspect of this invention is that the pharmaceutical composition is in a solid dosage form comprising a compound of Formulae I and II or a pharmaceutical acceptable salt, ester, solvate or prodrug thereof and a least one pharmaceutically acceptable carrier, adjuvant or vehicle.

Another aspect of this invention is a liquid, aqueous pharmaceutical composition is comprising a compound of Formulae I and II or a pharmaceutical acceptable salt, ester, solvate or prodrug thereof and a least one pharmaceutically acceptable carrier, adjuvant or vehicle provided that the adjuvant is not a solubility enhancing component, such as those described in U.S. Pat. No. 6,673,337 (discussed above).

Another aspect of this invention is a liquid, aqueous pharmaceutical composition is comprising a compound of Formulae I and II or a pharmaceutical acceptable salt, ester, solvate or prodrug thereof and a least one pharmaceutically acceptable carrier, adjuvant or vehicle wherein if a solubility enhancement component is present it is cyclodextrin.

Another aspect of this invention is a pharmaceutical formulation that is a nasal spray wherein the pH is equal to or less that about 6.5, more preferably between about 6.1 to 6.2.

Another aspect of this invention the formulation is a nasal spray wherein the adjuvants include a suspending agent (e.g., AVICEL (such as AVICIL RC-581, RC-591 and CL-611), which are microcrystalline cellulose and carboxymethylcellulose sodium; hydroxypropylmethyl cellulose; methyl cellulose; polyvinyl alcohol; or CARBOPOL) and a humectant (e.g., glycerin, propylene glycol; polyethylene glycol; povidone; or dextrose).

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formulae I and II, or a pharmaceutically acceptable salt or solvate of said compound and a pharmaceutically acceptable carrier, vehicle or diluent.

Yet another aspect of this invention is a kit comprising an amount of at least one compound of Formulae I and II, or a pharmaceutically acceptable salt or solvate of said compound and an amount of at least one therapeutic agent listed above, wherein the amounts of the two or more ingredients result in desired therapeutic effect.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, $^1$H spectra were obtained on either a Varian VXR-400 (400 MHz, $^1$H), Varian Gemini-300 (300 MHz), Varian Mercury VX-400 (400 MHz), or Bruker-Biospin AV-500 (500 MHz), and chemical shifts are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me=methyl; Et=ethyl; Pr=propyl; Bu=butyl; t-Bu=tert-butyl; Ph=phenyl, and Ac=acetyl
μl=microliters
AcOEt or EtOAc=ethyl acetate
AcOH or HOAc=acetic acid
ACN=acetonitrile
aq=aqueous
atm=atmosphere
Boc or BOC=tert-butoxycarbonyl
BINAP=2,2'-bis(diphenylphosphino)-1,1'-bisnaphthyl
cat=catalyst or catalytic
Cbz=benzyloxycarbonyl
DEA=diethylamine
DEAD=diethylazodicarboxylate
DCM or $CH_2Cl_2$: dichloromethane:
DMAP=4-dimethylaminopyridine
DIBAL=diisobutylaluminum hydride
DIPEA=diisopropylethylamine
DME=1,2-dimethoxyethane
DMF=dimethylformamide
DMS=dimethylsulfide
DMSO=dimethyl sulfoxide
Dppf=1,1'-bis(diphenylphosphino)ferrocene
EDCl or DEC=1-(3-dimethylaminopropyl)-3-ethylcarbodiimide
Eq=equivalents
g=grams
h or hr=hour
HOBt=1-hydroxybenzotriazole
IPA=isopropyl alcohol
Im=imidazole
LAH=lithium aluminum hydride
LDA=lithium diisopropylamide
LCMS=liquid chromatography mass spectrometry
M=molar
mCPBA=m-chloroperoxybenzoic acid
min=minute
mg=milligrams
mL=milliliters
mmol=millimoles
MeOH=methanol
MS=mass spectrometry N=normal
NBS=N-bromosuccimide
NMO=N-methylmorpholine N-oxide
NMR=nuclear magnetic resonance spectroscopy
PG=protecting group
Pyr=pyridine
rac or (±)=racemic mixture or enantiomers
RT or rt=room temperature (ambient, about 25° C.)
sat=saturated
SFC=supercritical fluid chromatography
SM=starting material
TBSCl=t-butyldimethylsilyl chloride
TBS=t-butyldimethyl silyl
TEA=triethylamine (Et$_3$N)
TEMPO=2,2,6,6-Tetramethylpiperidine-1-oxyl
TFA=trifluoroacetic acid
THF=tetrahydrofuran
TLC=thin layer chromatography
TMS=trimethylsilyl
Tos or Ts=p-toluenesulfonyl (tosyl)
Tol=toluene
TosMIC=Toluenesulfonylmethyl isocyanide
TPAP=tetrapropylammonium perruthenate
Tr=triphenylmethyl

EXAMPLES

The compounds of this invention can be prepared through the general approach outlined in the following schemes. These schemes are being provided to illustrate the present invention. While the schemes depict $J^1$-$J^4$ as —CH—, wherein the hydrogen may be replaced by A, this is for exemplary purposes only and one of ordinary skill in the art would be able to prepare compounds containing one of the other definitions for $J^1$-$J^4$ by modifying schemes using other procedures known to one in the art. To assist one in this endeavor the ordinary practitioner would have full knowledge of literature sources such as *Chemical Abstracts, Beilstein*, etc.

Scheme 1 shows an approach in which S1 (X=CH$_2$— and n=0-2; or X=O—, —NH— or substituted N and n=1-2) is converted to hydantoin S2 by reaction with ammonium carbonate and a cyanide source (such as KCN, NaCN or TMSCN; or related conditions such as CO$_2$/NH$_4$OH/NaCN/H$_2$O$_2$). Subsequent hydrolysis to the amino acid S3a with base (LiOH, NaOH, Ba(OH)$_2$, or the like) is followed by conversion to the amino ester S3b and reduction to the alcohol S4 (with reagents such as DIBAL, NaBH$_4$, borane, or LAH). Alternatively, the amino acid S3a is directly reduced to S4. In various embodiments, the amino alcohol (S4) is then cyclized to provide the following moieties:
  substituted 2-aminooxazoline S5a (Z=NHC(O)R), with an isothiocyanate (such as benzoyl isothiocyanate).
  2-aminooxazoline S5b (Z=NH$_2$ via treatment with, for example, cyanogen bromide with or without a base (such as diisopropylethylamine) or by treatment with an thioisocyanate, such as (EtO$_2$C)NCS or BzNCS, followed by treatment with a base or acid or catalyst such as Hg(O), Hg(OAc)$_2$ or 2-chloro-3-ethylbenzoxazolium tetrafluoroborate and hydrolysis with LiOH);
  oxazoline S5c (Z=H, by treatment with methyl formate/DAST, trialkoxyformate, dimethylformamide dimethyl acetal or other similar reagent);
  oxazolidinone (S5d, Z=OH) by treatment with reagents known in the literature (e.g., carbonyldiimidazole, triphosgene, or related carbonates or chloroformates etc.);
  oxazolidinethione (S5e, Z=SH, by treatment with a known reagent such as EtOCS$_2$H, Im$_2$CS, CS$_2$, Cl$_2$CS, NaSCH, or MeSC(S)OEt etc.); and
  an oxazoline S5f with a carbon linkage at Z (by numerous literature methods such as treatment with RC(=NH)OEt, RCN/ZnCl$_2$, RCO$_2$H, RC(OMe)$_3$ an anhydride, RCHO with an appropriate oxidant or other methods).

2-aminooxazoline S5b (Z=NH$_2$) may also be obtained from S5a (Z=NHC(O)R), by treatment with a hydroxide source such as LiOH. Oxazolidinethione S5e (Z=SH) may also be obtained from 5d (Z=OH) by treatment with a sulfur reagent (such as Lawesson's reagent). The oxazolidinone (S5d, Z=OH) or oxazolidinethione (S5e, Z=SH) may be further substituted by alkylation or acylation chemistry known in the literature (to Z=OR or Z=SR respectively). An alkylated oxazolidinethione (S5e, Z=SR, where R=alkyl or the like) is optionally oxidized to provide Z=S(O)$_p$R (where p=1 or 2).

The biaryl coupling transformation (A=halogen or activated alcohol to A=the various definitions of R$^1$, such as aryl, cycloalkenyl, heterocyclenyl, or heteroaryl) occurs via a metal catalyzed or metal-facilitated process (such as Stille coupling, Suzuki coupling, Negishi coupling or nucleophilic substitution reaction) with an appropriately substituted aryl or heteroaryl partner. Installation of the biaryl group may be done at various stages in the sequence.

The functionalized R$^2$ and R$^3$ groups may exist in the starting material S1 or its precursor. Alternatively, S1 or its precursor may be functionalized with R$^2$ and R$^3$ groups at various stages in the sequence.

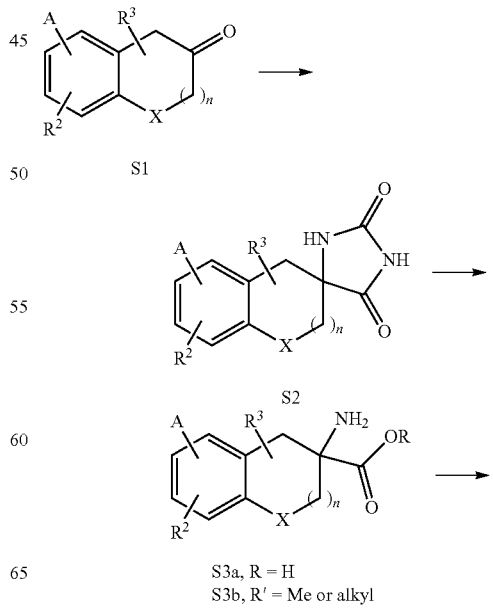

SCHEME 1

-continued

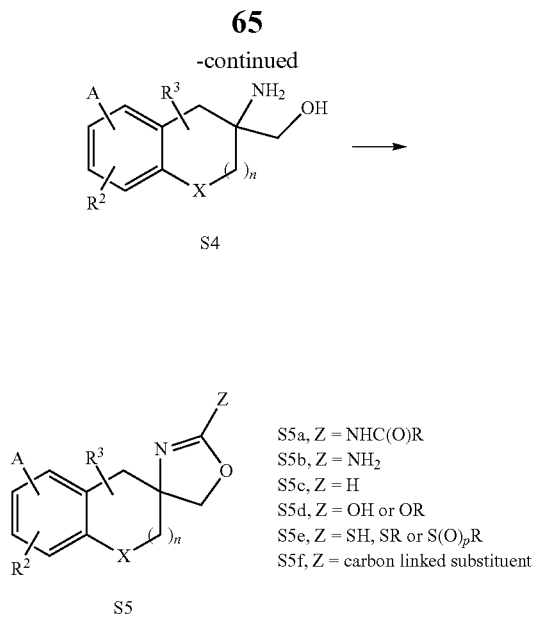

S5a, Z = NHC(O)R
S5b, Z = NH₂
S5c, Z = H
S5d, Z = OH or OR
S5e, Z = SH, SR or S(O)$_p$R
S5f, Z = carbon linked substituent

S5

According to another embodiment (Scheme 2), compound S1 is converted to S6 by a Strecker reaction (with a cyanide source and an amine such as NH₄Cl/KCN or alkylamine/NaCN). The nitrile is reduced (with LAH or a similar reagent) to S7, which may be cyclized to provide S8 or S9. In another embodiment, compound S6 is converted to amino acid S3a (Scheme 1) by hydrolysis.

SCHEME 2

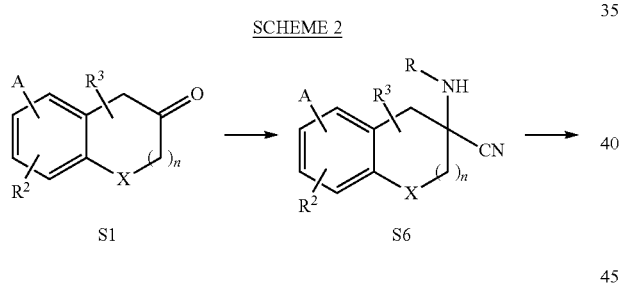

S1    S6

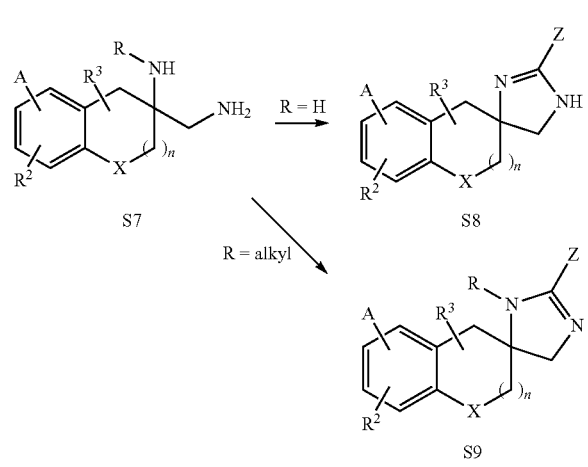

According to another embodiment (Scheme 3), compound S5d or S5e is converted to S10 (via chlorination with SOCl₂, POCl₃, PCl₃, PCl₅, Cl₂ or the like). In various embodiments, intermediate S10 is displaced with an amine, oxygen or carbon nucleophile or alternatively reacted in a metal catalyzed or metal-facilitated process (such as a palladium-catalyzed Suzuki or Stille coupling) to provide S5 (in which Z is a carbon, oxygen or nitrogen linked substituent).

SCHEME 3

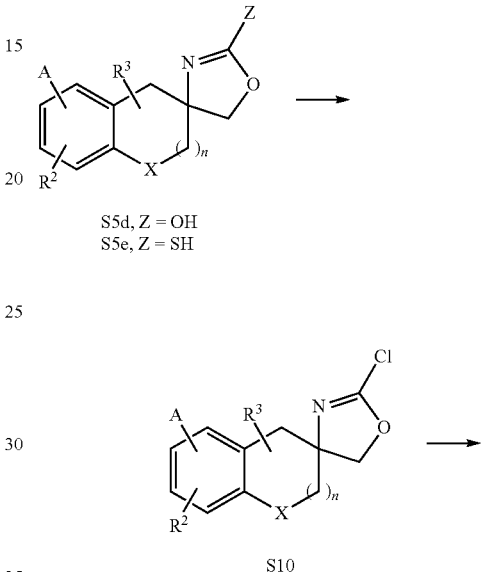

Scheme 4 shows an approach in which amino alcohol S4 is reacted with an acid under standard coupling conditions (with reagents such as EDCl, HOBt etc.) or with an acid chloride to provide the amide S11 (wherein R is defined as Z in Formula I or a group that may be converted into Z). In one embodiment, compound S11 is then treated with sulfur reagent such as Lawesson's Reagent, P₂S₅, or Deoxy-Fluor to affect incorporation of S with concomitant cyclization to S12. Alternatively, S4 may be converted to thioamide or thiourea S13 (by reaction with a thioester, thioacid, or thioisocyanate) and then cyclized to S12 (under a variety of conditions including treatment with HCl, SOCl₂, Deoxy-Fluor, DAST, Hg(0), Hg(OAc)₂ or 2-chloro-3-ethylbenzoxazolium tetrafluoroborate or other reagents). In another embodiment, S11 is first converted to S13 (by treatment with a sulfur reagent such as Lawesson's Reagent, DAST or the like) and then cyclized to S12 in a step-wise fashion.

SCHEME 4

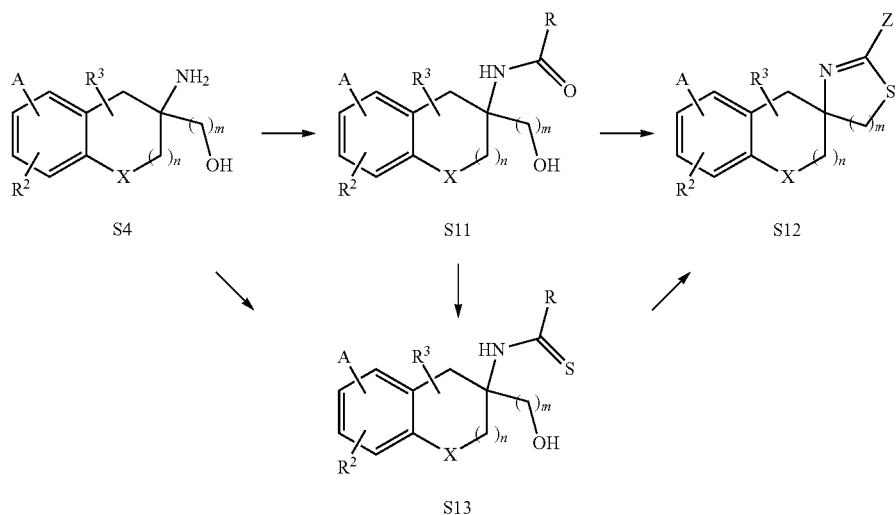

According to another embodiment (Scheme 5), aminoester S3b (optionally protected) is sequentially treated with an organometallic reagent (such as a RMgBr, a Grignard reagent, or RLi, an alkyllithium compound, to give a ketone S15), followed by reduction to afford S17 (wherein R is defined as R⁴ in Formula I or a group that may be converted into R⁴). The substituted aminoalcohol S17 is then cyclized to a substituted oxazoline S18 as previously described. Alternatively, this general approach may be taken starting with the amino nitrile S6 or Weinreb amide S14 (accessed from aminoacid S3a by amide coupling with HN(Me)OMe or from aminoester S3b reaction with HN(Me)OMe/AlMe₃). In another embodiment, S3b, S6, or S14 are reduced (or reduced/oxidized) to aldehyde S16 which is then subsequentially reacted with an organometallic reagent to provide S17. The reduction of ketone S15 may optionally be undertaken in a stereoselective manner to preferentially provide one stereoisomeric alcohol S17. Reagents for a stereoselective reduction are well known in the art, and include, but are not limited to the CBS-oxazaborolidine/borane reagent, LAH/N-methylephedrine, BINAL-H, Ipc₂BCl, DIBAL-H, Li-selectride, NaBH₄/CeCl₃, and enzymatic catalysis.

SCHEME 5

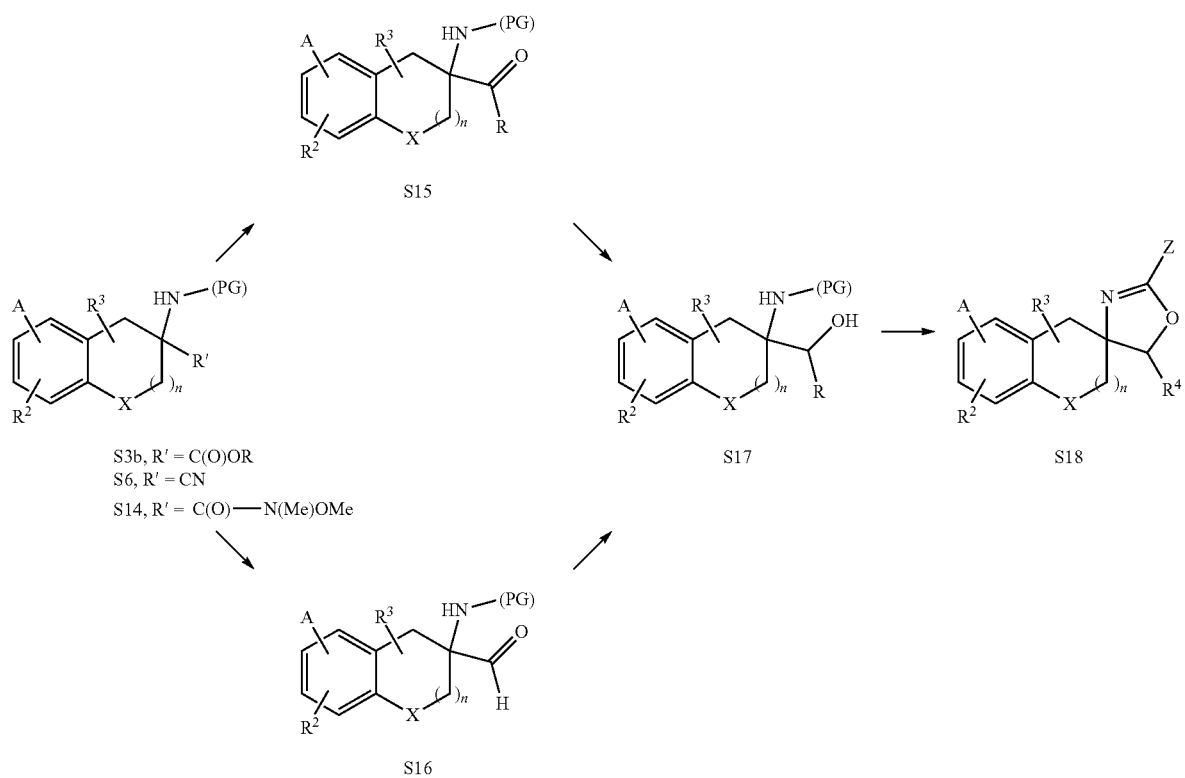

According to another embodiment (Scheme 6), ketone S15 (optionally protected) undergoes an olefination (Wittig, Horner-Emmons, Tebbe reaction etc.)-hydroboration sequence to provide alcohol S20 (wherein R is defined as $R^4$ in Formula I or a group that may be converted into $R^4$), which is then cyclized to S21.

SCHEME 6

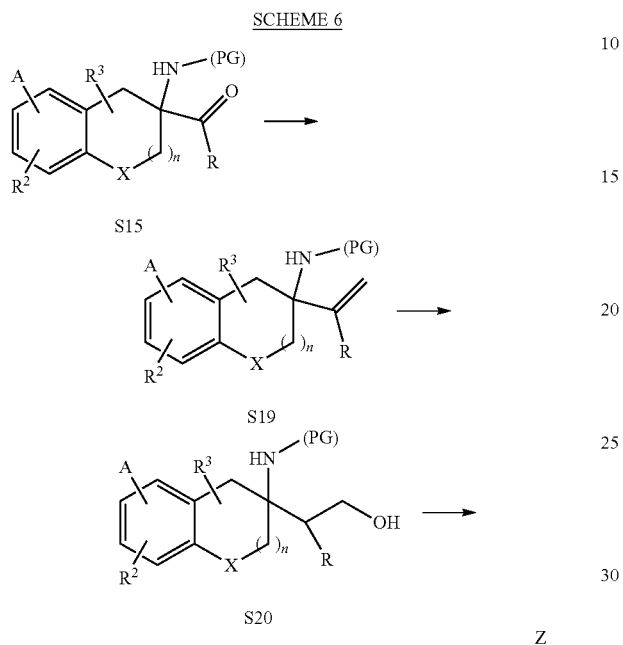

According to another embodiment (Scheme 7), ketone S15 (optionally protected) undergoes an olefination (Wittig, Horner-Emmons etc.) to a 1,2-disubstituted olefin. Hydroboration of S22 (wherein R and R' are independently defined as $R^4$ in Formula I or a group that may be converted into $R^4$) provides alcohol S23, which is then cyclized to S24.

SCHEME 7

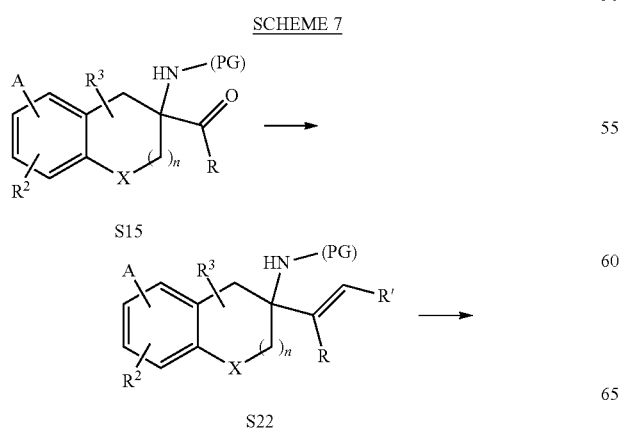

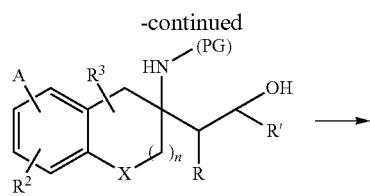

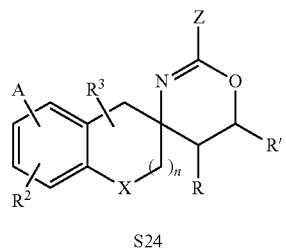

According to another embodiment (Scheme 8), alcohol S20 (optionally protected) is sequentially oxidized and treated with an organometallic reagent to provide S23 (wherein R and R' are independently defined as $R^4$ in Formula I or a group that may be converted into $R^4$). Compound S23 is then cyclized to provide S24.

SCHEME 8

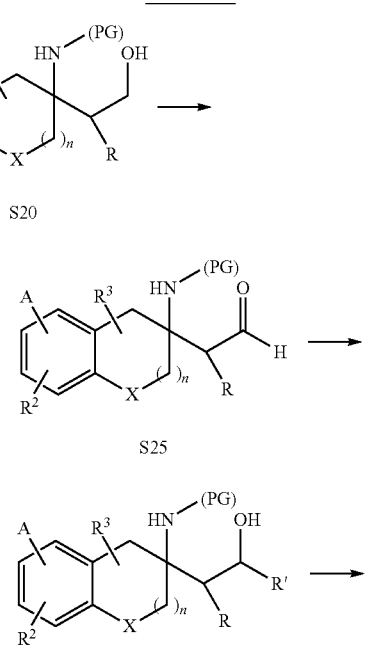

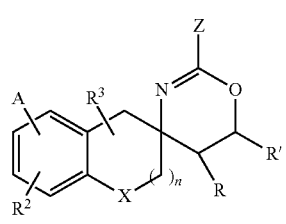

According to another embodiment (Scheme 9), chiral alcohol S28 is prepared by the addition of the anion of a chiral sulfoxide S27 onto ketone S26. An intramolecular $S_N2$ reaction provides epoxides S29, which are opened using nitrogen nucleophiles such as ammonia or by addition of $NH_2$ precursors such as azides, phthalimides, benzyl amines or benzhydryl amines to give aldehyde S30. Alcohols S31 and S32 are prepared by addition of an organometallic compound (such as an organomagnesium) and amine deprotection.

In another embodiment (Scheme 10), chiral sulfoxide S33 contains an alkyl group R'. Following an approach similar to Scheme 9, epoxide opening provides ketone S36. Alcohols S31 and S32 are obtained by reduction of the ketone by known methods (such as treatment with as $NaBH_4$) and amine deprotection. Alternatively, the ketone is reduced in an asymmetrical fashion using chiral reduction methods known for those skilled in the art (such as CBS reduction).

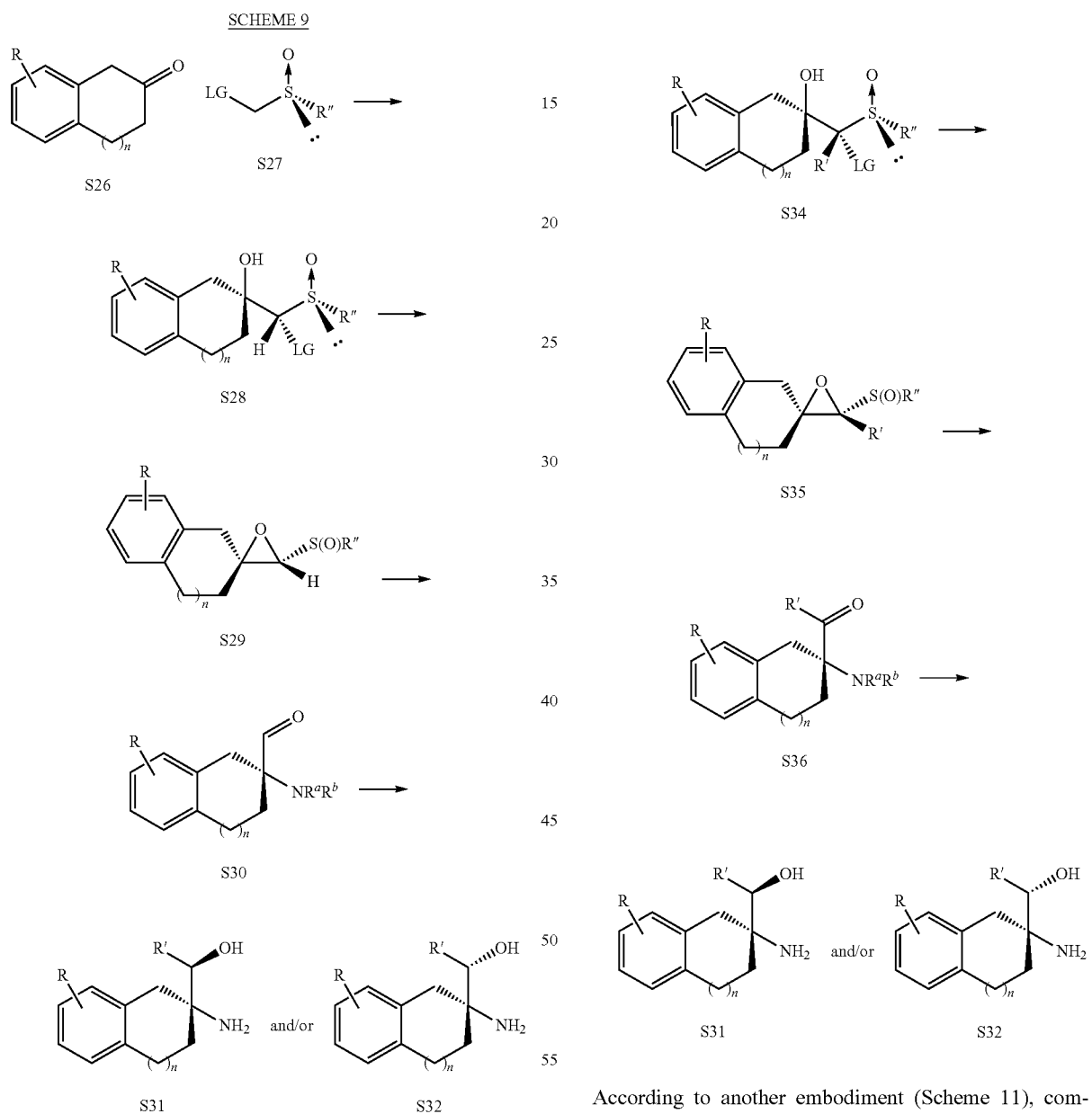

According to another embodiment (Scheme 11), compound S1 is treated with a chiral amine (such as (R)-phenylglycine or other chiral amine) and then treated with a cyanide source (such of KCN, NaCN or TMSCN) to provide converted to S6 as a pure enantiomer or in enantiomerically enriched form. Reduction of the nitrile, cleavage of the chiral auxiliary, and cyclization provides imidazoline S8 as previously described. Alternatively, S6 is converted to S3b by hydrolysis (with MeOH/HCl or other approach) and cleavage of the chiral auxiliary.

SCHEME 11

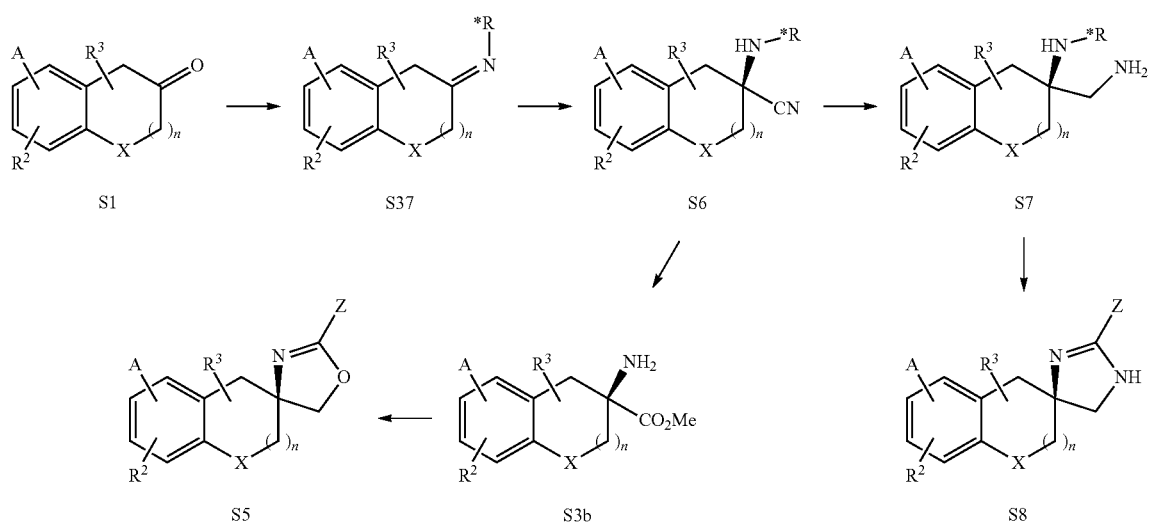

According to another embodiment (Scheme 12), the ester S3b is converted to amide S3c (by treatment with ammonia or an amine) and then reduced (with LAH, $BH_3$ or a similar reagent) to diamine S38, which may be cyclized to provide:

S39a, via treatment with amidine reagents such as formamidine, acetamidine, or benzamidine);
S39b, via treatment with diphenyl cyanocarbonimidate;
S39c, via treatment with cyanogen bromide; and
S39d, via treatment with carbonyldiimidazole, triphosgene, or related carbonates or chloroformates etc.).

SCHEME 12

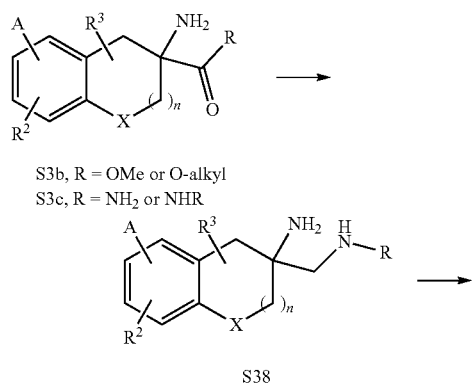

S3b, R = OMe or O-alkyl
S3c, R = $NH_2$ or NHR

-continued

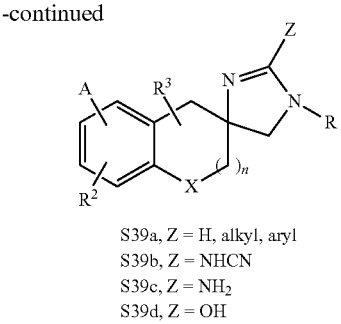

S39a, Z = H, alkyl, aryl
S39b, Z = NHCN
S39c, Z = $NH_2$
S39d, Z = OH

According to another embodiment (Scheme 13), a Functionalized xylene 40b (R=LG such as Br, synthesized from S40a with NBS or similar) is condensed with a N-protected glycine ester (such as N-(diphenylmethylene)glycine ethyl ester or N-benzylideneglycine ethyl ester) to provide S41 which is further elaborated to S42. Use of chiral N-protected glycine ester or use of a chiral phase-transfer catalyst with a nonchiral N-protected glycine ester provides enantioselective enhancement in the condensation.

Alternatively, S40b is condensed with a malonate ester (such as dimethyl malonate) to provide S43. Selective enzymatic hydrolysis of one ester (by an esterase or similar enzyme) provides S44 which is converted to S45 by a Curtuis rearrangement and then further elaborated to S42.

SCHEME 13

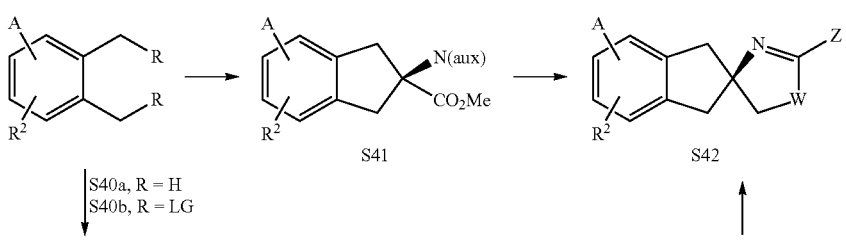

S40a, R = H
S40b, R = LG

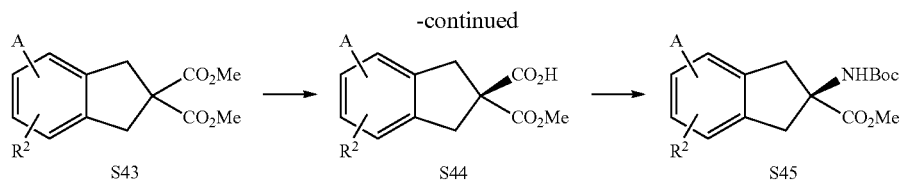

The starting materials, including compound S1, S26, and S40, and reagents used in preparing compounds described are either available from commercial suppliers such as Aldrich Chemical Co. (Wisconsin, USA) and Acros Organics Co. (New Jersey, USA) or were prepared by literature methods known to those skilled in the art. When unavailable from commercial suppliers, compound S1 (optionally substituted with $R^2$ and $R^3$, or with substituents that are converted into $R^2$ and $R^3$) is synthesized from S46, S47, S48, S49, or other starting materials according to methods known in the literature.

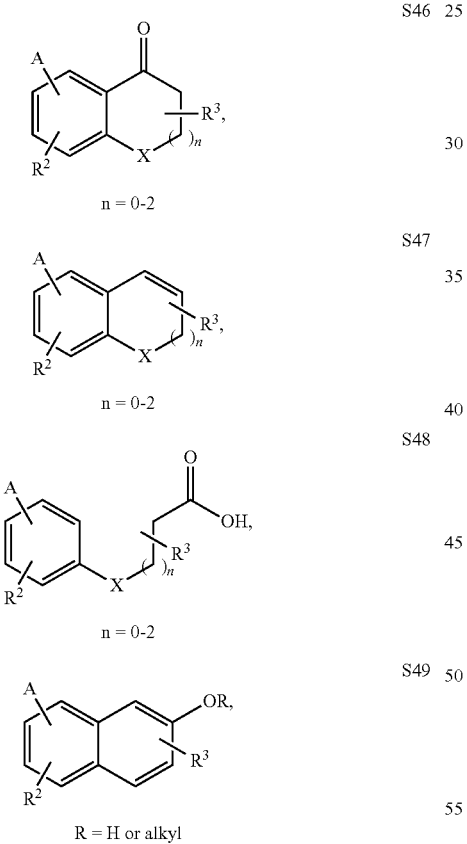

Compounds of formulae S5, S8, S9, S10, S12, S18, S21, S24, S39, S42 and S45 can be prepared by the general methods outlined above. Exemplary compounds were prepared as described in the examples below or from starting materials known in the art. These examples are being provided to further illustrate the present invention. They are for illustrative purposes only; the scope of the invention is not to be considered limited in any way thereby.

Preparative Example 1

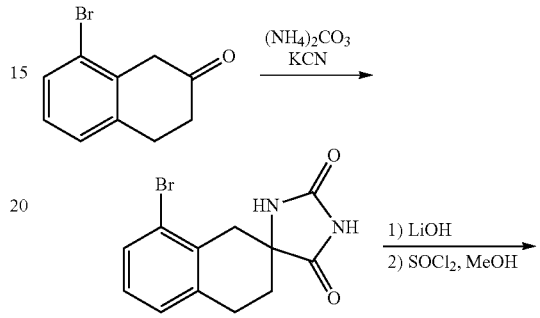

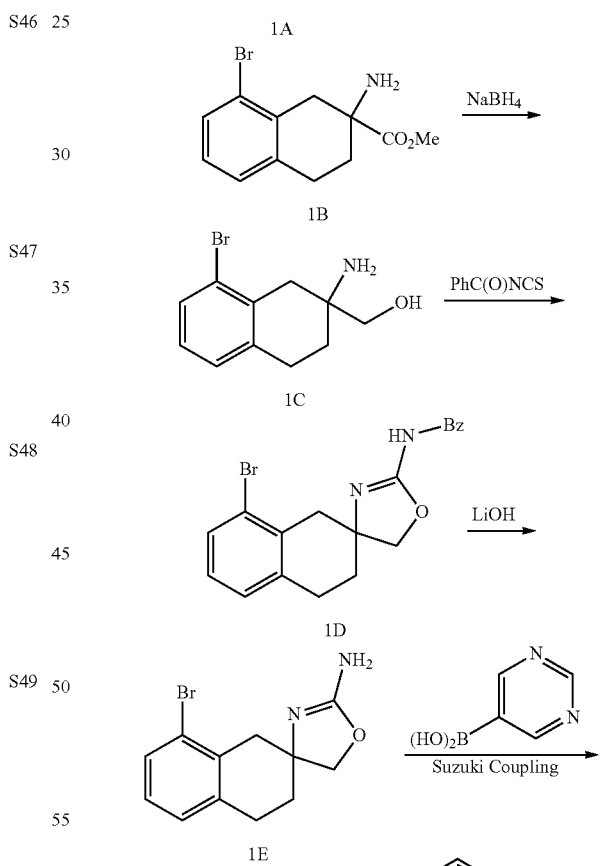

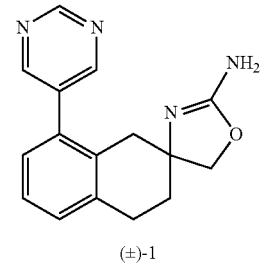

Step 1

A mixture of 8-bromo-2-tetralone (5.0 g, 22.2 mmol), (NH$_4$)$_2$CO$_3$ (15.0 g, 156 mmol), and KCN (2.16 g, 33.2 mmol) in 1:1 EtOH—H$_2$O (50 mL) was heated in a sealed tube overnight at 85° C. The reaction was then cooled to RT, diluted with water (~400 mL) and stirred for 2 h. The precipitate was filtered and dried in vacuo overnight to provide hydantoin 1A (5.95 g, 91%). LCMS m/z 295 (MH+).

Steps 2-3

A mixture of 1A (4.46 g, 15.1 mmol) and LiOH—H$_2$O (3.18 g, 75.6 mmol) in H$_2$O (100 mL) was refluxed overnight. The reaction was then cooled to 0° C., acidified with 12 N HCl, and concentrated to give the amino acid as a solid. LCMS m/z 270 (MH+).

Thionyl chloride (9 mL) was carefully added to MeOH (300 mL) at 0° C. The resulting mixture was then added to a flask charged with the amino acid product. The reaction was heated to reflux overnight and then cooled and concentrated. The residue was taken up in sat. aq. NaHCO$_3$ and extracted EtOAc (2×). The combined organic layers were dried over Na$_2$SO$_4$ and concentrated. Chromatography (0-50% EtOAc/hex) provided 1B as a red oil. LCMS m/z 284 (MH+).

Steps 4-5

Compound 1B (8.16 g, 28.7 mmol) was dissolved in anhydrous MeOH and then treated with NaBH$_4$ (2.72 g, 71.8 mmol, bubbling and heat generation noted). A second portion of NaBH$_4$ (2.72 g, 71.8 mmol) was added after 15 min. The reaction was concentrated after TLC indicated consumption of 1B (~15 min). THF (100 mL) was added to the residue and then removed in vacuo to give the yellow foam 1C, which was used in the next step without purification or aqueous workup. LCMS m/z 256 (MH+).

The crude aminoalcohol 1C (~28.7 mmol) was dissolved in anhydrous THF (250 mL) and treated with benzoyl isothiocyanate (8.5 mL, 63 mmol). After stirring for 20 min at RT, additional benzoyl isothiocyanate (4.3 mL, 32 mmol) was added. The reaction was concentrated after TLC and MS indicated consumption of 1C (~20 min). The residue was diluted with water and extracted with DCM (3×). The combined organic layers were dried over Na$_2$SO$_4$, concentrated and chromatographed (20-40% EtOAc/hex) to provide provided 1D as a yellow foam. LCMS m/z 385 (MH+).

Step 6

A mixture of 1D (~38.7 mmol) and LiOH—H$_2$O (6.03 g, 144 mmol) in 1:1 MeOH—H$_2$O (200 mL) was refluxed for 1.5 h. The reaction was concentrated to one-half volume and extracted with DCM (4×). The combined organic layers were dried over Na$_2$SO$_4$, concentrated and chromatographed (2% of NH$_3$-MeOH/DCM) to give the desired product 1E (white solid 2.49 g, ~38% for 3-steps, LCMS m/z 281 MH+) and a small amount of a byproduct from Step 5 (1F, LCMS m/z 298 MH+).

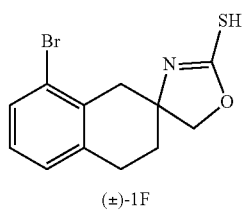

(±)-1F

Step 7

A mixture of 1E (3.03 g, 10.8 mmol), pyrimidine-5-boronic acid (2.00 g, 16.2 mmol), Pd(PPh$_3$)$_4$ (1.25 g, 1.08 mmol), K$_2$CO$_3$ (2.98 g, 21.6 mmol) in 1:1 DMF-H$_2$O (60 mL) were heated at 110° C. in a sealed tube for 1 h. The reaction concentrated, diluted with water and extracted with DCM (4×). The layers were separated. The combined organic layers were dried over Na$_2$SO$_4$, concentrated and chromatographed (2-5% of NH$_3$-MeOH/DCM) to give the title compound (±)-1 (2.74 g, 90%). LCMS m/z 281 (MH+).

The pure single enanantiomers (2D and 2E) of compound (±)-1 were separated as described in Example 2. Alternatively, the pure enantiomers of compound 1D were also separated by chiral prep HPLC. An alternative synthesis of compound (±)-1 is given in Example 6.

In a manner similar to that described above, 1E was coupled with an appropriate aryl boronic acid or aryl boronic ester to provide the following compounds:

| Cmpd No. | Compound | LCMS (MH+) |
|---|---|---|
| (±)-1G | | 279 |
| (±)-1H | | 280 |

Preparative Example 2

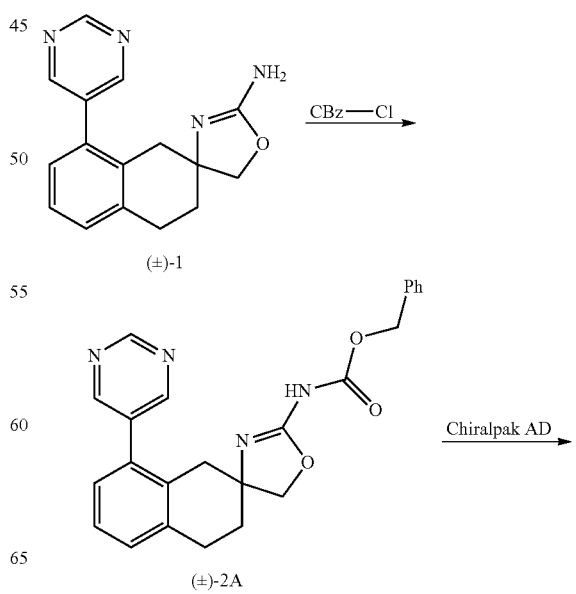

-continued

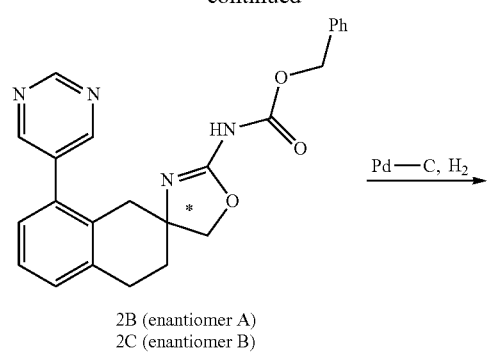

2B (enantiomer A)
2C (enantiomer B)

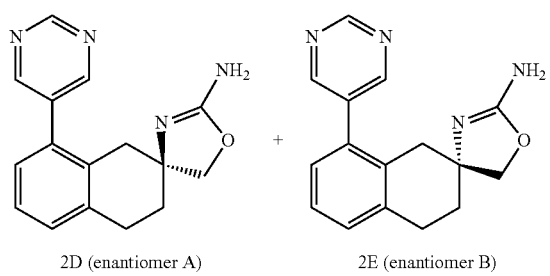

2D (enantiomer A)  2E (enantiomer B)

Step 1

A mixture of compound (±)-1 (2.74 g, 9.77 mmol), CbzCl (3.5 mL, 24.4 mmol), TEA (4.1 mL, 29.3 mmol) and DMAP (0.24 g, 1.95 mmol) in DCM (100 mL) was stirred at RT for 30 min and then treated with additional portions of CbzCl (3.5 mL, 24.4 mmol) and TEA (4.1 mL, 29.3 mmol). After 1 h, the reaction was concentrated, treated with water and extracted with DCM (4×). The organic layer was dried over $Na_2SO_4$, filtered, concentrated and chromatographed (2% MeOH/DCM) to provide (±)-2A.

Steps 2-3

The racemic mixture (±)-2A was separated on a preparative Chiralpak AD column with 50% isopropanol-hexanes to provide the pure enantiomers 2B (>95% ee) and 2C (>95% ee). The enantiomers 2B and 2C were each subjected to hydrogenation with Pd/C and $H_2$ (40 psi, overnight, MeOH), followed by chromatography (5% $NH_3$-MeOH/DCM) to provide 2D (enantiomer A of 1; LCMS m/z 281, MH+) and 2E (enantiomer B of 1; LCMS m/z 281, MH+), respectively. The HCl salts of 2D and 2E could each be made by stirring in 4N HCl-dioxane followed by concentration.

Preparative Example 3

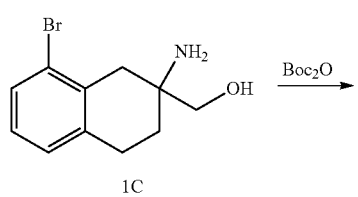

1C

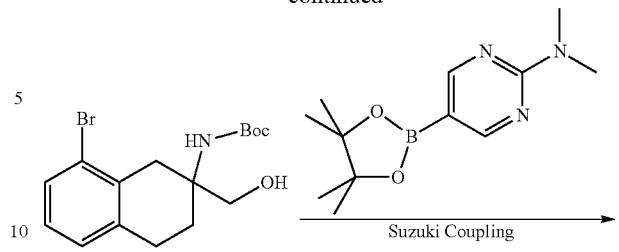

3A

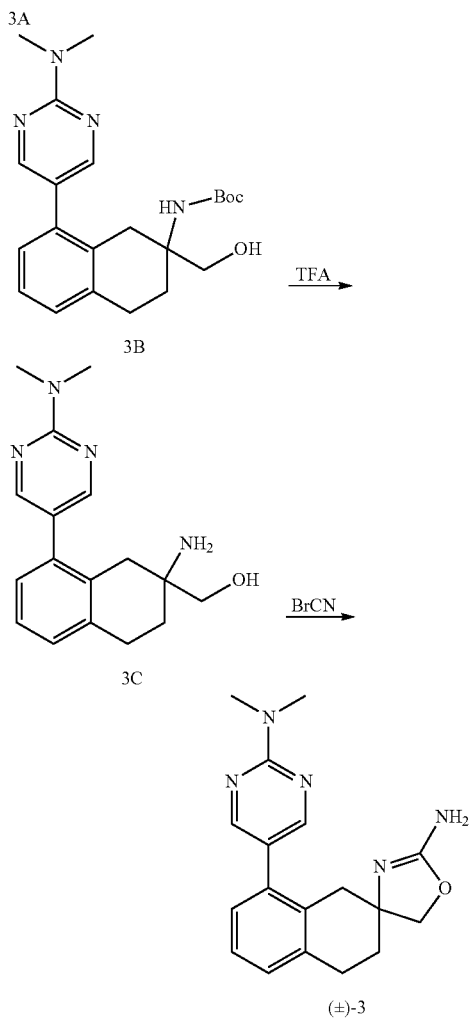

Step 1

A mixture of compound 1C (0.25 g, 0.98 mmol), $Boc_2O$ (0.24 g, 1.07 mmol), and $Et_3N$ (0.4 mL, 2.9 mmol) in DCM (10 mL) was stirred at RT overnight and then concentrated. Chromatography (2-10% $NH_3$-MeOH/DCM) provided 3A (300 mg, 86%).

Step 2

A mixture of 3A (70 mg, 0.20 mmol), 2-(dimethylamino)pyrimidine-5-boronic acid pinacol ester, (98 mg, 0.39 mmol), Pd(dppf)$Cl_2$—$CH_2Cl_2$ (16 mg, 0.02 mmol), $K_3PO_4$ (125 mg, 0.59 mmol) in 3:1 DME-$H_2O$ (2 mL) were microwaved at 120° C. for 15 min. The reaction was diluted with EtOAc and washed with water (3×). The organic layer were dried over $Na_2SO_4$, concentrated and chromatographed (2% of $NH_3$-MeOH/DCM) to give 3B (50 mg, 65%) as a yellow solid. LCMS m/z 399 (MH+).

Step 3

Compound 3B (50 mg, 0.12 mmol) was taken up in DCM (5 mL) and treated with TFA (1 mL). The reaction was stirred at RT for 2 h, concentrated, and chromatographed (5-10% of NH$_3$-MeOH/DCM) to give 3C. LCMS m/z 299 (MH+).

Step 4

A mixture of 3C (40 mg, 0.13 mmol) and cyanogen bromide (17 mg, 0.16 mmol) in DCM (5 mL) was stirred overnight at RT and concentrated. Chromatographed (C18, 10-90% MeCN/H$_2$O with 0.1% TFA) to give the title compound (±)-3. LCMS m/z 324 (MH+).

Following an analogous sequence to that described above, the following compound was prepared:

| Cmpd No. | Compound | LCMS (MH+) |
|---|---|---|
| (±)-3D | 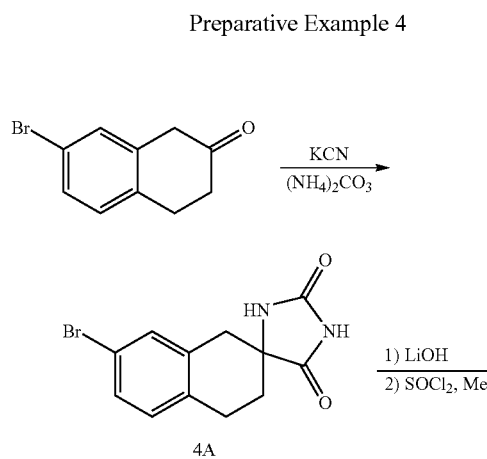 | 306 |

Preparative Example 4

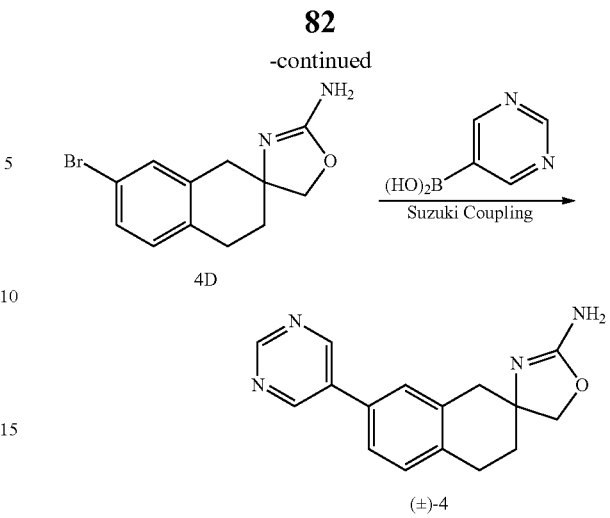

Compound (±)-4 was prepared from 7-bromo-2-tetralone in a manner similar to that described in Example 1: hydantoin formation with (NH$_4$)$_2$CO$_3$/KCN, hydrolysis with LiOH, methyl ester formation with SOCl$_2$/MeOH, reduction with NaBH$_4$, cyclization with benzoyl isothiocyanate, and hydrolysis with LiOH to provide 4D (LCMS m/z 281/283, MH+). Final Suzuki coupling with pyrimidine-5-boronic acid/Pd(PPh$_3$)$_4$ afforded the title compound (±)-4. LCMS m/z 281 (MH+).

Preparative Example 5

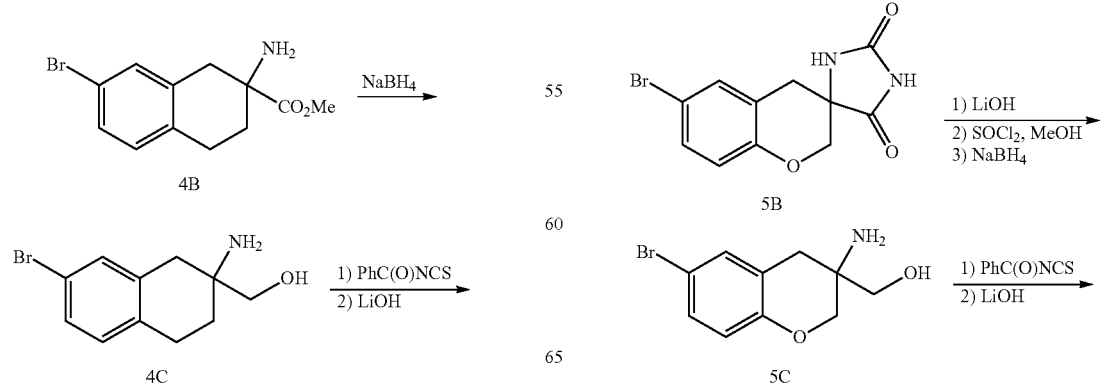

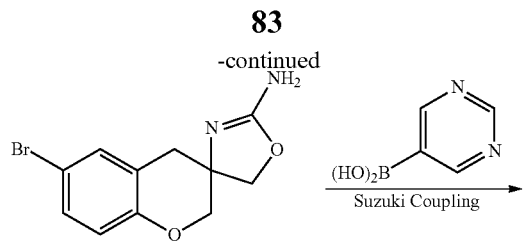

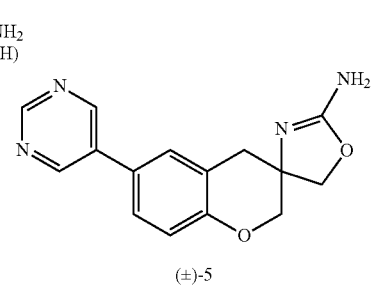

The starting material 6-bromochroman-3-one (5A) was prepared from 6-bromochroman-4-one in a manner similar to that described in the literature (Synthesis, 1980, 621): 6-bromochroman-4-one was reduced with $NaBH_4$ (1.2 eq, MeOH-DCM, 0° C. to RT, 2 h) and then eliminated with pTsOH (cat., toluene, reflux, 3 h, 90% for 2-steps). The resulting 6-bromochromene was subjected to osmylation (cat. $OsO_4$, 1 eq. NMO, water-acetone-tBuOH, RT, overnight) and subsequent treatment with pTsOH (cat., toluene, reflux, 15 min, 86% for 2-steps) to provide 6-bromochroman-3-one (5A).

Compound (±)-5D was prepared from 6-bromochroman-3-one in a manner similar to that described in Example 1: hydantoin formation with $(NH_4)_2CO_3/KCN$, hydrolysis with LiOH, methyl ester formation with $SOCl_2/MeOH$, reduction with $NaBH_4$, cyclization with benzoyl isothiocyanate, and hydrolysis with LiOH. A small amount of compound 5E (LCMS m/z 300/302, MH+) was formed during the benzoyl isothiocyanate cyclization step. The title compound (±)-5 was prepared from (±)-5D via Suzuki coupling with pyrimidine-5-boronic acid/Pd(dppf)Cl$_2$ in a manner similar to that described in Example 3 (Step 2). LCMS m/z 283 (MH+).

Alternatively, and in a manner similar to that that described in Example 3 (Step 4), compound 5C was reacted with 1.2 eq. cyanogen bromide (4 h, RT, EtOH) to directly provide (±)-5D (LCMS m/z 283/285, MH+) in ~50% yield with ~40% recovered starting material 5C.

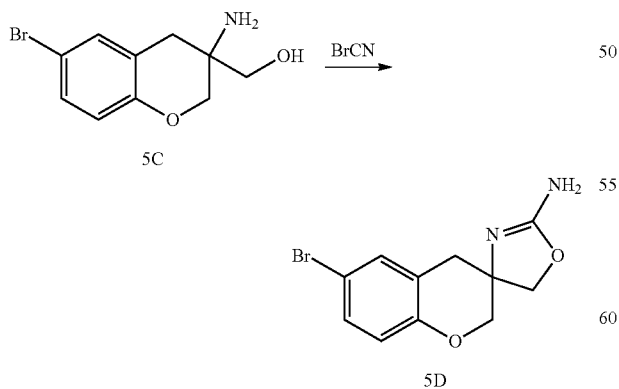

In a manner similar to that described above, 5D was coupled with an appropriate aryl boronic acid or aryl boronic ester to provide the following compounds:

| Cmpd No. | Compound | LCMS (MH+) |
|---|---|---|
| (±)-5F | | 285 |
| (±)-5G | | 299 |
| (±)-5H | | 300 |
| (±)-5I | | 301 |
| (±)-5J | | 296 |
| (±)-5K | | 281 |
| (±)-5L | | 309 |
| (±)-5M | | 349 |

-continued

| Cmpd No. | Compound | LCMS (MH+) |
|---|---|---|
| (±)-5N | | 311 |
| (±)-5P | | 282 |
| (±)-5Q | | 312 |
| (±)-5R | | 296 |
| (±)-5S | | 271 |
| (±)-5T | | 287 |
| (±)-5U | | 313 |
| (±)-5V | | 271 |

-continued

| Cmpd No. | Compound | LCMS (MH+) |
|---|---|---|
| (±)-5W | | 321 |

Preparative Example 6

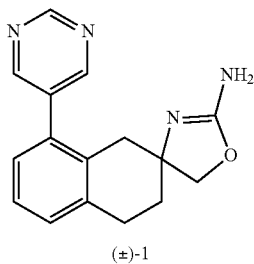

(±)-1

An alternative synthesis of (±)-1 is given below:

Step 1

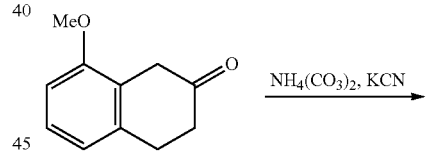

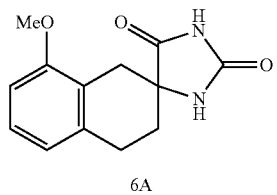

6A

To a solution of 8-methoxy-2-tetralone (600 mg, 3.4 mmol) in EtOH—H$_2$O (1:1, 12 mL) in a sealed tube was added ammonium carbonate (2.28 g, 23.8 mmol) and KCN (420 mg, 6.8 mmol) in one portion. The mixture was heated at 80° C. for 12 h before it was cooled to RT. Water (20 mL) was added to precipitate the product 6A. The light grey solid was collected by filtration and washed with water and dried in air (835 mg, 100%, LCMS m/z 247, MH+).

Steps 2-3

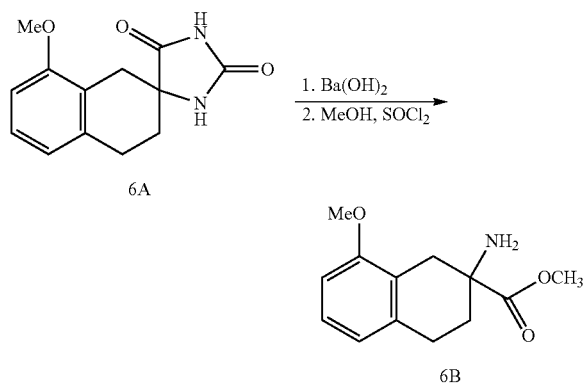

Step 5

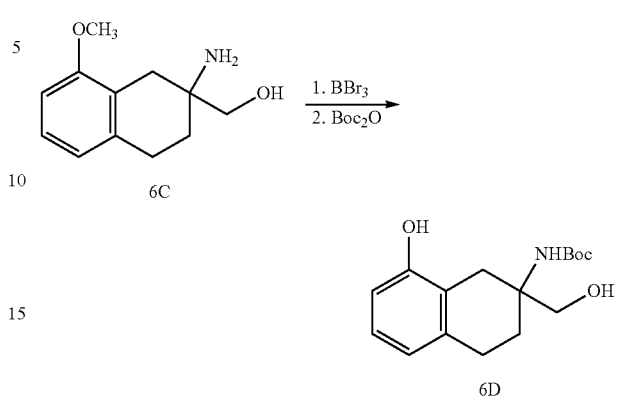

A suspension of 6A (200 mg, 0.813 mmol) and Ba(OH)$_2$ (460 mg, 3.25 mmol) in water (2 mL) was heated in a sealed tube at 120° C. for 36 h. The mixture was acidified with 6 N H$_2$SO$_4$, and filtered and the filter pad was washed with MeOH repeatedly. The combined filtrate was concentrated under reduced pressure to yield the amino acid as an off-white solid. The crude product was added to a mixture of SOCl$_2$ (145 mg, 1.219 mmol) and MeOH (10 mL). The mixture was stirred at reflux for 3 h, cooled to RT and concentrated under reduced pressure. The methyl ester HCl salt was suspended in EtOAc (20 mL) and neutralized with sat. NaHCO$_3$. The aqueous phase was extracted with EtOAc (2×10 mL). The combined organic layers were dried (Na$_2$SO$_4$), filtered and concentrated under reduced pressure. The residue was purified by column chromatography (80% EtOAc/Hexanes) to give 6B as a pale yellow oil (105 mg, 55%, LCMS m/z 236, MH+).

Step 4

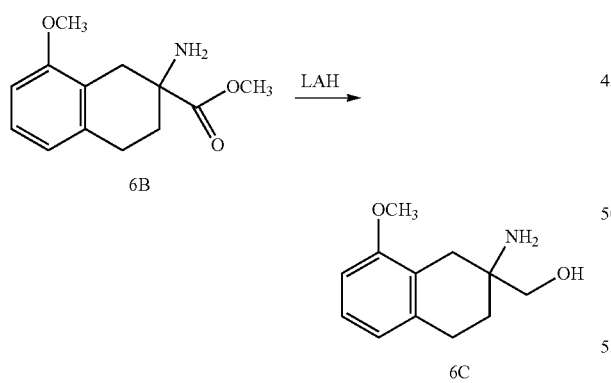

To a stirred solution of 6B (3.17 g, 13.5 mmol) in THF (50 mL) was added LiAlH$_4$ (1.02 g, 27 mmol) in small portions at 0° C. The mixture was stirred at RT overnight and quenched with slow addition of water (1 mL), 1 N NaOH (3 mL) and water (1 mL). The grey suspension was filtered and the filtrate was dried (Na$_2$SO$_4$), filtered and concentrated under reduced pressure to yield compound 6C (2.79 g, 100%, LCMS m/z 208, MH+) as a white solid.

To a stirred solution of 6C (2.79 g, 13.5 mmol) in CH$_2$Cl$_2$ (25 mL) was added BBr$_3$ (1M CH$_2$Cl$_2$ solution, 32.5 mL) at 0° C. The bright yellow solution was stirred at this temperature for 3 h and quenched with addition of sat. NaHCO$_3$ until pH equals 7. The mixture was concentrated under reduced pressure to give an off-white solid. To a solution of the crude phenol in dioxane-H$_2$O (1:1, 25 mL) was added Boc$_2$O (5.9 g, 27 mmol) and NaHCO$_3$ (1.7 g, 20.25 mmol). The mixture was stirred overnight, acidified with 1 N HCl, and extracted with EtOAc (4×60 mL). The combined organic layers were washed with brine (10 mL), dried (Na$_2$SO$_4$), filtered and concentrated under reduced pressure. The residue was purified by column chromatography (50% EtOAc/Hexanes) to give compound 6D as pale yellow oil (2.555 g, 64%, LCMS m/z 294, MH+).

Step 6

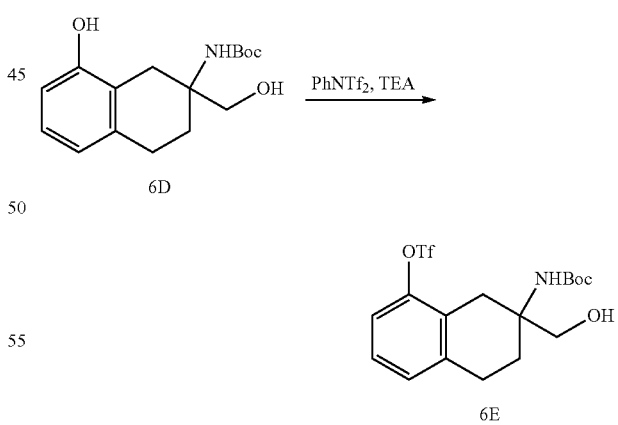

To a solution of 6D (1.555 g, 5.3 mmol) in THF (20 mL) was added triethylamine (2.2 mL, 15.9 mmoL) and PhNTf$_2$ (2.276 g, 6.37 mmol). The solution was stirred at RT overnight and concentrated under reduced pressure. The residue was purified by column chromatography (50% EtOAc/Hexanes) to give compound 6E as a white solid (1.99 g, 85%).

Step 7

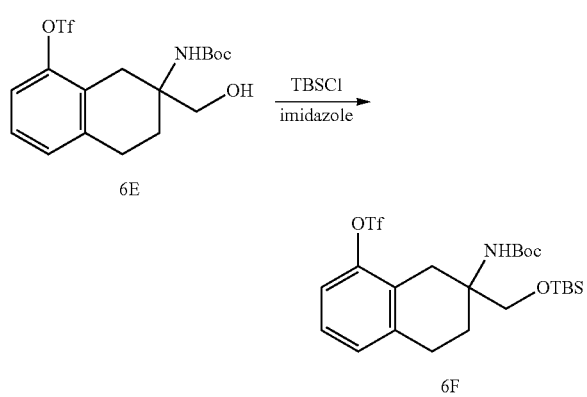

To a solution of 6E (1.45 g, 3.4 mmol) in DMF (2 mL) was added TBSCl (614.9 mg, 4.08 mmol) and imidazole (554.9 mg, 8.16 mmol). The mixture was stirred at RT overnight and quenched with addition of water (30 mL). This was extracted with EtOAc (30 mL) and the resulting organic phase was washed with $H_2O$ (3×30 mL). The organic layer was dried ($Na_2SO_4$), filtered and concentrated under reduced pressure. The residue was purified by column chromatography (5% EtOAc/Hexanes) to give compound 6F as a pale yellow oil (1.759 g, 96%, LCMS m/z 540, MH+).

Step 8

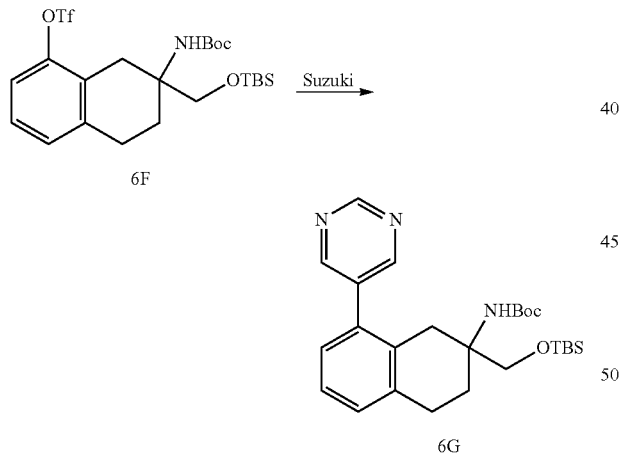

To a solution of 6F (91.8 mg, 0.17 mmol) in DME-water (3:1, 1.6 mL) was added Pd(PPh$_3$)$_4$ (19.7 mg, 0.017 mmol), 5-pyrimidylboronic acid (31.6 mg, 0.255 mmol), and NaHCO$_3$ (1 M solution, 0.34 mL). The mixture was heated using microwave (120° C., 15 min) and treated with EtOAc (15 mL) and 1 N NaOH (5 mL). The organic layer was dried (Na$_2$SO$_4$), filtered and concentrated under reduced pressure. The residue was purified by column chromatography (15% EtOAc/Hexanes) to give compound 6G as a white solid (71 mg, 89%, LCMS m/z 470, MH+).

Step 9

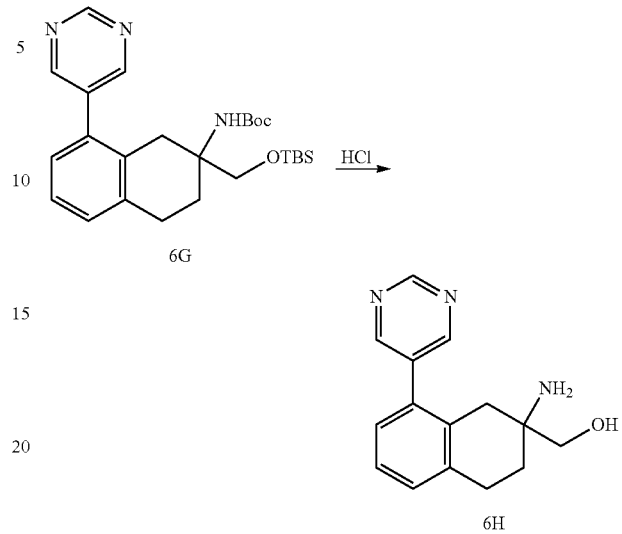

To a stirred solution of 6G (772 mg, 1.646 mmol) in MeOH (5 mL) was added HCl (4 M in dioxane, 8.23 mL, 32.9 mmol). The mixture was stirred at RT for 4 h and concentrated under reduced pressure. The residue was purified by column chromatography (10% MeOH/CH$_2$Cl$_2$, 1% NH$_4$OH) to give compound 6H as a white solid (277.9 mg, 66%).

Step 10

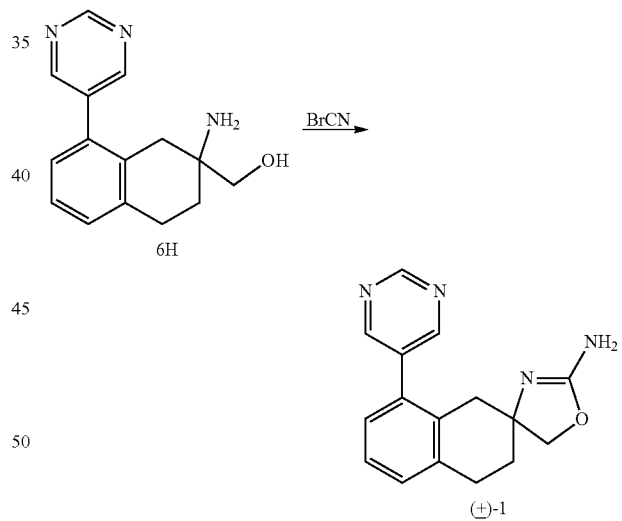

To a stirred solution of 6H (91.2 mg, 0.355 mmol) in EtOH (2 mL) was added BrCN (45.1 mg, 0.426 mmol) at 0° C. The mixture was stirred at RT for 4 h and concentrated under reduced pressure. The residue was purified by prep-HPLC (0-50% CH$_3$CN/H$_2$O) to give compound (±)-1 as a white solid (35.8 mg, 36%, LCMS m/z 281, MH+) and recovered 6H (45.6 mg, 50%).

In a separate experiment, a mixture of compound 6H (0.076 mmol) and BrCN (5M/CH$_3$CN, 18 μL, 0.091 mmol) in CH$_3$CN (0.8 mL) was stirred overnight, treated with an additional BrCN (1 eq) and TEA (1 eq) and then stirred an additional 18 h to provide (±)-6I as the major product. LCMS m/z 306 (MH+).

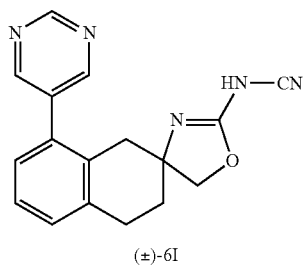

(±)-6I

In a manner analogous to that described above (Steps 6-8), 6F was coupled with an appropriate aryl boronic acid or aryl boronic ester and then further elaborated to provide the following compounds:

| Cmpd No. | Compound | LCMS (MH+) |
|---|---|---|
| (±)-6J | | 304 |
| (±)-6K | | 304 |
| (±)-6L | | 283 |

Preparative Example 7

In a manner similar to that described in Example 6 (Steps 1-10), the following compounds were synthesized from 5-methoxy-2-tetralone:

| Cmpd No. | Compound | LCMS (MH+) |
|---|---|---|
| (±)-7A | | 283 |
| (±)-7B | | 281 |
| (±)-7C | | 298 |

Preparative Example 8

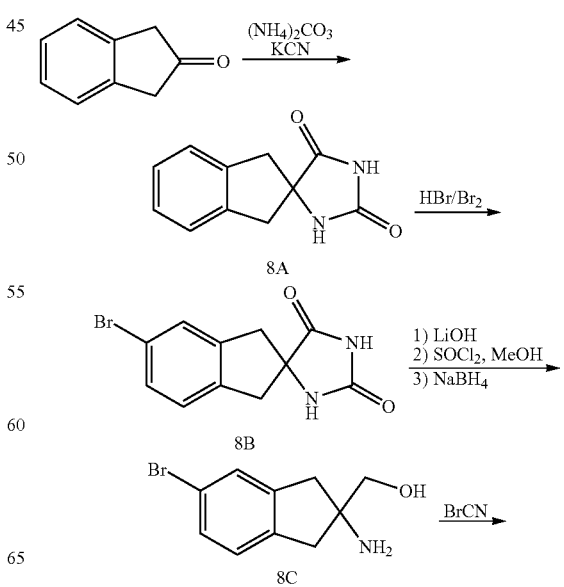

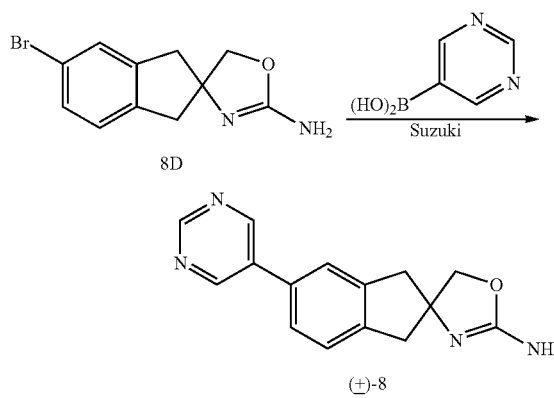

Steps 1-2

In a manner similar to that described in Example 1 (Step 1), 2-indanone was treated with $(NH_4)_2CO_3$ and KCN to provide hydantoin 8A. The hydantoin was subjected to bromination (HBr/Br$_2$) as described in WO2004/082602 to provide 8B.

Steps 3-5

In a manner similar to that described in Example 1 (Steps 2-4), compound 8B was sequentially treated with LiOH, SOCl$_2$-MeOH, and NaBH$_4$ to provide 8C.

Steps 6-7

In a manner similar to that described in Example 3 (Steps 4 and 2), compound 8C was sequentially cyclized with cyanogen bromide and then coupled with pyrimidine-5-boronic acid to provide the title compound (±)-8. LCMS m/z 267 (MH+).

The following compounds were prepared by coupling 8D with an appropriate boronic acid or ester:

| Cpd | Structure | LCMS (MH+) |
|---|---|---|
| (±)-8E | | 265 |
| (±)-8F | | 292 |
| (±)-8G | | 266 |
| (±)-8H | 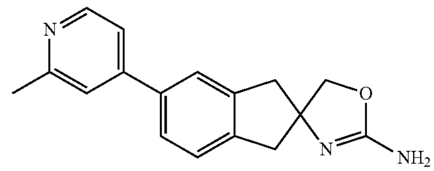 | 280 |
| (±)-8I | 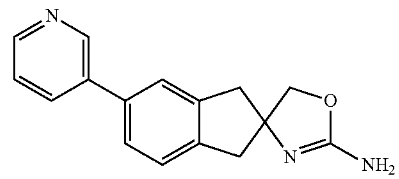 | 266 |
| (±)-8J | 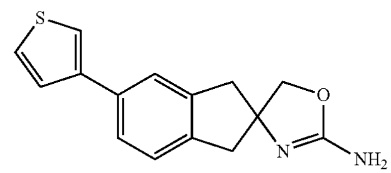 | 271 |
| (±)-8K | 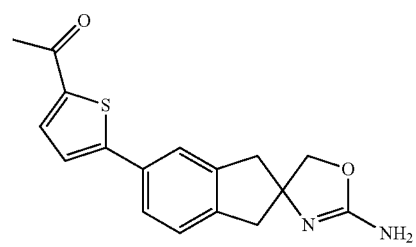 | 313 |
| (±)-8L | 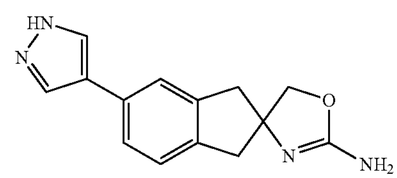 | 255 |
| (±)-8M | 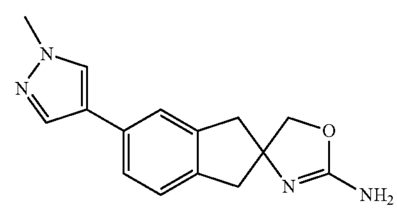 | 269 |
| (±)-8N | 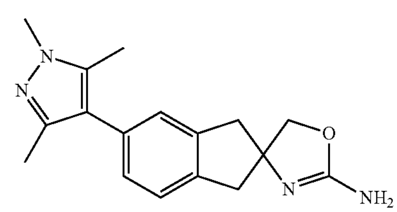 | 297 |
| (±)-8P | 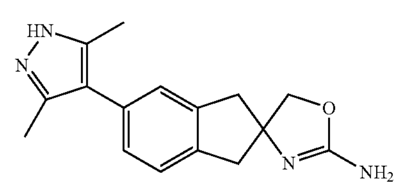 | 283 |

-continued

| Cpd | Structure | LCMS (MH+) |
|---|---|---|
| (±)-8Q | 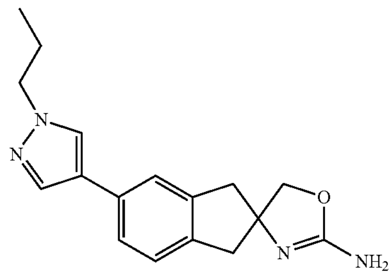 | 297 |
| (±)-8R | 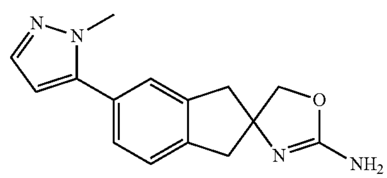 | 269 |
| (±)-8S | 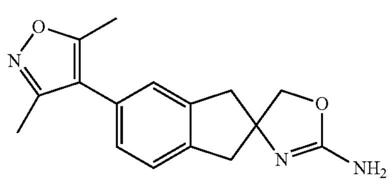 | 284 |
| (±)-8T | 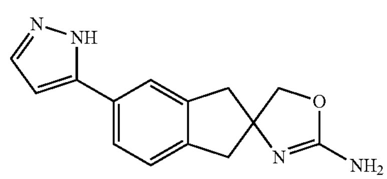 | 255 |
| (±)-8U | 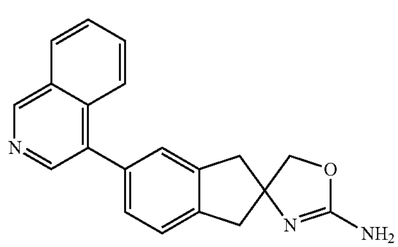 | 316 |

Preparative Example 9

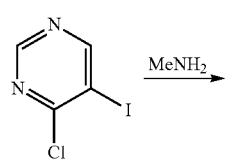

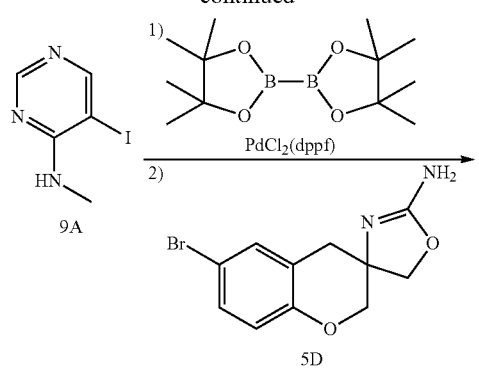

5-iodo-N-methylpyrimidin-4-amine (9A) was prepared from 4-chloro-5-iodopyrimidine and methylamine as described in WO2008100456. Compound 9A (37.5 mg, 0.160 mmol.) was then mixed with bis(pinacolato)diboron (46.6 mmg, 0.184 mmol), KOAc (78.3 mg, 0.798 mmol), and PdCl$_2$(dppf) (32.6 mg, 0.040 mmol) in dioxane (2.0 mL). The mixture was heated at 105° C. overnight in a 5 mL sealed tube and then cooled to RT. The reaction was then treated with compound 5D (22.59 mg, 0.0800 mmol), K$_2$CO$_3$ (66.2 mg, 0.48 mmol), PdCl$_2$(dppf) (16.3 mg, 0.020 mmol) and water (1.0 mL) and microwaved for 15 min at 125° C. The mixture was diluted with aq Na$_2$CO$_3$ and extracted with DCM. The organic extracts were dried over MgSO$_4$ and concentrated. Chromatography (0-10% of (9:1 MeOH/NH$_3$) in CH$_2$Cl$_2$) afforded (±)-9 (657 mg). LCMS m/z 312 (MH+).

Preparative Example 10

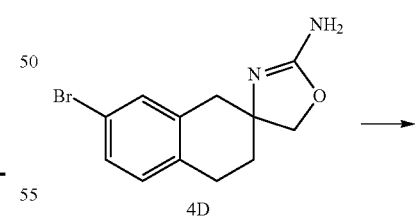

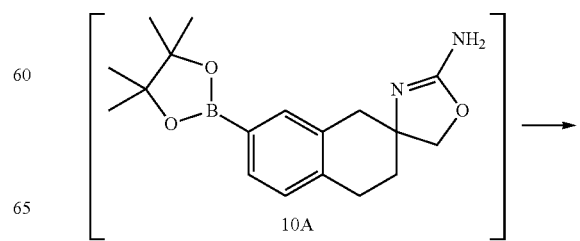

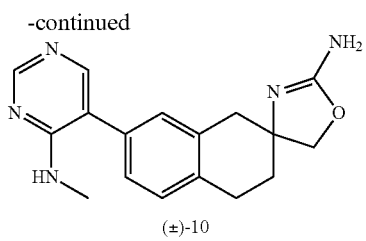

(±)-10

A mixture of 4D (224 mg, 0.797 mmol), bis(pinacol)diboronate (405 mg, 1.59 mmol), KOAc (313 mg, 2.39 mmol) and PdCl$_2$dppf·DCM (15 mg, 0.013 mmol) in 1,4-dioxane (4.0 mL) was irradiated with microwaves for 15 min at 110° C. Then iodopyrimidine 9A (468 mg, 1.99 mmol) was added followed by sodium carbonate (338 mg, 3.19 mmol), 1,4-dioxane (2.0 mL) and water (4.0 mL). The resulting mixture was irradiated with microwaves for 15 min at 130° C. The mixture was cooled to RT, diluted with water and extracted twice with DCM. The combined organic phase was dried over anhydrous Na$_2$SO$_4$ and the solvent removed in vacuo. The product was purified by column chromatography (SiO$_2$, 10% MeOH(NH$_3$)/DCM) to give the title compound (±)-10 as a brown oily solid. LCMS m/z 310 (MH+).

In a similar manner, compound 4D was sequentially coupled with bis(pinacol)diboronate and 4,6-dimethyl-5-bromopyrimidine to provide compound (±)-10B. LCMS m/z 309 (MH+).

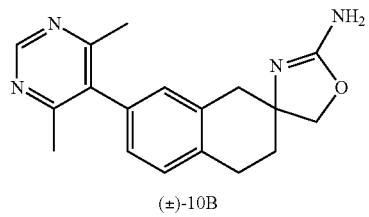

(±)-10B

Preparative Example 11

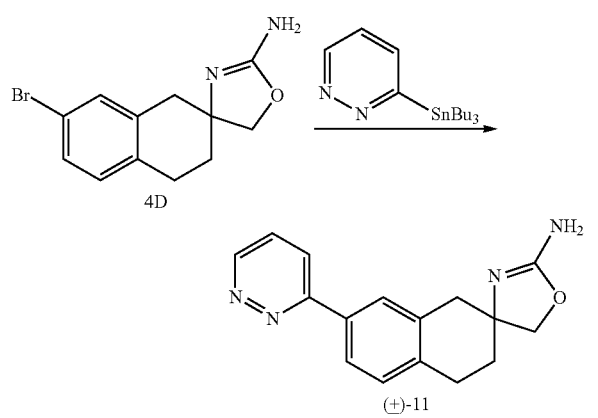

A mixture of 4D (21 mg, 0.075 mmol), 3-tributyltin-pyridazine (83 mg, 0.22 mmol) and PdCl$_2$dppf·DCM (15 mg, 0.013 mmol) in DMF (2.0 mL) was irradiated with microwaves for 15 min at 130° C. The mixture was extracted with DCM, washed with water and dried over anhydrous Na$_2$SO$_4$.

The product was purified by column chromatography followed by preparative TLC (SiO$_2$, 10% MeOH(NH$_3$)/DCM) to give (±)-11. LCMS m/z 281 (MH+).

Preparative Example 12

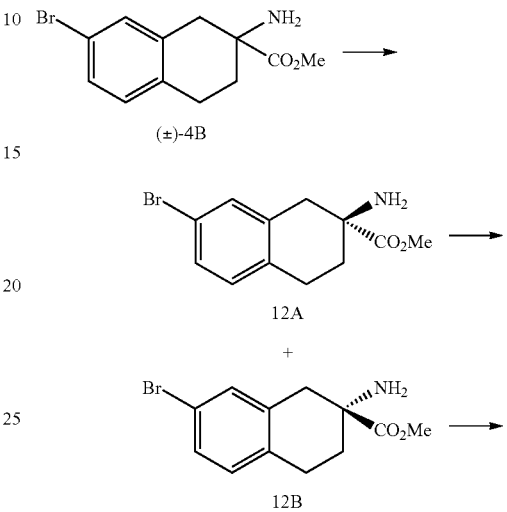

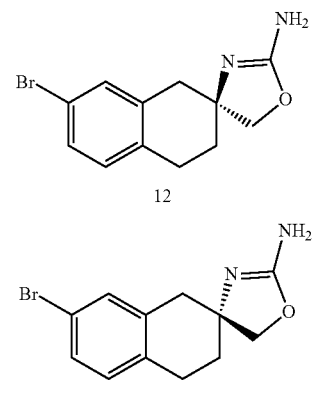

The racemic mixture (±)-4B was separated on a preparative Chiralpak AD column (SFC Chromatography with 20% MeOH-0.2% DEA) to provide the pure enantiomers 12A and 12B (>99% ee), which were separately advanced to provide compound 12 (LCMS m/z 281/283, MH+) and compound 12C (LCMS m/z 281/283, MH+), respectively, as described in Example 4.

Preparative Example 13

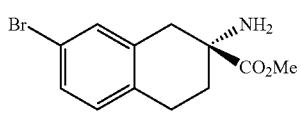

Step 1

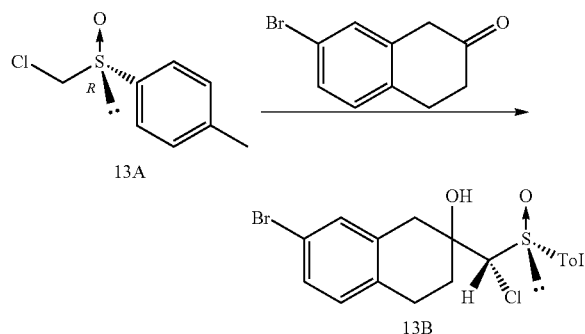

LDA 2.0 M (0.62 mL, 1.14 mmol) was dropwise added to a solution of sulfoxide 13A (J. Org. Chem. 1989, 54, 3130; 0.197 g, 1.039 mmol) in dry THF (4 mL) at −75° C. under nitrogen. The mixture was stirred for 10 min and a solution of 7-bromo-2-tetrolone (242 mg, 1.044 mmol) in dry THF (2 mL) was added dropwise over a period of 3 min. The resulting mixture was stirred for 30 min at −75° C. and then TFA was added (0.40 mL). The mixture was warmed to RT, diluted with water, and extracted with DCM. The combined organic phase was dried and the solvent removed in vacuo to give an orange oil. $Et_2O$ was added and the title compound 13B precipitated as a white solid (205 mg, 47%, 3:1 mixture of diastereomers).

Step 2

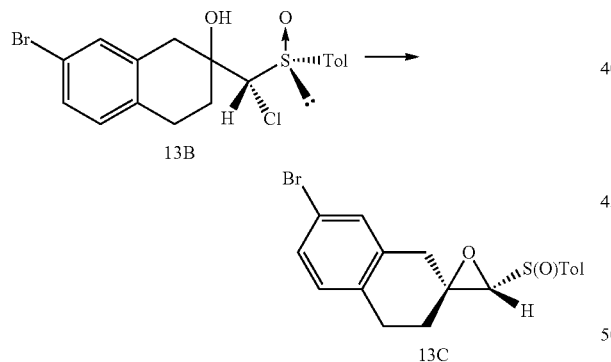

KOtBu (39 mg, 0.35 mmol) was added to a solution of a mixture of diastereomeric alcohols 13B (120 mg, 0.29 mmol) in a 1:1 mixture of dry tBuOH and dry THF (20 mL) at RT. The resulting mixture was stirred for 1.5 h and KOtBu (13 mg, 0.12 mmol) was added. The mixture was stirred for another 30 min and the solvent evaporated. Water was added and the mixture was extracted with DCM. The combined organic phase was dried and the solvent removed in vacuo to give an orange oil which was purified by column chromatography (AcOEt:hexanes 1% to 100%) to afford major epoxide 13C (104 mg, 95% considering isolation of 16 mg of minor epoxide).

Step 3

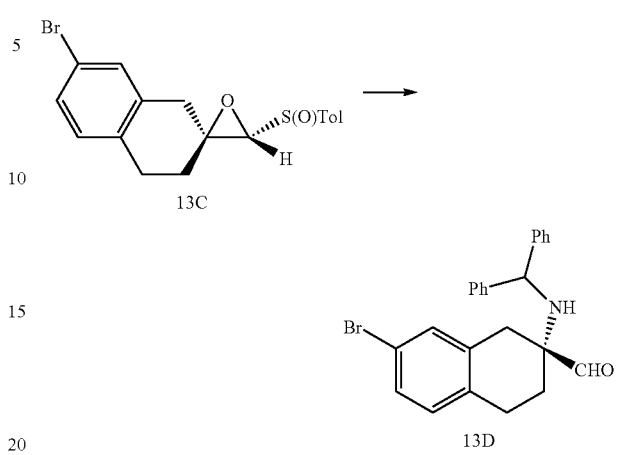

Diphenylamino methane (0.185 mL, 1.06 mmol) was added to a solution of epoxide 13C (80 mg, 0.212 mmol) in IPA (3 mL) at RT. The resulting mixture was heated at 90° C. for 17 h then cooled at RT. The solvent was evaporated and the residue was purified by column chromatography (AcOEt: hexanes 1% to 10%) to afford the title compound 13D (38 mg, 43%) as a pale brown glass.

Step 4

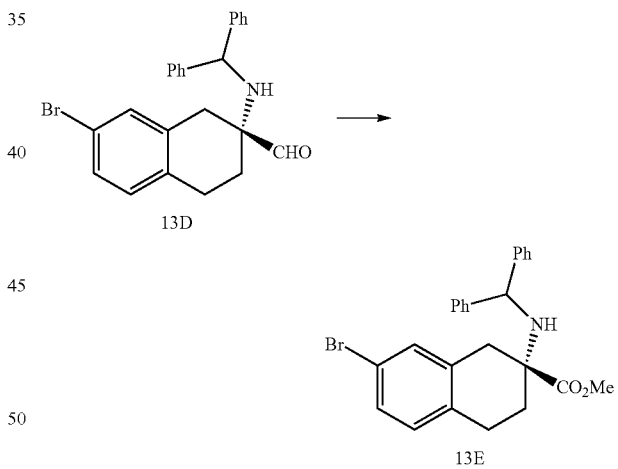

A solution of KOH (136 mg, 2.17 mmol) in dry MeOH (2 mL) was added to a solution of iodine (242 mg, 0.95 mmol) in dry MeOH (2 mL) and stirred for 10 min. The resulting mixture was added to a solution of aldehyde 13D (57 mg, 0.136 mmol) in MeOH (3 mL). The mixture was stirred for 25 min, quenched with aq sat $Na_2S_2O_3$ and extracted with DCM. The combined organic phase was dried and the solvent evaporated in vacuo to give a brown glass that was purified by column chromatography (AcOEt: hexanes 1% to 10%) to afford the title compound 13E (37 mg, 61%) as a colorless glass.

Step 5

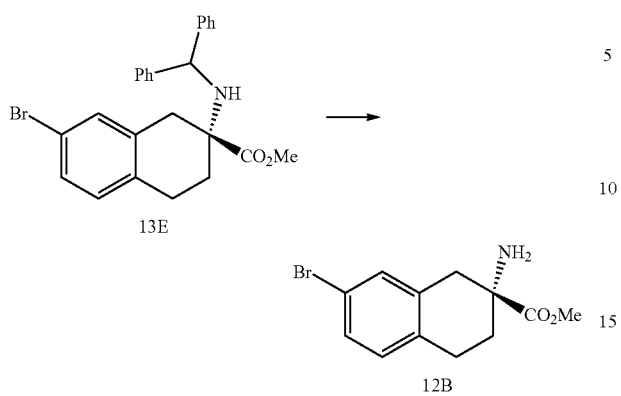

A solution of benzhydryl-protected aminoester 13E (37 mg, 0.082 mmol) in trifluoroacetic acid (3 mL) was heated in a 15 mL sealed tube at 90° C. for 1 h and 20 min. The mixture was cooled to RT, the solvent was removed and the residue quenched with $NH_3$ in MeOH solution (0.4 N). The solvent was evaporated and the residue was purified by column chromatography (AcOEt: hexanes 1% to 100%) to afford the title compound 12B (23 mg, 100%) as a pale brown glass.

Preparative Example 14

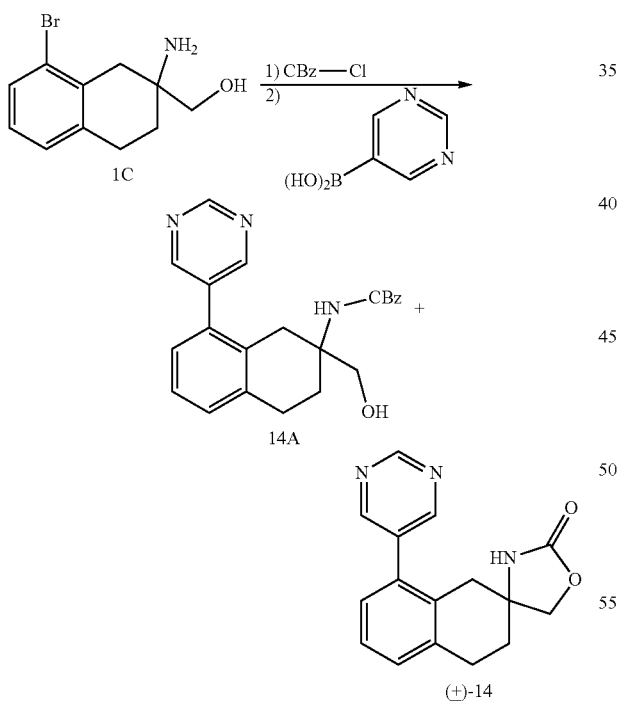

In a manner similar to that described in Example 2 (Step 1) and Example 1 (Step 7), compound 1C was sequentially treated with CBzCl and then subjected to a Suzuki reaction with pyrmidine-5-boronic acid to obtain compound 14A and (±)-14. LCMS m/z 282 (MH+).

Compound (±)-14B was obtained in a similar fashion. LCMS m/z 311 (MH+).

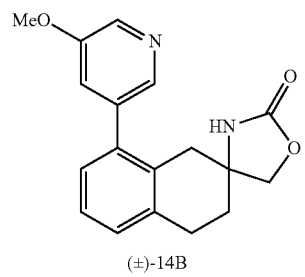

Preparative Example 15

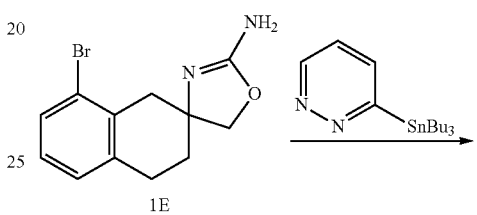

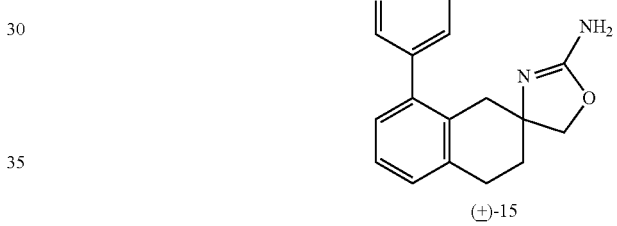

In a manner similar to Example 11, a mixture of compound 1E (40 mg, 0.142 mmol), $Pd(PPh_3)_4$ (16.4 mg, 0.0142 mmol), KF (25 mg, 0.426 mmol), and 3-tributyltin-pyridazine (78.8 mg, 0.214 mmol) in dioxane (1.5 mL) was heated at 100° C. overnight. The mixture was cooled to RT and treated with EtOAc (15 mL) and water (5 mL). The organic layer was dried ($Na_2SO_4$), filtered and concentrated under reduced pressure. The residue was purified by column chromatography (10% MeOH/DCM) to give compound (±)-15 as a white solid. LCMS m/z 281 (MH+).

The following compounds were prepared in a similar fashion:

| Cpd | Structure | LCMS (MH+) |
|---|---|---|
| (±)-15A | 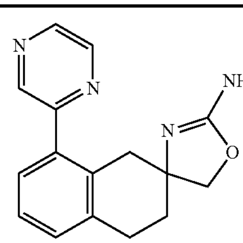 | 281 |

-continued

| Cpd | Structure | LCMS (MH+) |
|---|---|---|
| (±)-15B | 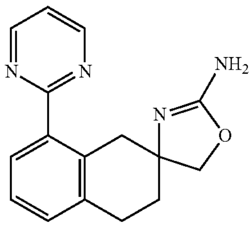 | 281 |
| (±)-15C | 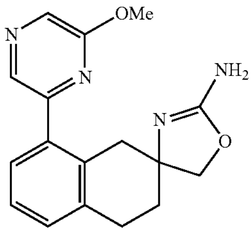 | 311 |

Preparative Example 16

(±)-16

Steps 1-2

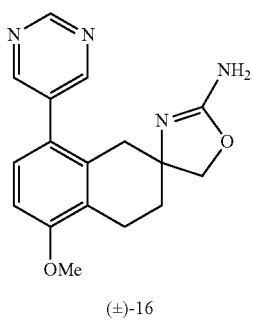

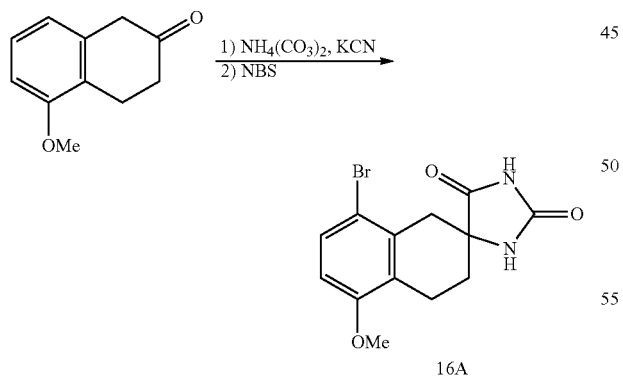

In a manner similar to that described in Example 6 (Step 1), 5-methoxy-2-tetralone was treated with ammonium carbonate and KCN.

A solution of the resulting hydantoin (7.02 g, 28.5 mmol) in DMF (80 mL) was treated with NBS (5.58 g, 31.4 mmol) at RT. The mixture was stirred for 30 min and poured into water (200 mL). The slurry was filtered and washed with water. The beige solid was dried in air to give 16A (quantitative yield).

Steps 3-8

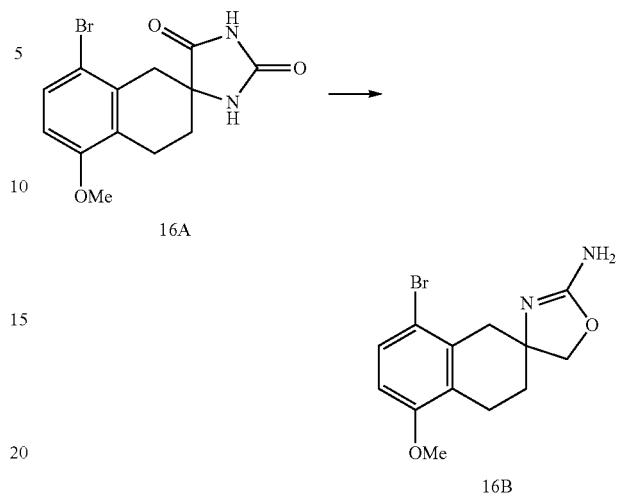

Using the sequence described in Example 1 (Steps 2-7), 16A was converted into 16B and then coupled with pyrimidine-5-boronic acid under Suzuki conditions to provide the title compound (±)-16. LCMS m/z 311 (MH+).

The following compounds were prepared in an analogous fashion from 16B:

| Cpd | Structure | LCMS (MH+) |
|---|---|---|
| (±)-16C | 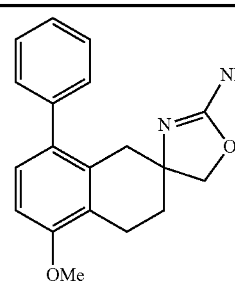 | 309 |
| (±)-16D | 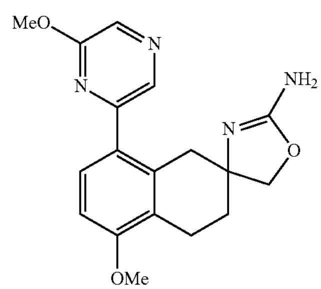 | 341 |
| (±)-16E | 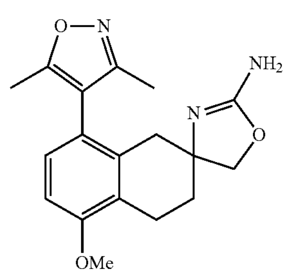 | 328 |

Preparative Example 17

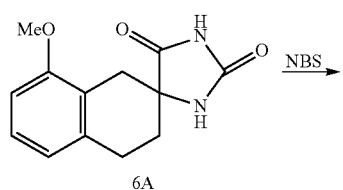
6A

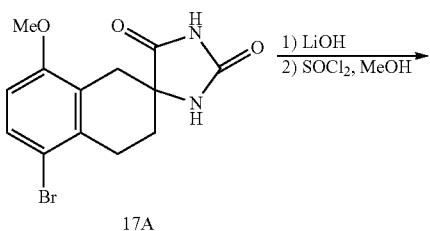
17A

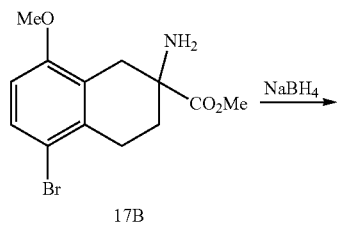
17B

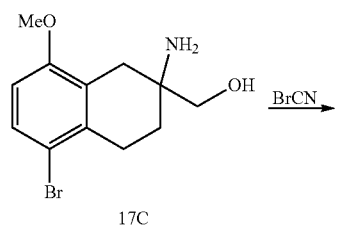
17C

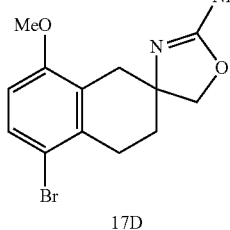
17D

Compound 6A was brominated as described in Example 16 (Step 2) to provide 17A, which was further advanced to compound 17D as previously described.

The following compounds were prepared from 17D by Suzuki coupling as previously described:

| Cpd | Structure | LCMS (MH+) |
|---|---|---|
| (±)-17 | 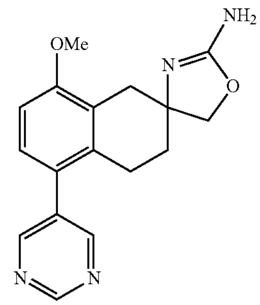 | 311 |
| (±)-17E | 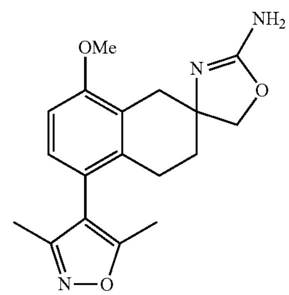 | 327 |
| (±)-17F | 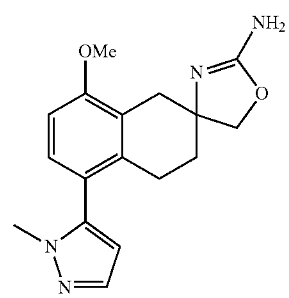 | 313 |

Preparative Example 18

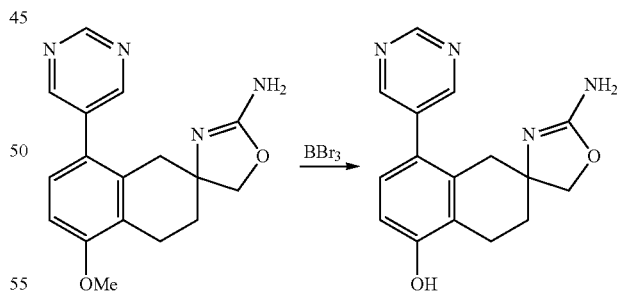

To a stirred solution of (±)-16 (109 mg, 0.352 mmol) in $CH_2Cl_2$ (2.5 mL) was added $BBr_3$ (1M in DCM, 1.05 mL, 1.05 mmol) at 0° C. The mixture was stirred at this temperature for 5 h and quenched with the addition of sat. $NaHCO_3$ until pH 7. The mixture was extracted with EtOAc (50 mL), dried ($Na_2SO_4$), filtered, and concentrated under reduced pressure. The residue was purified by column chromatography (10% $MeOH/CH_2Cl_2$, 1% $NH_4OH$) to give compound (±)-18 as a white solid. LCMS m/z 297 (MH+).

Compound (±)-18A (LCMS m/z 297, MH+) was prepared from (±)-17 in a similar fashion.

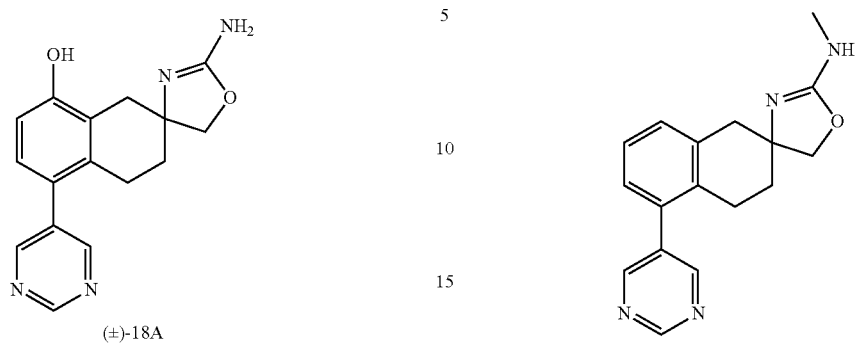

(±)-18A

Preparative Example 19

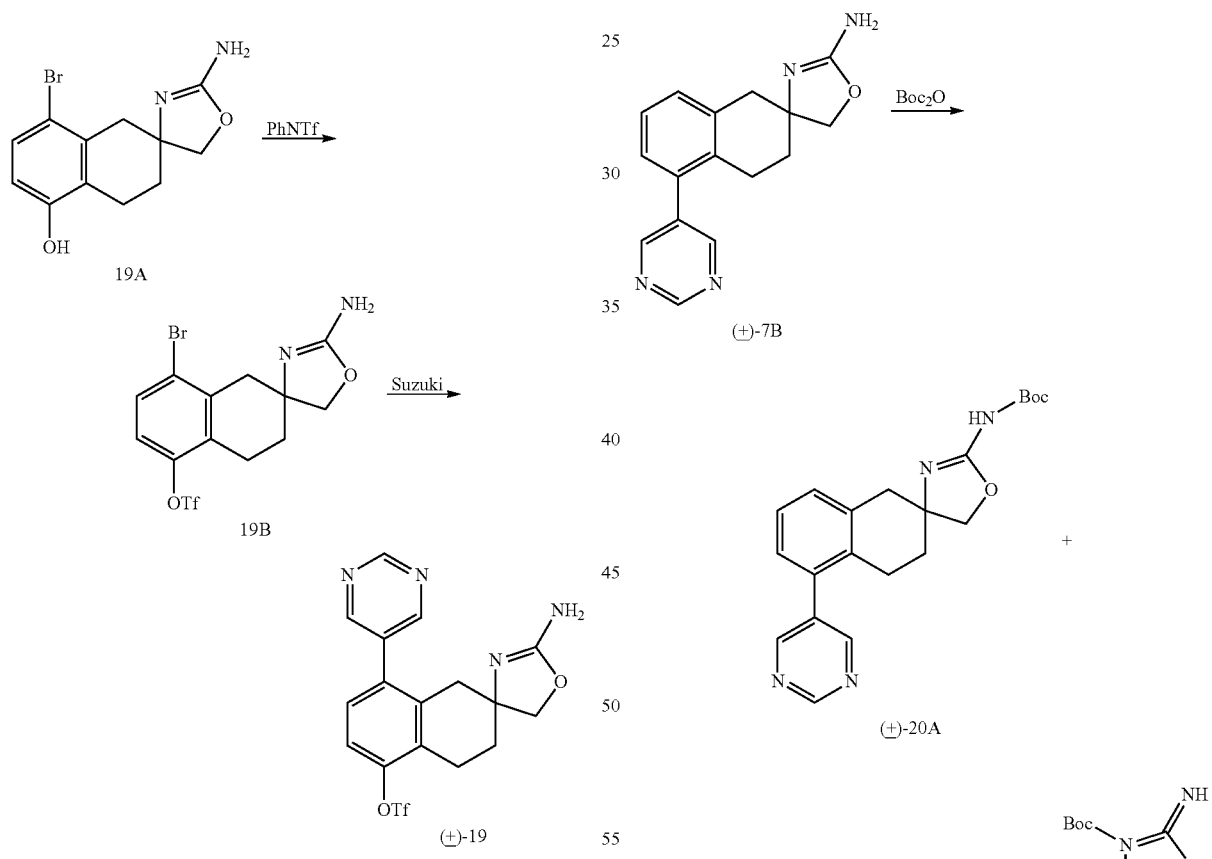

To a solution of compound 19A (prepared from 16B and BBr₃ as previously described in Example 18, 640 mg, 1.6 mmol) in THF (10 mL) was added PhNTf₂ (571.6 mg, 1.6 mmol) and TEA (0.556 mL, 4 mmol) at RT. The reaction mixture was stirred overnight and concentrated under reduced pressure. The crude was purified with column chromatography (10% MeOH/DCM) to give compound 19B as a white foam. Suzuki reaction of 19B produced compound (±)-19 as a clear glass. LCMS m/z 429 (MH+).

Preparative Example 20

Step 1

In a manner similar to that described in Example 2 (Step 1), (±)-7B was protected with Boc$_2$O to provide (±)-20A as the major product and (±)-20B (LCMS m/z 381, MH+) as the minor product.

Steps 2-3

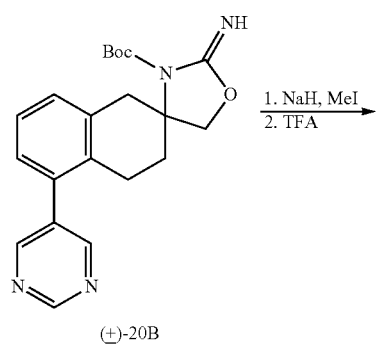

(±)-20B

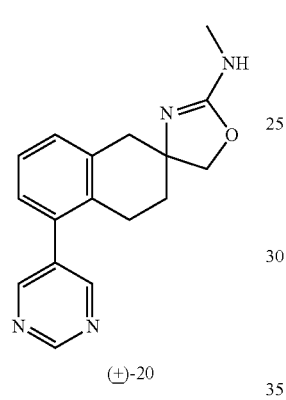

(±)-20

To a solution of (±)-20B (40.8 mg, 0.107 mmol) in THF (1 mL) was added MeI (0.02 mL, 0.321 mmol) and NaH (60% dispersion in mineral oil, 6.4 mg, 0.16 mmol) at RT. The mixture was stirred for 1 hr before it was quenched with the addition of water and extracted with EtOAc. The organic layer was dried (Na$_2$SO$_4$), filtered and concentrated to give the crude product (30.6 mg).

The crude material was dissolved in DCM (1 mL) and treated with TFA (1 mL) at RT. After 2 hr, the mixture was concentrated under reduced pressure and purified using column chromatography (10% MeOH/DCM) to give the title compound (±)-20 as a white foam (11.2 mg, 50%). LCMS m/z 295 (MH+).

Compound (±)-20C (LCMS m/z 295, MH+) was prepared from compound 1 in a similar fashion.

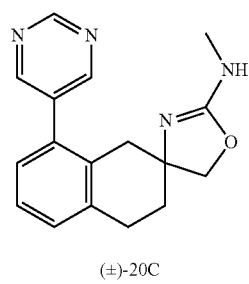

(±)-20C

Preparative Example 21

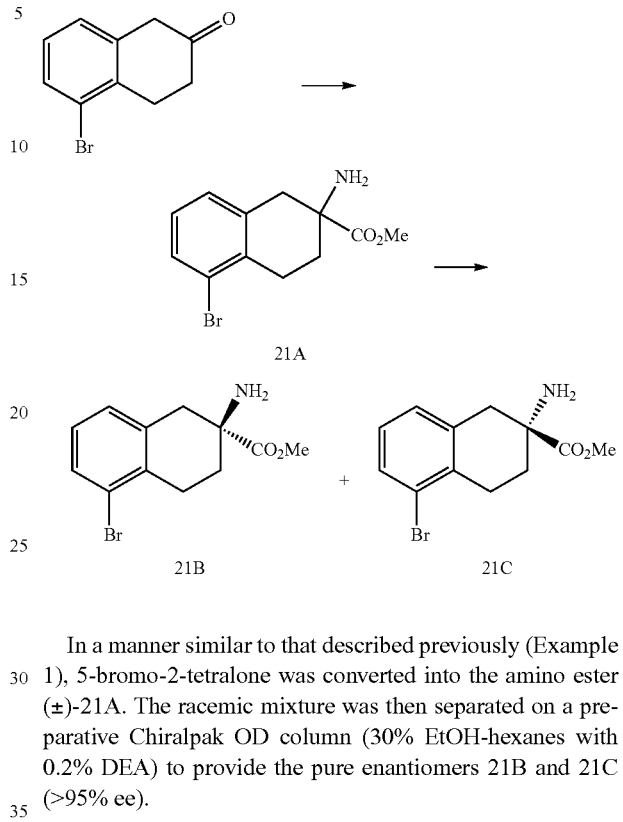

In a manner similar to that described previously (Example 1), 5-bromo-2-tetralone was converted into the amino ester (±)-21A. The racemic mixture was then separated on a preparative Chiralpak OD column (30% EtOH-hexanes with 0.2% DEA) to provide the pure enantiomers 21B and 21C (>95% ee).

Alternatively, 21B and 21C were synthesized by an asymmetric approach outlined below:

Step 1

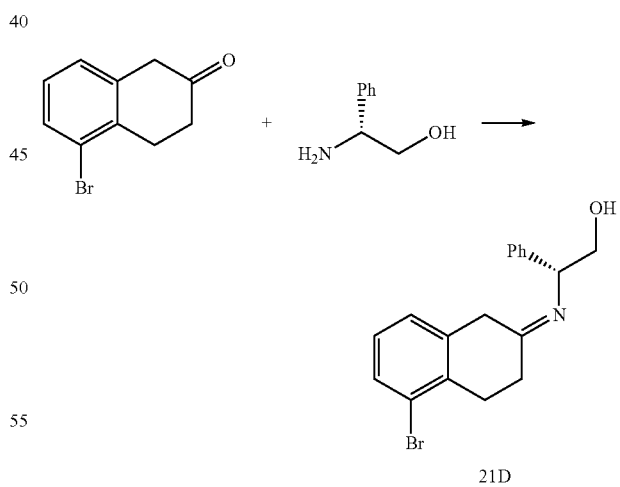

21D

A mixture of 5-bromo-2-tetralone (2.0 g, 8.89 mmol), (R)-phenylglycinol (1.22 g, 8.89 mmol, 1.0 eq), and 4 Å molecular sieves in CHCl$_3$ (50 mL) was refluxed until the starting material disappeared (monitored by $^1$H NMR). After filtering the molecular sieves the solvent was removed under reduced pressure, the residual oil 21D was used for the next step without further purification.

Step 2

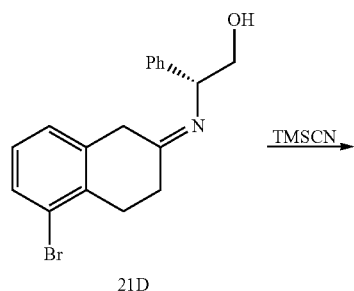

To a solution of 21D in 10 mL CH₂Cl₂ at 0° C. was added TMSCN (1.67 mL, 13.34 mmol, 1.5 eq) followed by MeOH (3.5 mL). The cooling bath was removed and the reaction mixture was stirred at RT for 24 h. The solution was concentrated at reduced pressure and the residue 21E was used for the next step without any purification.

Step 3

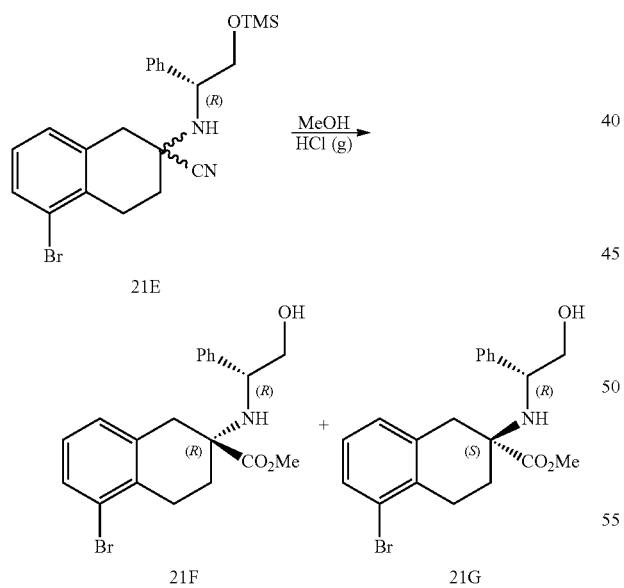

The oily residue 21E was dissolved in 10 mL MeOH and cooled in an ice-water bath. Anhydrous HCl (g) was bubbled through the solution until saturation. After stirring for 1 h, the MeOH was evaporated and the residue was diluted with 100 mL of EtOAc. The organic layer was washed with 10% aq NaHCO₃, brine and dried over Na₂SO₄. After removal of the solvent, the amino ester was purified by SFC chromatography to yield 21F (1.75 g) and 21G (0.43 g).

Step 4

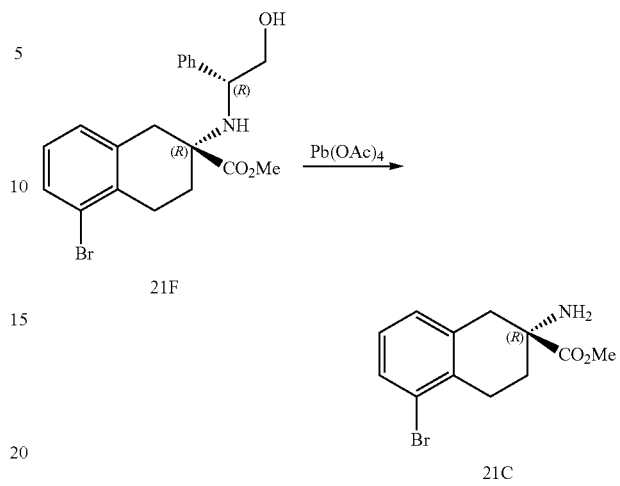

To a solution of 21F (330 mg, 0.82 mmol) in DCM (3.5 mL) and MeOH (1.8 mL) was added lead tetraacetate (362 mg, 0.82 mmol, 1.0 eq) at 0° C. After the resultant mixture was stirred for 30 min, 10 mL of phosphate buffer (pH 7) was added to quench the reaction. The mixture was filtered through celite, and the organic layer was separated, washed with water, and concentrated to dryness. The residual oil was purified by flash chromatography (1% MeOH/CH₂Cl₂) to yield 111 mg of the R-amino ester 21C.

In a manner similar to that described previously (Examples 1 and 3), the individual enantiomers 21B and 21C were subjected to the following sequence to provide compounds listed in the table below: reduction with NaBH₄, cyclization with BrCN, and Suzuki coupling with the appropriate boronic acid or boronic ester.

| Cpd | Structure | LCMS (MH+) |
| --- | --- | --- |
| 21H | 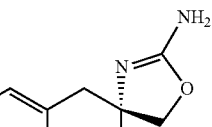 | 285 |
| 21I | 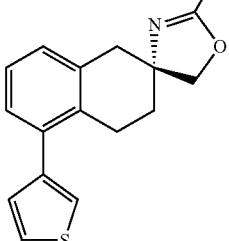 | 269 |

-continued
| Cpd | Structure | LCMS (MH+) |
|---|---|---|
| 21J | 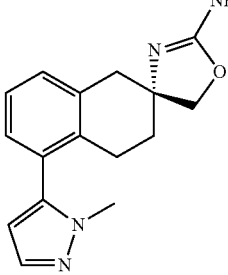 | 283 |
| 21K | 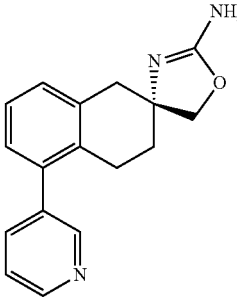 | 280 |
| 21L | 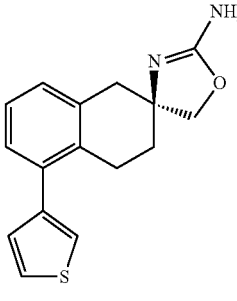 | 285 |
| 21M | 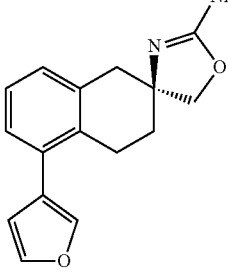 | 269 |
| 21N | 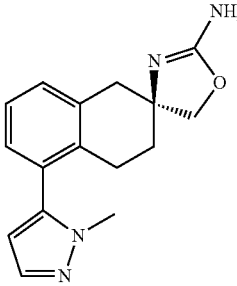 | 283 |
-continued
| Cpd | Structure | LCMS (MH+) |
|---|---|---|
| 21O | 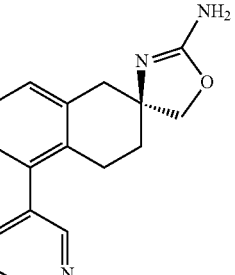 | 280 |
Preparative Example 22
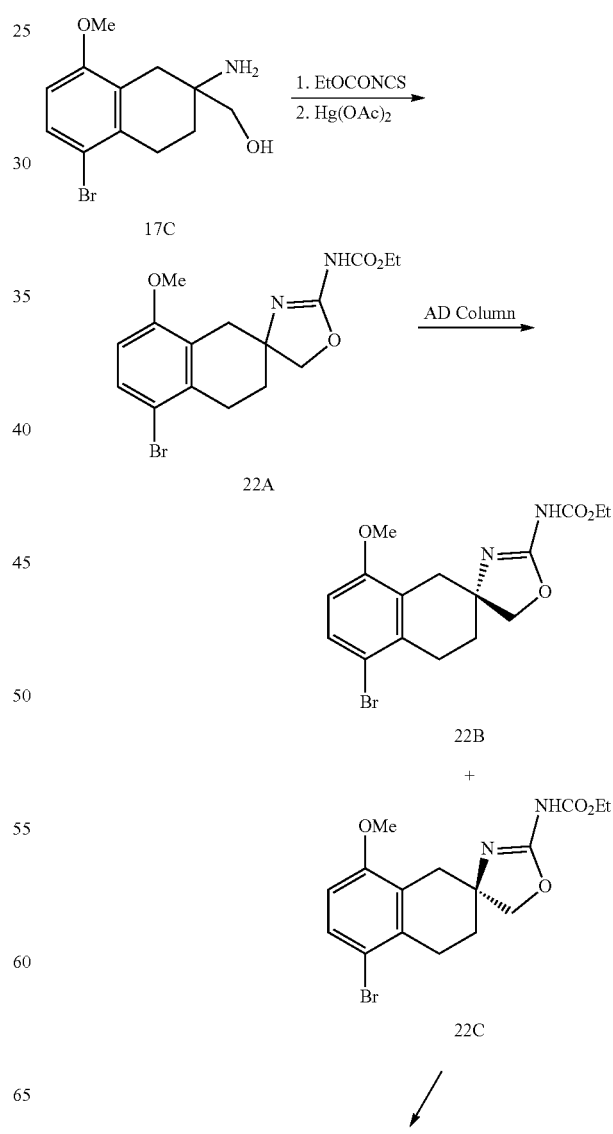

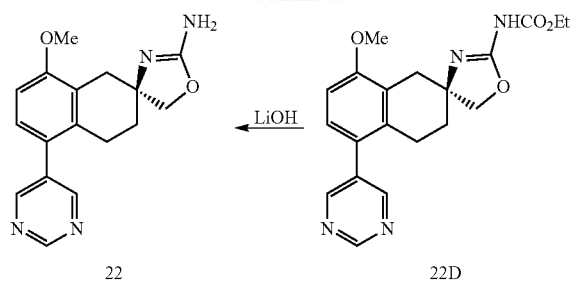

Steps 1-3

To a stirred solution of 17C (1.53 g, 5.33 mmol) in THF (20 mL) was added EtOCONCS (0.7 g, 5.33 mmol). The mixture was stirred at RT for 2 h and concentrated under reduced pressure. The residue was dissolved in EtOH (40 mL) and then treated with $Hg(OAc)_2$ (1.698 g, 5.33 mmol) in one portion. After stirred for 2 h, the dark suspension was filtered through a pad of celite and concentrated under reduced pressure. The crude material was purified by column chromatography (55% hexanes/EtOAc) to give 22A. This material was separated by Chiralpak AD HPLC (12% IPA/hexanes) to give compound 22B (LCMS m/z 383, MH+) and 22C (LCMS m/z 383, MH+) as white solid (total 1.02 g, 50%).

Steps 4-5

Employing previously described procedures for the Suzuki reaction (microwave, 110° C., 15 min), compound 22D was prepared from 22C.

To a solution of 22D (25 mg, 0.065 mmol) in MeOH/water (1:1, 3 mL) was added LiOH (27.3 mg, 0.65 mmol). The mixture was refluxed for 2 hr and concentrated under reduced pressure to remove MeOH. The residue was extracted with EtOAc and dried ($Na_2SO_4$), filtered, and concentrated under reduce pressure. The crude material was purified by column chromatography (10% MeOH/DCM) to give compound 22 as a white solid (14.1 mg, 70%). LCMS m/z 311 (MH+).

In a similar manner, compound 22E was prepared from 22B. LCMS m/z 311 (MH+).

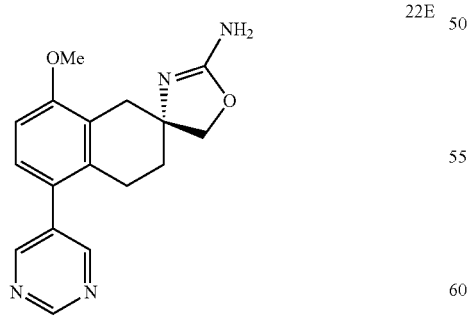

Compounds 22F (LCMS m/z 297, MH+) was prepared from 22 in a manner similar to that described in Example 18. Likewise, compound 22G (LCMS m/z 297, MH+) was prepared from 22E.

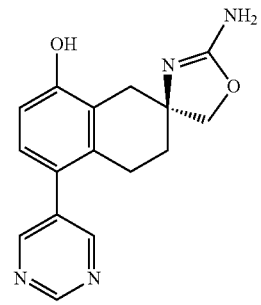

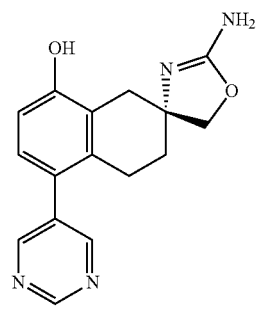

Preparative Example 23

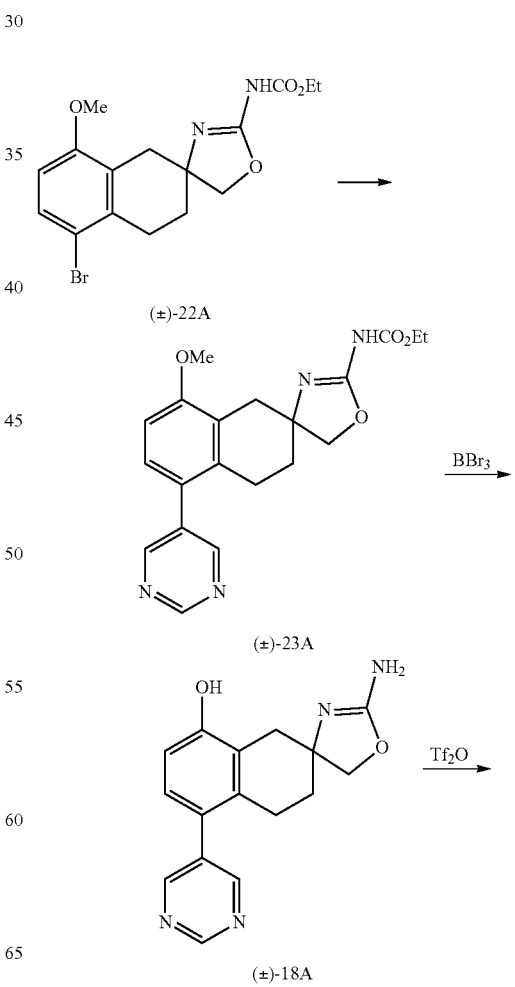

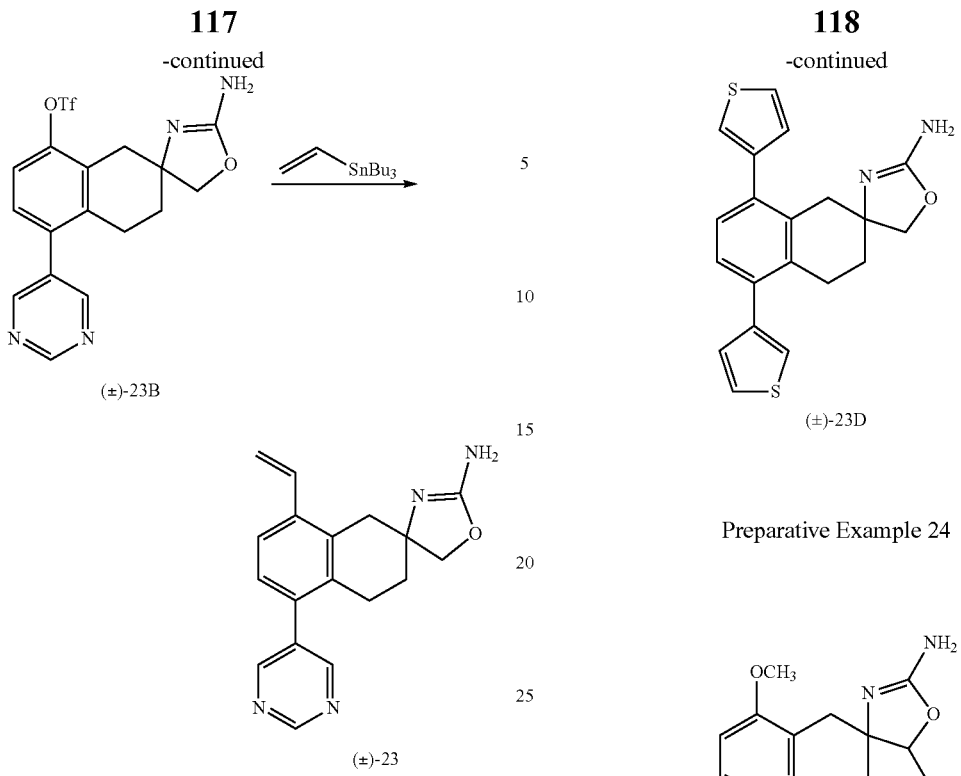

(±)-23B (±)-23

In a manner similar to that previously described, compound (±)-22A was sequentially subjected to Suzuki conditions with pyrimidine-5-boronic acid, treated with BBr₃, and reacted with Tf₂O to provide (±)-23B.

A solution of (±)-23B (14.3 mg, 0.0336 mmol) in dixane (1 mL) was treated with Pd(PPh₃)₄ (4 mg, 0.0034 mmol), vinyltributyl tin (0.020 mL, 0.0672 mmol), and LiCl (4.3 mg, 0.101 mmol). After being stirred at 100° C. overnight, the mixture was cooled and treated with EtOAc (5 mL) and water (2 mL). The organic layer was separated, dried (Na₂SO₄), filtered, and concentrated under reduced pressure. The crude material was purified by prep-HPLC (0-50% CH₃CN/H₂O) to give compound (±)-23 as a clear glass (2.0 mg, 20%). LCMS m/z 307 (MH+).

Compounds (±)-23C (LCMS m/z 359, MH+) and (±)-23D (LCMS m/z 267, MH+) were synthesized using a similar approach (Suzuki reaction in the final step):

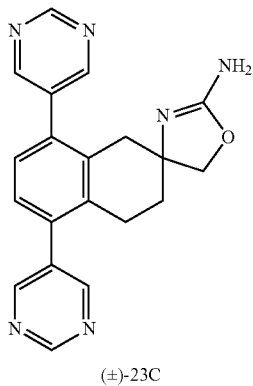

(±)-23C (±)-23D

Preparative Example 24

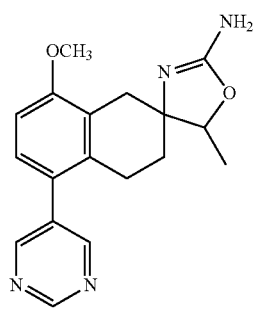

(±)-24

Step 1

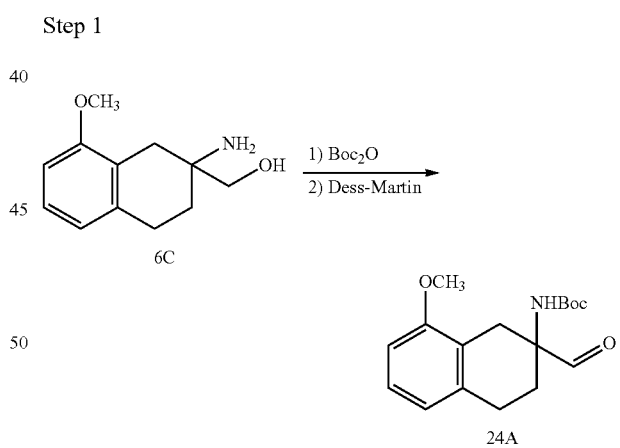

In a manner similar to that described in Example 6 (Step 5), compound 6C was treated with Boc₂O. To a solution of the resulting product (1.767 g, 5.756 mmol) in CH₂Cl₂ (30 mL) was added Dess-Martin periodinate (3.66 g, 8.634 mmol) at RT. The mixture was stirred for 1 h and quenched with addition of NaS₂O₅ solution (1 M, 20 mL). The organic layer was separated and washed with saturated NaHCO₃ solution and brine. The organic phase was dried (Na₂SO₄), filtered, and concentrated under reduced pressure. The crude material was purified by column chromatography (15% EtOA/hexanes) to give aldehyde 24A as a white solid (1.637 g, 95%).

Step 2

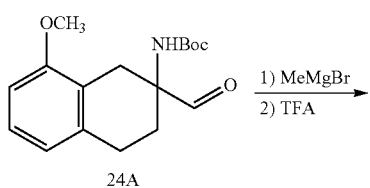

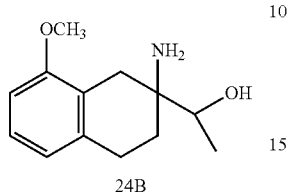

To a solution of compound 24A (1.673 g, 5.485 mmol) in CH$_2$Cl$_2$ (30 mL) was added MeMgBr (3 M solution in THF, 4.2 mL, 12.6 mmol) at −78° C. The mixture was stirred at this temperature for 1 h and quenched with addition of saturated NH$_4$Cl solution (20 mL) and EtOAc (80 mL). The organic layer was separated, washed with brine, dried (Na$_2$SO$_4$), filtered, and concentrated under reduced pressure. The crude material (white solid, 1.756 g, 97%) was deprotected with TFA in a manner similar to that described in Example 3 (Step 3) to provide 24B.

Step 3

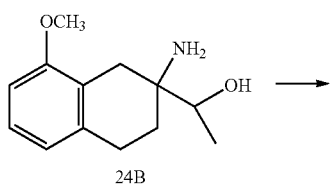

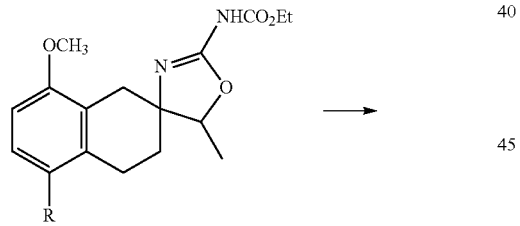

24C, R = H
24D, R = Br
24E, R = 5-pyrmidyl

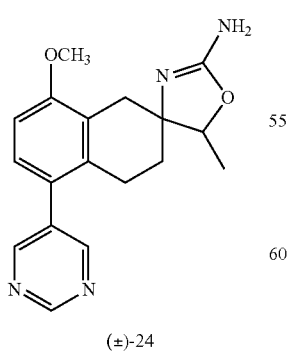

(±)-24

In a manner similar to that previously described, compound 24B was cyclized (Example 22, Steps 1-2), brominated (Example 16, Step 2), coupled with the 5-pyrimidine-5-boronic acid (Example 1, Step 7), and deprotected (Example 22, Step 5) to give compound (±)-24. LCMS m/z 325 (MH+).

Separation of 24E (Chiralpak AD, SFC Prep-HPLC) followed by deprotection provided the four pure diastereomers 24F (LCMS m/z 325, MH+), 24G(LCMS m/z 325, MH+), 24H(LCMS m/z 325, MH+), and 24I (LCMS m/z 325, MH+).

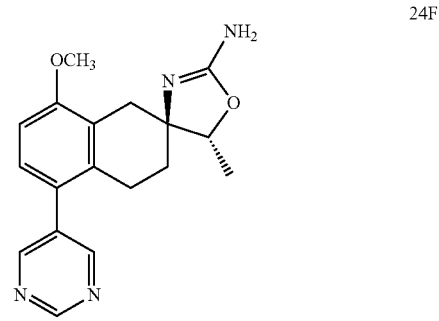

24F

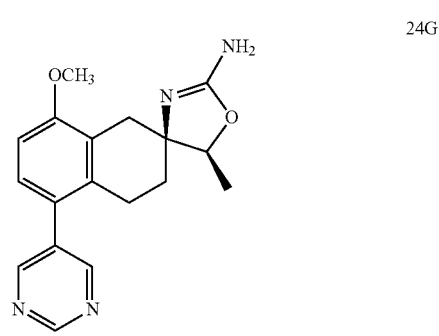

24G

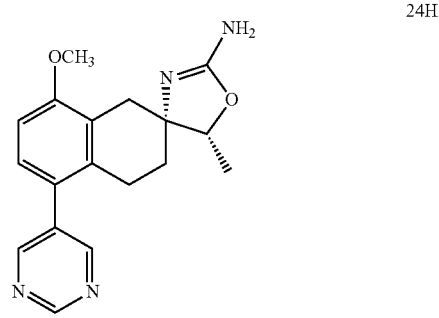

24H

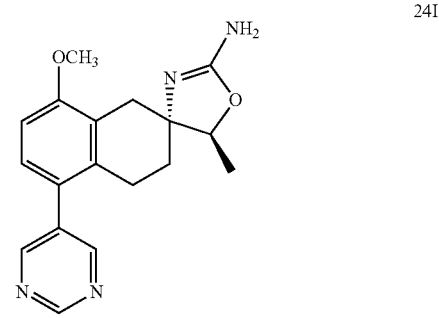

24I

Preparative Example 25

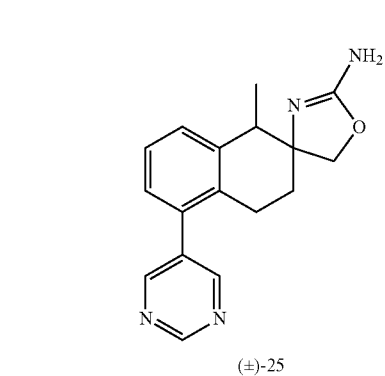

(±)-25

Steps 1-3

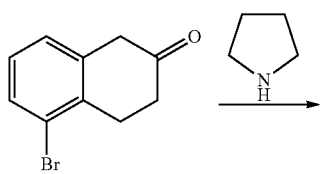

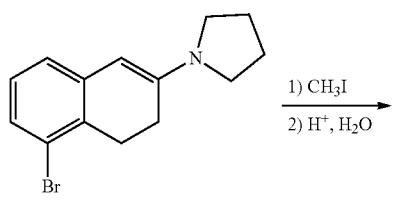

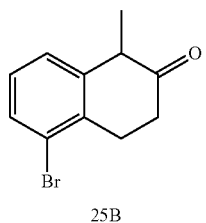

25B

A mixture of 5-bromotetralone (5.5 g, 24.4 mmol) and pyrrolidine (2.6 g, 36.6 mmol) in toluene (100 mL) was heated at reflux with a Dean Stark trap for 48 h. The reaction was then concentrated to give 25A as a dark foam. LCMS m/z 278/280 (MH+).

The enamine 25A was dissolved in 100 mL of 1,4-dioxane, tread with 15 mL of MeI and heated at reflux overnight. The reaction was cooled down in an ice bath and then treated with 40 mL H$_2$O and 1.5 mL AcOH. After heating at reflux for 3 h, the reaction was concentrated and chromatographed (5% to 15% ether/hexanes) to give a light yellow oil 25B (2.85 g, 49% for 2 steps).

Steps 4-10

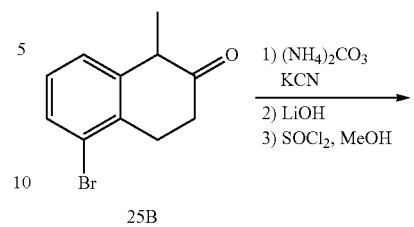

25B

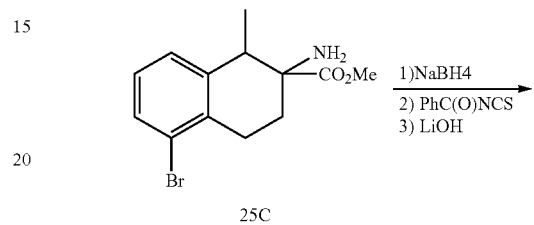

25C

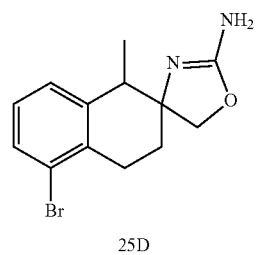

25D

In a manner similar to that described in Example 1, compound 25B was advanced to 25D (LCMS m/z 295/297, MH+). Final Suzuki coupling with pyrimidine-5-boronic acid provided the title compound (±)-25 as a mixture of 4 stereoisomers. LCMS m/z 295 (MH+).

The four stereoisomers of compound 25 were separated first by semi-prep AD column (10% EtOH/Hex with 0.1% DEA) to give a mixture of 25E and 25F and pure samples of 25G and 25H. The mixture of 25E and 25F was separated by semi-prep OJ (10% EtOH/Hex with 0.1% DEA) to give pure samples of 25E and 25F.

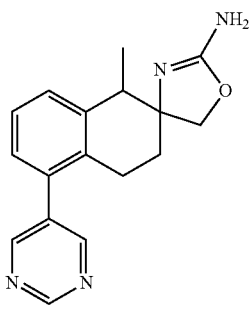

25E (Diastereomer 1)
25F (Diastereomer 2)
25G (Diastereomer 3)
25H (Diastereomer 4)

Preparative Example 26

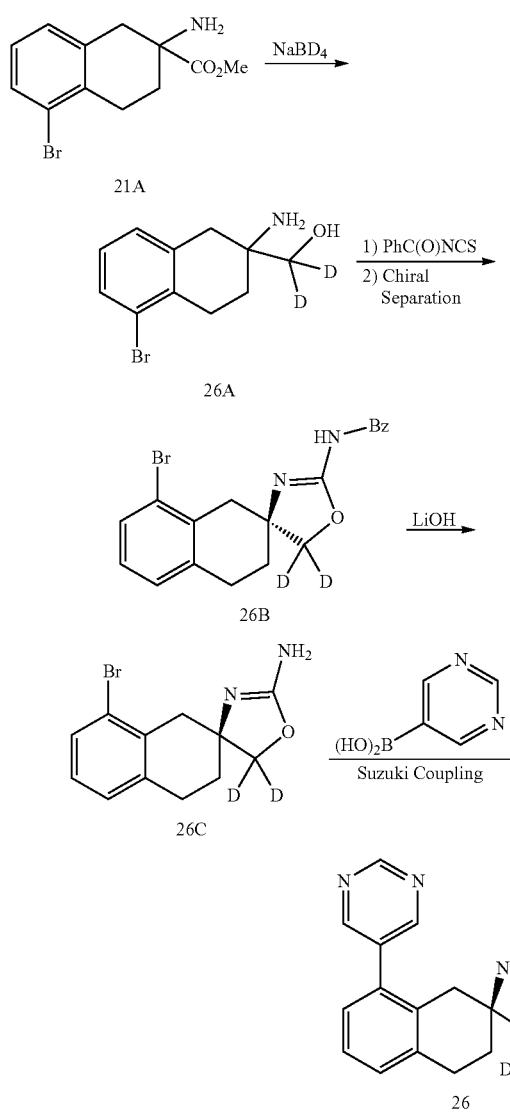

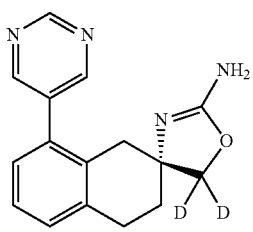

In a manner similar to that described in Example 1, 21A was reduced with NaBD$_4$ and then cyclized with PhC(O)NCS. Chiral separation, hydrolysis and Suzuki coupling provided the S-enantiomer 26. LCMS m/z 283 (MH+). Likewise, the R-enantiomer 26D was also synthesized. LCMS m/z 283 (MH+).

Preparative Example 27

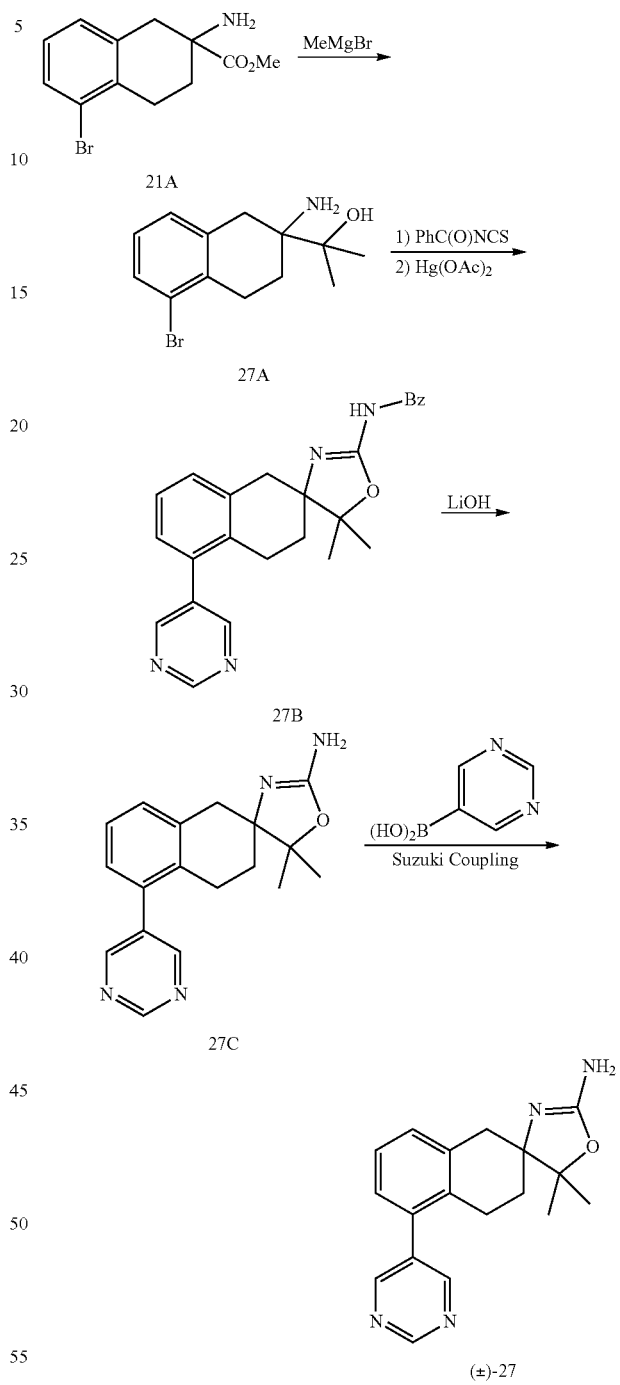

A solution of compound 21A (0.92 g, 3.24 mmol) in THF (15 mL) was treated slowly with MeMgBr (6 mL of a 3.0M solution/Et$_2$O) and then stirred overnight at RT. The reaction was cooled in an ice bath, quenched with sat. aq. NH$_4$Cl, and stirred for 30 min. The mixture was then treated with 1.0 M NaOH (~10 mL) and then extracted with DCM (3×), dried over Na$_2$SO$_4$, and concentrated to give 27A as a brown foam (0.92 g).

In a manner similar to that described in Example 22, 27A was cyclized with PhC(O)NCS/Hg(OAc)$_2$, hydrolyzed and coupled with pyrimidine-5-boronic acid to provide the title compound (±)-27. LCMS m/z 309 (MH+). The pure enantiomers 27D (LCMS m/z 309, MH+) and 27E (LCMS m/z 309, MH+) were separated by chiral HPLC (AD column, 10% EtOH-hexanes with 0.1% DEA).

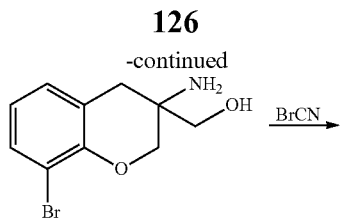

Preparative Example 28

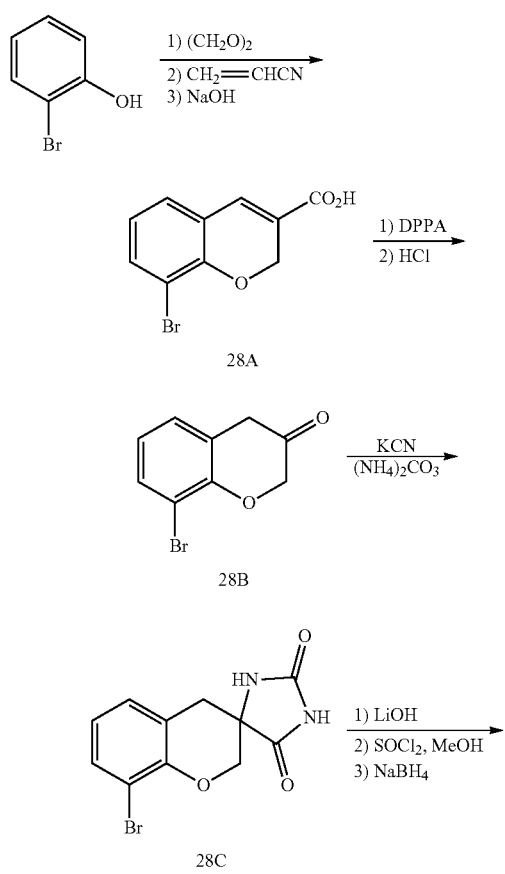

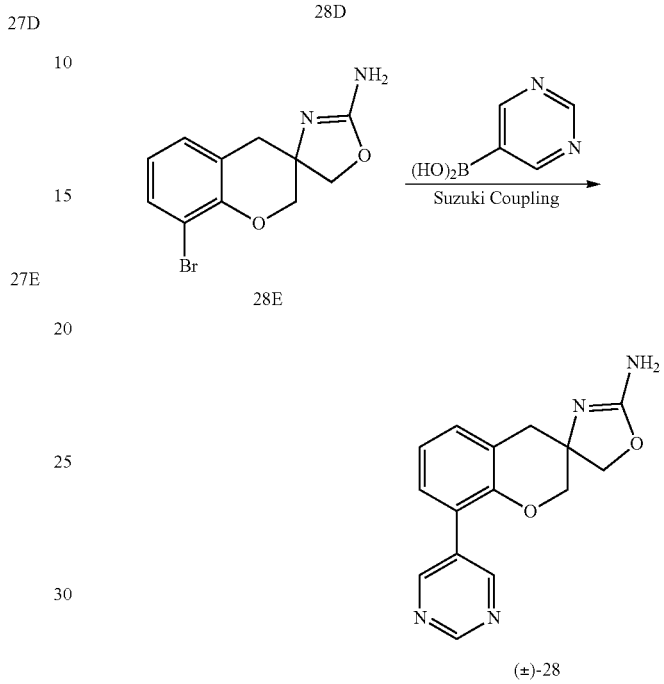

Steps 1-5

8-Bromochroman-3-one 28B was prepared from 2-bromophenol in a manner similar to that described in the literature (J. Med. Chem., 1988, 689): Reaction of 2-bromophenol with paraformadehyde (MgCl$_2$, NEt$_3$, THF, 75° C., 4 h), followed by treatment with acrylonitrile (neat, Dabco, 95° C., 18 h), and hydrolysis with 10% NaOH (100° C., 4 h) afforded 28A. Compound 28A was reacted with DPPA (NEt$_3$, toluene, 110° C., 2 h) followed by treatment with 6N HCl (85° C., 2 h) to afford 8-bromochroman-3-one 28B.

Steps 6-11

Compound 28D was prepared from 28B in a manner similar to that described in Example 1: hydantoin formation with (NH$_4$)$_2$CO$_3$/KCN, hydrolysis with LiOH, methyl ester formation with SOCl$_2$/MeOH, and reduction with NaBH$_4$. The reaction of compound 28D with cyanogen bromide provided 28E (THF, RT, 3 h, in a manner similar to that described in Example 3, Step 4). The title compound (±)-28 was prepared from 28E via Suzuki coupling with pyrimidine-5-boronic acid/Pd(dppf)Cl$_2$ in a manner similar to that described in Example 1 (Step 7). LCMS m/z 283 (MH+).

The racemic mixture (±)-28 was separated on a preparative Chiralpak AD column with 10% EtOH-hexanes to provide the pure enantiomers (R)-28F (LCMS m/z 283, MH+) and (S)-28G (LCMS m/z 283, MH+).

Preparative Example 29

Preparative Example 30

Compound 28E (20 mg, 0.07 mmol), 2-(tributylstannyl) pyrazine (41 mg, 0.11 mmol), Pd(PPh₃)₄ (8 mg, 0.007 mmol) and KF (12 mg, 0.21 mmol) were placed in a microwave reactor and sealed. The inside air was exchanged with N₂. Dioxane was added (2.0 mL) and the reaction was heated at 120° C. in an oil bath for 20 h. The reaction was concentrated and purified (silica, CH₂Cl₂ with 1-4% 7N NH₃-MeOH) to provide compound (±)-29 (11 mg, 55%) as pale yellow solid. LCMS m/z 283 (MH+).

Compound (±)-29A was prepared from 28E in a manner similar to that described as above (coupling with 4-(tributyl-stannyl)thiazole). LCMS m/z 288 (MH+).

Compound 30A was prepared by the Boc protection of the amino group in compound 28D with Boc₂O (NEt₃, THF, RT, overnight) followed by oxidation of hydroxymethyl group with Dess-Martin periodinane (CH$_2$Cl$_2$, RT, 30 min) in a manner similar to that described in Example 24 (Step 1). Subsequent reaction with MeMgBr (CH$_2$Cl$_2$, RT, 30 min) in a manner similar to that described in Example 24 (Step 2) provided compound 30B. Deprotecton of 30B (1:5 TFA-CH$_2$Cl$_2$, RT, 4 h) was followed by reaction with EtOC(O)NCS (THF, RT, 40 min), cyclization with Hg(OAc)$_2$ (EtOH, RT, 2 h) and treatment with LiOH (MeOH—H$_2$O, 2:1, 100° C., 3 h) in a manner similar to that previously described. The compound (±)-30 was prepared by Suzuki coupling of compound 30C with pyrimidine-5-boronic acid/Pd(dppf)Cl$_2$ in a manner similar to that described in Example 1 (Step 7). LCMS m/z 297 (MH+).

the pure enantiomers 30D (LCMS m/z 297, MH+), 30E (LCMS m/z 297, MH+) and a mixture of two isomers. This mixture could be separated on a preparative Chiralpak OD column (10% EtOH-hexanes) to provide the pure enantiomers 30F (LCMS m/z 297, MH+) and 30G (LCMS m/z 297, MH+).

Preparative Example 31

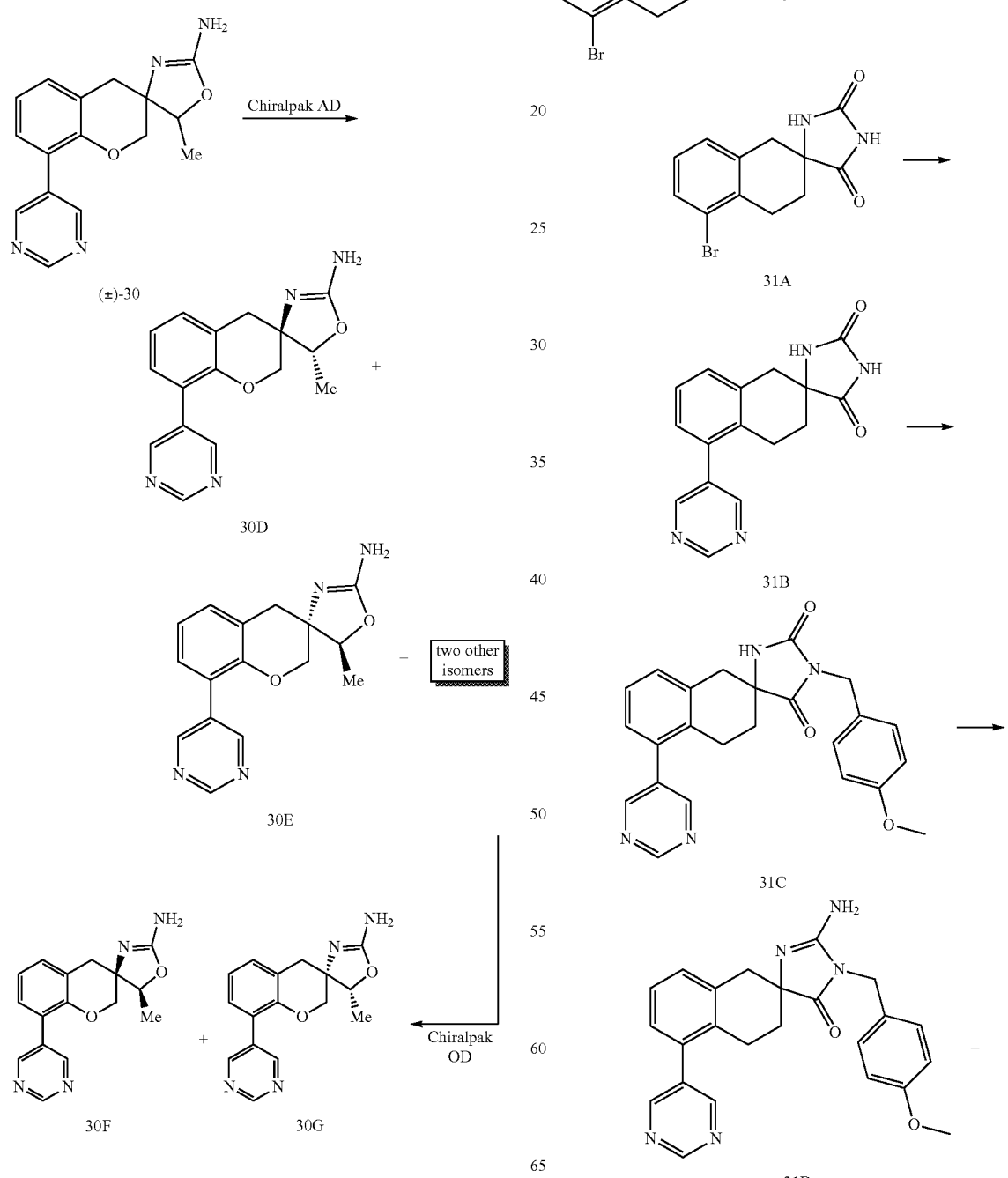

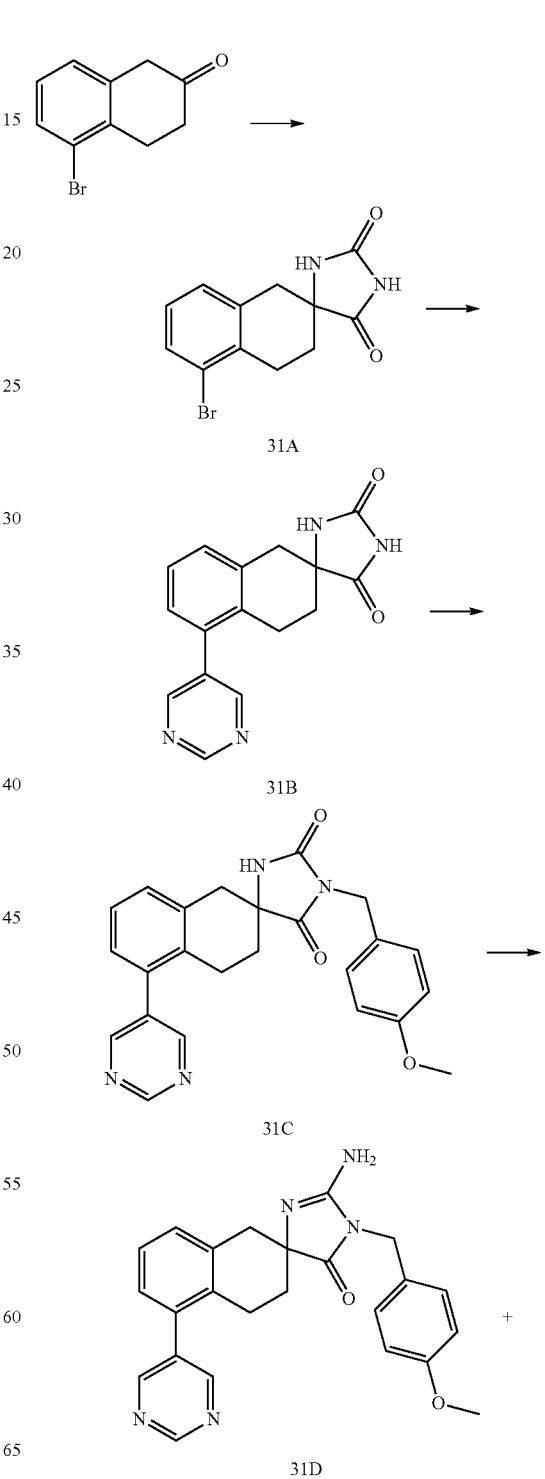

The racemic mixture (±)-30 was further purified on a preparative Chiralpak AD column (15% IPA-hexanes) to provide

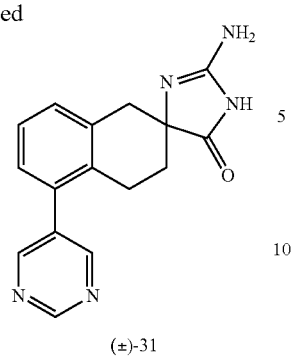

(±)-31

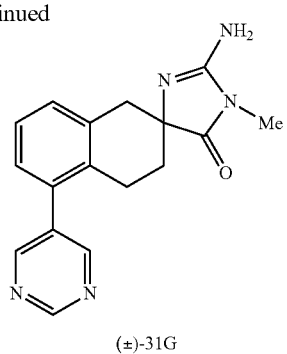

(±)-31G

In a manner similar to Example 1 (Steps 1 and 7), 5-bromo-2-tetralone was converted to 31B. LCMS m/z 295 (MH+).

A solution of crude 31B (0.5 g, 1.7 mmol) in DMF (5 mL) was treated with KHCO₃ (0.48 g, 4.76 mmol) and 4-methoxybenzyl chloride (0.53 mL, 3.91 mmol). After stirring at 60° C. for 20 h, the mixture was extracted with EtOAc and brine, dried over Na₂SO₄, concentrated and purified to give 31C (0.1 g).

Compound 31C (0.045 g) was suspended in POCl₃ (1.5 mL) and heated at 170° C. in a microwave reactor for 1.5 h. The reaction was then concentrated, dissolved in NH₃/MeOH (10 mL, 7N), transferred to a sealed tube, and heated at 85° C. for 20 h. The solvent was removed; the products were purified by reverse-phase HPLC to afford 31D (0.009 g, LCMS m/z 414, MH+), (±)-31 (0.002 g, LCMS m/z 294, MH+), and 31C (0.025 g, LCMS m/z 415, MH+).

In a similar fashion, compound (±)-31G was synthesized:

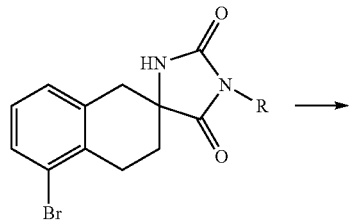

(±)-31A, R = H
(±)-31E, R = Me

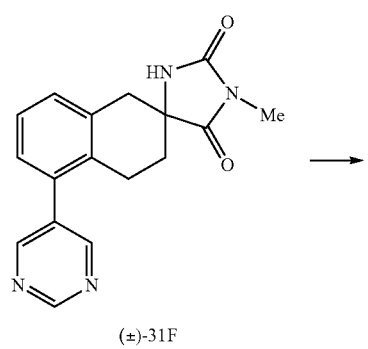

(±)-31F

A solution of crude compound 31A (0.2 g, 0.68 mmol) in DMF (5 mL) was treated with CsHCO₃ (0.26 g, 1.36 mmol) and MeI (0.17 mL, 2.72 mmol). After stirring at RT for 20 h, the mixture was extracted with EtOAc and brine, dried over Na₂SO₄, concentrated and purified by silica gel chromatography to give (±)-31E (0.07 g). In a manner similar to that described in Example 1 (Step 7), compound 31E was subjected to Suzuki coupling with pyrimidine-5-boronic acid to provide (±)-31F (LCMS m/z 309, MH+). Treatment with POCl₃/NH₃ as described earlier in this example provided (±)-31G. LCMS m/z 308, (MH+).

Preparative Example 32

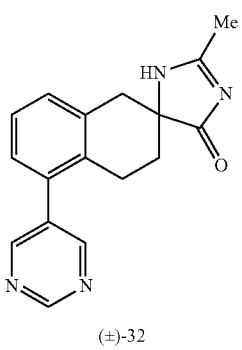

(±)-32

Step 1

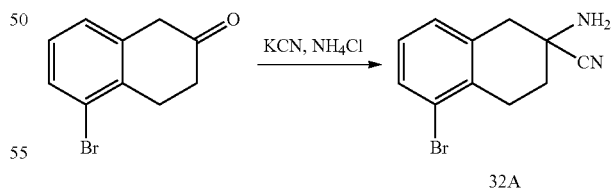

32A

A solution of 5-bromo-2-tetralone (1.5 g, 6.66 mmol) in a 1:1 mixture of EtOH/H₂O (50 mL) was treated with KCN (1.3 g, 19.99 mmol, 3.0 eq) and NH₄Cl (1.78 g, 33.3 mmol, 5.0 eq). The reaction mixture was heated to 60° C. for 16 h after which it cooled to RT. Saturated NaHCO₃ (40 mL) was added and extracted with CH₂Cl₂ (3×50 mL). The combined organic layer was dried over Na₂SO₄, filtered, and concentrated to yield crude 32A which was carried to the next step without purification.

Step 2

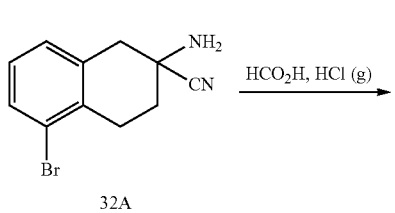

A solution of the crude amino nitrile 32A in HCO₂H (20 mL) was cooled to 0° C. and saturated with anhydrous HCl (g). After 10 min, the excess formic acid was evaporated and the residue was taken up in acetone (25 mL). Filtration of the white solid afforded compound 32B (1.25 g).

Step 3

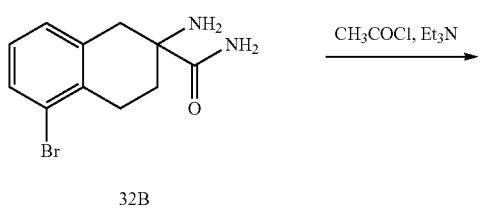

To a suspension of compound 32B (500 mg, 1.86 mmol) in CH₂Cl₂ (10 mL) was added Et₃N (0.52 mL, 3.72 mmol, 2.0 eq). Acetyl chloride (0.16 mL, 2.23 mmol, 1.2 eq) was slowly added and the reaction was left to stir at RT overnight. After the reaction was complete, aq. NaHCO₃ (15 mL) was added. Extraction with CH₂Cl₂ (2×20 mL), drying over Na₂SO₄, and evaporation under reduced pressure gave a crude mixture which was purified by flash chromatography using a gradient of DCM/MeOH (98/2) to yield 32C (525 mg). LCMS m/z 293/295 (MH+).

Step 4

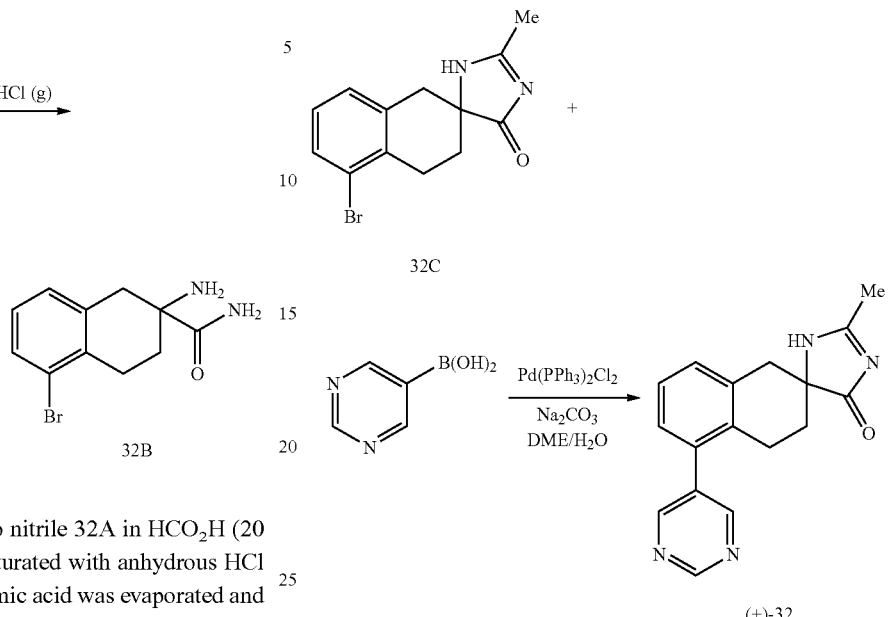

A mixture of 32C (100 mg, 0.34 mmol), pyrimidine-5-boronic acid hemihydrate (82 mg, 0.61 mmol, 1.8 eq), PdCl₂(PPh₃)₂ (24 mg, 0.034 mmol, 10 mol %) and Na₂CO₃ (108 mg, 1.025 mmol, 3 eq) in 3.0 mL of DME/H₂O (4:1) was heated to 120° C. for 20 min in a microwave. After cooling, the reaction mixture was loaded onto a flash column and purified by eluting with 1% to 3% MeOH/CH₂Cl₂ to yield 75 mg of (±)-32 as a white powder. LCMS m/z 293 (MH+).

Preparative Example 33

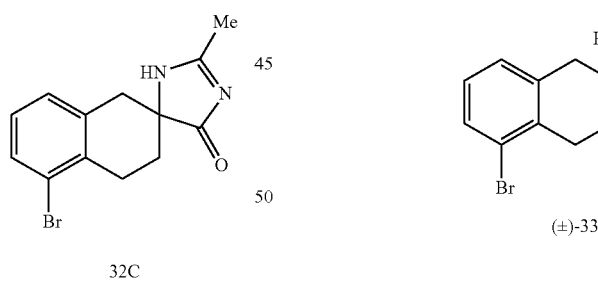

A solution of 32B (100 mg, 0.37 mmol) and trimethyl orthoformate (0.049 mL, 0.44 mmol, 1.2 eq) in 1 mL DMF was microwaved at 140° C. for 40 min. Upon cooling, H₂O (5 mL) was added and the mixture was extracted with EtOAc (2×10 mL), dried over Na₂SO₄, filtered, and evaporated under reduced pressure. The crude product was purified by flash chromatography by eluting with 2-4% MeOH/CH₂Cl₂ to yield 30 mg of compound (±)-33. LCMS m/z 279/281 (MH+).

In a manner similar to that described in Example (Step 7), (±)-33 is coupled with pyrimidine-5-boronic acid to give (±)-33A.

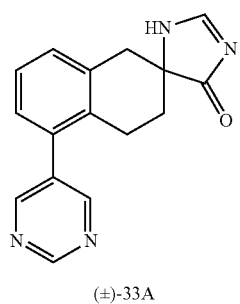
(±)-33A
Preparative Example 34
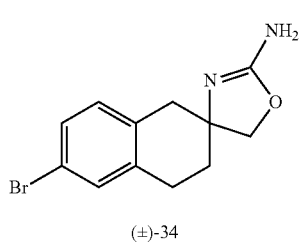
(±)-34
In a manner similar to that previously described, compound (±)-34 (LCMS m/z 281/283, MH+) was synthesized from 6-bromo-2-tetralone. The following compounds were prepared from (±)-34 following procedures similar to those exemplified in the examples above:
| Cpd | Structure | LCMS (MH+) |
|---|---|---|
| (±)-34A | | 281 |
| 34B | | 281 |
| 34C | 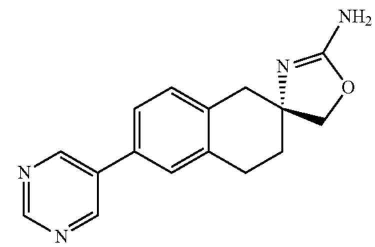 | 281 |
| (±)-34D | 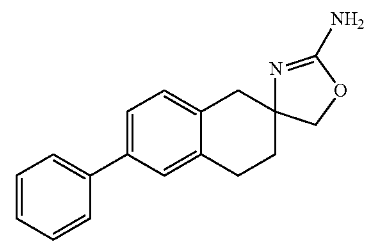 | 279 |
| (±)-34E | 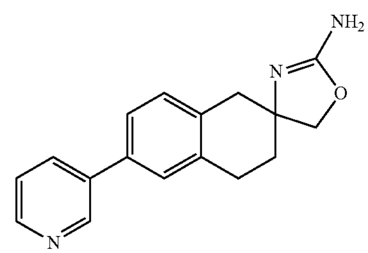 | 280 |
| (±)-34F | 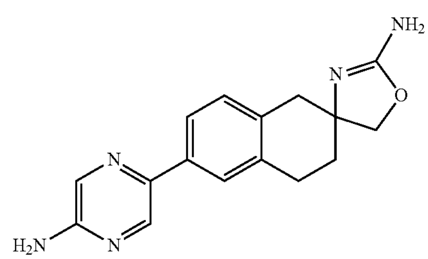 | 296 |
| (±)-34G | | 268 |
| (±)-34G | | 283 |

137
-continued
| Cpd | Structure | LCMS (MH+) |
|---|---|---|
| (±)-34I | 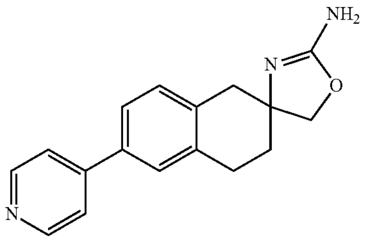 | 280 |
| (±)-34J | 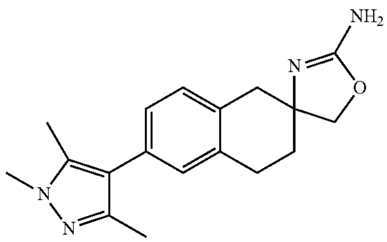 | 311 |
| (±)-34K | 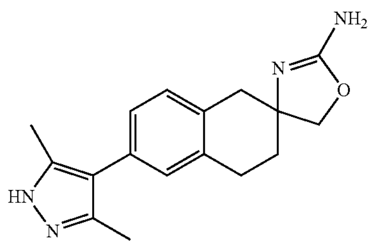 | 297 |
| 34L | 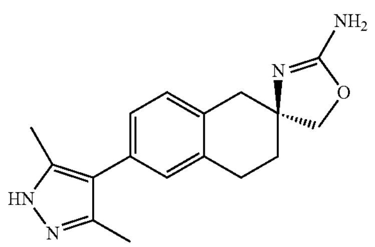 | 297 |
| 34M | 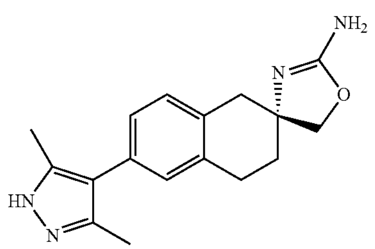 | 297 |
| (±)-34N | 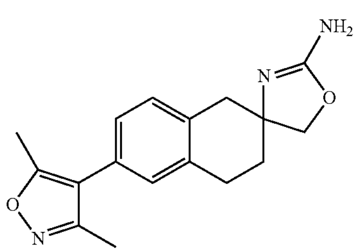 | 298 |
138
-continued
| Cpd | Structure | LCMS (MH+) |
|---|---|---|
| 34O | | 281/283 |
| 34P | | 281/283 |
Preparative Example 35
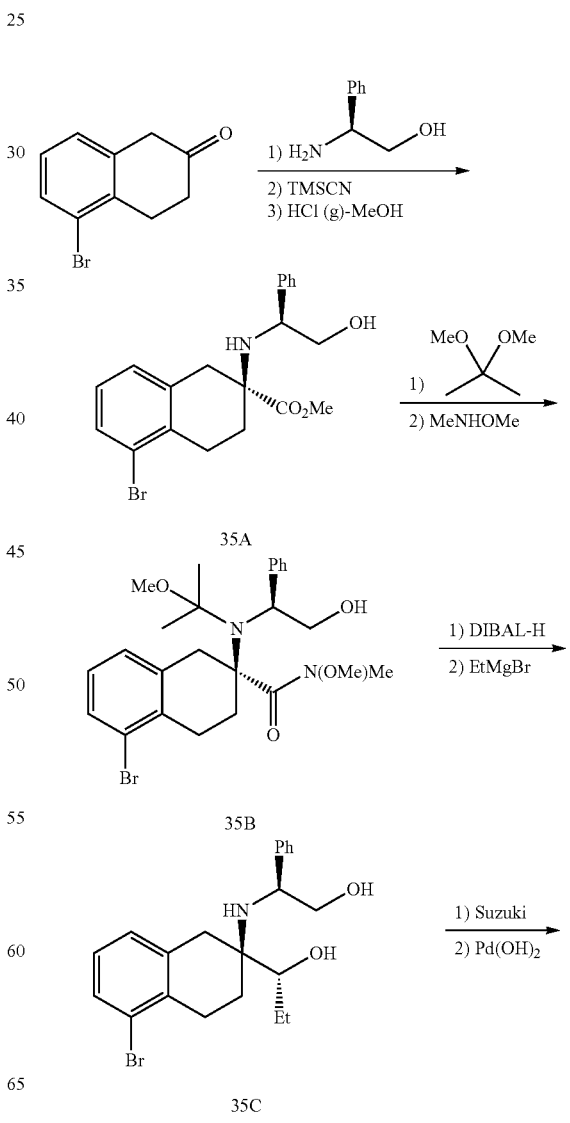

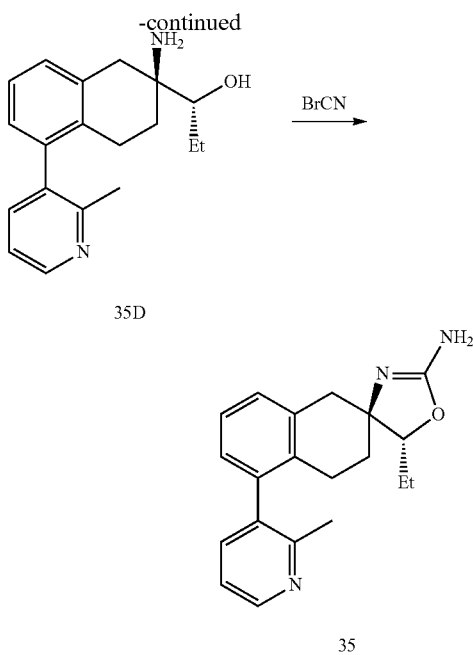

35D

35

Steps 1-3

In a manner similar to that described in Example 21, 5-bromo-2-tetralone was sequentially treated with (S)-phenylglycinol, TMSCN and HCl (g)-MeOH to provide 35A.

Steps 4-5

A mixture of 35A (3.0 g, 7.42 mmol), acetone dimethyl acetal (22.7 mL, 185.5 mmol, 25.0 equiv), and p-toluenesulfonic acid (71 mg, 0.37 mmol, 0.05 equiv) in $C_6H_6$ (10 mL) was refluxed in the presence of 4 Å molecular sieves for 12 h. After cooling, the molecular sieves were filtered, the solvent was removed under reduced pressure, and the residual oil was purified by flash chromatography (5% EtOAc/hexanes, 1.8 g product).

n-Butyllithium (23.1 mL, 36.96 mmol, 10.0 equiv, 1.6 M in hexanes) was added dropwise to a solution of N,O-dimethylhydroxylamine-HCl (1.8 g, 18.48 mmol, 5.0 equiv) in THF (50 mL) at −78° C. The cooling bath was removed and the reaction was stirred at RT for a period of 30 minutes. A solution of the product from the previous step (1.76 g, 3.7 mmol) in 10 mL THF was added dropwise to the reaction mixture at −78° C. After 1 h of stirring at −78° C., sat. $NH_4Cl$ (30 mL) was added to the reaction mixture and warmed to RT. The mixture was extracted with EtOAc (2×25 mL), washed with brine and dried over $Na_2SO_4$. After concentration, the crude mixture was purified by flash chromatography (10-20% EtOAc/hexanes) to yield 1.8 g of 35B.

Steps 6-7

DIBAL-H (7.5 mL, 7.5 mmol, 2.1 equiv, 1.0 M in hexanes) was added dropwise to a solution of 35B (1.8 g, 3.58 mmol) in THF (25 mL) at −78° C. After 1 h of stirring, the reaction was quenched by the addition of sat. $NH_4Cl$ (10 mL). The reaction mixture was extracted with EtOAc (2×20 mL), washed with brine and dried over $Na_2SO_4$. After concentration, the crude reaction mixture was purified by flash chromatography (10% EtOAc/hexanes, 1.5 g product).

Ethylmagnesium bromide (1.57 mL, 4.7 mmol, 2.1 equiv, 3.0 M in $Et_2O$) was added dropwise to a solution of the product from the previous step (1.0 g, 2.24 mmol) in $CH_2Cl_2$ (15 mL) at −78° C. After stirring at −78° C. for 1.5 h, the reaction was quenched by the addition of sat. $NH_4Cl$ (5 mL).

The organic layer was separated and the aqueous layer was extracted with $CH_2Cl_2$ (2×10 mL). The combined organic layers were washed with 4 N HCl (20 mL), neutralized with sat. $NaHCO_3$ and extracted with $CH_2Cl_2$ (2×20 mL). The organic layer was washed with brine, dried over $Na_2SO_4$ and concentrated. The crude alcohol was purified by flash chromatography (5% $MeOH/CH_2Cl_2$) to yield 700 mg of 35C as a white solid.

Steps 8-9

A mixture of 35C (200 mg, 0.49 mmol), 2-methylpyridine-3-boronic acid (101 mg, 0.74 mmol, 1.8 equiv), $PdCl_2(PPh_3)_2$ (34 mg, 0.049 mmol, 10 mol %) and $Na_2CO_3$ (156 mg, 1.47 mmol, 3 equiv) in 3.0 mL of $DME/H_2O$ (4:1) was heated to 120° C. for 20 min in a microwave. After cooling, the reaction mixture was chromatographed (1-3% $MeOH/CH_2Cl_2$ to yield the desired product (190 mg) as an off white powder.

To a solution of the product (184 mg, 0.44 mmol) in 10 mL MeOH was added $Pd(OH)_2$ (310 mg, 0.44 mmol). The reaction mixture was hydrogenated at 40 psi using a Parr shaker for 24 h after which it was filtered through celite and concentrated. The crude product was purified by flash chromatography (20% MeOH/DCM) to yield 43 mg of the desired product 35D.

Step 10

To a solution of 35D (40 mg, 0.14 mmol) in 5 mL $CH_3CN$ was added TEA (31 µL, 0.21 mmol, 1.5 equiv) followed by BrCN (36 µL, 0.18 mmol, 1.25 equiv, 5 M in $CH_3CN$). The reaction was stirred at RT overnight after which 10 mL of water was added, extracted with EtOAc (2×10 mL), dried over $Na_2SO_4$ and concentrated. The crude product was purified by flash chromatography (10% MeOH/DCM) to yield 12 mg of the desired product 35. LCMS m/z 322 (MH+).

Preparative Example 36

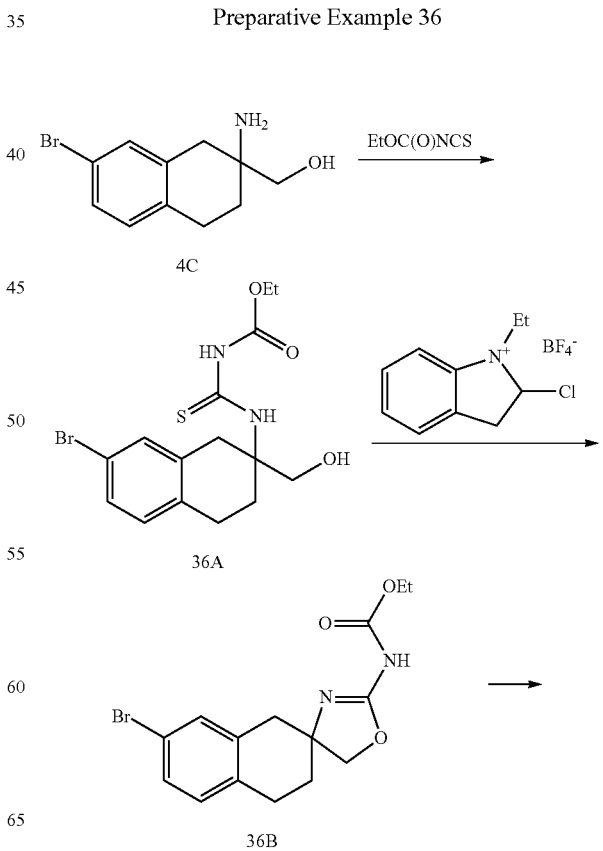

4C

36A

36B

-continued

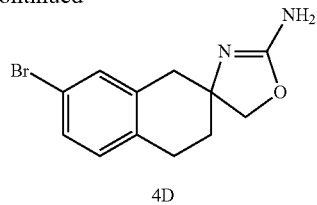

4D

In a manner similar to that previously described, a solution of compound 4C is treated with EtOC(O)NCS (1.2 eq) in THF, stirred for 3 h at RT, and then concentrated to provide 36A.

Crude compound 36A is taken up in $CH_3CN$, cooled in an ice bath, and treated with 2-chloro-3-ethylbenzoxazolium tetrafluoroborate (1.2 eq) portionwise. The reaction is stirred for 1.5 h and then sequentially quenched with TEA and water. The mixture is extracted with DCM (2×) and concentrated to provide 36B.

Compound 36B is then deprotected with LiOH in a manner similar to that previously described to provide 4D.

Preparative Example 37

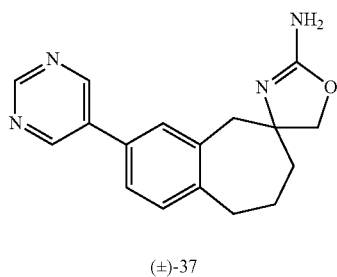

(±)-37

Step 1

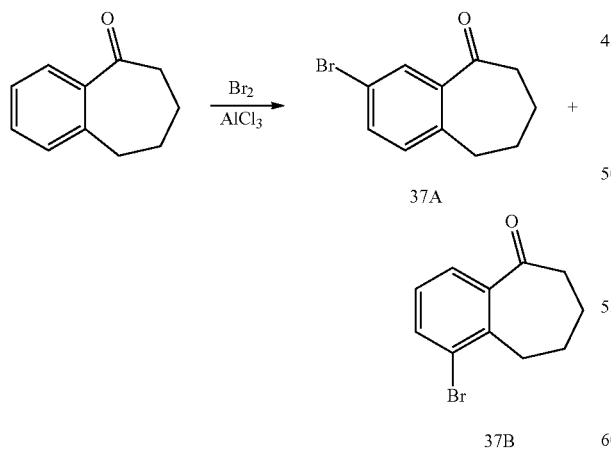

A 3-neck round bottom flask fitted with a condenser was charged with $AlCl_3$ (41.6 g, 0.31 mol) and then heated to 75° C. 1-Benzosuberone (20 g, 0.13 mol) was added dropwise to the hot $AlCl_3$. To the resulting brown slurry was added $Br_2$ (24 g, 0.15 mol) dropwise. The reaction mixture was stirred for 5 min before it was cooled to 0° C. The reaction mixture was quenched with ice chips. Concentrated HCl was added slowing with stirring to get the mixture into solution. The mixture was diluted with $H_2O$ and extracted the organic layer with $Et_2O$ (2×). The combined organic layers were dried ($MgSO_4$), filtered and concentrated under reduced pressure to give a mixture of 6-bromocyclohepta-1-one 37A and 8-bromocyclohepta-1-one 37B (in a 1:2 ratio)

Step 2

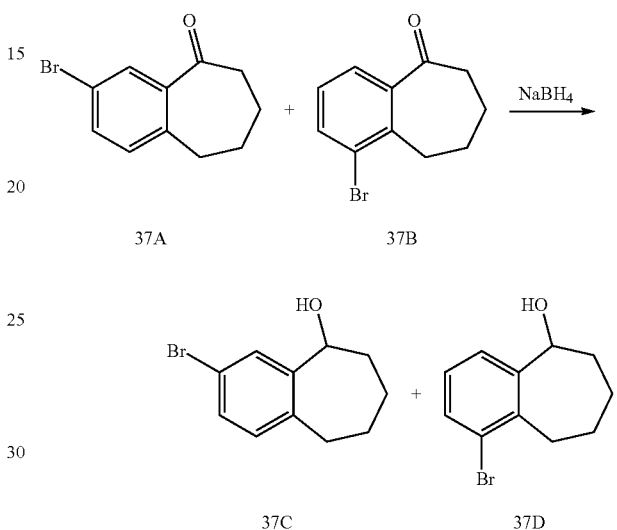

To a 1:2 mixture of 37A and 37B in MeOH (20 mL) and THF (40 mL) was added $NaBH_4$ at 0° C. The reaction mixture was stirred at RT for 1 h, neutralized with 1N HCl, diluted with $H_2O$ and extracted the organic layer with $Et_2O$. The combined organic layers were dried ($MgSO_4$), filtered and concentrated under reduced pressure. The residue was purified by column chromatography (5-10% EtOAc/Hexanes) to give 1-hydroxy-8-bromo-benzocycloheptane 37C (9.1 g) and 1-hydroxy-6-bromo-benzocycloheptane 37D (19.7 g).

Step 3

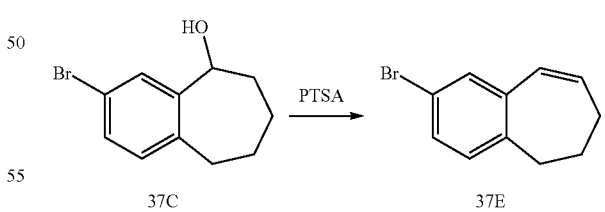

To a solution of 37C (4.4 g, 0.02 mol) in toluene (50 mL) was added molecular sieves and p-toluenesulfonic acid monohydrate (347 mg, 1.82 mmol). The reaction mixture was refluxed for 3 h, cooled to RT, quenched with sat. $NaHCO_3$ solution and extracted with $CH_2Cl_2$ (2×). The combined organic layers were dried ($MgSO_4$), filtered and concentrated under reduced pressure to give the alkene 37E (used directly in next step).

Step 4

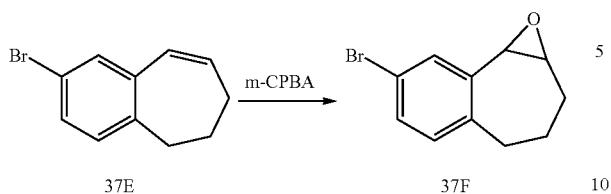

To a solution of 37E in toluene (50 mL) was added mCPBA (4.4 g, 0.03 mol) in 3 portions. The reaction mixture was stirred at RT for 1 h, quenched with aq sodium sulfite (10%), extracted with CH$_2$Cl$_2$. The organic layer was washed with 1N NaOH, dried (MgSO$_4$), filtered and concentrated under reduced pressure to give the epoxide 37F (used directly in next step).

Step 5

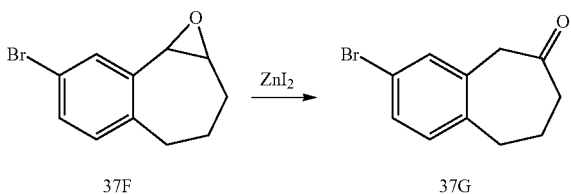

To a solution of 37F in toluene (50 mL) was added ZnI$_2$ (7.31 g, 0.02 mol) at 0° C. The reaction mixture was stirred at RT for 1.5 h, diluted with H$_2$O. The mixture was extracted with CH$_2$Cl$_2$. The combined organic layer was dried (MgSO$_4$), filtered and concentrated under reduced pressure. Flash chromatography (EtOAc/Hexanes, 1:9) afforded the desired product 37G (2.3 g, 53%).

Steps 6-10

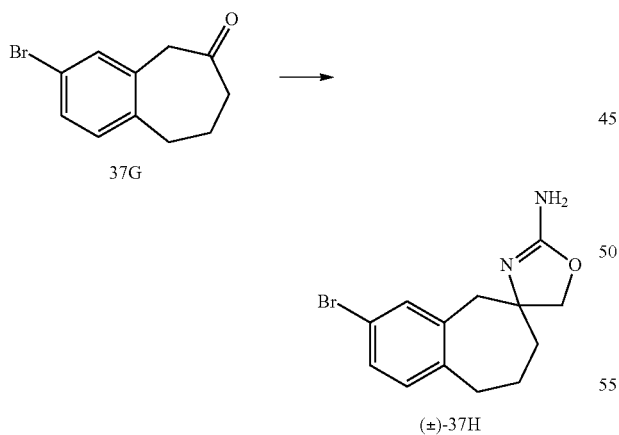

In a manner similar to that described previously (Example 1, Steps 1-4 and Example 3, Step 4), compound 37G was subjected to the following sequence: hydantoin formation with (NH$_4$)$_2$CO$_3$/KCN, hydrolysis with LiOH, methyl ester formation with SOCl$_2$/MeOH, reduction with NaBH$_4$, and cyclization with BrCN to provide (±)-37H (LCMS m/z 295/297, MH+). Final Suzuki coupling with pyrimidine-5-boronic acid afforded the title compound (±)-37. LCMS m/z 295 (MH+).

The racemic mixture (±)-37 was separated on a preparative Chiralpak OD column with 20% IPA-hexanes (with 0.5% DEA additive at 10 mL/min) to provide the pure enantiomers 37I (LCMS m/z 295, MH+) and 37J (LCMS m/z 295, MH+).

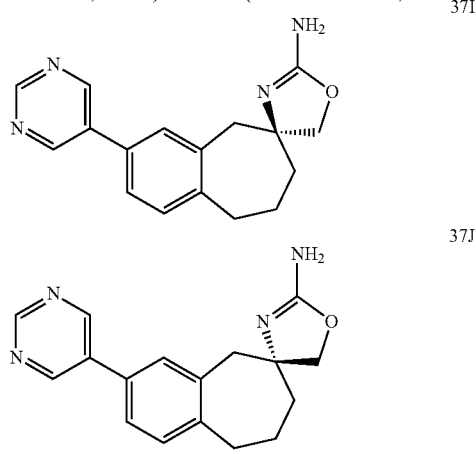

Compounds 37K, (±)-37L (LCMS m/z 295/297, MH+), and (±)-37M (LCMS m/z 295, MH+) were synthesized from 37D in a similar manner:

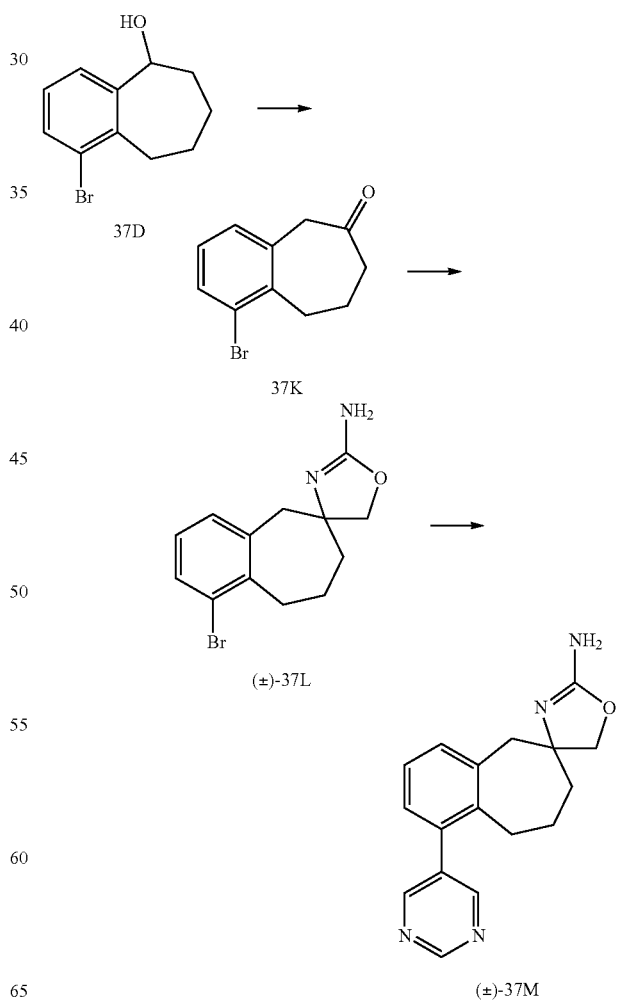

The racemic mixture (±)-37M was separated on a preparative Chiralpak AD column with 18% IPA-hexanes (with 0.5% DEA additive at 10 ml/min) to provide the pure enantiomers 37N (LCMS m/z 295, MH+) and 37M (LCMS m/z 295, MH+).

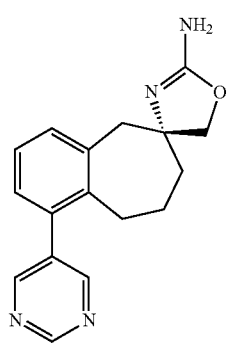

37M

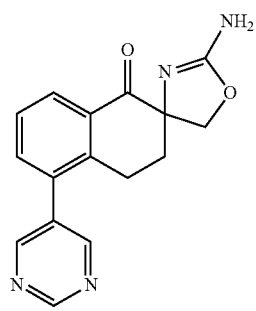

37N

Preparative Example 38

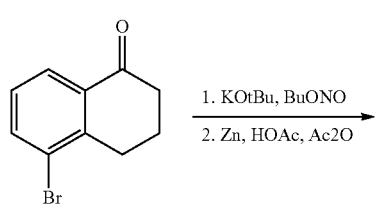

(±)-38

Steps 1-2

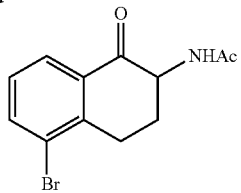

1. KOtBu, BuONO
2. Zn, HOAc, Ac2O

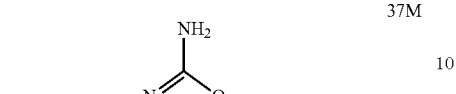

38A

To an ice cooled solution of KOtBu (1.0M in THF, 42 mL, 0.042 mol) in Et₂O was added a solution of 5-bromo-1-teralone (9.0 g, 0.04 mol) in Et₂O (50 mL) dropwise. followed by a solution of BuONO (4.94 g, 0.048 mol) in Et₂O (20 mL). The mixture was stirred at RT for 30 min, acidified with 1N HCl, and diluted with DCM. The organic layer was dried (MgSO₄), filtered and concentrated under reduced pressure. The residue was dissolved in HOAc (30 mL) and Ac₂O (20 mL). Zn powder (7.8 g, 0.12 mol) was added in 3 portions. The mixture was stirred at RT for 1 h, and then filtered. The filtrate was concentrated in vacuo. Flash chromatography (EtOAc/Hexanes, 1:2 then 2:1) afforded the product 38A (5.0 g).

Step 3

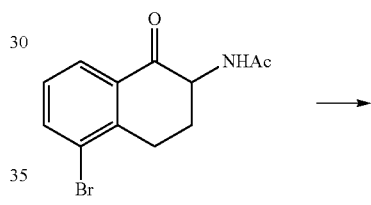

38A

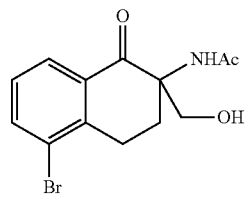

38B

To a solution of 38A (5.0 g, 0.018 mol) in EtOH (50 mL) and H₂O (8 mL) was added formaldehyde (37% in H₂O, 6 mL) and K₂CO₃ (1.23 g, 0.009 mol). The mixture was stirred at RT for 18 h, and then diluted with DCM. The organic phase was dried (MgSO₄), filtered and concentrated in vacuo. Flash chromatography (EtOAc/Hexanes, 1:2 then 2:1) afforded the alcohol 38B (5.0 g).

Step 4

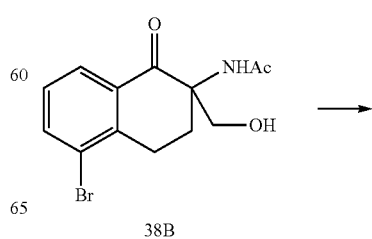

38B

-continued

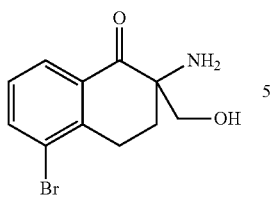

38C

A mixture of 38B (5 g) in 1N HCl (150 mL) was refluxed for 1.5 h and then cooled to RT. The mixture was concentrated in vacuo. Flash chromatography (MeOH (7N NH₃)/Hexanes, 1:10) afforded the alcohol 38C (3.1 g).

Steps 5-6

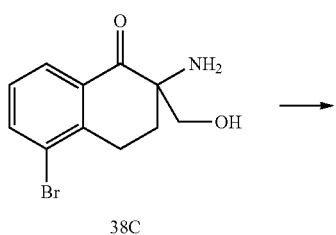

38C

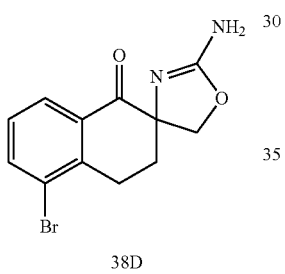

38D

In a manner similar to that previously described (Example 3, Step 4), compound 38C was cyclized with BrCN to provide 38D. LCMS m/z 295/297 (MH+). Final Suzuki coupling with pyrimidine-5-boronic acid afforded the title compound (±)-38. LCMS m/z 295 (MH+).

The racemic mixture (±)-38 was separated on a preparative Chiralpak OD column with 14% IPA-hexanes (with 0.5% DEA additive at 10 mL/min) to provide the pure enantiomers 38E (LCMS m/z 295, MH+) and 38F (LCMS m/z 295, MH+).

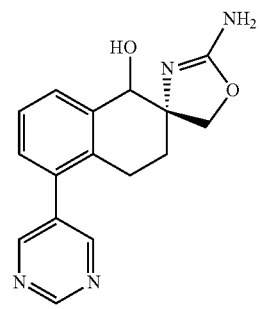

38E

-continued

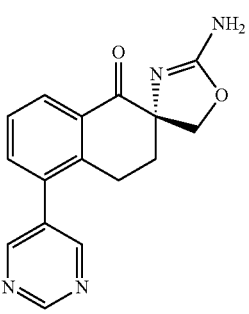

38F

Reduction of 38E (3 eq. NaHB(OAc)₃ then 3 eq. NaBH₄ in 1:1 MeOH-DCM) followed by chromatographic separation (prep TLC with 10% of 7N NH₃-MeOH in DCM) provided the stereoisomers 38G (LCMS m/z 297, MH+) and 38H (LCMS m/z 297, MH+). Similar treatment of 38F provided 38I (LCMS m/z 297, MH+) and 38J (LCMS m/z 297, MH+). Likewise, treatment of 38D provided (±)-38K as a mixture of stereoisomers. (LCMS m/z 297/299, MH+).

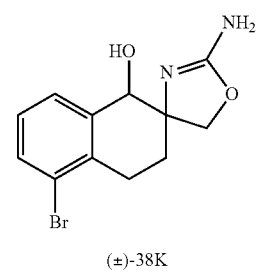

38G (diastereomer 1)      38I (diastereomer 1)
38H (diastereomer 2)      38J (diastereomer 2)

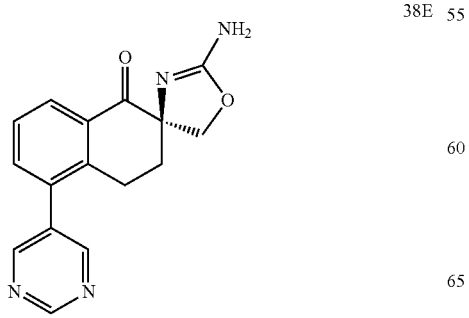

(±)-38K

Preparative Example 39

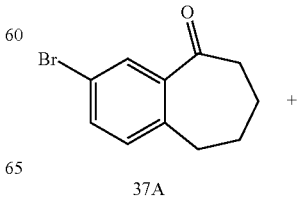

37A

-continued

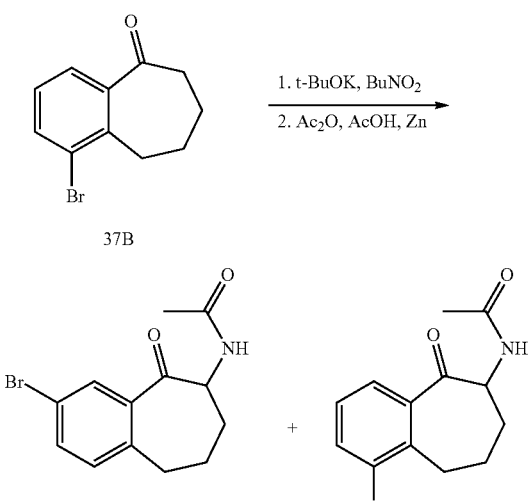

To a solution of KOtBu (13.2 g, 0.12 mol) in Et$_2$O (100 mL) at 0° C., was added the mixture of 37A and 37B (26.7 g, 0.11 mol) in Et$_2$O (250 mL) slowly, followed by n-butyl nitrite (13.8 g, 0.13 mol). The reaction mixture was stirred at RT for 30 min, diluted with H$_2$O, acidified to pH 3 with 1N HCl, and then extracted with CH$_2$Cl$_2$. The combined organic layers were dried (MgSO$_4$), filtered and concentrated in vacuo.

The crude residue was dissolved in AcOH (30 mL) and Ac$_2$O (25 mL) at 0° C. Zn powder (36.0 g, 0.55 mol) was added to reaction mixture in portions. The reaction mixture was stirred at RT for 1 h, filtered through a pad of celite, washing with CH$_2$Cl$_2$. The filtrate was concentrated in vacuo. Flash chromatography (EtOAc/Hexanes, 2:1) provided 39A (6 g) and 39B (6.7 g).

In a manner similar to that described in Example 38, the following compounds were synthesized from 39A and 39B.

| Cpd | Structure | LCMS (MH+) |
|---|---|---|
| (±)-39C | | 309/311 |
| (±)-39D | | 309 |
| 39E | 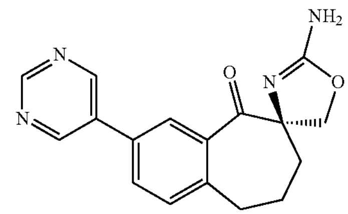 | 309 |
| 39F | 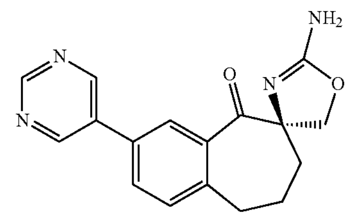 | 309 |
| (±)-39G | 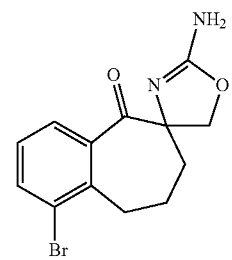 | 309/311 |
| (±)-39H | 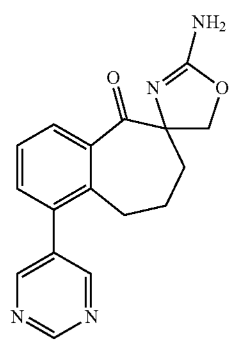 | 309 |
| (±)-39I | 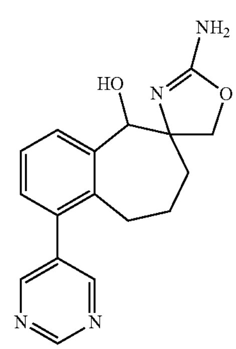 | 311 |

Preparative Example 40

In a manner similar to that described in Example 38, the compounds were synthesized from the appropriate bromo-2-tetralone.

| Cpd | Structure | SM | LCMS (MH+) |
|---|---|---|---|
| (±)-40A | 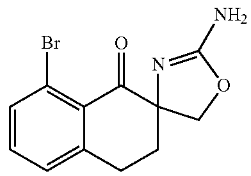 | | 295/297 |
| (±)-40B | 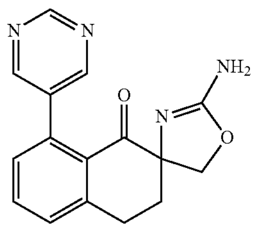 | | 295 |
| (±)-40C | 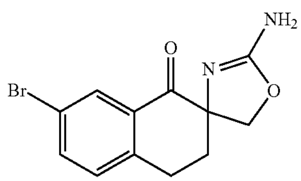 | | 295/297 |
| (±)-40D | 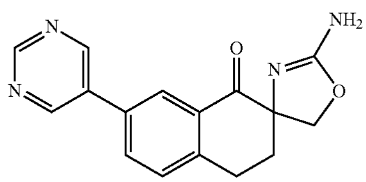 | | 295 |

Preparative Example 41

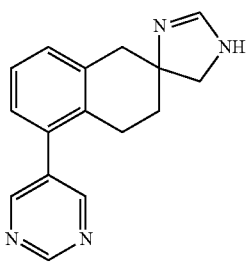

(±)-41

Steps 1-2

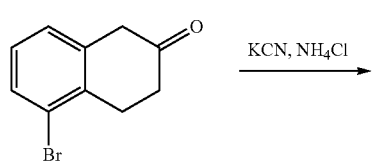

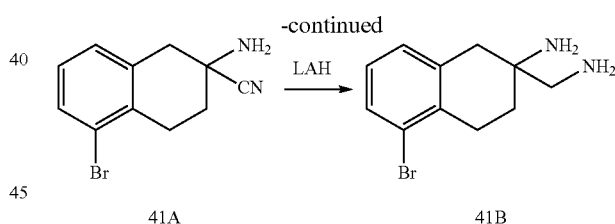

In a sealed tube 5-bromo-2-tetralone (2.00 g, 8.88 mmol) was dissolved in EtOH (40.0 mL, 685 mmol) and Water (33.0 mL, 1830 mmol). KCN (1.157 g, 17.77 mmol) followed by $NH_4Cl$ (1.901 g, 35.54 mmol) were added. The reaction was heated to 60° C. and stirred overnight. The mixture was diluted with DCM and sat. $NaHCO_3$. The biphasic solution was separated and the aqueous layer was extracted with DCM in three portions. The combined organic phase was dried over anhydrous sodium sulfate and concentrated to dryness to provide 41A (2.3 g, 100%).

A solution of 41A (2.20 g, 8.76 mmol) in THF (20.0 mL, 246 mmol) was treated with LAH (2.0 M/THF, 6.57 mL) and stirred at RT for 30 min. The reaction was cooled in an ice/water bath and slowly quenched with water (dropwise) followed by 10% NaOH. The mixture was warmed to RT and stirred for 3 h. The material was filtered through celite, washed with a solution of 1:1 MeOH/DCM in three portions and concentrated to dryness to provide 41B (2.14 g, 96%).

Steps 3-4

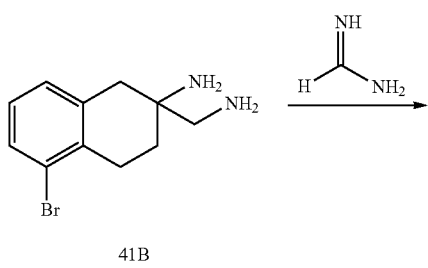

41B

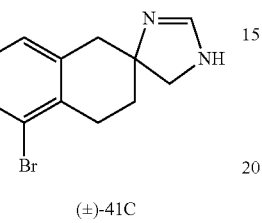

(±)-41C

A mixture of 41B (200 mg, 0.78 mmol) and formamidine acetate (106 mg, 1.02 mmol) in EtOH (10 mL, 171 mmol) under Ar was stirred for 1 h at RT. The mixture was diluted with DCM and sat. sodium bicarbonate. The biphasic solution was separated and the aqueous layer was extracted with DCM in three portions. The combined organic phase was dried over anhydrous sodium sulfate and concentrated to provide (±)-41C (201 mg, 97%). LCMS m/z 265/267 (MH+).

In a manner to that described in Example 1 (Step 7), 41C was coupled with pyrimidine-5-boronic acid to provide the title compound (±)-41. LCMS m/z 265 (MH+).

The following compounds were synthesized by coupling with 41C as previously described.

| Cpd | Structure | LCMS (MH+) |
|---|---|---|
| (±)-41D |  | 263 |
| (±)-41E |  | 267 |
| (±)-41F | 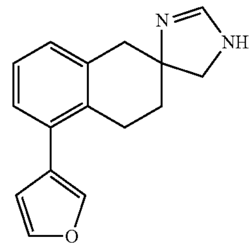 | 253 |
| (±)-41G | 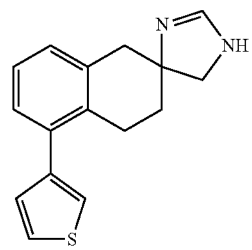 | 269 |
| (±)-41H | 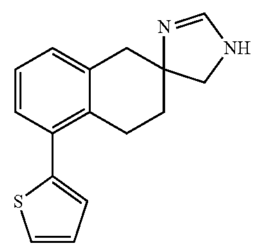 | 269 |

Steps 5-6

Alternatively, compound 41B was synthesized from 21A by the following two-step procedure:

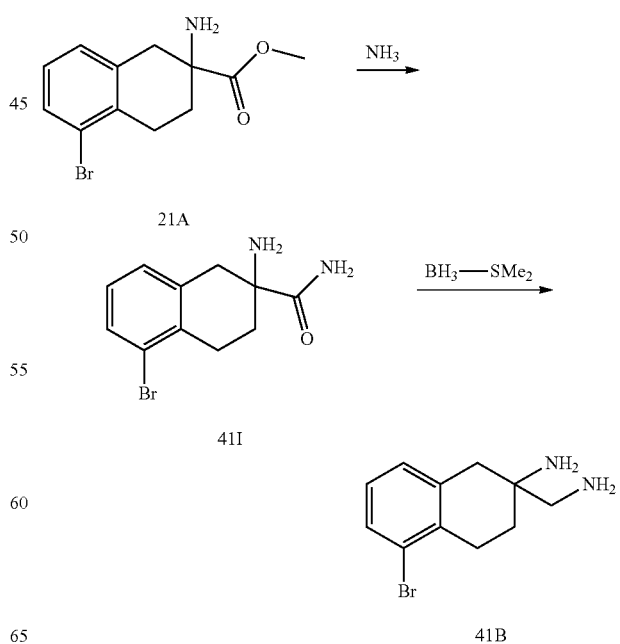

21A

41I

41B

A solution of 21A (190 mg, 0.67 mmol) in NH₃-MeOH (7N, 12 mL) was heated to 105° C. overnight in a sealed tube. The reaction mixture was concentrated to provide 41I (191 mg, 106%).

A solution of compound 41I (180 mg, 0.67 mmol) in THF (10 mL) in a sealed tube was treated slowly with BH₃—SMe₂ (2M/THF, 1 mL). The reaction mixture was heated to 105° C. for 2 h, then cooled to 0° C. in an ice/water bath and quenched with EtOH followed by K₂CO₃. The mixture was warmed to RT and stirred for 2 h. The material was filtered through celite, washed with EtOH in three portions and concentrated. The crude mixture was diluted with DCM and sat. sodium bicarbonate. The biphasic solution was separated and the aqueous layer was extracted with DCM in three portions. The combined organic phase was dried over anhydrous sodium sulfate and concentrated to provide 41B (161 mg, 94%).

Preparative Example 42

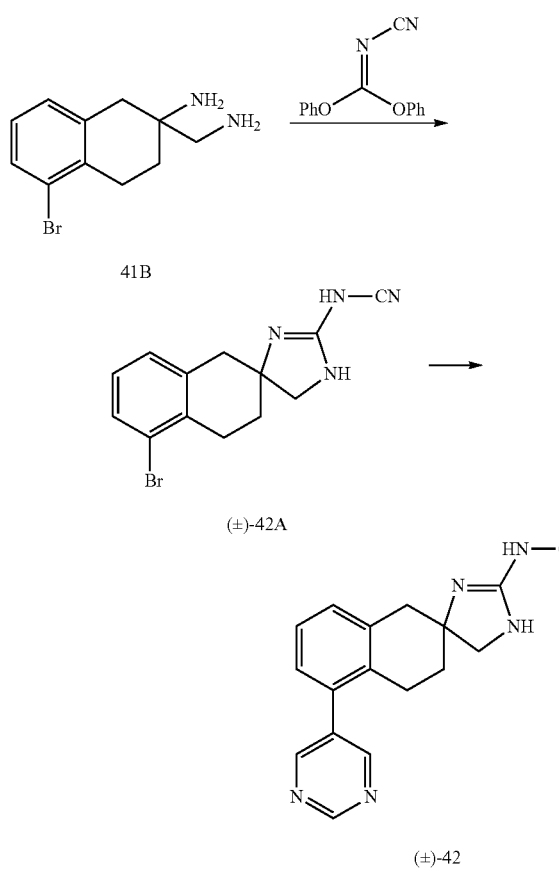

A solution of 41B (200.mg, 0.78 mmol) in THF (10 mL) was treated with diphenyl cyanocarbonimidate (280 mg, 1.18 mmol) and then heated to 85° C. for 1 h. The mixture was diluted with DCM and sat. sodium bicarbonate. The biphasic solution was separated and the aqueous layer was extracted with DCM in three portions. The combined organic phase was dried over anhydrous sodium sulfate and concentrated to provide (±)-42A (228 mg, 95%). LCMS m/z 305/307 (MH+).

In a manner to that described in Example 1 (Step 7), 42A was coupled with pyrimidine-5-boronic acid to provide the title compound (±)-42. LCMS m/z 305 (MH+).

Preparative Example 43

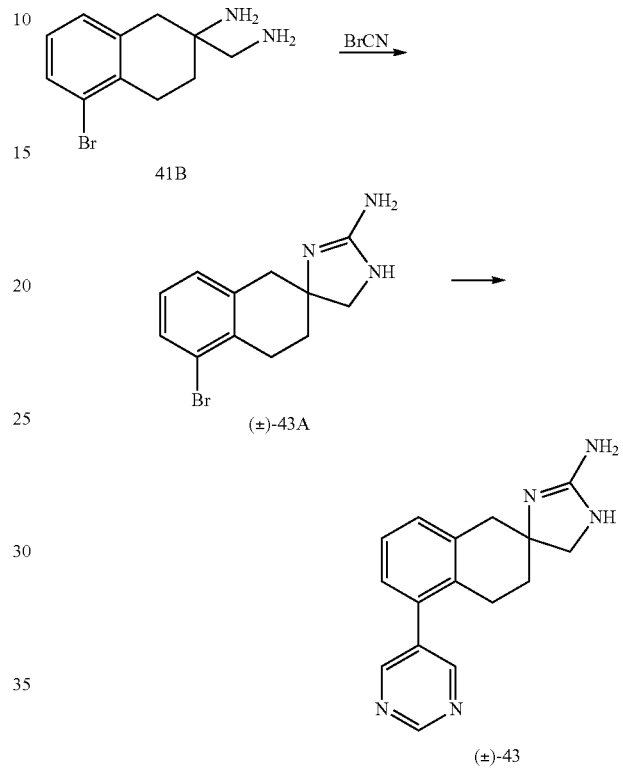

A solution of 41B (200 mg, 0.78 mmol) in THF (10 mL) was treated with BrCN (5M/MeCN, 204 uL) and then stirred at RT for 1 h. The mixture was diluted with DCM and sat. sodium bicarbonate. The biphasic solution was separated and the aqueous layer was extracted with DCM in three portions. The combined organic phase was dried over anhydrous sodium sulfate and concentrated to provide (±)-43A (224 mg, 100%). LCMS m/z 280/282 (MH+).

In a manner to that described in Example 1 (Step 7), 43A was coupled with pyrimidine-5-boronic acid to provide the title compound (±)-43. LCMS m/z 280 (MH+).

Preparative Example 44

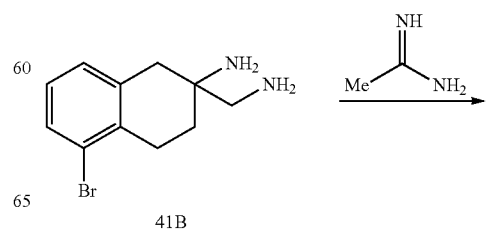

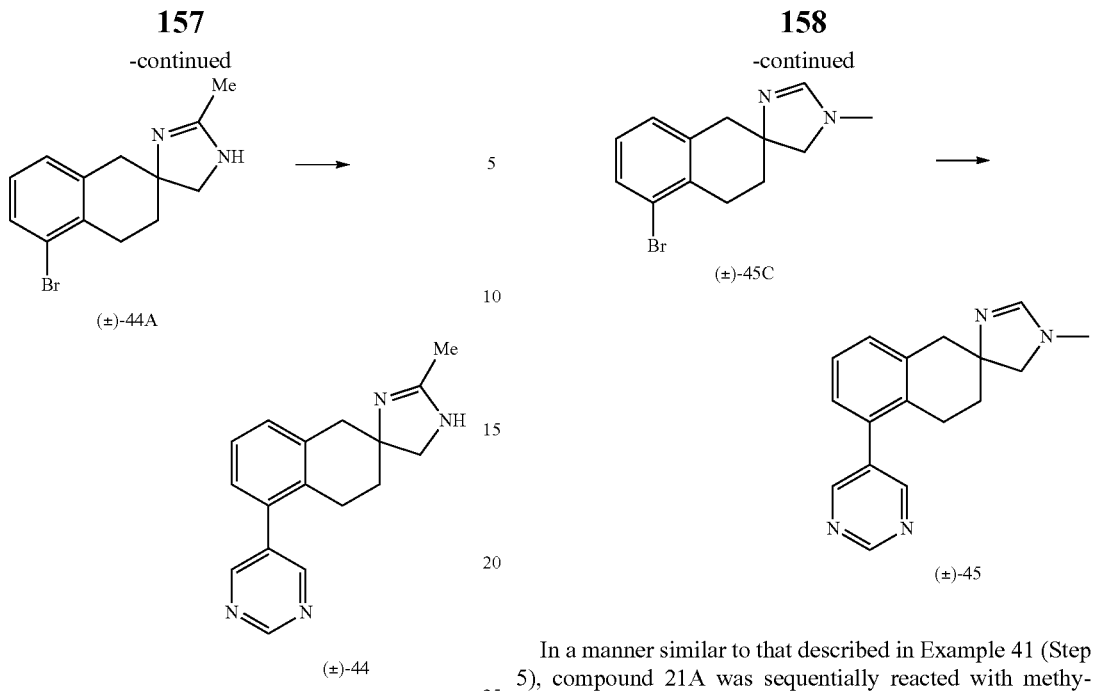

In a manner similar to that described in Example 41, compound 41B was reacted with acetamidine hydrochloride (EtOH, RT, 2 h) to provide (±)-44A. LCMS m/z 279/281 (MH+).

In a manner to that described in Example 1 (Step 7), 44A was coupled with pyrimidine-5-boronic acid to provide the title compound (±)-44. LCMS m/z 279 (MH+).

Preparative Example 45

In a manner similar to that described in Example 41 (Step 5), compound 21A was sequentially reacted with methylamine (2M/MeOH, 105° C. overnight in a sealed tube), $BH_3$—$SMe_2$, and formamidine acetate to provide (±)-45C. LCMS m/z 279/281 (MH+).

In a manner to that described in Example 1 (Step 7), 45C was coupled with pyrimidine-5-boronic acid to provide the title compound (±)-45. LCMS m/z 279 (MH+).

Likewise, reaction of 21A with ethylamine followed by reduction with $BH_3$—$SMe_2$, provided 45E, which was cyclized with formamidine acetate to provide (±)-45F and acetamidine hydrochloride to provide (±)-45G (LCMS m/z 307/309, MH+), respectively. Coupling of (±)-45F with pyrimidine-5-boronic acid provides (±)-45H. Coupling of (±)-45G with pyrimidine-5-boronic acid provides (±)-45I.

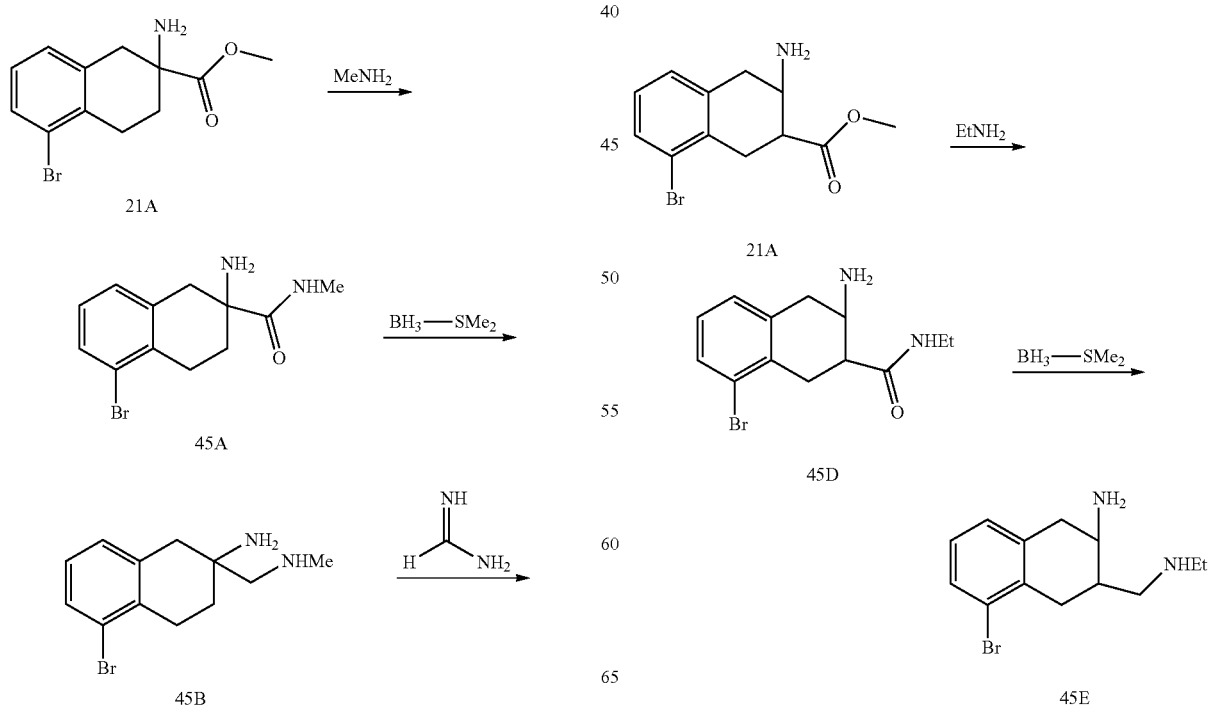

-continued

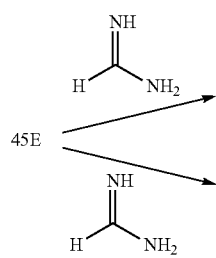

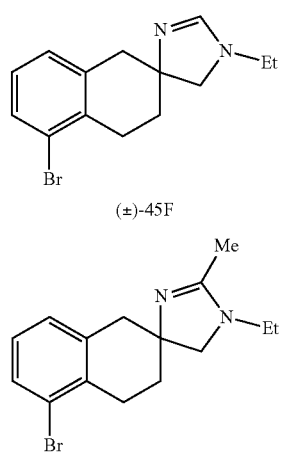

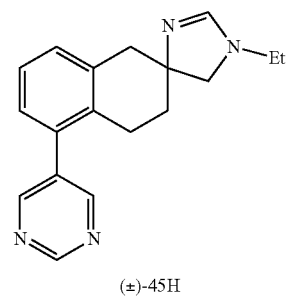

(±)-45H

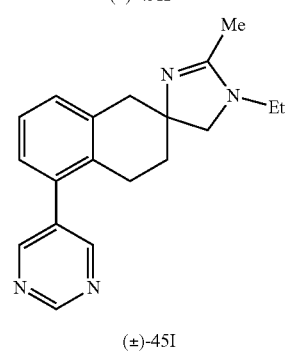

(±)-45I

Preparative Example 46

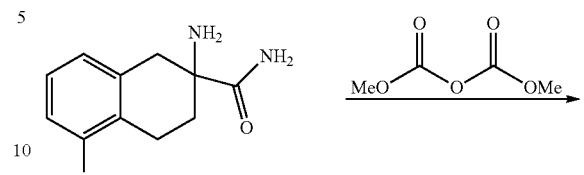

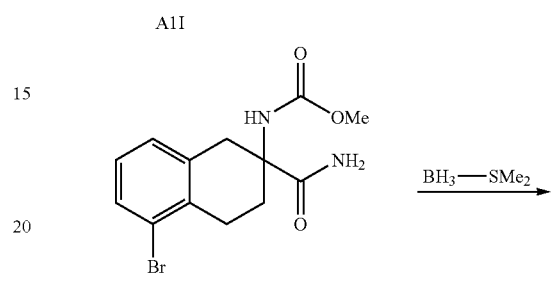

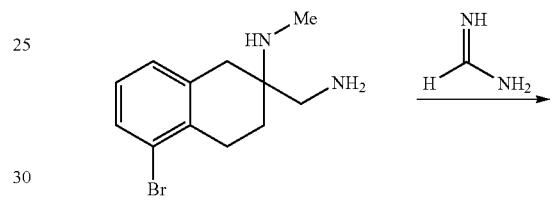

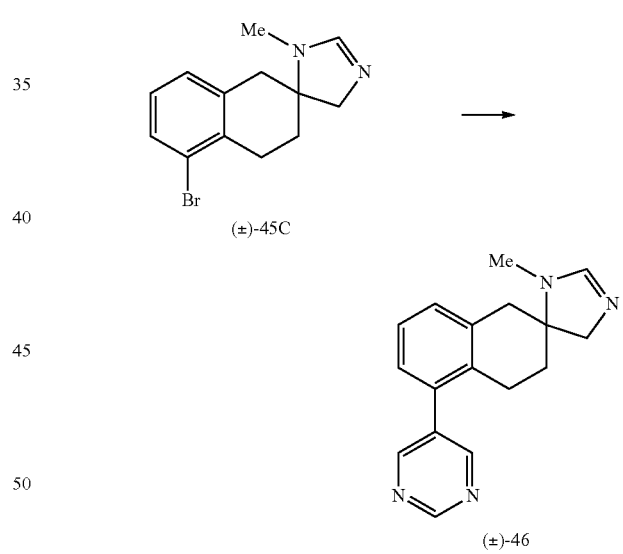

(±)-46

A solution of 41I (100 mg, 0.37 mmol) in THF (5 mL) was treated with dimethyl dicarbonate (119 uL, 1.12 mmol) followed by TEA (207 uL, 1.49 mmol) and stirred at RT for 2 h. The mixture was diluted with DCM and sat. sodium bicarbonate. The biphasic solution was separated and the aqueous layer was extracted with DCM in three portions. The combined organic phase was dried over anhydrous sodium sulfate and concentrated to provide 46A (135 mg).

In a manner similar to that described in Example 41, compound 46A was sequentially reacted with $BH_3$—$SMe_2$ and formamidine acetate to provide (±)-46C. LCMS m/z 279/281 (MH+).

In a manner to that described in Example 1 (Step 7), 46C was coupled with pyrimidine-5-boronic acid to provide the title compound (±)-46. LCMS m/z 279 (MH+).

Preparative Example 47

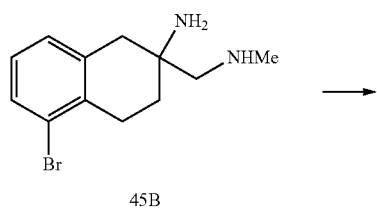

45B

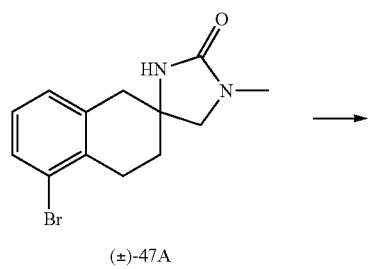

(±)-47A

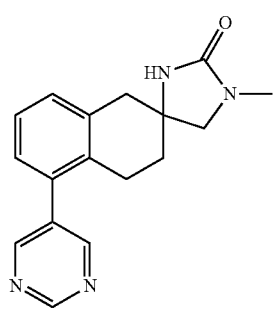

(±)-47

A solution of 45B (21 mg, 0.079 mmol) in DCM (3 mL) was treated with TEA (33. uL, 0.24 mmol) followed by triphosgene (7.8 mg, 0.026 mmol) and stirred at RT for 2 h. The mixture was diluted with DCM and sat. sodium bicarbonate. The biphasic solution was separated and the aqueous layer was extracted with DCM in three portions. The combined organic phase was dried over anhydrous sodium sulfate and concentrated. The crude mixture was purified (C18 reverse phase HPLC: 5 to 75% water/acetonitrile with 0.1% formic acid, over 10 min) to provide (±)-47A (11 mg, 47%). LCMS m/z 295/297 (MH+).

In a manner to that described in Example 1 (Step 7), 47A is coupled with pyrimidine-5-boronic acid to provide the title compound (±)-47.

Preparative Example 48

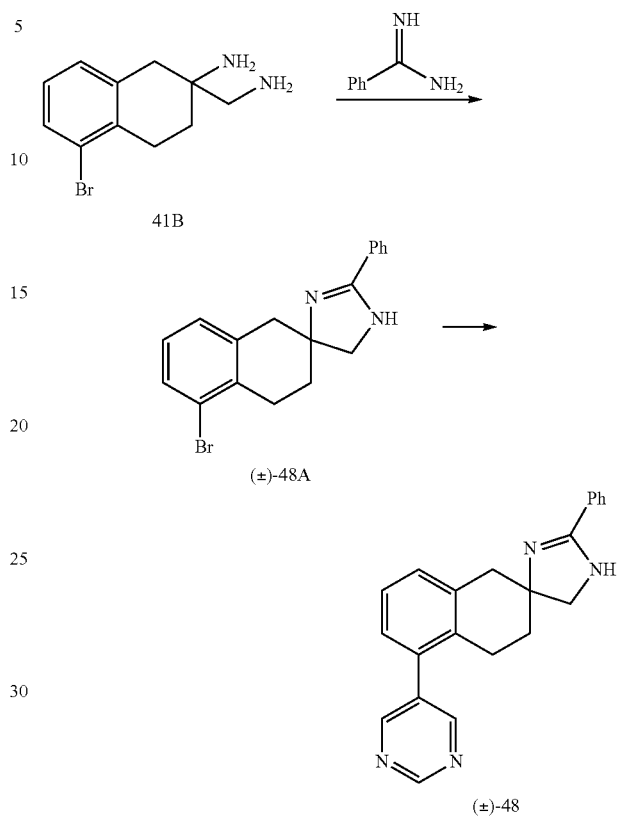

In a manner similar to that described in Example 41 (Step 3), 41B was reacted with benzamidine HCl (EtOH, 2 h, RT) to provide (±)-48A. LCMS m/z 342 (MH+).

In a manner to that described in Example 1 (Step 7), 48A is coupled with pyrimidine-5-boronic acid to provide the title compound (±)-48.

Preparative Example 49

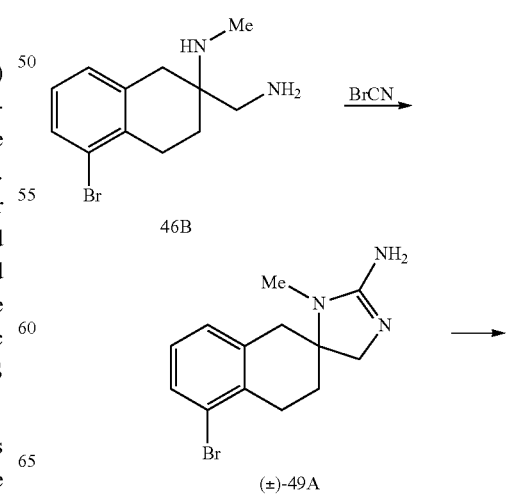

-continued

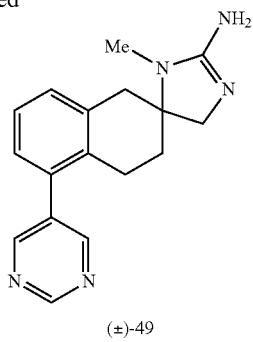

(±)-49

In a manner similar to that described in Example 43, compound 46B was reacted with BrCN (1.3 eq, THF, 1 h) to provide (±)-49A. LCMS m/z 294/296 (MH+).

In a manner to that described in Example 1 (Step 7), 49A is coupled with pyrimidine-5-boronic acid to provide the title compound (±)-49.

Preparative Example 50

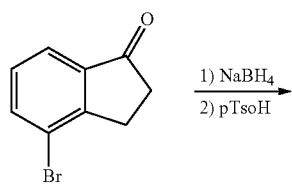

50A

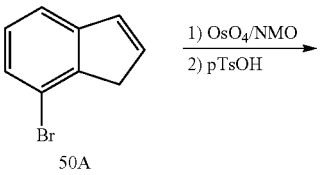

50B

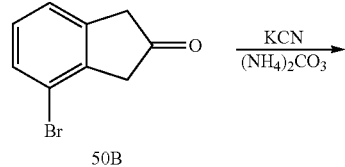

50C

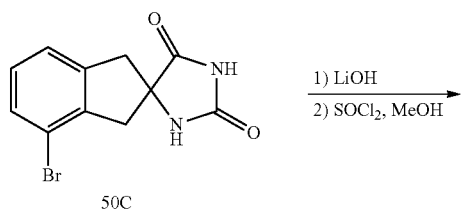

50D

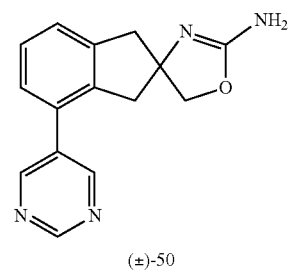

50E (±)-50F (±)-50

In a manner similar to that previously described (Examples 1, 3 and 5), 4-bromo-1-indanone was converted to 4-bromo-2-indanone (50B) and then further to (±)-50F (LCMS m/z 267/269, MH+) and the title compound (±)-50 (LCMS m/z 267, MH+)

An alternative conversion of 50A to 50B is described below:

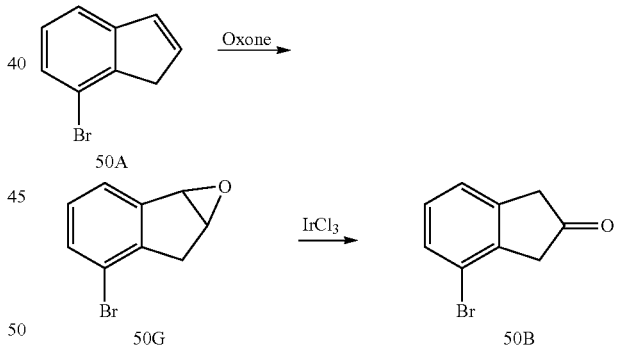

To a solution of compound 50A (0.047 mol, prepared from 10 g 4-bromo-1-indanone) in EtOAc/water (220 mL/220 mL) was added NaHCO₃ (19.74 g, 0.235 mol) and acetone (34.5 mL, 0.47 mol) at RT. To the above mixture was added dropwise over 1 hr a solution of Oxone (57.8 g, 0.094 mol) in water (220 mL). The reaction mixture was stirred vigorously overnight before the layers were separated. The organic phase was washed with brine (20 mL), dried (Na₂SO₄), filtered, and concentrated under reduced pressure to give crude compound 50G.

To a solution of the crude 50G in THF/CH₂Cl₂ (65 mL/130 mL) was added IrCl₃ hydrate (158 mg, 0.47 mmol) at RT. The suspension was stirred for 2 hrs and filtered through a pad of Celite. The filtrate was concentrated under reduced pressure and purified by column chromatography (15% EtOAc/hexanes) to give compound 50B as an off-white solid (6.65 g, 67% over four steps from 4-bromo-1-indanone).

Another alternative conversion of 50A to 50B is described below:

To an ice-cooled mixture of the 50A (crude, 22 g, 0.113 mol) in DCM (360 mL) was added sodium bicarbonate (28.5 g, 0.339 mol) followed by mCPBA (35.4 g, 0.16 mol) portionwise. The reaction was slowly warmed to RT and vigorously stirred for 4 h. The mixture was quenched/washed with 10% solution of aq sodium sulfite followed by a final wash with brine. The organic phase was dried over anhydrous sodium sulfate and concentrated to dryness to provide 50G (100%).

In a dry round-bottom flask under an atmosphere of nitrogen the crude epoxide 50G (0.113 mol) was dissolved in benzene (360 mL). The flask was cooled to 0° C. in an ice/water bath and anhydrous zinc diiodide (43.4 g, 0.136 mol) was gradually added. The resulting mixture was stirred at 0° C. for 10 min before it was warmed to RT and stirred for 4 h. The mixture washed with water in two portions followed by a final wash with brine. The organic phase was dried over anhydrous sodium sulfate and concentrated to dryness to provide 50B (99%).

Another alternative preparation of 50E is described below:

solution of compound 50H (343 mg) in THF was added and the reaction was stirred 1 h at −78° C. and then 2 h at RT. The mixture was again cooled to −78° C. and treated with NaHMDS (1.0N/THF, 1.1 mL, 1.1 eq). The reaction was slowly warmed to RT, stirred overnight, quenched with sat. aq. NH$_4$Cl and extracted with DCM. The organic phase was dried over anhydrous sodium sulfate and concentrated. The residue was taken up in ethyl ether, treated with 1N HCl, and stirred vigorously for 2 h. The benzophenone byproduct was removed from reaction mixture by extracting with diethyl ether. The product was isolated by cooling the aqueous layer in an ice bath, neutralizing with 1N NaOH, and extracting with diethyl ether. The ether extract was concentrated to provide 50I.

In a manner similar to that previously described (Example 1), compound 50I is reduced with NaBH$_4$ to provide 50E.

The following compounds were prepared from (±)-50F by Suzuki coupling with the appropriate boronic ester (1.5 eq) in a fashion similar to that previously described (0.25 eq Pd(dppf)Cl$_2$, 3 eq Na$_2$CO$_3$, 4:1 DME-water, microwave 15 min at 125° C.):

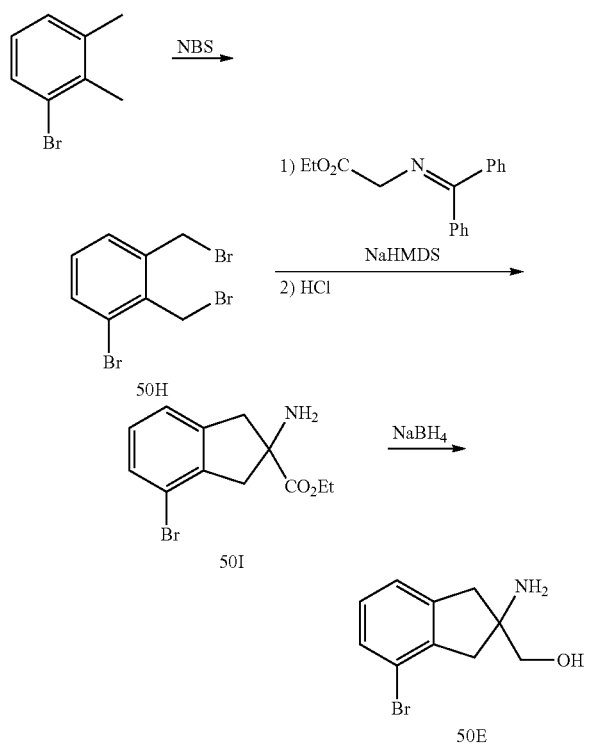

A mixture of 3-bromo-o-xylene (20 g, 0.108 mol) in CCl$_4$ (200 mL) was treated with NBS (38.5 g, 2.0 eq) and benzoyl peroxide (263 mg, 0.01 eq) and refluxed overnight. The reaction was then cooled to 0° C. and filtered. The filtrate was concentrated and purified (silica gel, hexanes) to give 50H as a light red oil.

In a manner similar to those described in the literature (Tetrahedon, 1999, 55, 14281 and Tetrahedron Letters, 1992, 33, 1565), a mixture of N-(diphenylmethylene)-glycine ethyl ester (267 mg, 1 mmol) in THF at −78° C. was treated with NaHMDS (1.0N/THF, 1.1 mL, 1.1 eq) and stirred 30 min. A

| Cpd | Structure | LCMS (MH+) |
|---|---|---|
| (±)-50J | 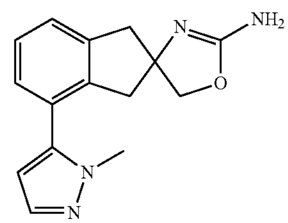 | 269 |
| (±)-50K | 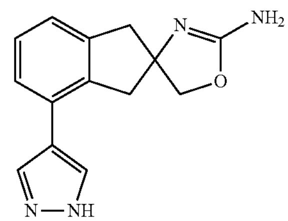 | 255 |
| (±)-50L | 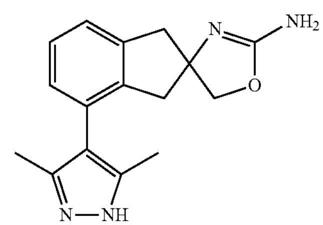 | 283 |
| (±)-50M | 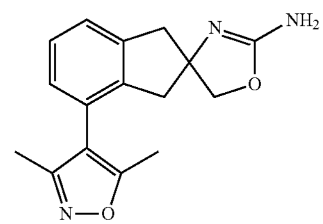 | 284 |

Preparative Example 51

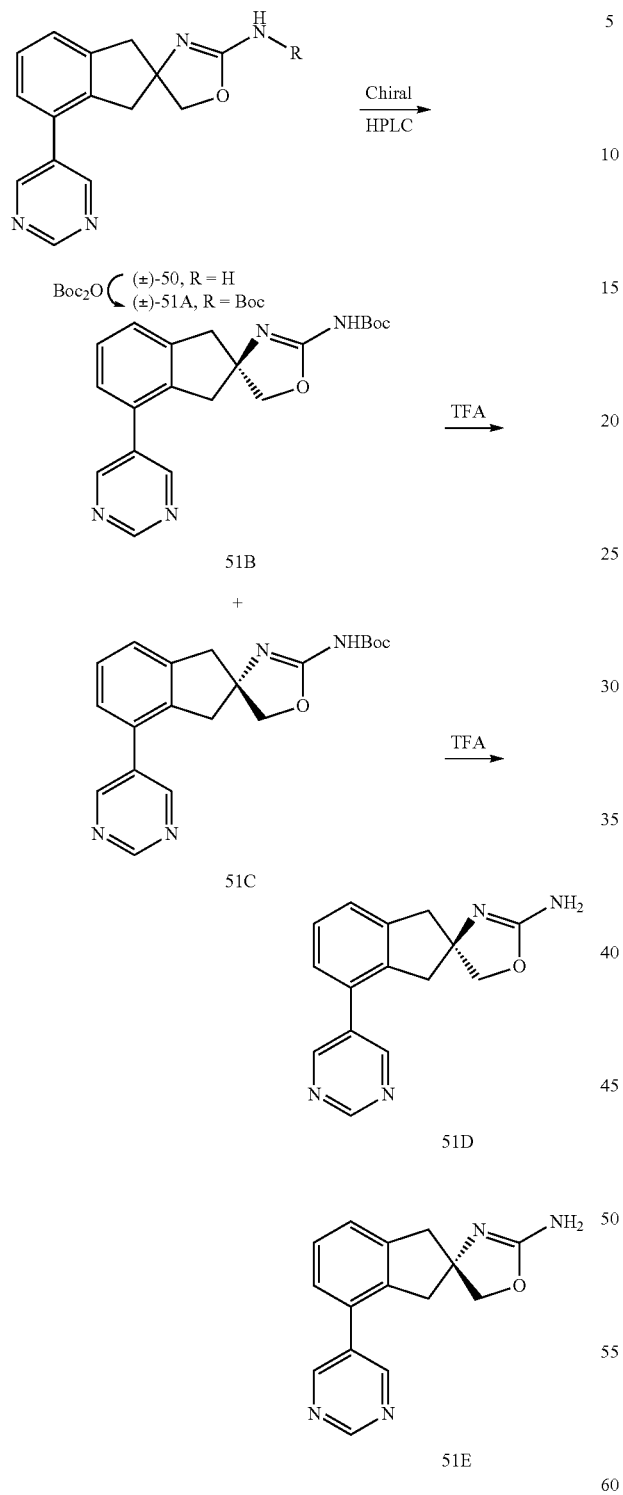

anes) to provide pure material. Compounds 51B and 51C were each deprotected (5:1 DCM:TFA, 3 h) to provide 51D (LCMS m/z 267, MH+) and 51E (LCMS m/z 267, MH+), respectively.

Preparative Example 52

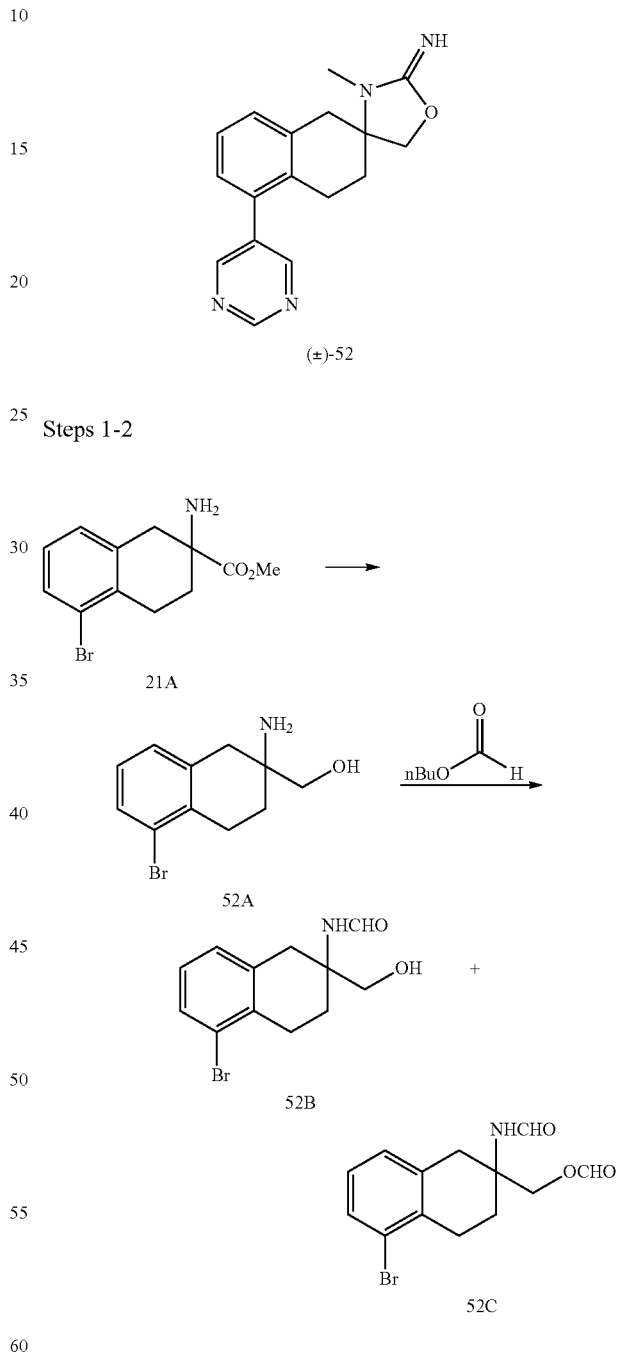

Steps 1-2

In a manner similar to that described in Example 2, compound (±)-50 was treated with 1.5 eq. Boc$_2$O (1.5 eq NaHCO, THF-water) to provide (±)-51A. The racemic mixture (±)-51A was purified by chiral HPLC (OD column, 25% IPA-hexanes) to provide impure 51B and pure 51C. Compound 51B was purified further on an AD column (25% IPA-hexanes) to provide pure material.

In a manner similar to that described in Example 1 (Step 4), compound 21A was reduced with NaBH$_4$ to provide 52A.

A mixture of 52A (200 mg, 0.78 mmol) and n-butyl formate (2 mL) were heated in a sealed tube for 2d at 130° C. and then cooled to RT. Silica column purification provided the products 52B and 52C.

Steps 3-5

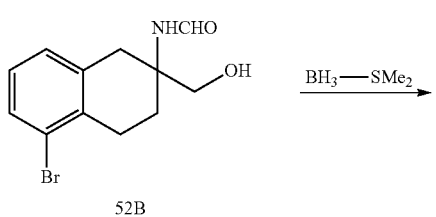

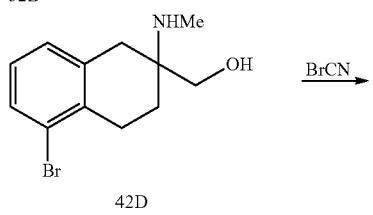

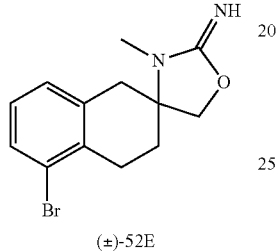

A mixture of 52B (0.78 mmol) in THF (5 mL) was treated with BH$_3$—SMe$_2$ (2.0 N/THF, 0.78 mL) and then heated at reflux overnight. The reaction was cooled to RT, treated with EtOH (10 mL) and K$_2$CO$_3$ (2 eq), and then heated at 80° C. for 2 h. The mixture was again cooled and filtered. The filtrate was concentrated and purified by column chromatography to provide 52D (130 mg).

A solution of 52D (130 mg) in EtOH (5 mL) was treated with BrCN (5.0 N/MeCN, 0.12 mL) and stirred at RT for 4 h. The mixture was concentrated and purified by column chromatography (7N NH$_3$-MeOH in DCM) to provide (±)-52E (72 mg, 51%). LCMS m/z 295/297 (MH+).

In a manner similar to that previously described, Suzuki coupling of (±)-52E with 1.5 eq pyrimidine-5-boronic acid (0.2 eq Pd(dppf)Cl$_2$, 3 eq Na$_2$CO$_3$, 4:1 DME-water, microwave 15 min at 120° C.) provided (±)-52. LCMS m/z 295 (MH+).

The enantiomers of (±)-52 were separated (OD semi-prep column, 35% IPA-hexanes, 10 mL/min) to provide 52F (LCMS m/z 295, MH+) and 52G (LCMS m/z 295, MH+).

Preparative Example 53

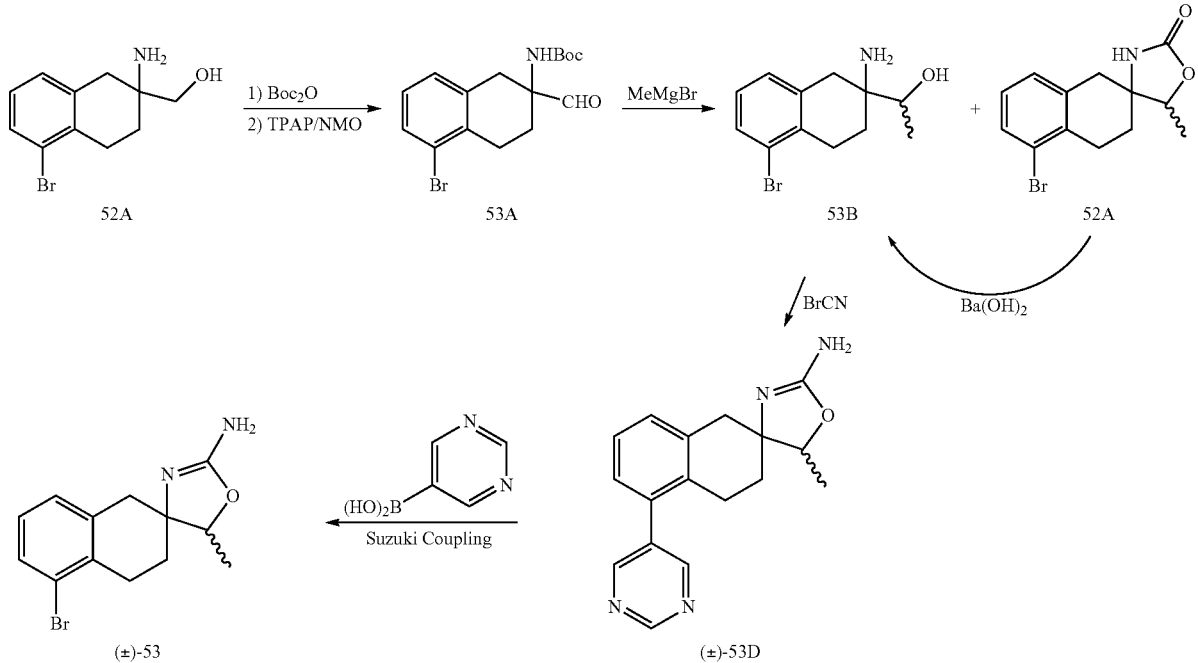

Steps 1-2

A mixture of 50E (1.0 g, 3.9 mmol) in THF-water (1:1, 40 mL) was treated with Boc$_2$O (1.28 g, 1.5 eq) and Na$_2$CO$_3$ (491 mg, 1.5 eq), stirred at RT, and then extracted with EtOAc. The organic layers were combined and concentrated to give the protected product (1.25 g, 90%) as a cream colored solid.

A mixture of the Boc protected alcohol (660 mg, 1.85 mmol) in DCM (20 mL) was treated with TPAP (65 mg, 0.1 eq) and NMO (282 mg, 1.3 eq) and stirred at RT for 3 h. The reaction was then diluted with hexane (20 mL), stirred 10 min, and filtered. The filtrate was concentrated and purified by silica gel chromatography to provide 53A (490 mg).

Steps 3-4

A solution of 53A (430 mg, 1.21 mmol) in THF (15 mL) was cooled to −78° C. and treated with MeMgBr (3.0 N/THF, 0.93 mL, 2.3 eq) dropwise. The mixture was allowed to warm to RT slowly and then was quenched with sat. aq. NH$_4$Cl at 0° C. The reaction was extracted with DCM. The combined organic extracts were dried over Na$_2$SO$_4$, concentrated and purified to provide a mixture of 53B (minor product) and 53C (major product).

Compound 53C was converted to 53B by the following procedure: A mixture of 53C (145 mg, 0.5 mmol) and Ba(OH)$_2$ in dioxane-water (1:1, 30 mL) was heated at 100° C. until LCMS analysis indicated consumption of the SM. The mixture was cooled and diluted with EtOAc and water. The organic layer was separated, dried over Na$_2$SO$_4$, concentrated and purified to provide a mixture of 53B (110 mg, 81%).

Alternatively, compound 53A was converted directly to compound 53B by use of DCM as solvent: A mixture of 53A (3.49 g, 9.8 mmol) in DCM (50 mL) was cooled to −78° C. and treated with MeMgBr (3.0 N/THF, 8.2 mL, 2.5 eq) dropwise. The mixture was allowed to warm to RT, stirred 1 h, and then was quenched with sat. aq. NH$_4$Cl at 0° C. The reaction was extracted with DCM. The organic layer was dried over Na$_2$SO$_4$, concentrated and purified to provide 53B (3.61 g) as a white foam.

Steps 5-6

A mixture of the amino alcohol 53B (100 mg, 0.37 mmol) and BrCN (5.0 N/MeCN, 0.09 mL) in EtOH (7 mL) was stirred at RT for 4 h. The mixture was concentrated and purified by column chromatography (7N NH$_3$-MeOH in DCM) to provide (±)-53D.

Compound (±)-53D was subjected to Suzuki coupling with pyrimidine-5-boronic acid (cat. Pd(dppf)Cl$_2$, Na$_2$CO$_3$, 4:1 DME-water, microwave 15 min at 120° C.) to provide (±)-53. LCMS m/z 295 (MH+).

The two sets of disastereomers were separated by silica gel chromatography. The less polar set was further purified by chiral HPLC (AD column, 15% IPA-hexanes with 0.1% DEA) to provide 53E (LCMS m/z 295, MH+) and 53F (LCMS m/z 295, MH+). The more polar set was further purified by chiral HPLC (OD column, 10% EtOH-hexanes with 0.1% DEA) to provide 53G (LCMS m/z 295, MH+) and 53H (LCMS m/z 295, MH+).

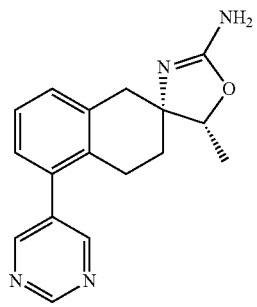

53E

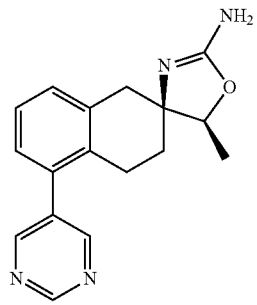

53F

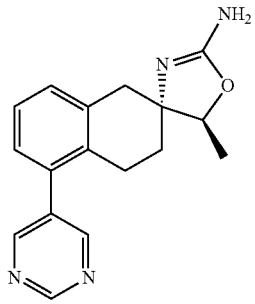

53G

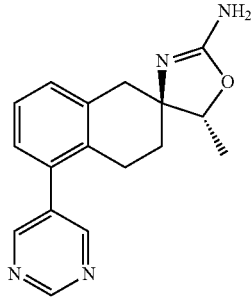

53H

Alternatively, enantiomerically pure amino ester 21B was brought through the sequence outlined above to provide a mixture of 53F and 53H, which were separated by chiral HPLC (OD column, 10% EtOH-hexanes with 0.1% DEA and then AD column, 15% IPA-hexanes with 0.1% DEA).

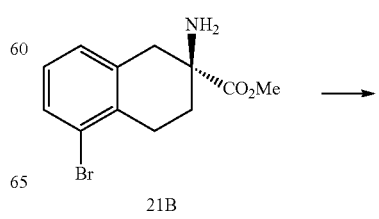

21B

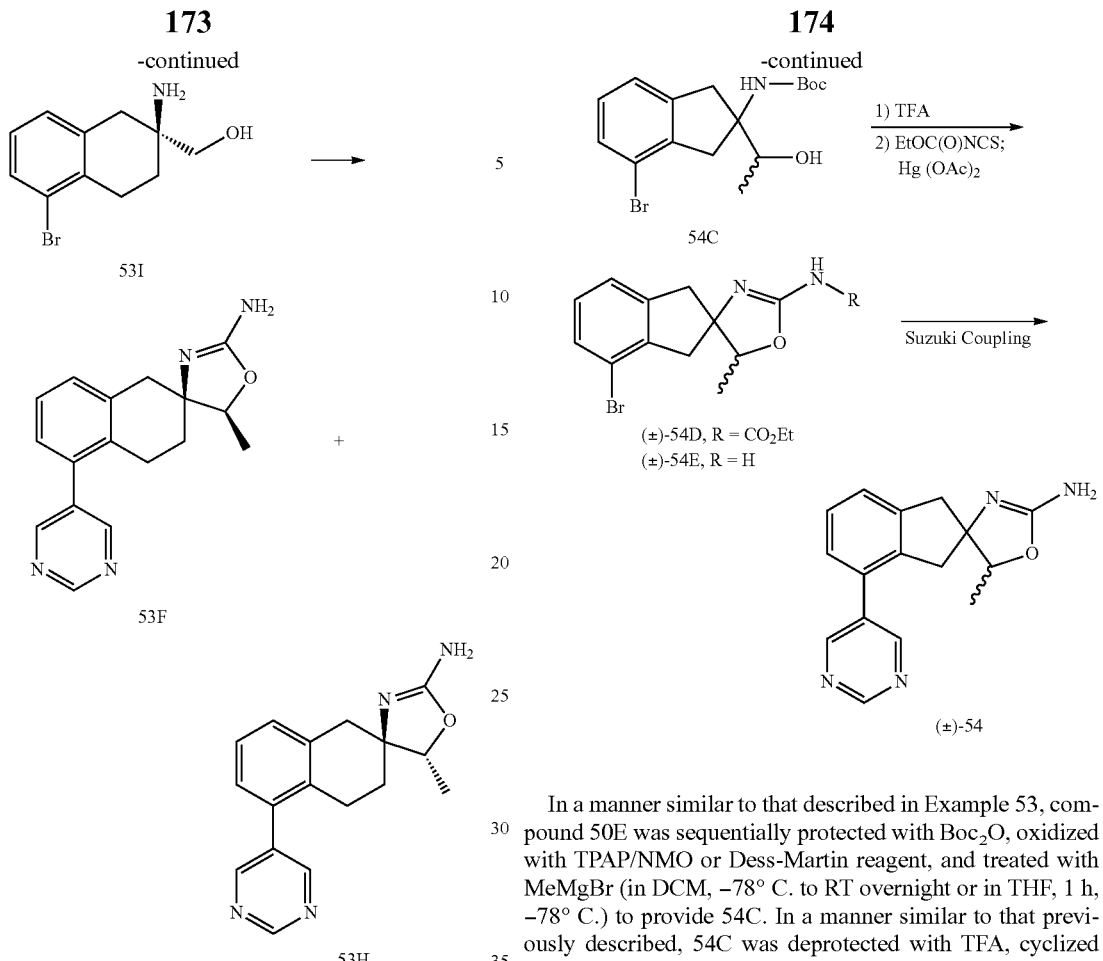

In a manner similar to that described in Example 53, compound 50E was sequentially protected with Boc₂O, oxidized with TPAP/NMO or Dess-Martin reagent, and treated with MeMgBr (in DCM, −78° C. to RT overnight or in THF, 1 h, −78° C.) to provide 54C. In a manner similar to that previously described, 54C was deprotected with TFA, cyclized with EtOC(O)NCS/Hg(OAc)₂, and hydrolyzed with LiOH to provide (±)-54E. Suzuki coupling with pyrimidine-5-boronic acid provided (±)-54 (LCMS m/z 281, MH+) as a mixture of four stereoisomers.

The four stereoisomers of (±)-54 were separated by chiral HPLC (Lux Cellulose-2 column using 15% IPA-hexanes with 0.1% DEA followed by AD column using 15% IPA-hexanes with 0.1% DEA) to provide 54G (LCMS m/z 281, MH+), 54H (LCMS m/z 281, MH+), 54I (LCMS m/z 281, MH+), and 54J (LCMS m/z 281, MH+).

Preparative Example 54

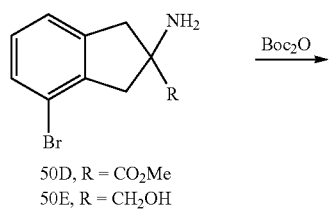

50D, R = CO₂Me
50E, R = CH₂OH

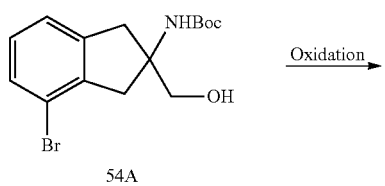

54A

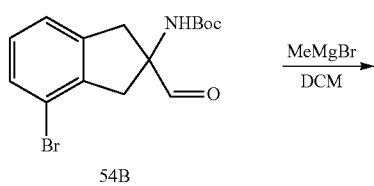

54B

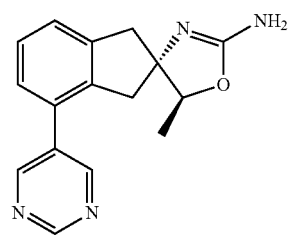

54G

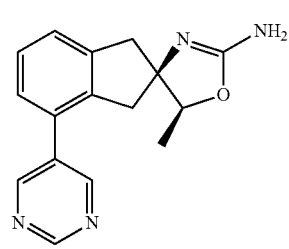

54H

54I

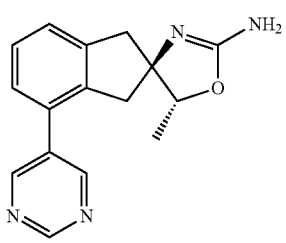

54J

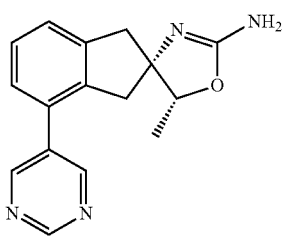

Alternatively, the enantiomers of compound 50D and 54A were separated by SFC (OD column with 10% MeOH and AD with 20% MeOH, respectively). The diastereomers of alcohols (54K and 54L) were separated by silica chromatography (2-25% EtOAc/hexanes).

54K

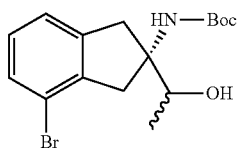

54L

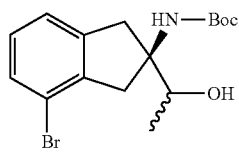

Preparative Example 55

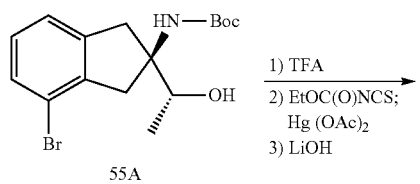

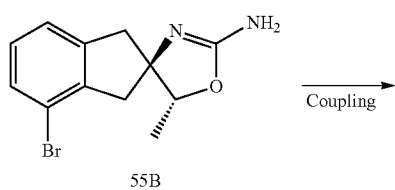

-continued

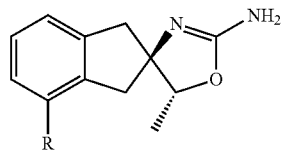

Compound 55A (prepared from 54L as described in Example 54) was deprotected, cyclized, and hydrolyzed as described above to provide 55B. In a manner similar to that described in previous examples, 55B is coupled with the appropriate boronic ester, boronic acid, or tin compound to provide the following compounds.

55C

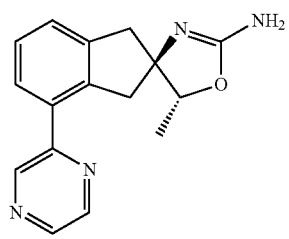

55D

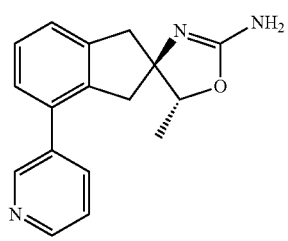

55E

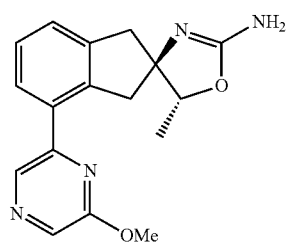

55F

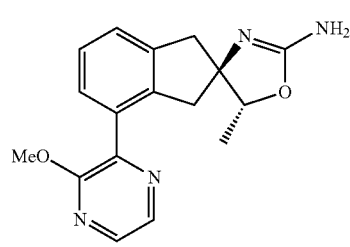

55G

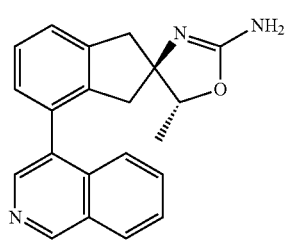

| | |
|---|---|
| 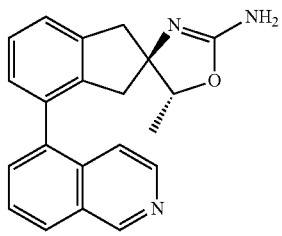 55H | 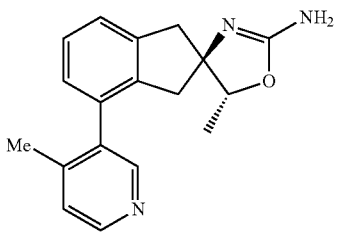 55N |
| 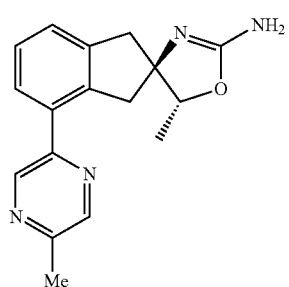 55I | 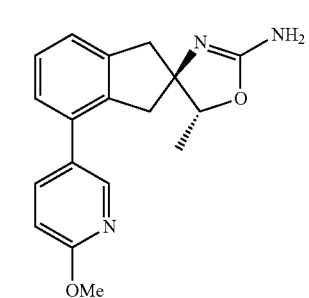 55O |
| 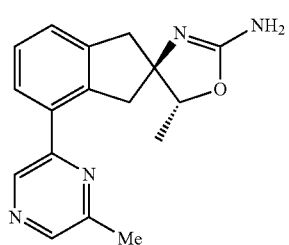 55J | 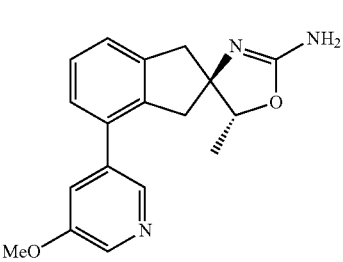 55P |
| 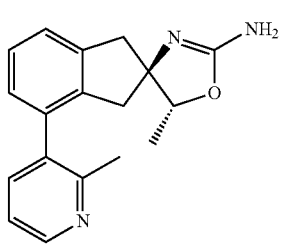 55K | 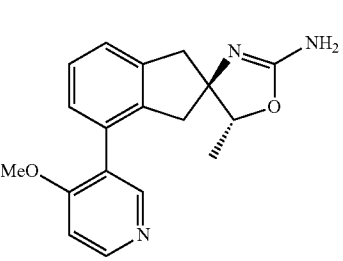 55Q |
| 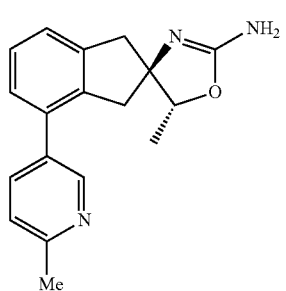 55L | 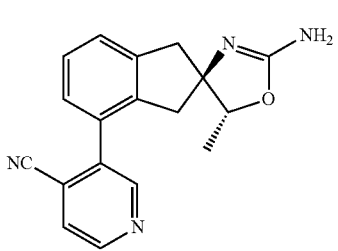 55R |
| 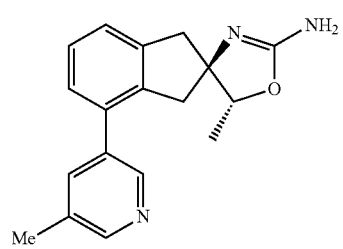 55M | 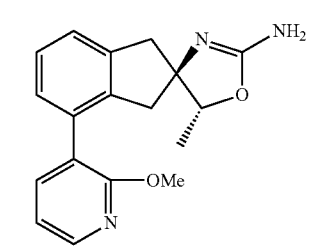 55S |

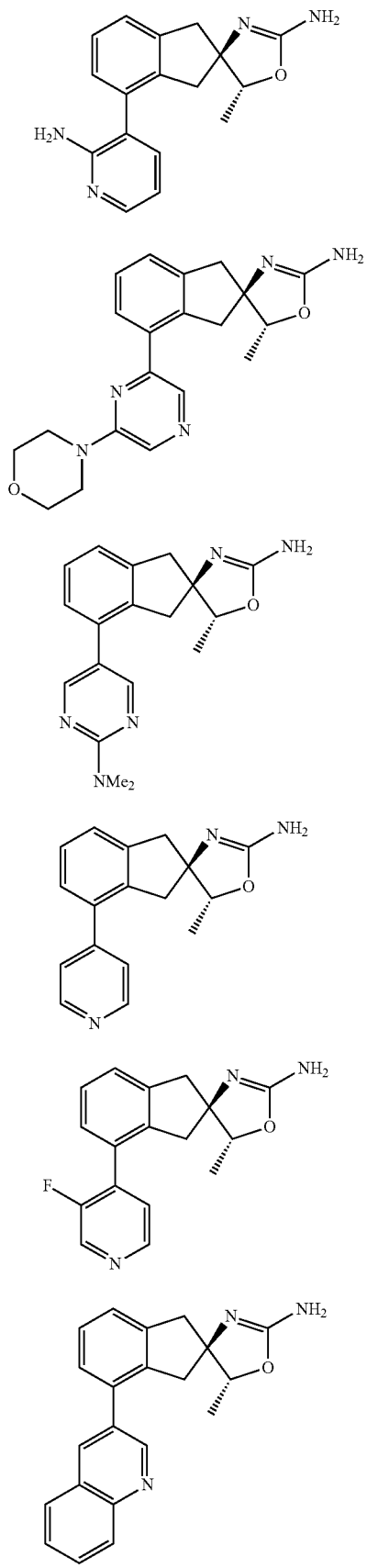

| 181 -continued | | 182 -continued | |
|---|---|---|---|
| | 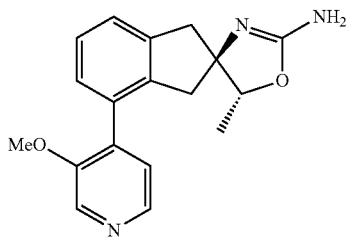 | 55AF | 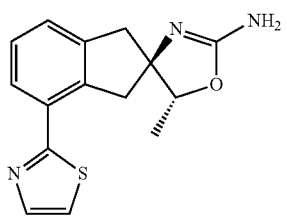 55AL |
| | 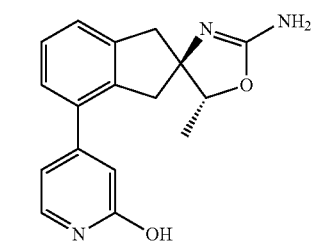 55AG | | 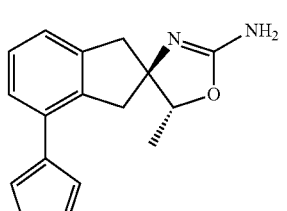 55AM |
| | 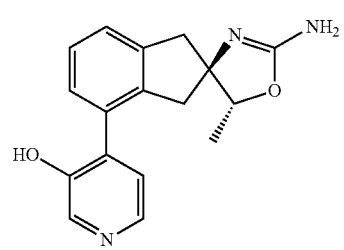 55AH | | 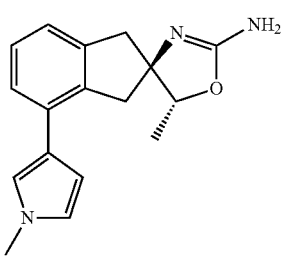 55AN |
| | 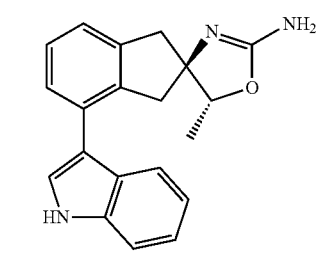 55AI | | 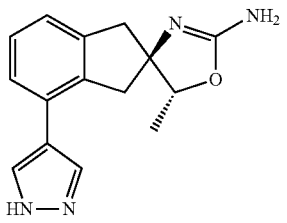 55AO |
| | 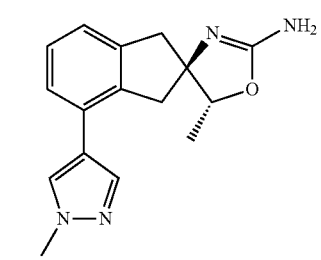 55AJ | | 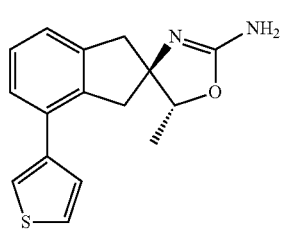 55AP |
| | 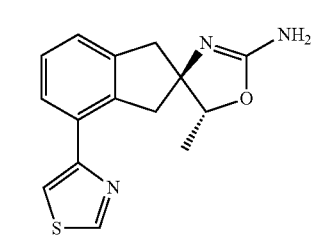 55AK | | 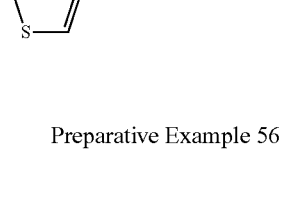 |
Preparative Example 56
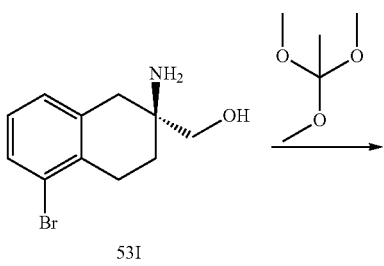
53I

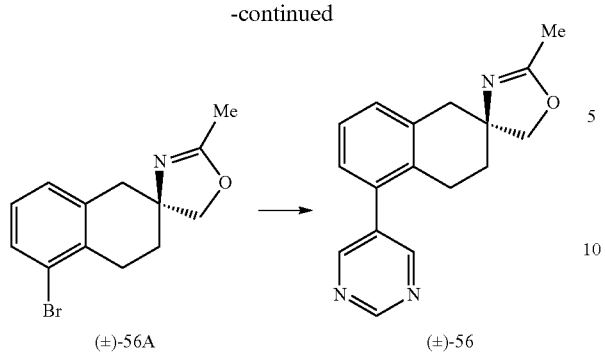

To the mixture of 53I (93 mg, 0.360 mmol, derived by reduction of 21B with NaBH₄) and DIPEA (78 µL, 0.432 mmol) in DMF (3 mL) was added trimethylorthoacetate (55 µL, 0.432 mmol). The mixture was kept stirring at 115° C. for 16 h. The mixture was diluted H₂O (5 mL) and then extracted with EtOAc (2×10 mL). The combined organic layer was washed with brine (10 mL), dried over anhydrous MgSO₄, and concentrated. The residue was purified (silica gel, 1:1 EtOAc-Hexane) to obtain (±)-56A as a white solid (50 mg). LCMS m/z 280/282, (MH+).

A mixture of compound (±)-56A (50 g, 0.178 mol), pyrimidine-5-boronic acid (36 mg, 0.268 mmol), Pd(PPh₃)₂Cl₂ (19 mg, 0.15 mol %) and Na₂CO₃ (57 mg, 0.534 mmol) in DME-H₂O (2 mL-0.5 mL) was microwaved (120° C., 30 min) and then extracted with CH₂Cl₂ (2×10 mL). The organic layer was washed with brine (6 mL), dried over anhydrous MgSO₄, and concentrated. The residue was purified by PTLC (1:12 mixture of 2N NH₃-MeOH in DCM) to obtain (±)-56 as a white foam (20 mg). LCMS m/z 280 (MH+).

Preparative Example 57

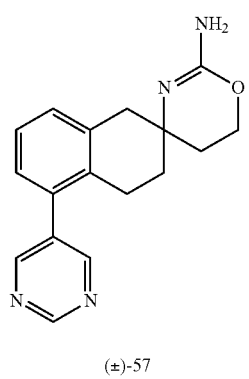

(±)-57

Step 1

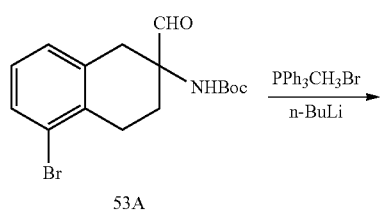

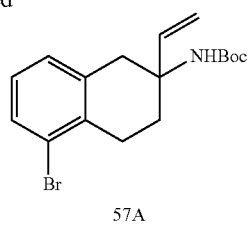

57A 2.5M n-BuLi in hexane (260 µL, 0.650 mmol) was added to a suspension of methyltriphenylphosphonium bromide (211 mg, 0.600 mmol) in THF (3 mL). The mixture turned into an orange suspension. After stirring at RT for 30 min, the solution of aldehyde 53A (200 mg, 0.565 mmol) in THF (1 mL) was added dropwise. The resultant mixture was kept stirring at RT for 1 h and a white precipitate formed. The mixture was diluted with sat. aq. NH₄Cl (3 mL) and extracted with EtOAc (2×10 mL). The combined organic was washed with brine (10 mL), dried over anhydrous MgSO₄, and concentrated. The residue was purified (silica gel, 1:10 EtOAc-Hexane) to obtain 57A as a white solid (120 mg). LCMS m/z 352/354 (MH+).

Step 2

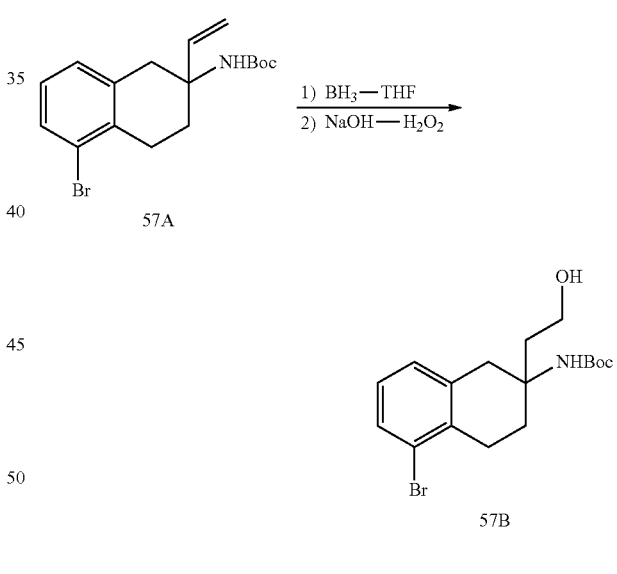

A solution of 57A in THF (1 mL) solution at 0° C. was treated with BH₃-THE (1M, 1.56 mL, 1.56 mmol) and stirred at 0° C. for 1 h. The reaction was treated with 1N NaOH (1.5 mL), immediately followed by H₂O₂ (30%). The ice bath was removed, and the reaction mixture was kept stirring at RT for 1 h. The reaction was extracted with EtOAc (2×10 mL). The combined organic was washed with H₂O (10 mL), dried over anhydrous MgSO₄, and concentrated. The residue was purified (silica gel, 1:2 EtOAc-Hexane) to obtain 57B as a white solid (31 mg). LCMS m/z 370/372 (MH+).

Step 3:

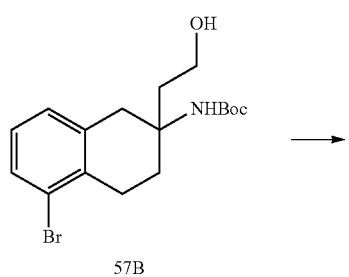

57B

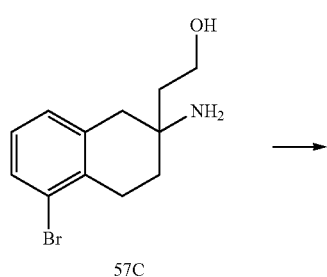

57C

TFA (1 mL) was added to the solution of compound 57B (120 mg, 0.324 mmol) in CH$_2$Cl$_2$ (2 mL). The reaction was kept stirring at RT for 2 h. The mixture was diluted with CH$_2$Cl$_2$ (10 mL) and basified with 50% NH$_4$OH (v/v, 6 mL). The aqueous layer was extracted once more with CH$_2$Cl$_2$ (10 mL). The combined organic was dried over anhydrous MgSO$_4$, and concentrated to obtain compound 57C as a white solid (67 mg). LCMS m/z 270/272 (MH+).

Step 4

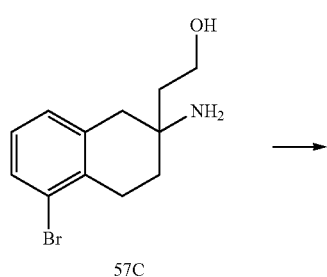

57C

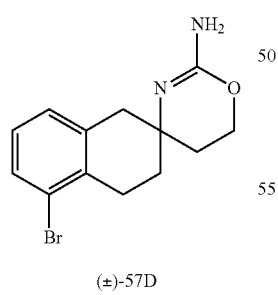

(±)-57D

A solution of 57C (67 mg, 0.248 mmol) in EtOH (1 mL) at 0° C. was treated with BrCN (5M/CH$_3$CN, 60 μL, 0.3 mmol) and then stirred at RT for 16 h. The mixture was concentrated, diluted with CH$_2$Cl$_2$ (10 mL), and basified with sat. aq. NaHCO$_3$ (5 mL). The aqueous layer was extracted once more with CH$_2$Cl$_2$ (10 mL). The combined organic layers were dried over anhydrous MgSO$_4$, and concentrated. The residue was purified (PTLC eluting with DCM-MeOH (2N NH$_3$)=10:1) to obtain (±)-57D as a white foam (15 mg). LCMS m/z 295/297 (MH+).

Step 5

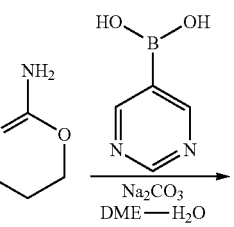

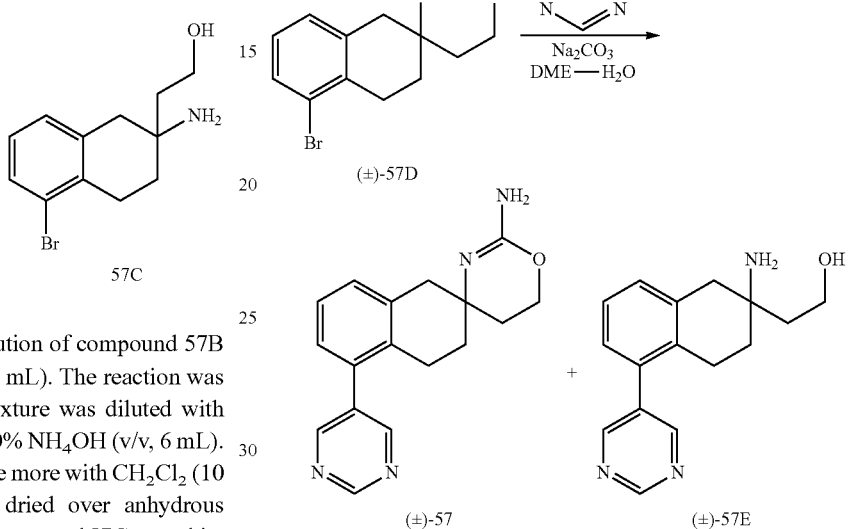

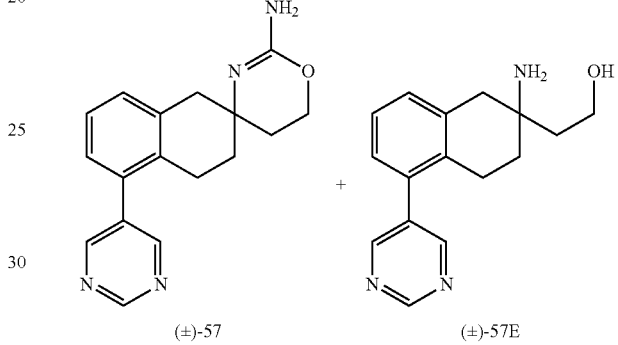

Compound (±)-57D (15 mg, 0.05 mmol), pyrimidine-5-boronic acid (7.6 mg, 0.06 mmol), Pd(PPh$_3$)$_2$Cl$_2$ (5.2 mg, 0.15 mol %) and Na$_2$CO$_3$ (21 mg, 0.2 mmol) were mixed in DME-H$_2$O (1 mL-0.25 mL) and microwaved at 120° C. for 45 min. The mixture was extracted with CH$_2$Cl$_2$ (2×10 mL). The organic was washed with brine (6 mL), dried over anhydrous MgSO$_4$, and concentrated. The residue was purified (PTLC eluting with DCM-MeOH (2N NH$_3$)=10:1) to obtain the title compound (±)-57 as a white film (1.2 mg, LCMS m/z 295, MH+), and (±)-57E as a white film (1.4 mg, LCMS m/z 270, MH+).

Preparative Example 58

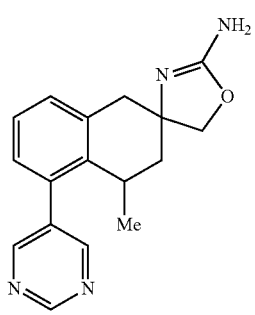

(±)-58

Step 1

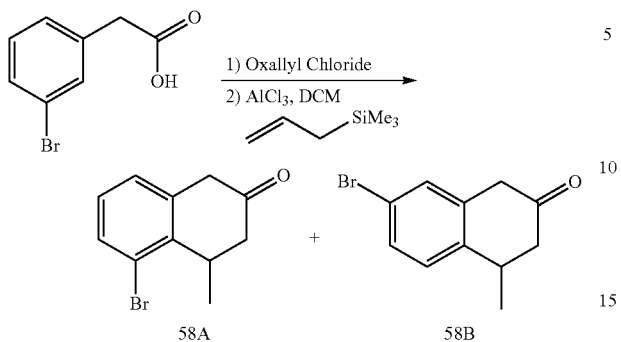

3-bromo-phenylacetic acid (6.5 g, 30 mmol) was treated with oxallyl chloride (10 mL) at RT for 2 h, and then refluxed at 80° C. for 4 hr. The mixture was cooled to RT and concentrated to give crude acetyl chloride without further purification.

A mixture of AlCl₃ (12 g, 90 mmol) in DCM (90 mL) at -20° C. was added to the crude acetyl chloride in DCM (10 mL) and stirred for 0.5 h at -20° C. Allyl trimethylsilane (5.14 g, 54 mmol) was added dropwise. The mixture was further stirred at -20° C. for 2 h and then refluxed for 1.5 h before cooling to RT. An aq. HCl solution (2N, 30 mL) was slowly added to the reaction at 0° C., then extracted with Et₂O thoroughly. The combined organic layers were dried over Na₂SO₄, concentrated and chromatographed (0% to 10% EtOAc/Hexane) to give the desired product 58A and 58B as a mixture (1/1.5, 3 g, 42%).

Steps 2-7

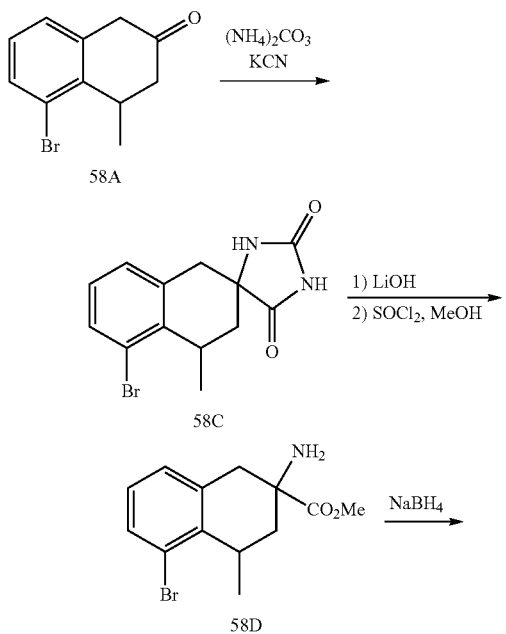

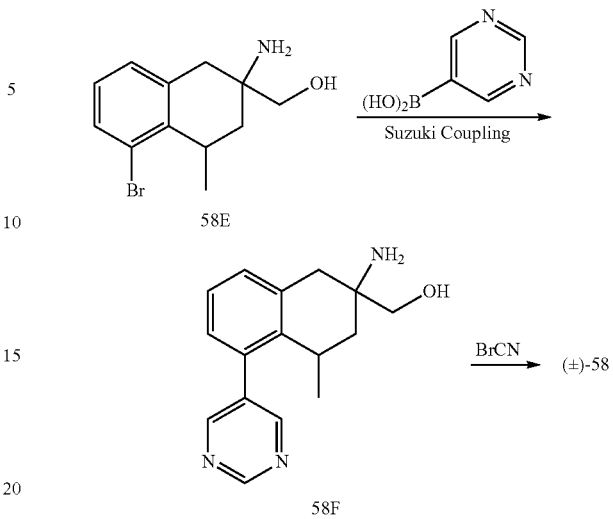

A mixture of 58A and 58B (1/1.5, 3.0 g, 12.5 mmol, 58B not shown), (NH₄)₂CO₃ (5 g, 50 mmol), and KCN (1.63 g, 25 mmol) in 1:1 EtOH—H₂O (20 mL) was heated in a sealed tube overnight at 85° C. The reaction was then cooled to RT, diluted with water (~400 mL) and stirred for 2 h. The precipitate was filtered and dried in vacuo overnight to provide a mixture of 5- and 7-Br hydantoins as exemplified by 58C (3.5 g, 90%, 5-sub/7-sub=1/1.5, 7-bromo not shown).

A mixture of 5- and 7-Br hydantoins (as exemplified by 58C, 3.5 g, 11.3 mmol) and LiOH—H₂O (3.18 g, 75.6 mmol) in H₂O (100 mL) was refluxed overnight. The reaction was then cooled to 0° C., acidified with 12 N HCl, and concentrated to give a mixture of 5- and 7-Br amino acids as a solid.

Thionyl chloride (9 mL) was carefully added to MeOH (300 mL) at 0° C. The resulting mixture was then added to a flask charged with the amino acid product. The reaction was heated to reflux overnight and then cooled and concentrated. The residue was taken up in sat. aq. NaHCO₃ and extracted EtOAc (2×). The combined organic layers were dried over Na₂SO₄ and concentrated. Chromatography (0-50% EtOAc/hex) provided a mixture of 5- and 7-Br aminoesters (as exemplified by 58D) as a red oil.

The mixture of aminoesters (270 mg, 0.98 mmol) was dissolved in anhydrous MeOH (2 mL) and then treated with NaBH₄ (60 mg, 1.5 mmol). The reaction was concentrated after TLC indicated consumption of SM (1 h). DCM (20 mL) was added to the residue and washed with brine (10 mL). The organic layers were dried over Na₂SO₄, concentrated and chromatographed (0% to 20% MeOH/DCM) to give the desired aminoalcohols (as exemplified by 58E, LCMS m/z 270/272, MH+).

A mixture of aminoalcohols (120 mg, 0.45 mmol), pyrimidine-5-boronic acid (62 mg, 0.5 mmol), Pd(PPh₃)₄ (63 mg, 0.09 mmol), Na₂CO₃ (144 mg, 1.35 mmol) in 4:1 DME-H₂O (5 mL) were heated at 120° C. in a microwave for 1 h. The reaction concentrated, diluted with water and extracted with DCM (4×). The layers were separated. The combined organic layers were dried over Na₂SO₄, concentrated and chromatographed (2-5% of NH₃-MeOH/DCM) to give the desired product (100 mg, 83%, mixture of 5- and 7-substitutions as exemplified by 58F, LCMS m/z 270, MH+).

A solution of 58F (82 mg, 0.31 mmol) in EtOH/DCM (1:1, 2 mL) was treated with BrCN (0.1 mL, 5.0 M in CH₃CN) and was stirred at RT overnight. The mixture was diluted with water and extracted with DCM (4×). The layers were separated. The combined organic layers were dried over Na₂SO₄, concentrated and chromatographed (2-5% of NH₃-MeOH/DCM) to give (±)-58 (40 mg, 44%). LCMS m/z 295 (MH+)

Compounds 58G (LCMS m/z 295, MH+) and 58H (LCMS m/z 295, MH+) were also isolated during this procedure:

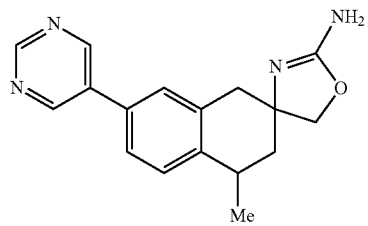

58G: Diastereomer 1
58H: Diastereomer 2

Preparative Example 59

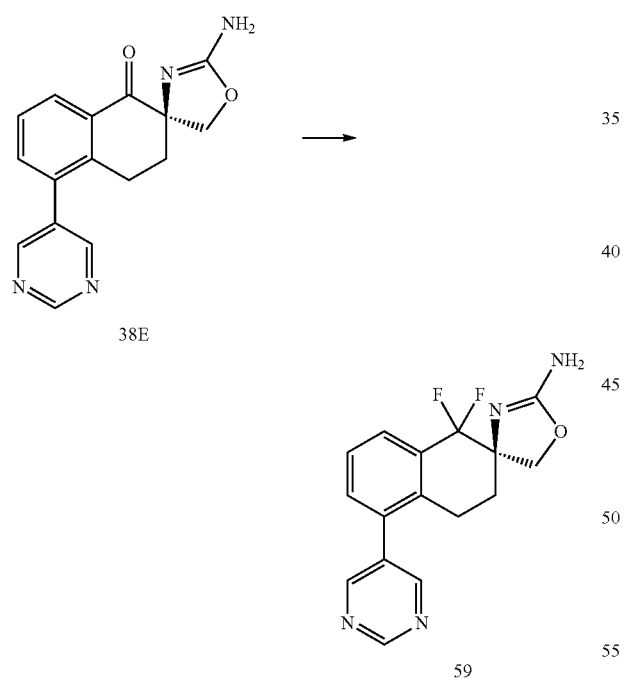

A solution of compound 38E in DCM is treated with Deoxy-Fluor (F₃S—N(CH₂CH₂OMe)₂) and refluxed until the starting material is consumed. The reaction is cooled to RT, poured onto sat. aq. NaHCO₃ and extracted with DCM (2×). The organic layers are dried over Na₂SO₄, concentrated and chromatographed on silica gel to provide the product 59. Alternatively, DAST (F₃S-NEt₂) is used as the fluorinating reagent.

The following compounds are synthesized in a similar manner from the indicated starting materials:

| Cpd | Structure | SM |
|---|---|---|
| 59A | 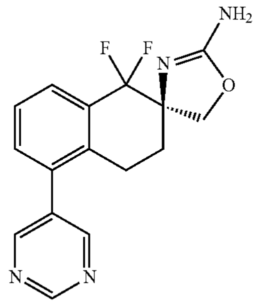 | 38F |
| 59B | diastereomer 1 | 38G (diastereomer 1) |
| 59C | diastereomer 2 | 38H (diastereomer 2) |
| 59D | diastereomer 1 | 38I (diastereomer 1) |

Preparative Example 60

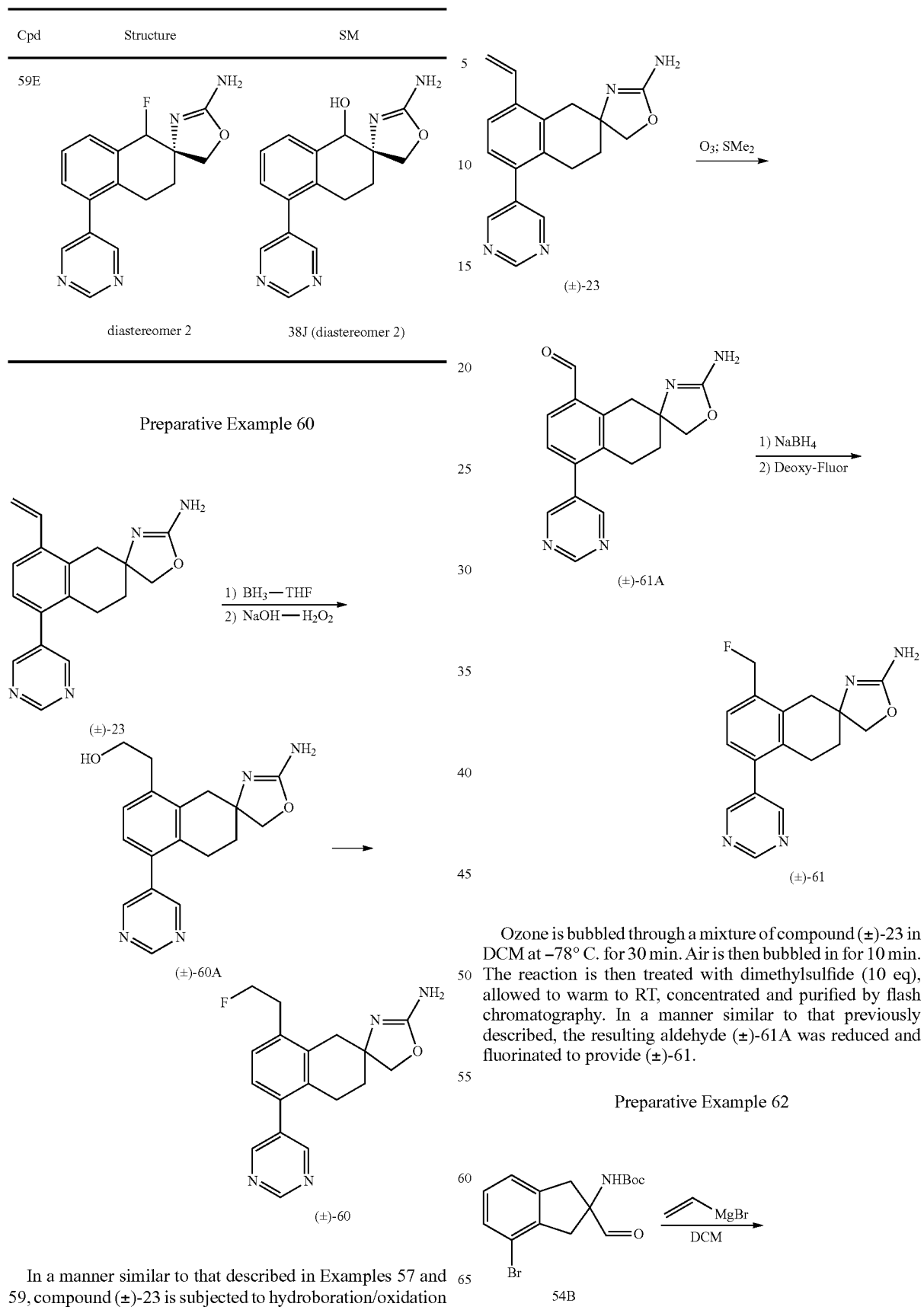

In a manner similar to that described in Examples 57 and 59, compound (±)-23 is subjected to hydroboration/oxidation and fluorination to provide (±)-60.

Preparative Example 61

Ozone is bubbled through a mixture of compound (±)-23 in DCM at −78° C. for 30 min. Air is then bubbled in for 10 min. The reaction is then treated with dimethylsulfide (10 eq), allowed to warm to RT, concentrated and purified by flash chromatography. In a manner similar to that previously described, the resulting aldehyde (±)-61A was reduced and fluorinated to provide (±)-61.

Preparative Example 62

-continued

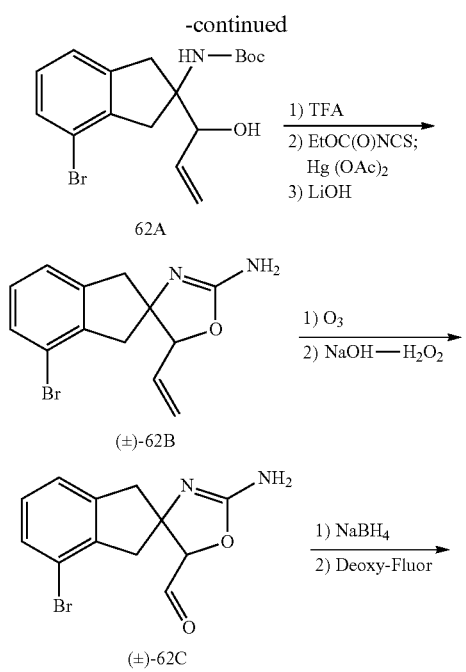

In a manner similar to that described in Example 53, vinyl-magnesium bromide is added to compound 54B. In a manner similar to that previously described, the resulting product 62A is deprotected, cyclized, and hydrolyzed to give (±)-62B. Following the sequence described previously, (±)-62B is advanced to (±)-62D and then coupled with pyrdimine-5-boronic acid to provide the title compound (±)-62.

Preparative Example 63

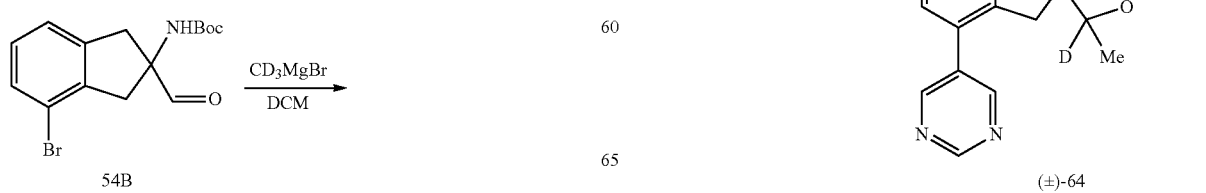

-continued

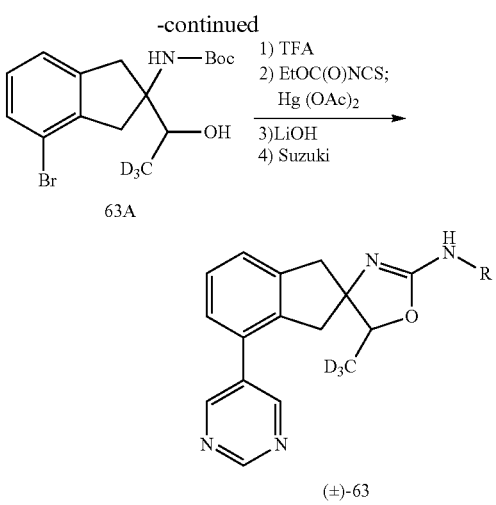

In a manner similar to that described in Example 53, compound 54B is treated with $CD_3MgBr$ (prepared from $CD_3Br$, see J. Am. Chem. Soc. 1989, 111, 3897) and then advanced to (±)-63.

Preparative Example 64

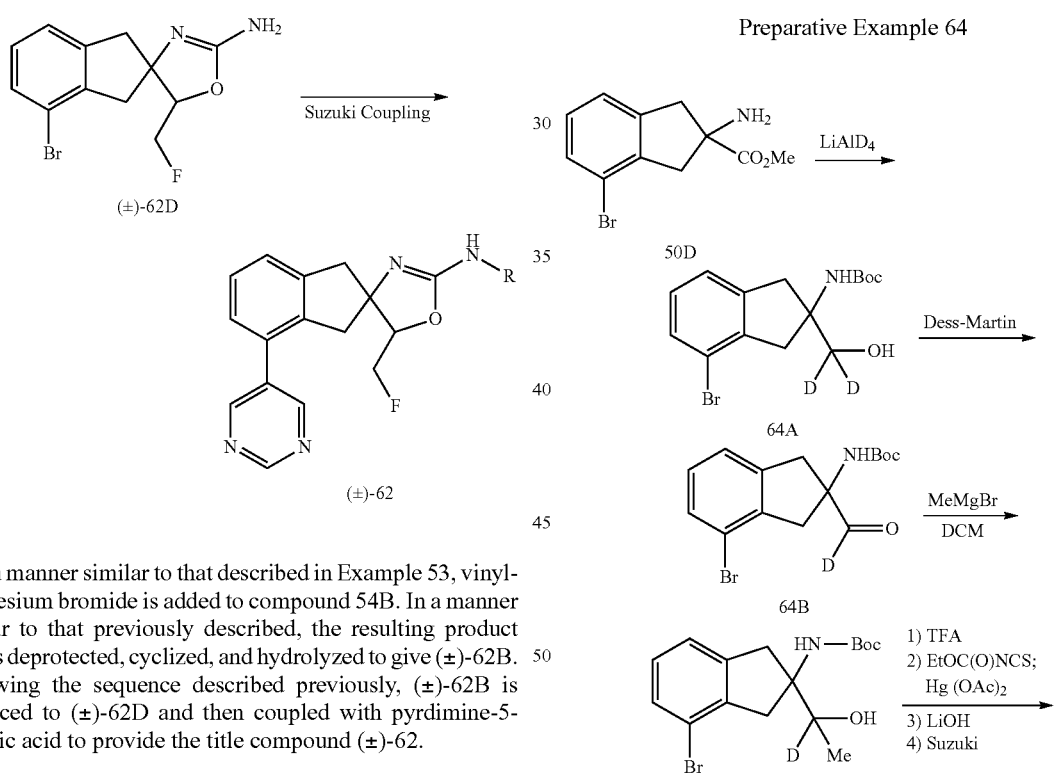

A solution of 50D in THF is treated with LiAlD$_4$ at RT for 1 h to provide 64A, which is further progressed to (±)-64 in a manner similar to that outlined in Example 54.

Preparative Example 65

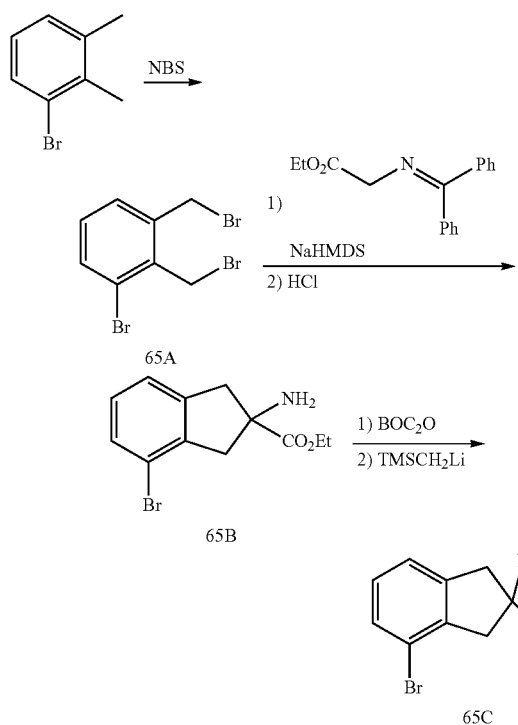

Step 1

A suspension of 3-bromo-o-xylene (80 g, 432 mmol), NBS (154 g, 864 mmol) and AIBN (2,2'-azobis(2-methylpropionitrile, 2.0 g, 12.3 mmol) in anhydrous CCl$_4$ (400 mL) was gradually warmed to boiling and then refluxed for 2 h. The mixture was cooled to RT and filtered. The filtrate was concentrated and filtered through a silica pad, eluting with 10% EtOAc-hexanes. The resulting product was concentrated, cooled in the freezer and then triturated with cold hexanes to obtain 65A (110 g). Additional product could be obtained from the mother liquor.

Steps 2-3

A solution of NaHMDS (1.0M/THF, 200 mL, 1.05 eq) in THF was cooled to −78° C. and treated dropwise with a solution of N-(diphenylmethylene)glycine ethyl ester (50.68 g, 1.0 eq) in THF. The reaction was stirred 30 min at −78° C. and then treated with tribromide 65A (65 g, 1.0 eq) in THF dropwise. The reaction was allowed to slowly warm to RT overnight. The mixture was then cooled to −78° C. and treated dropwise with NaHMDS (1.0M/THF, 209 mL, 1.1 eq). The reaction was again allowed to slowly warm to RT overnight. The mixture was quenched with ice and extracted with Et$_2$O.

The organic layer was treated with HCl (2N, 1 L) and stirred vigorously until analysis indicated complete conversion of the intermediate imine to 65B. The layers were then separated, discarding the organic layer. The aqueous layer was cooled in an ice-bath and neutralized with 5% NaOH (or aq. NH4OH) and extracted with DCM. The DCM layer was dried over Na$_2$SO$_4$, concentrated and chromatographed (5-50% EtOAc/hex) to give 65B.

Steps 4-5

Compound 65B was treated with Boc$_2$O as previously described. The resulting protected amino ester (0.14 g, 0.364 mmol) was taken up in anhydrous pentane (3 mL) and treated with TMS-methyllithium (1.0 M/pentane, 1.1 mL, 3.0 eq) at 0° C. The reaction was stirred 2.5 h at 0° C., quenched with MeOH (1 mL), and stirred at RT for 1 h. The mixture was diluted with water and extracted with ether (3×50 mL). The ether layer was dried over Na$_2$SO$_4$, concentrated and chromatographed to give 65C.

Compound 65C is reduced with NaBH$_4$ to give alcohol 54C. Alternatively, 65C is reduced in a steroselective manner with (S)-2-methyl-CBS-oxazaborolidine/borane or (R)-2-methyl-CBS-oxazaborolidine/borane as described in Example 66.

Preparative Example 66

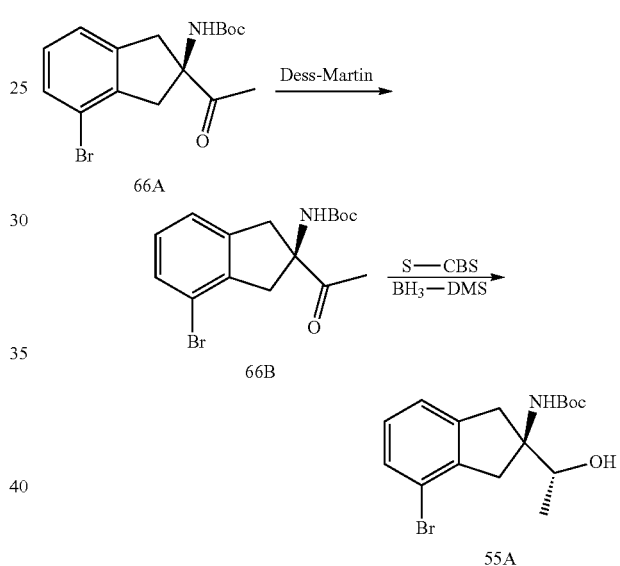

A solution of compound 66A (995 mg, 2.79 mmol, prepared from 54L as described in Example 54) in DCM (25 mL) was treated with the Dess-Martin periodinane reagent (1.78 g, 4.19 mmol) and stirred for 3 h at RT. The reaction was then quenched with a solution of Na$_2$S$_2$O$_3$ in water and stirred at RT. The organic layer was separated, washed with aqueous Na$_2$S$_2$O$_3$. The aqueous layer was further extracted with EtOAc. The combined organic layers were sequentially washed with sat. aq. NaHCO$_3$ (2×), brine and water. The organic layer was then dried over Na$_2$SO$_4$, concentrated and chromatographed (5-20% EtOAc/hex) to give 66B as a light yellow foam. LCMS m/z 352/354 (MH+)

A mixture of BH$_3$-DMS (2.54 mL of 2.0N solution/THF) and (S)-2-methyl-CBS-oxazaborolidine (5.08 mL of 2.0N solution/THF) in THF (30 min) was stirred for 10 min at RT. The reaction was cooled to 0° C. and then slowly treated with a solution of compound 65C (1.63 g, 4.62 mmol) in THF (30 mL) via addition funnel. The reaction was allowed to warm to RT slowly, stirred overnight, quenched with water, and stirred an additional 2 h. The mixture was then extracted with EtOAc, dried over Na$_2$SO$_4$, concentrated and chromatographed (5-20% EtOAc/hex) to give 55A as a white solid (1.45 g). LCMS m/z 356/358 (MH+).

Preparative Example 67

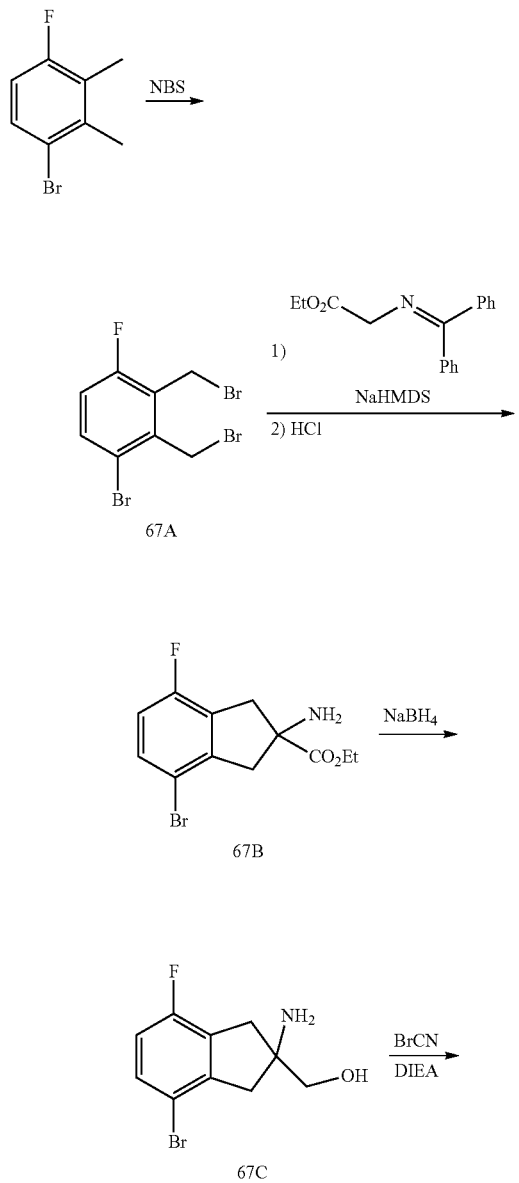

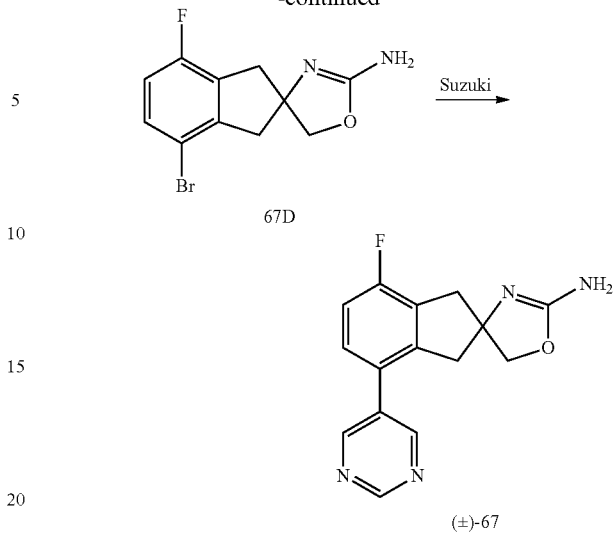

Step 1

A mixture of 3-bromo-6-fluoro-o-xylene (25.37 g, 432 mmol) in anhydrous $CCl_4$ (250 mL) was treated with NBS (44.5 g, 864 mmol) and benzoyl peroxide (310 mg) and then heated at reflux overnight. The mixture was cooled to 0° C. and filtered, washing with hexanes. The filtrate was concentrated and chromatographed (hexanes) to give 67A as an colorless oil (41.57 g, with minor mono-bromo impurities).

Steps 2-4

In a manner similar to that described previously (Example 65, Steps 2-3 and Example 1, Step 4), compound 67A was sequentially treated with N-(diphenylmethylene)glycine ethyl ester, HCl, and $NaBH_4$ to provide 67C.

Steps 5-6

A mixture of amino alcohol 67C (671 mg, 2.6 mmol) in anhydrous acetonitrile (14 mL) was treated with BrCN (3M/DCM, 1.06 mL, 1.24 eq) and $iPr_2NEt$ (0.53 mL, 1.19 eq). The reaction was stirred at RT for 18 h and then quenched with aq. $NH_3$ and extracted with DCM. The organic extracts were concentrated to give 67D (730 mg) as a white crystalline solid.

In a manner similar to that previously described, 67D was coupled with pyrimidine-5-boronic acid to provide (±)-67. MS m/z 285 (MH+).

The following compounds were prepared following procedures similar to those exemplified in the examples above.

| Cpd | Structure | LCMS (MH+) |
| --- | --- | --- |
| (±)-100 | 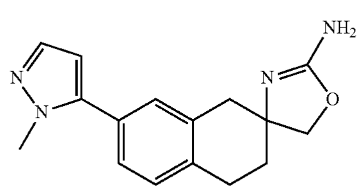 | 283 |

-continued

| Cpd | Structure | LCMS (MH+) |
|---|---|---|
| (±)-101 | 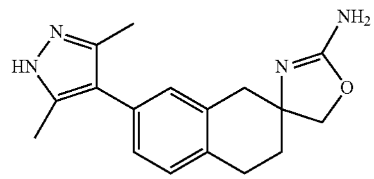 | 297 |
| (±)-102 | 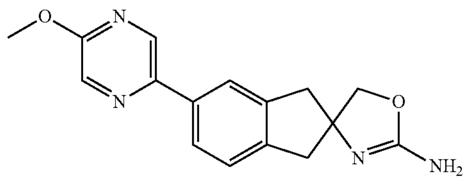 | 297 |
| (±)-103 | 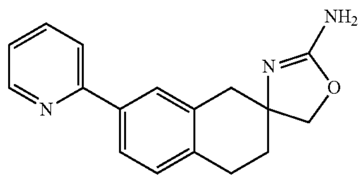 | 280 |
| (±)-104 | 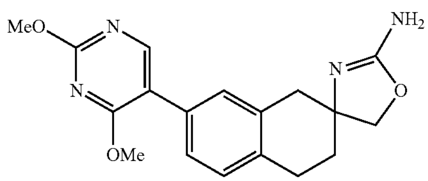 | 341 |
| (±)-105 | 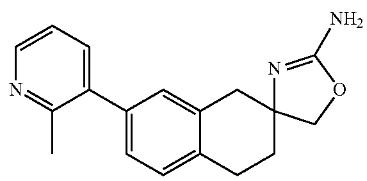 | 294 |
| (±)-106 | 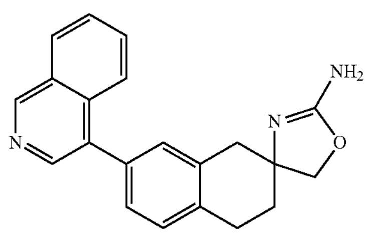 | 330 |
| (±)-107 | 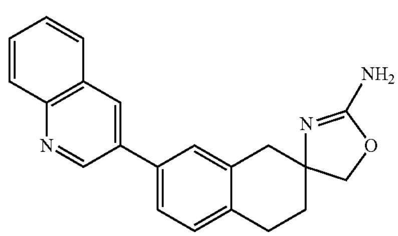 | 330 |
| (±)-108 | 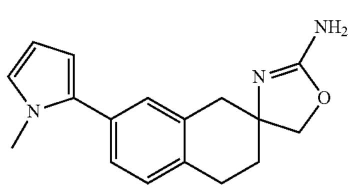 | 282 |

-continued

| Cpd | Structure | LCMS (MH+) |
|---|---|---|
| 109 | 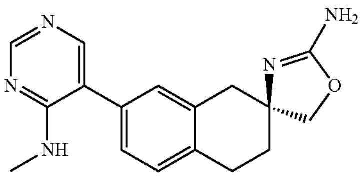 | 310 |
| 110 | 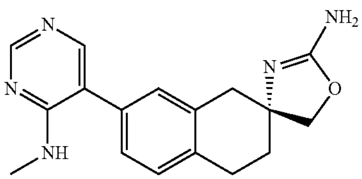 | 310 |
| 111 | 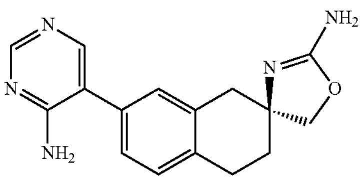 | 296 |
| (±)-112 | 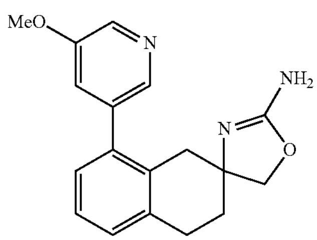 | 310 |
| (±)-113 | 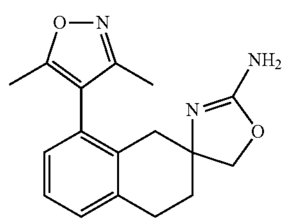 | 298 |
| (±)-114 | 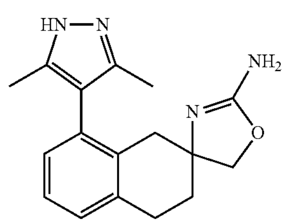 | 297 |
| 115 | 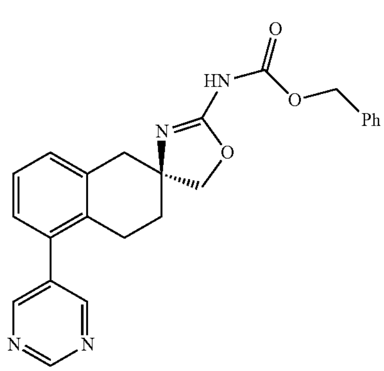 | 415 |

-continued

| Cpd | Structure | LCMS (MH+) |
|---|---|---|
| 116 | 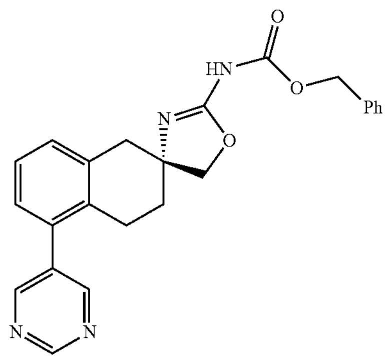 | 415 |
| 117 | 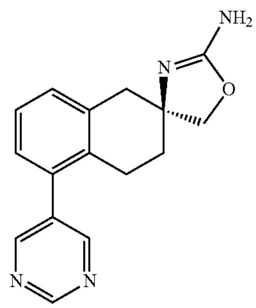 | 281 |
| 118 | 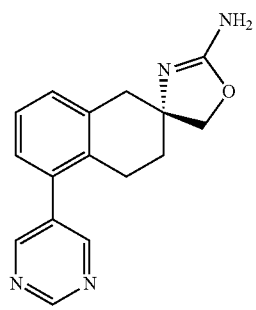 | 281 |
| 119 | 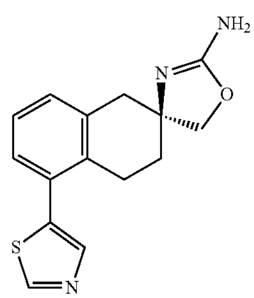 | 286 |
| 120 | 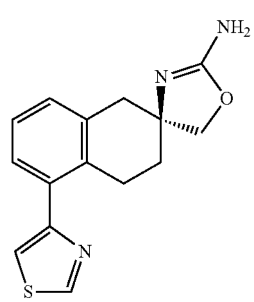 | 286 |

-continued
| Cpd | Structure | LCMS (MH+) |
|---|---|---|
| 121 | 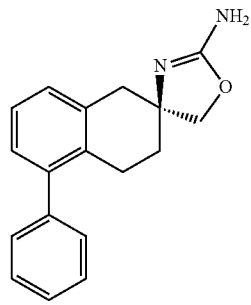 | 279 |
| 122 | 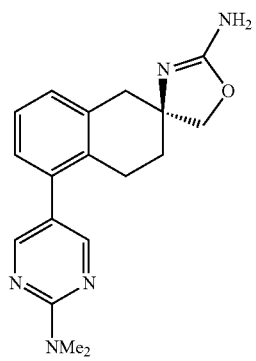 | 324 |
| 123 | 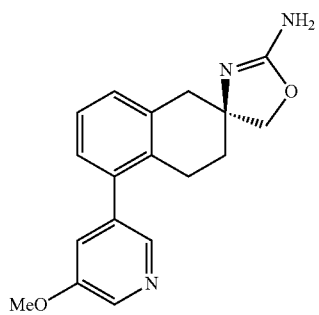 | 310 |
| 124 | 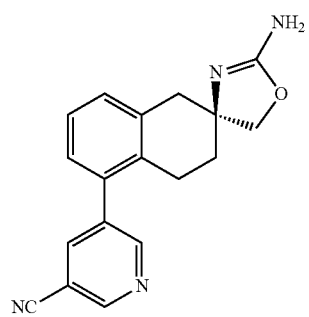 | 305 |

| Cpd | Structure | LCMS (MH+) |
|---|---|---|
| 125 | 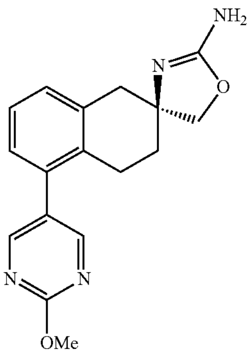 | 311 |
| 126 | 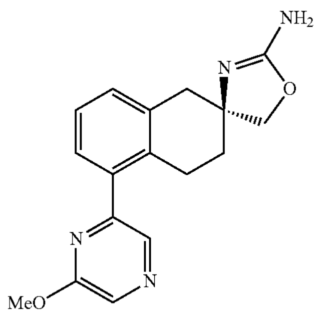 | 311 |
| (±)-127 | 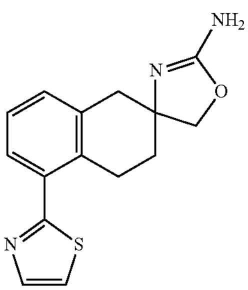 | 286 |
| (±)-128 | 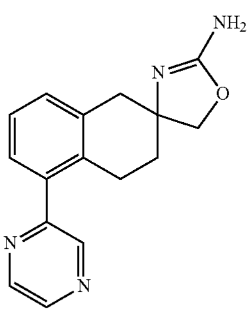 | 281 |
| (±)-129 | 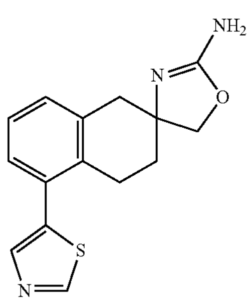 | 286 |

| Cpd | Structure | LCMS (MH+) |
|---|---|---|
| (±)-130 | 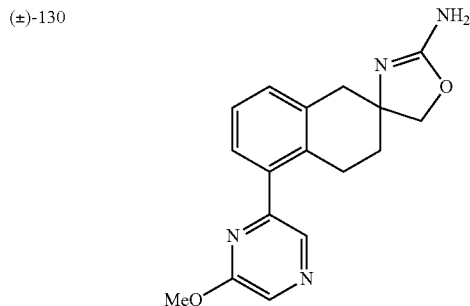 | 311 |
| (±)-131 | 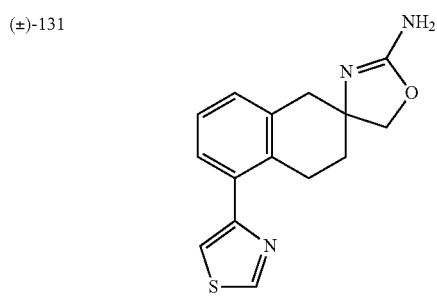 | 286 |
| (±)-132 | 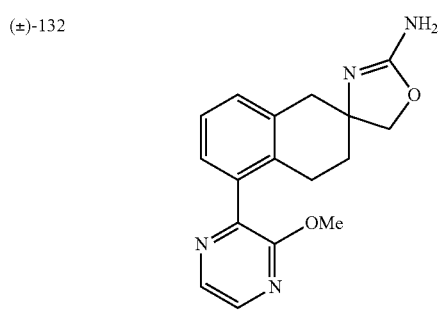 | 311 |
| (±)-133 | 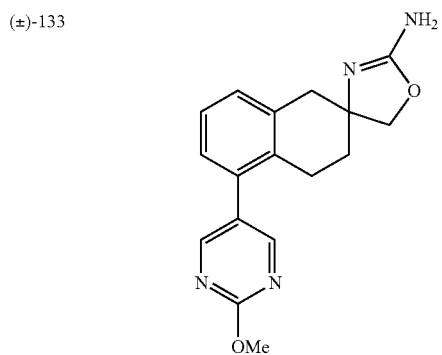 | 311 |

-continued

| Cpd | Structure | LCMS (MH+) |
|---|---|---|
| (±)-134 | 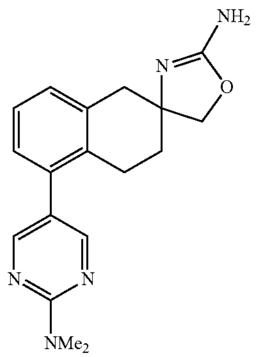 | 324 |
| 135 | 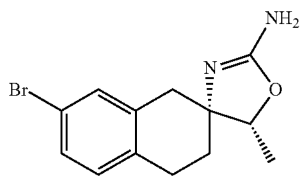 | 295/297 |
| 136 | 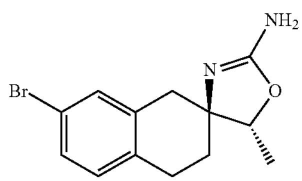 | 295/297 |
| 137 | 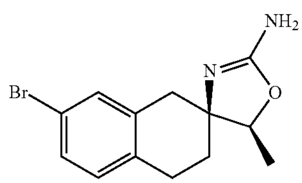 | 295/297 |
| 138 | 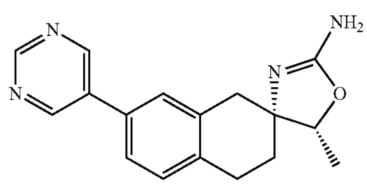 | 295 |
| 139 | 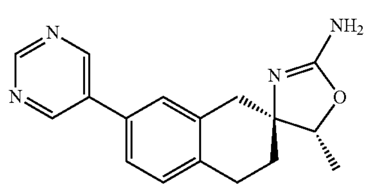 | 295 |
| 140 | 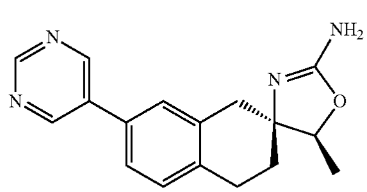 | 295 |

-continued

| Cpd | Structure | LCMS (MH+) |
|---|---|---|
| 141 | 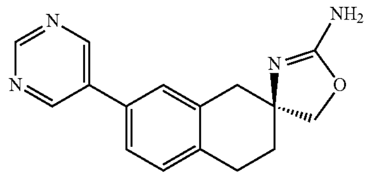 | 281 |
| 142 | 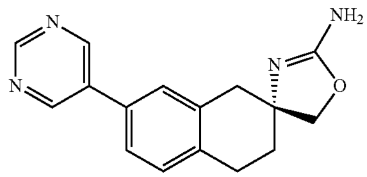 | 281 |
| 143 | 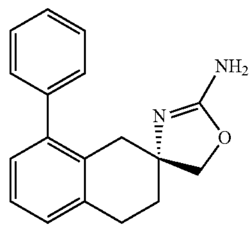 | 279 |
| 144 | 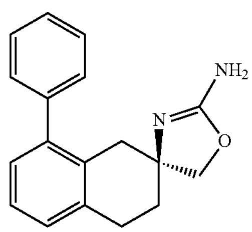 | 279 |
| 145 | 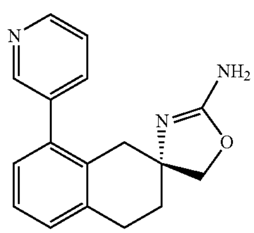 | 280 |
| 146 | 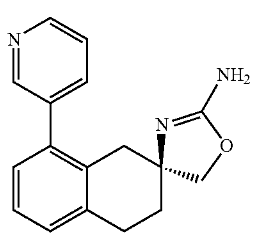 | 280 |
| 147 | 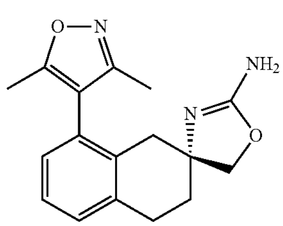 | 298 |

-continued

| Cpd | Structure | LCMS (MH+) |
|---|---|---|
| 148 | 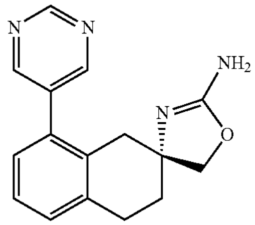 | 281 |
| 149 | 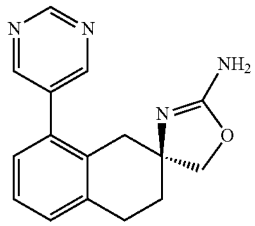 | 281 |
| 150 | 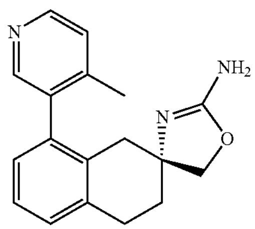 | 294 |
| 151 | 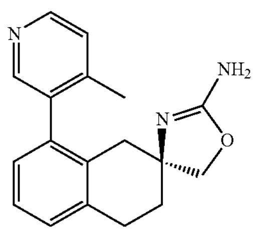 | 294 |
| 152 | 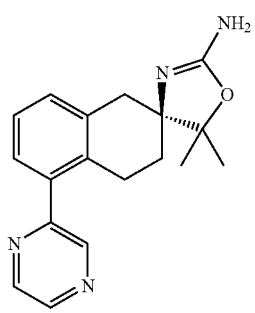 | 309 |
| 153 | 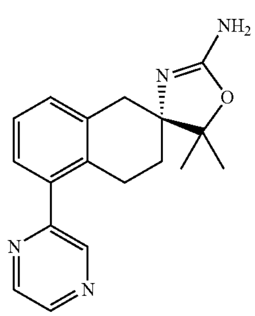 | 309 |

-continued

| Cpd | Structure | LCMS (MH+) |
| --- | --- | --- |
| (±)-154 | 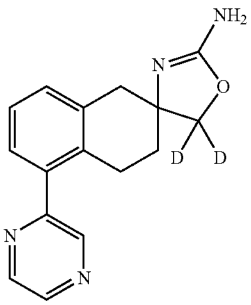 | 283 |
| (±)-155 | 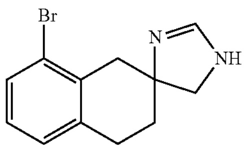 | 265/267 |
| (±)-156 | 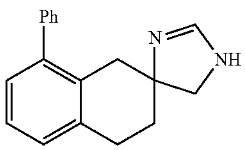 | 263 |
| (±)-157 | 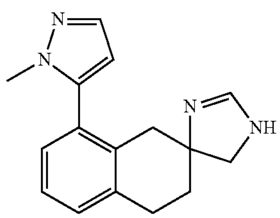 | 267 |
| (±)-158 | 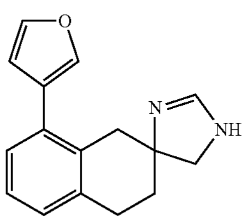 | 253 |
| (±)-159 | 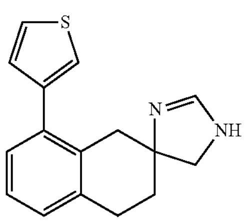 | 269 |
| (±)-160 | 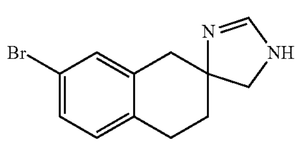 | 265/267 |
| (±)-161 | 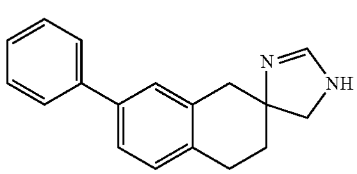 | 263 |

| Cpd | Structure | LCMS (MH+) |
| --- | --- | --- |
| (±)-162 | 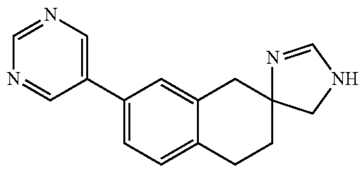 | 265 |
| (±)-163 | 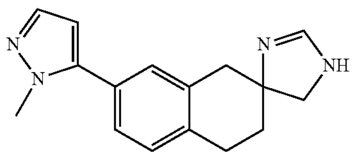 | 267 |
| (±)-164 | 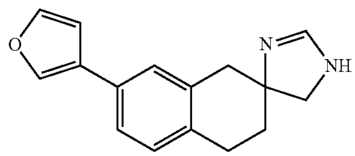 | 253 |
| (±)-165 | 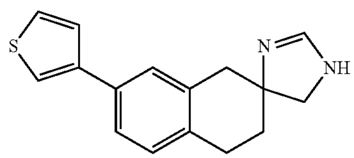 | 269 |
| (±)-166 | 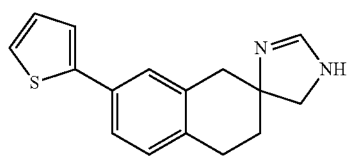 | 269 |
| (±)-167 | 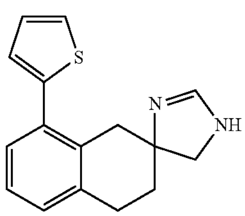 | 269 |
| (±)-168 | 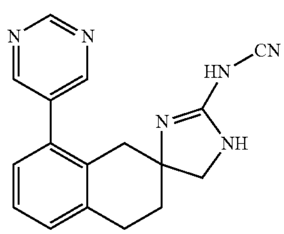 | 305 |
| (±)-169 | 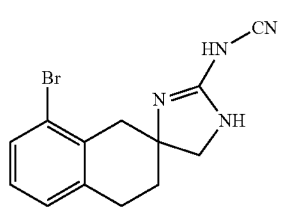 | 305/307 |

-continued
| Cpd | Structure | LCMS (MH+) |
|---|---|---|
| (±)-170 | 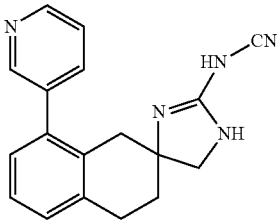 | 304 |
| (±)-171 | 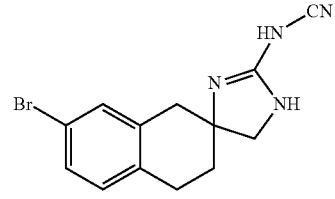 | 305/307 |
| (±)-172 | 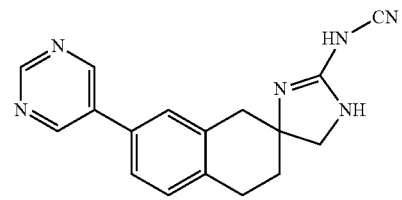 | 305 |
| (±)-173 | 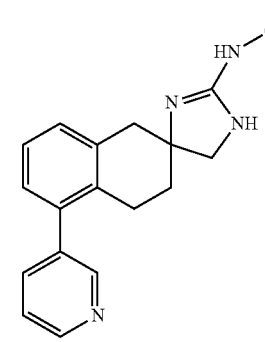 | 304 |
| (±)-174 | 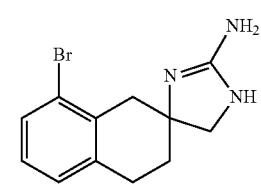 | 280/282 |
| (±)-175 | 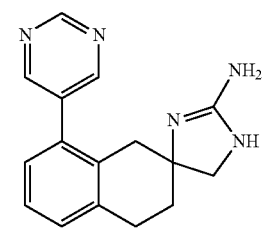 | 280 |

-continued

| Cpd | Structure | LCMS (MH+) |
|---|---|---|
| (±)-176 | 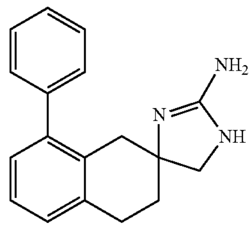 | 278 |
| (±)-177 | 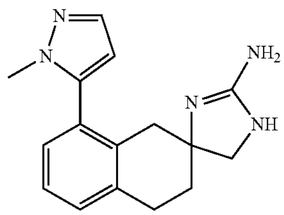 | 282 |
| (±)-178 | 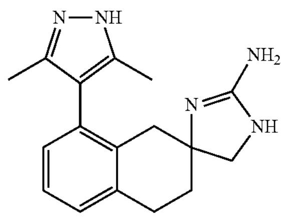 | 296 |
| (±)-179 | 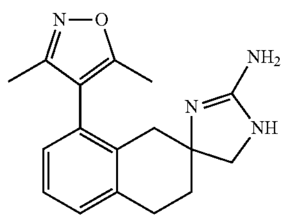 | 297 |
| (±)-180 | 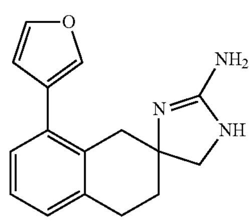 | 268 |
| (±)-181 | 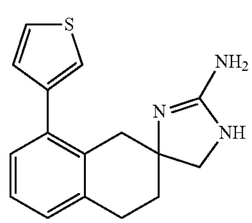 | 284 |
| (±)-182 | 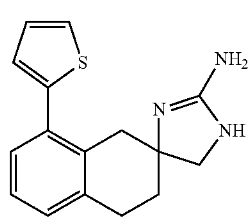 | 284 |

-continued

| Cpd | Structure | LCMS (MH+) |
|---|---|---|
| (±)-183 | 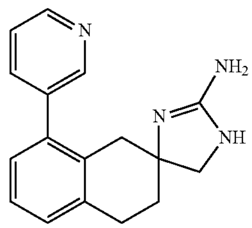 | 279 |
| (±)-184 | 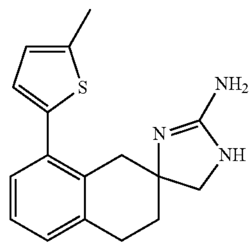 | 298 |
| (±)-185 | 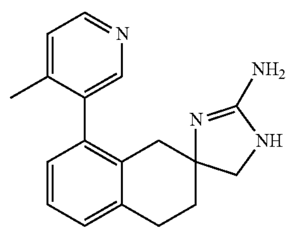 | 293 |
| (±)-186 | 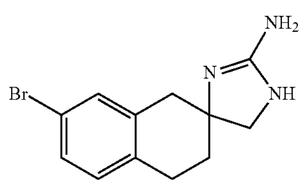 | 280/282 |
| (±)-187 | 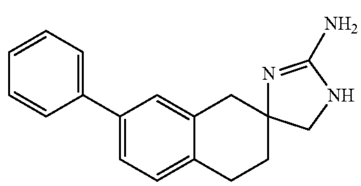 | 278 |
| (±)-188 | 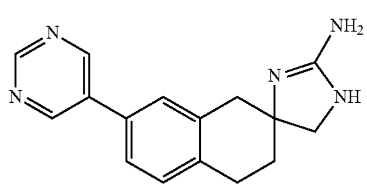 | 280 |
| (±)-189 | 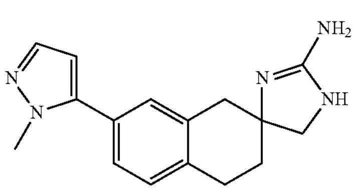 | 282 |

| Cpd | Structure | LCMS (MH+) |
|---|---|---|
| (±)-190 | 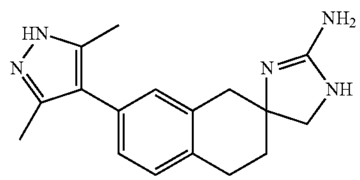 | 296 |
| (±)-191 | 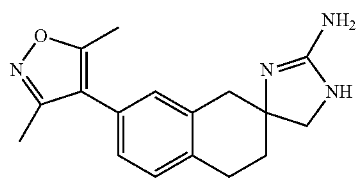 | 297 |
| (±)-192 | 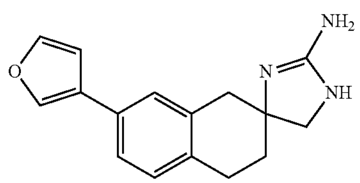 | 268 |
| (±)-193 | 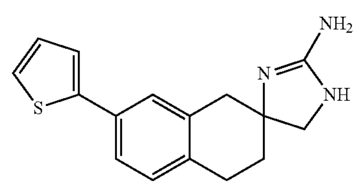 | 284 |
| (±)-194 | 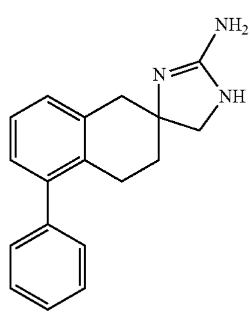 | 278 |
| (±)-195 | 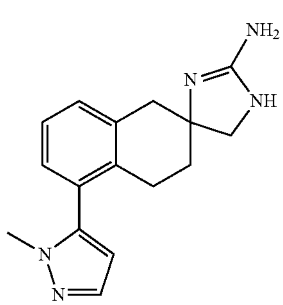 | 282 |

-continued

| Cpd | Structure | LCMS (MH+) |
|---|---|---|
| (±)-196 | 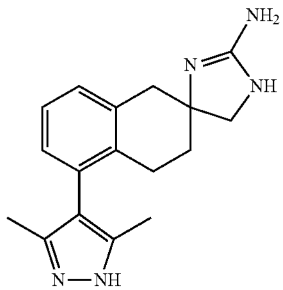 | 296 |
| (±)-197 | 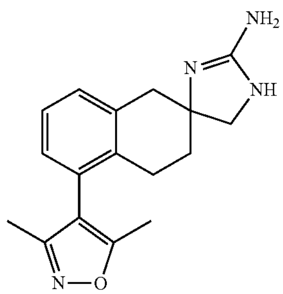 | 297 |
| (±)-198 | 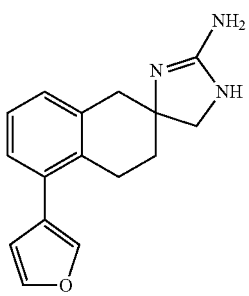 | 268 |
| (±)-199 | 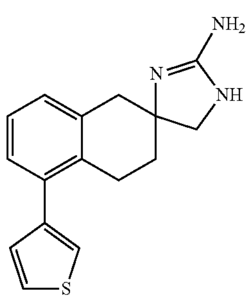 | 284 |
| (±)-200 | 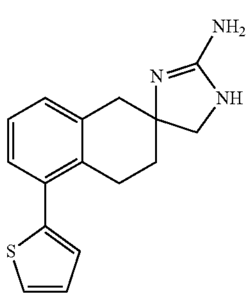 | 284 |

-continued
| Cpd | Structure | LCMS (MH+) |
|---|---|---|
| (±)-201 | 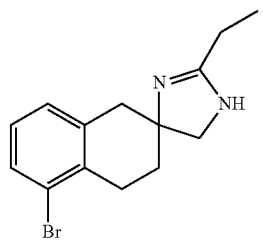 | 293/295 |
| (±)-202 | 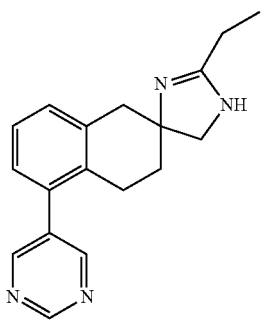 | 293 |
| (±)-203 | 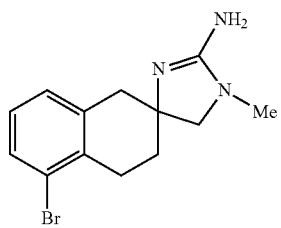 | 294/296 |
| (±)-204 | 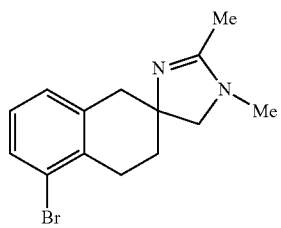 | 293/295 |
| (±)-205 | 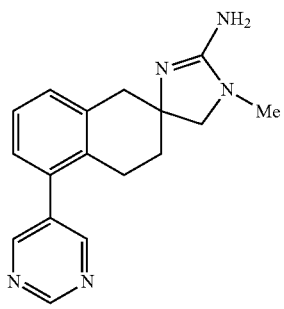 | 294 |

-continued

| Cpd | Structure | LCMS (MH+) |
|---|---|---|
| (±)-206 | 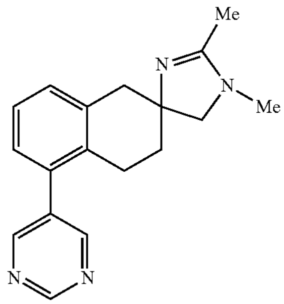 | 293 |
| (±)-207 | 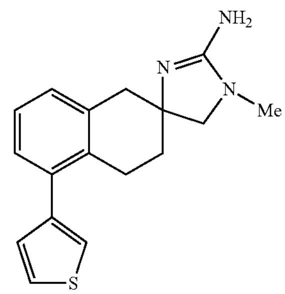 | 298 |
| (±)-208 | 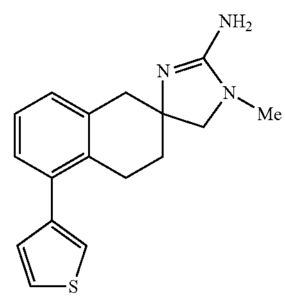 | 297 |
| (±)-209 | 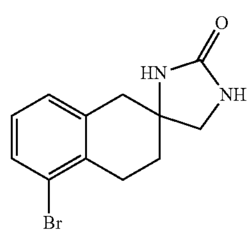 | 281/283 |
| (±)-210 | 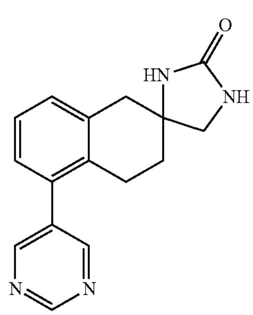 | 281 |

-continued

| Cpd | Structure | LCMS (MH+) |
|---|---|---|
| (±)-211 | 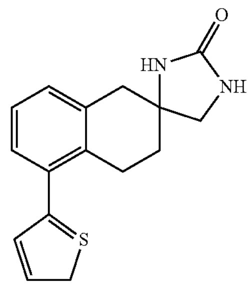 | 285 |
| 212 | 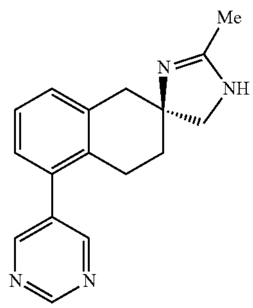 | 279 |
| 213 | 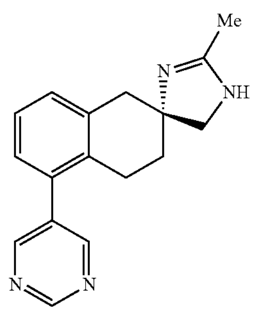 | 279 |
| 214 | 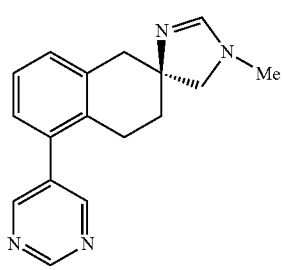 | 279 |
| 215 | 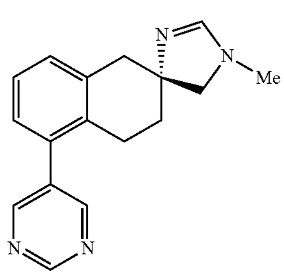 | 279 |

-continued

| Cpd | Structure | LCMS (MH+) |
|---|---|---|
| 216 | 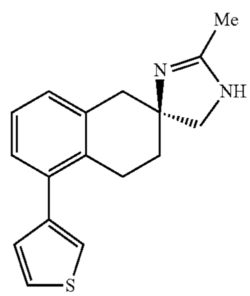 | 283 |
| 217 | 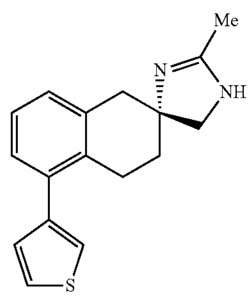 | 283 |
| 218 | 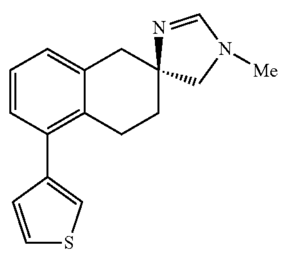 | 283 |
| 219 | 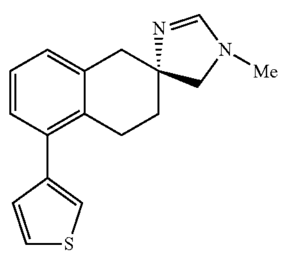 | 283 |
| 220 | 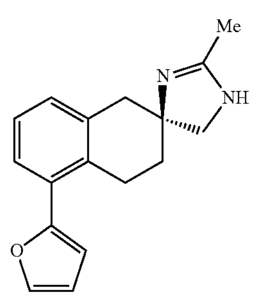 | 267 |

-continued

| Cpd | Structure | LCMS (MH+) |
|---|---|---|
| 221 | 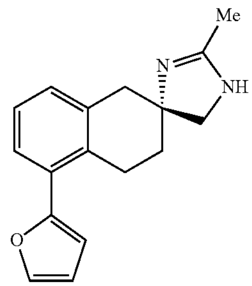 | 267 |
| 222 | 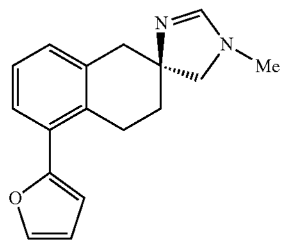 | 267 |
| 223 | 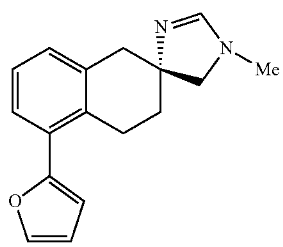 | 267 |
| 224 | 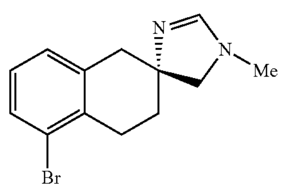 | 279/281 |
| 225 | 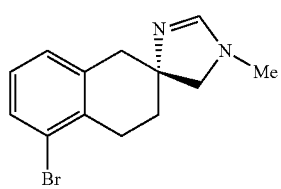 | 279/281 |
| 227 | 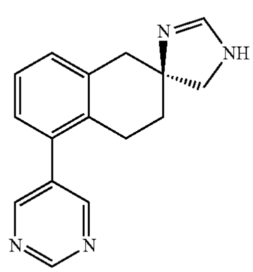 | 265 |

-continued

| Cpd | Structure | LCMS (MH+) |
|---|---|---|
| 228 | 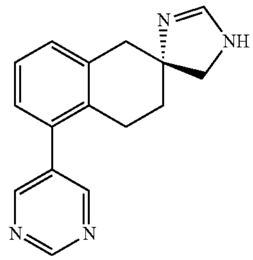 | 265 |
| 229 | 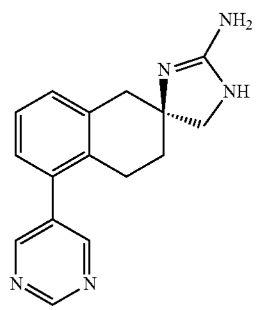 | 280 |
| 230 | 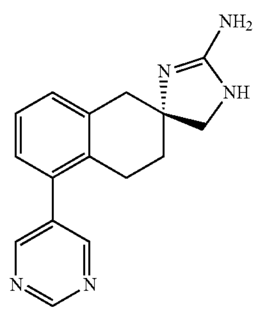 | 280 |
| 231 | 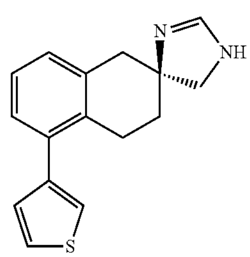 | 269 |
| 232 | 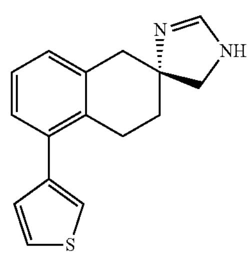 | 269 |

-continued

| Cpd | Structure | LCMS (MH+) |
|---|---|---|
| 233 | 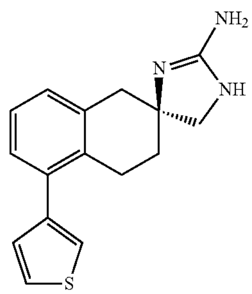 | 284 |
| 234 | 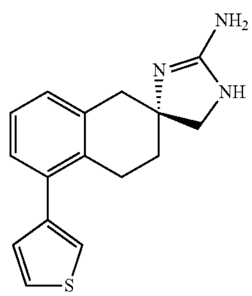 | 284 |
| 235 | 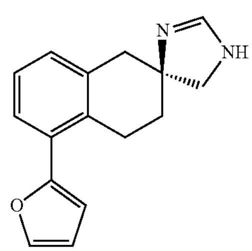 | 253 |
| 236 | 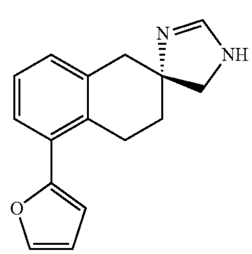 | 253 |
| 237 | 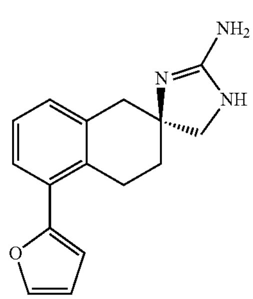 | 268 |

-continued

| Cpd | Structure | LCMS (MH+) |
| --- | --- | --- |
| 238 | 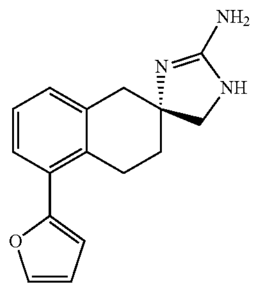 | 268 |
| 239 | 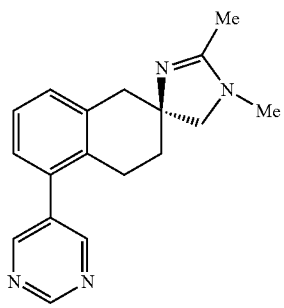 | 293 |
| 240 | 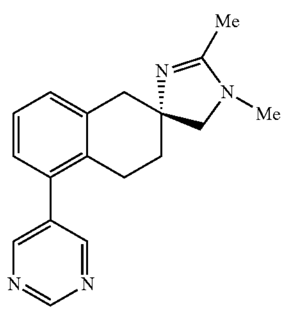 | 293 |
| 241 | 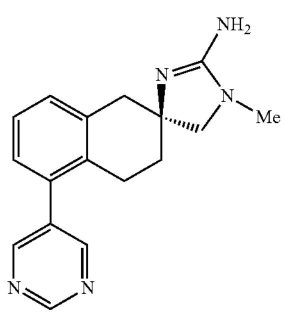 | 294 |
| 242 | 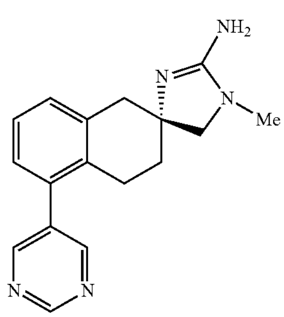 | 294 |

-continued

| Cpd | Structure | LCMS (MH+) |
|---|---|---|
| 243 | 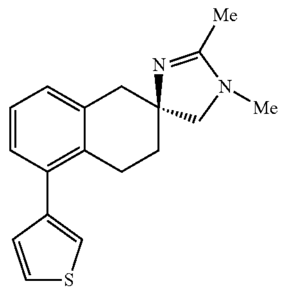 | 297 |
| 244 | 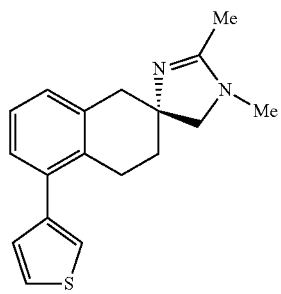 | 297 |
| 245 | 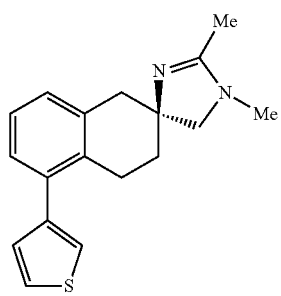 | 298 |
| 246 | 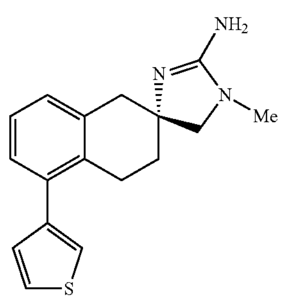 | 298 |
| 247 | 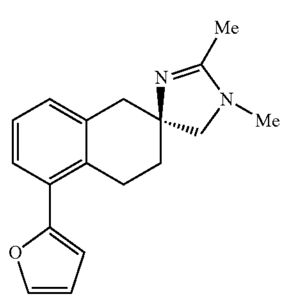 | 281 |

-continued

| Cpd | Structure | LCMS (MH+) |
|---|---|---|
| 248 | 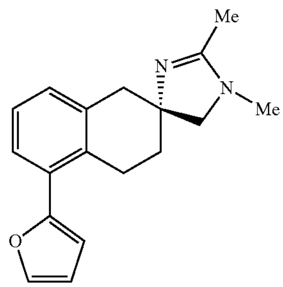 | 281 |
| 249 | 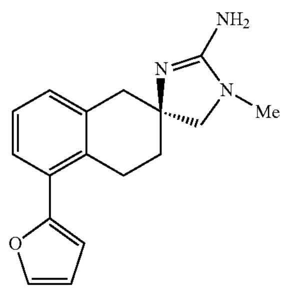 | 282 |
| 250 | 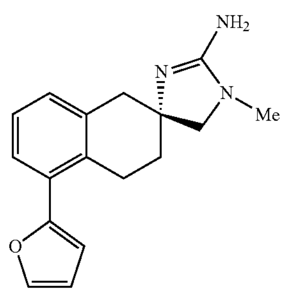 | 282 |
| 251 | 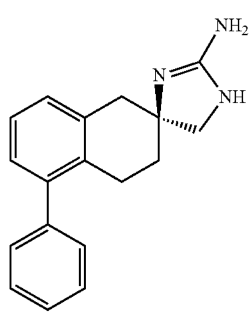 | 278 |
| 252 | 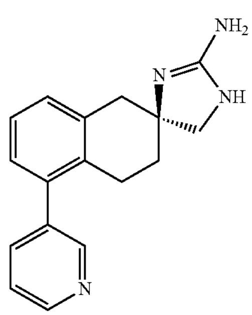 | 279 |

-continued

| Cpd | Structure | LCMS (MH+) |
|---|---|---|
| 253 | 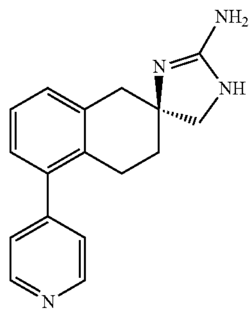 | 279 |
| 254 | 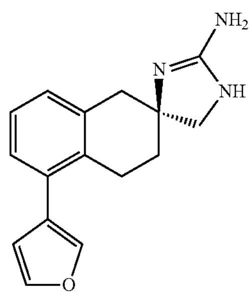 | 268 |
| 255 | 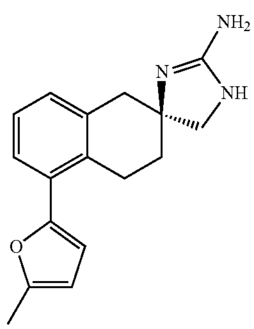 | 282 |
| 256 | 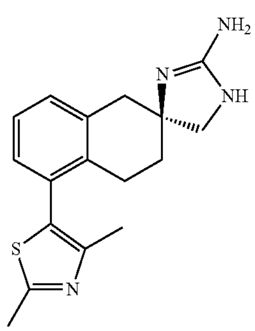 | 313 |
| 257 | 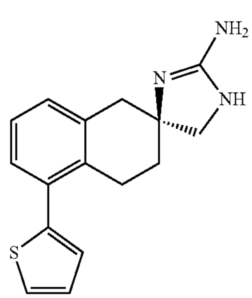 | 284 |

-continued
| Cpd | Structure | LCMS (MH+) |
|---|---|---|
| 258 | 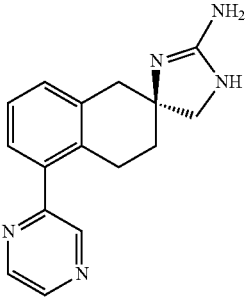 | 280 |
| 259 | 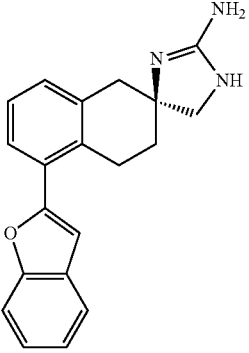 | 318 |
| 260 | 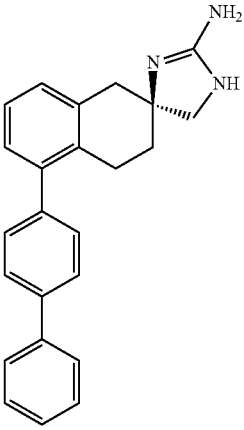 | 355 |
| 261 | 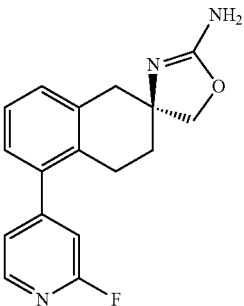 | 298 |

-continued

| Cpd | Structure | LCMS (MH+) |
|---|---|---|
| 262 | 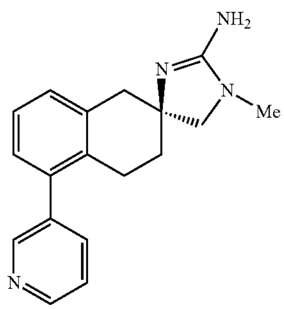 | 293 |
| (±)-263 | 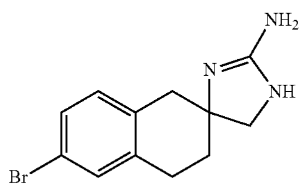 | 280/282 |
| (±)-264 | 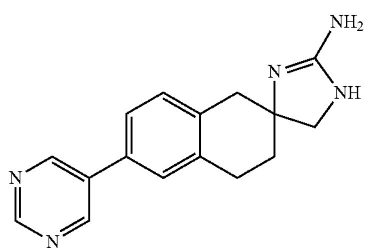 | 280 |
| (±)-265 | 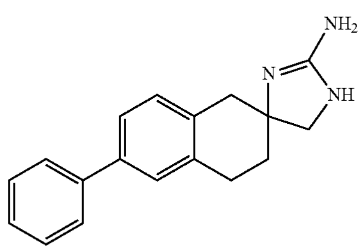 | 278 |
| (±)-266 | 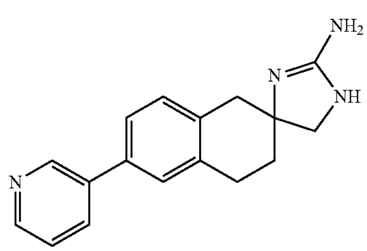 | 279 |
| (±)-267 | 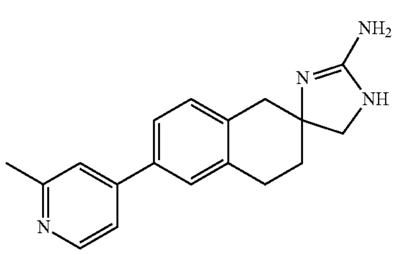 | 293 |

-continued

| Cpd | Structure | LCMS (MH+) |
|---|---|---|
| (±)-268 | 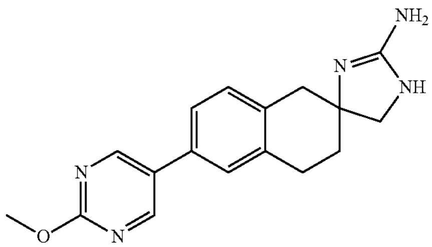 | 310 |
| (±)-269 | 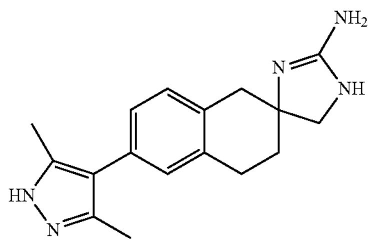 | 296 |
| (±)-270 | 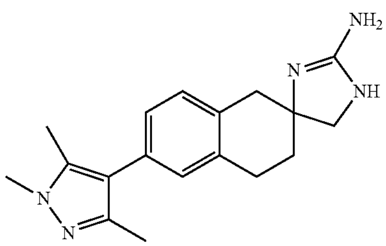 | 310 |
| (±)-271 | 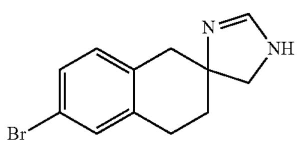 | 265/267 |
| (±)-272 | 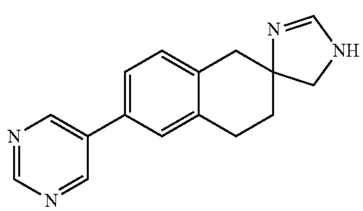 | 265 |
| (±)-273 | 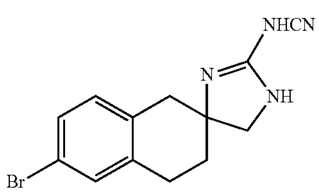 | 305/307 |
| (±)-274 | 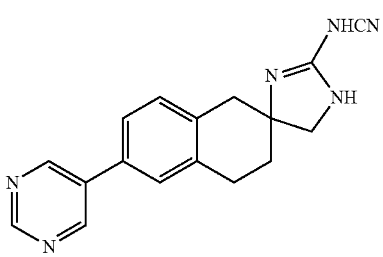 | 305 |

-continued

| Cpd | Structure | LCMS (MH+) |
|---|---|---|
| (±)-275 | 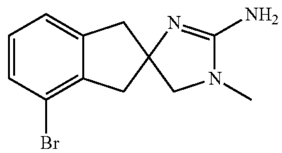 | 280/282 |
| (±)-276 | 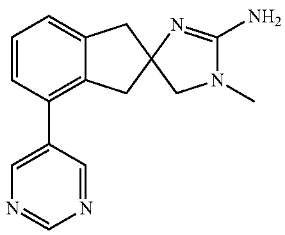 | 280 |
| (±)-277 | 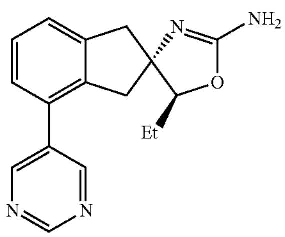 | 295 |
| (±)-278 | 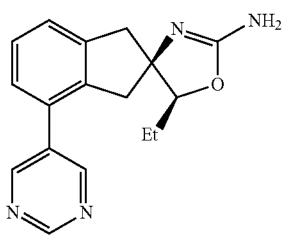 | 295 |
| (±)-279 | 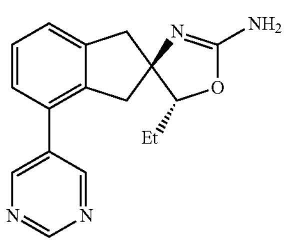 | 295 |
| (±)-280 | 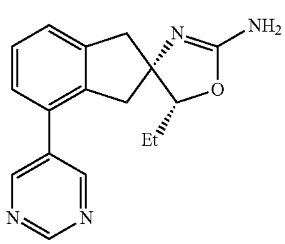 | 295 |

-continued

| Cpd | Structure | LCMS (MH+) |
|---|---|---|
| (±)-281 | 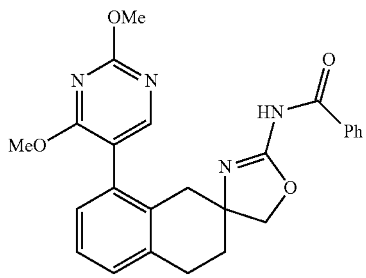 | 445 |
| (±)-282 | 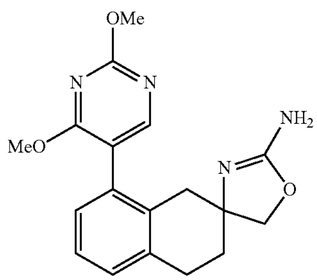 | 341 |
| (±)-283 | 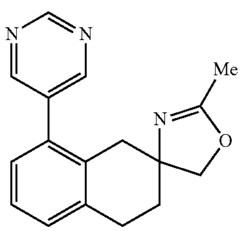 | 280 |
| (±)-284 | 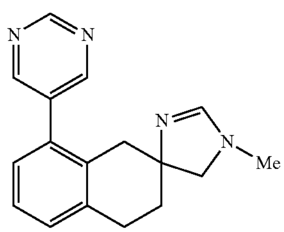 | 279 |
| (±)-285 | 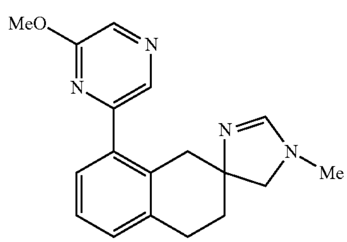 | 309 |
| (±)-286 | 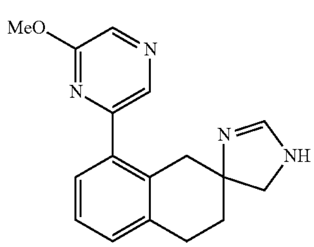 | 295 |

-continued

| Cpd | Structure | LCMS (MH+) |
|---|---|---|
| (±)-287 | 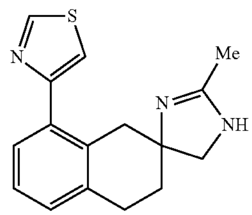 | 284 |
| 288 | 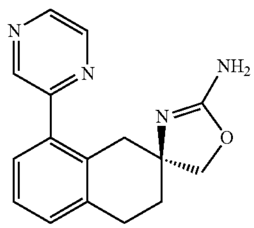 | 281 |
| (±)-289 | 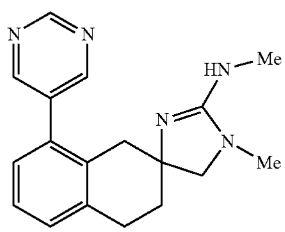 | 308 |
| (±)-290 | 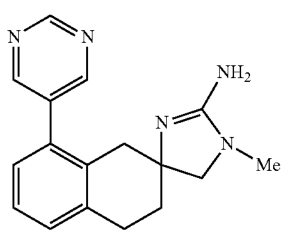 | 294 |
| (±)-291 | 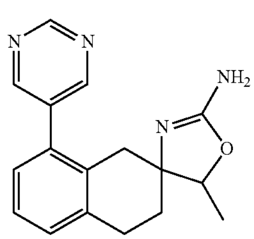 | 295 |
| (±)-292 | 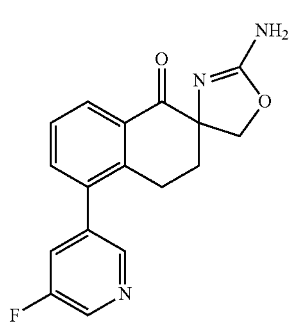 | 312 |

| Cpd | Structure | LCMS (MH+) |
|---|---|---|
| (±)-293 | 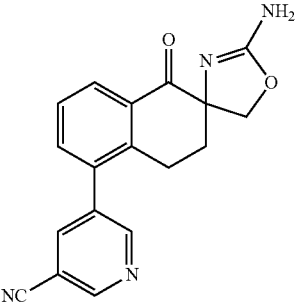 | 319 |
| (±)-294 | 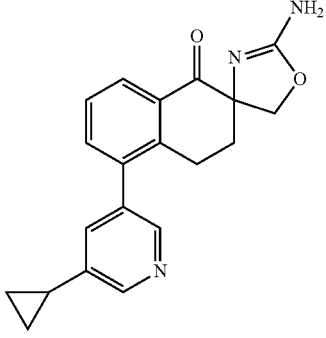 | 334 |
| (±)-295 | 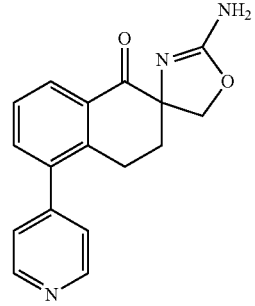 | 294 |
| (±)-296 | 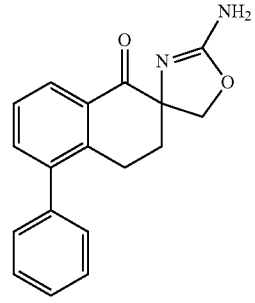 | 293 |
| (±)-297 | 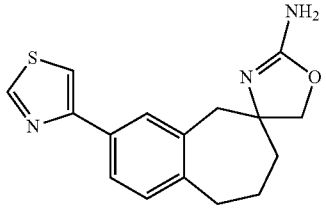 | 300 |

-continued

| Cpd | Structure | LCMS (MH+) |
|---|---|---|
| 298 | 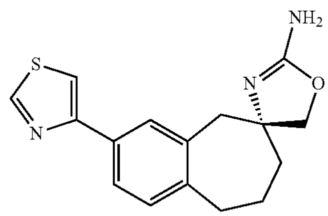 | 300 |
| 299 | 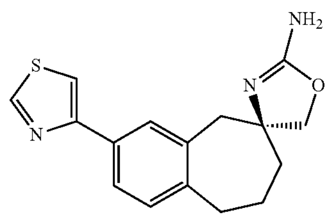 | 300 |
| (±)-300 | 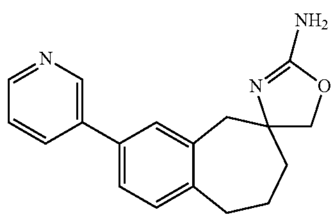 | 294 |
| 301 | 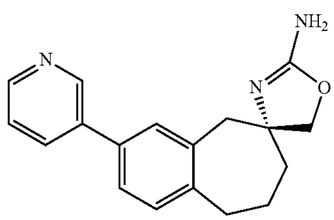 | 294 |
| 302 | 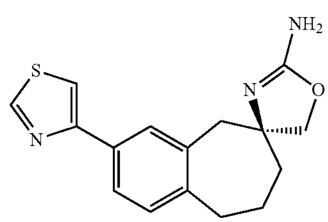 | 294 |
| (±)-303 | 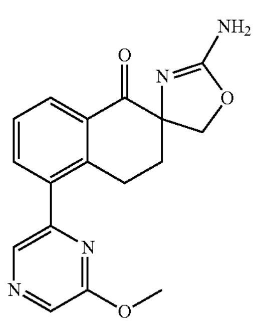 | 325 |

-continued

| Cpd | Structure | LCMS (MH+) |
|---|---|---|
| 304 | 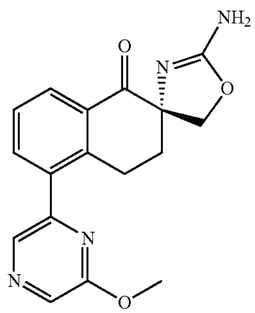 | 325 |
| 305 | 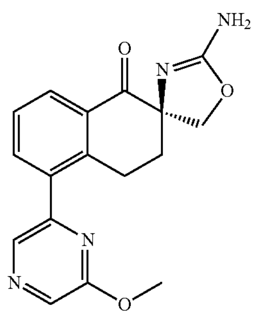 | 325 |
| (±)-306 | 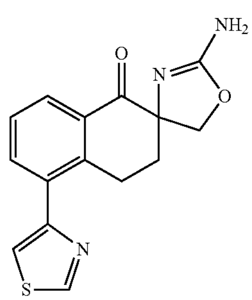 | 300 |
| 307 | 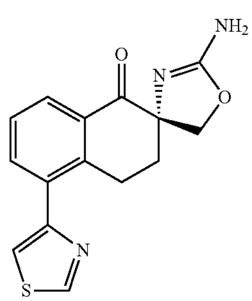 | 300 |
| 308 | 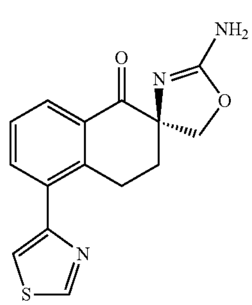 | 300 |

-continued

| Cpd | Structure | LCMS (MH+) |
|---|---|---|
| (±)-309 | 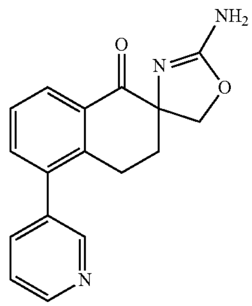 | 294 |
| (±)-310 | 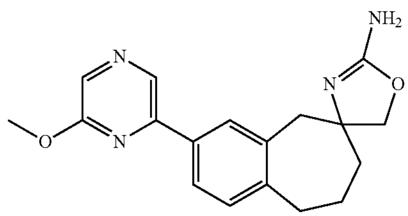 | 325 |
| 311 | 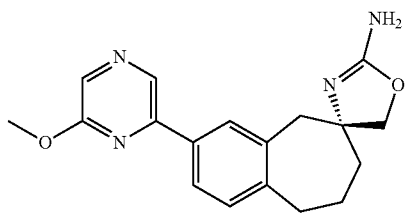 | 325 |
| 312 | 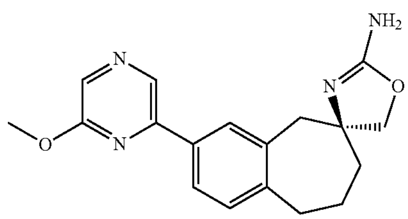 | 325 |
| 313 | 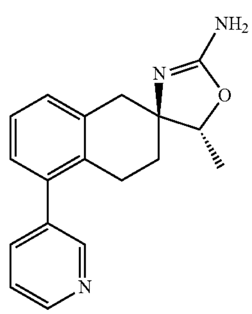 | 294 |
| 314 | 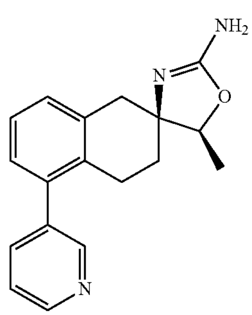 | 294 |

-continued

| Cpd | Structure | LCMS (MH+) |
|---|---|---|
| 315 | 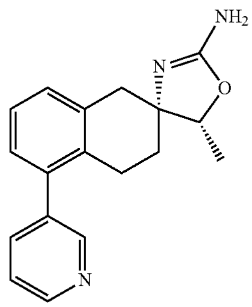 | 294 |
| 316 | 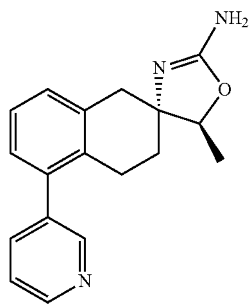 | 294 |
| 317 | 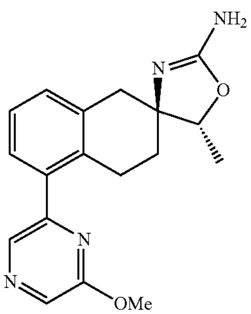 | 325 |
| 318 | 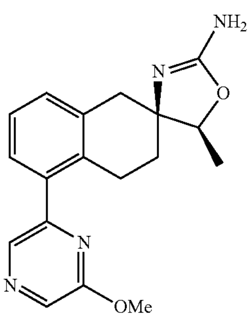 | 325 |
| 319 | 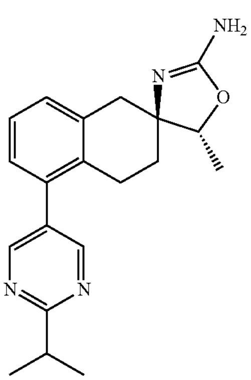 | 337 |

-continued
| Cpd | Structure | LCMS (MH+) |
|---|---|---|
| 320 | 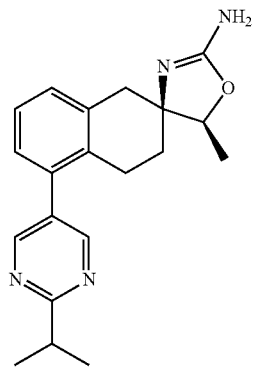 | 337 |
| 321 | 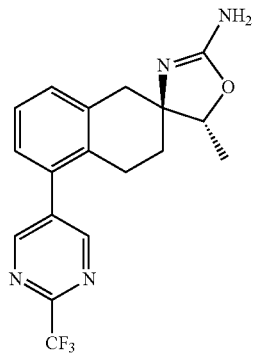 | 363 |
| 322 | 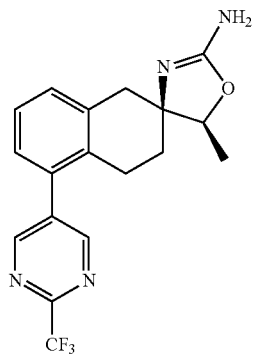 | 363 |
| 323 | 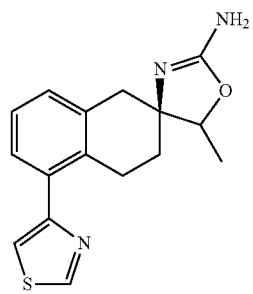 | 300 |

| Cpd | Structure | LCMS (MH+) |
|---|---|---|
| 324 | 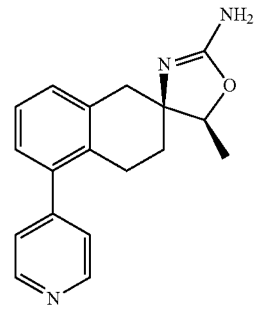 | 294 |
| (±)-325 | 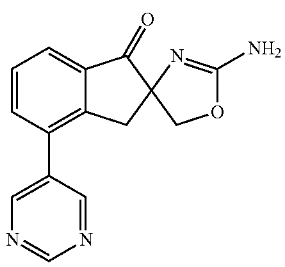 | 281 |

Assay:

Efficacy agonist activity values (Emax, GTPγS assay) for α2A and α2C were determined by following the general procedure detailed by Umland et. al ("Receptor reserve analysis of the human $\alpha_{2c}$-adrenoceptor using [$^{35}$S]GTPγS and cAMP functional assays" European Journal of Pharmacology 2001, 411, 211-221). For the purposes of the present invention, a compound is defined to be a specific or at least functionally selective agonist of the α2C receptor subtype if the compound's efficacy at the α2C receptor is ≧30% Emax (GTPγS assay) and its efficacy at the α2A receptor is ≦35% Emax (GTPγS assay). Additionally, for the purposes of this invention, a compound is defined to be an antagonist of the α2C receptor subtype if the compound's efficacy at the α2C receptor is <30% Emax (GTPγS assay) and the $K_i$ at the α2C receptor subtype was <500 nM, preferentially <200 nM, and most preferentially <20 nM.

The following compounds were evaluated to be active or functionally selective agonists of the α2C receptor subtype based on the previously defined definition:

(±)-1, (±)-1H, 2D, 2E, (±)-4, (±)-5H, (±)-5L, (±)-7A, (±)-7B, (±)-7C, (±)-10, (±)-15A, (±)-15C, (±)-17, (±)-18A, (±)-20, 21H, 21L, 21M, 21N, 21O, 22, 22E, 22F, 22G, (±)-23, (±)-23C, (±)-23D, (±)-24, 24F, 24H, 24I, 26, 26D, 28G, (±)-29, (±)-29A, (±)-30, 30D, 30F, (±)-34A, (±)-34I, (±)-34J, (±)-34K, (±)-37, (±)-37I, (±)-38, 38E, 38F, 38G, 38H, 38I, 38J, (±)-41, (±)-41D, (±)-41F, (±)-41G, (±)-41H, (±)-43, (±)-44, (±)-45, (±)-46, (±)-50, 51D, 51E, (±)-52, 52F, (±)-53, 53F, 53H, 54I, (±)-56, (±)-100, (±)-103, (±)-105, 110, 117, 118, 120, 121, 122, 123, 126, (±)-127, (±)-128, (±)-130, (±)-131, (±)-132, 141, 144, 146, (±)-154, (±)-159, (±)-165, (±)-175, (±)-194, (±)-205, (±)-206, (±)-207, 212, 214, 215, 216, 220, 222, 227, 228, 229, 230, 231, 233, 235, 237, 239, 240, 241, 242, 245, 249, 251, 252, 253, 254, 257, 259, 260, 261, 262, (±)-276, (±)-284, (±)-287, 288, (±)-290, 307, 309, 312, 313, and 323.

The following compounds were evaluated to be an antagonist of the α2C receptor subtype based on the previously defined definition ($K_i$<200 nM):

(±)-1G, (±)-3, (±)-3D, (±)-6J, (±)-6K, (±)-6L, (±)-8, (±)-8E, (±)-8I, (±)-8R, (±)-8S, (±)-10B, (±)-11, (±)-16, 21I, 21J, 21K, 25F, 25G, (±)-34D, (±)-50K, (±)-50L, (±)-50M, (±)-57, (±)-58, (±)-101, (±)-112, (±)-113, (±)-114, 119, (±)-129, (±)-133, 142, 143, 145, 149, 150, 151, 213, and 238.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by Formula I

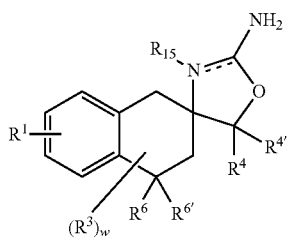

or a pharmaceutically acceptable salt thereof
wherein:
wherein ----- is a single bond when $R^{15}$ is present and is a double bond when $R^{15}$ is not present;
$R^1$ is a ring selected from the group consisting of cycloalkyl, cycloalkenyl, aryl, heterocyclyl, heterocyclenyl, and heteroaryl, each of which is optionally substituted with at least one $R^{12}$;
$R^3$ is independently selected from the group consisting of H, —OH, halo, —CN, —NO$_2$, —S(O)$_p$R$^7$, —NR$^7$R$^{7'}$, —S(O)$_p$NR$^7$R$^{7'}$, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$, provided that when w is 3, no more than 2 of the $R^3$ groups may be (=O);

$R^4$ is independently selected from the group consisting of H, D, —OH, halo, —CN, —S(O)$_p$R$^7$, —NR$^7$R$^{7'}$ and —S(O)$_p$NR$^7$R$^{7'}$, and alkyl, deuterated alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^{4'}$ is independently selected from the group consisting of H, D, halo, —OH, and alkyl, deuterated alkyl and alkoxy; or $R^4$ and $R^{4'}$ may be taken together to form (=O);

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O) groups, $R^6$ is selected from the group consisting of H, —OH, halo, —CN, —NO$_2$, —S(O)$_p$R$^7$, —NR$^7$R$^{7'}$, —S(O)$_p$NR$^7$R$^{7'}$, —C(O)—R$^{10}$, —C(O)—OR$^{10}$, and —C(O)—N(R$^7$)R$^{10}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with one or more moieties which are halo, —OH, —CN, —NO$_2$, —NR$^7$R$^{7'}$, —S(O)$_p$R$^7$ up to 2 (=O) groups, —C(=O)R$^7$, —C(=O)OR$^7$, —C(=O)NR$^7$R$^{7'}$, —SO$_2$R$^7$ or —SO$_2$NR$^7$R$^{7'}$;

$R^{6'}$ is selected from the group consisting of H, —S(O)$_p$R$^7$, —S(O)$_p$NR$^7$R$^{7'}$, —C(O)—R$^{10}$, —C(O)—OR$^{10}$, —C(O)—N(R$^7$)R$^{10}$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with one or more moieties which are halo, —OH, —CN, —NO$_2$, —NR$^7$R$^{7'}$, —S(O)$_p$R$^7$ up to 2 (=O) groups, —C(=O)R$^7$, —C(=O)OR$^7$, —C(=O)NR$^7$R$^{7'}$, —SO$_2$R$^7$ or —SO$_2$NR$^7$R$^{7'}$; or $R^6$ and $R^{6'}$ may be taken together to form (=O);

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$; or a) when a variable is —NR$^7$R$^{7'}$, —C(O)NR$^7$R$^{7'}$ or —SO$_2$NR$^7$R$^{7'}$, R$^7$ and R$^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected $R^{12}$ moieties and/or 1 or 2 (=O) groups, or b) when a variable is —(CH$_2$)$_q$ON=CR$^7$R$^{7'}$, R$^7$ and R$^{7'}$ together with the carbon atom to which they are attached independently form a 3- to 8-membered cycloalkyl, cycloalkenyl, aryl, heterocyclyl, heterocyclenyl or heteroaryl ring, wherein said heterocyclyl, heterocyclenyl or heteroaryl rings have 1-3 heteroatoms which are independently selected from the group consisting of O, N, —N(R$^9$)— and S, wherein said rings are optionally substituted by 1 to 5 independently selected $R^{12}$ moieties and/or 1 or 2 (=O) groups, $R^9$ is independently selected from the group consisting of H, —C(O)—R$^{10}$, —C(O)—OR$^{10}$, and —S(O)$_p$—R$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O) groups; and $R^{10}$ is independently selected from the group consisting of H, and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N(R$^{11'}$)$_2$, and —S(O)$_p$R$^{11'}$ and/or 1 or 2 (=O) groups;

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N(R$^{11}$)$_2$, —C(O)—OR$^{14}$, —N(R$^{14}$)—C(O)—R$^{14}$, —N(R$^{14}$)—C(O)$_2$—R$^{14}$, —C(O)—N(R$^{11}$)$_2$, —N(R$^{14}$)—S(O)$_2$—R$^{11}$, —S(O)$_2$—N(R$^{11}$)$_2$ and —S(O)$_p$R$^{11}$ and/or 1 or 2 (=O) groups, and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O) groups, wherein said optionally substituted alkoxy, aryloxy, optionally substituted cycloalkoxy, optionally substituted heteroaryloxy, and heterocyclenyloxy when substituted are substituted one or more times by $R^{11}$;

$R^{14}$ is independently H, alkyl, or aryl;

$R^{15}$ is absent or is independently selected from the group consisting of H, —C(O)—R$^{10}$, —C(O)—OR$^{10}$, —C(O)—N(R$^7$)(R$^{7'}$), and —S(O)$_p$—R$^{10}$, SO$_2$—NR$^7$R$^{7'}$ and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ and/or 1 or 2 (=O) groups substituents, and —C(=O)R$^7$, —C(=O)OR$^7$, —C(=O)NR$^7$R$^{7'}$, —SO$_2$R and —SO$_2$NR$^7$R$^{7'}$;

q is independently an integer from 0-10;

p is independently an integer from 0-2; and w is an integer from 0-3.

2. The compound according to claim 1 wherein

R$^1$ is optionally substituted aryl, optionally substituted arylalkyl, optionally substituted arylalkoxy, optionally substituted pyridyl, optionally substituted pyrimidyl, optionally substituted furanyl, optionally substituted thiophenyl, optionally substituted quinolinyl, optionally substituted indolyl, optionally substituted pyrrolyl, and optionally substituted pyrrolidinyl, optionally substituted pyrazolyl, optionally substituted oxazolyl, optionally substituted isoxazolyl, optionally substituted imidazole, optionally substituted pyridazinyl, optionally substituted pyrazinyl, optionally substituted tetrazolyl, optionally substituted imidazopyrimidinyl, optionally substituted thiazolyl, optionally substituted isothiazolyl, optionally substituted indazolyl, optionally substituted benzofuranyl, optionally substituted benzothiphenyl, optionally substituted isoquinolyl, optionally substituted benzimidazolyl, optionally substituted benzthiazolyl, optionally substituted quinoxalinyl, wherein said groups may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxyl;

R$^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$, provided that when w is 3, no more than 2 of the R$^3$ groups may be (=O);

R$^4$ is independently selected from the group consisting of H, halo, —OH, halo, and —CN, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;

R$^{4'}$ is independently selected from the group consisting of halo and alkyl;

R$^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O);

R$^6$ is independently selected from the group consisting of H and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O), and —C(=O)R$^7$, —C(=O)OR$^7$, —C(=O)NR$^7$R$^{7'}$, —SO$_2$R$^7$ and —SO$_2$NR$^7$R$^{7'}$;

R$^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by R$^{12}$;

R$^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by R$^{12}$;

R$^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N(R$^{11}$)$_2$, and —S(O)$_p$R$^{11}$ substituents and/or 1 or 2 (=O);

R$^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

R$^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkenyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least one by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more times by R$^{11}$;

$R^{14}$ is independently selected from the group consisting of H or alkyl; and $R^{15}$ is absent or selected from the group consisting of H and alkyl, cycloalkyl, aryl, arylalkyl, heteroaryl, and heteroarylalkyl groups, each of which is optionally substituted with at least one halo, —OH, —CN, —NO$_2$, —N($R^{11}$)$_2$, and —S(O)$_p R^{11}$ and/or 1 or 2 (=O); and q is 0 or 1, or a pharmaceutically acceptable salt thereof.

3. The compound according to claim 2, which has the formula

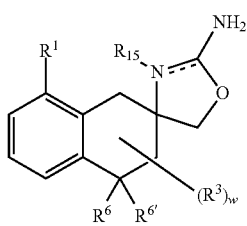

or a pharmaceutically acceptable salt thereof.

4. The compound according to claim 3, or a pharmaceutically acceptable salt thereof, wherein:

$R^1$ is a ring selected from the group consisting of phenyl, pyrazole, pyrimidine, oxazole and isoxazole wherein said rings may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy; and $R^{15}$ is absent.

5. The compound according to claim 2, which has the formula

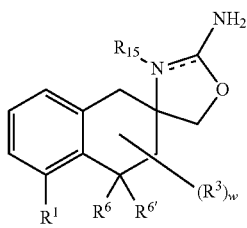

or a pharmaceutically acceptable salt thereof.

6. The compound according to claim 5, or a pharmaceutically acceptable salt thereof, wherein:

$R^1$ is a ring selected from the group consisting of phenyl, pyrazole, pyrimidine, oxazole and isoxazole wherein said rings may be optionally substituted 1 to 3 times with substitutents selected from the group consisting of alkyl, haloalkyl, nitro, cyano, halo, hydroxyl, amino, alkylamino, dialkylamino, —C(O)-amino; —C(O)-alkylamino, —C(O)-dialkylamino, —C(O)—OH, —C(O)—Oalkyl, amino-C(O)-alkyl, amino-C(O)—O-alkyl, amino-S(O)$_2$-alkyl, alkoxy, haloalkoxy, aryl, and heteroaryl, wherein said aryl and heteroaryl are optionally substituted 1 to 3 times by alkyl, haloalkyl, nitro, cyano, halo, hydroxyl, amino, alkylamino, dialkylamino, alkoxy, and haloalkoxy; and $R^{15}$ is absent.

7. The following compounds

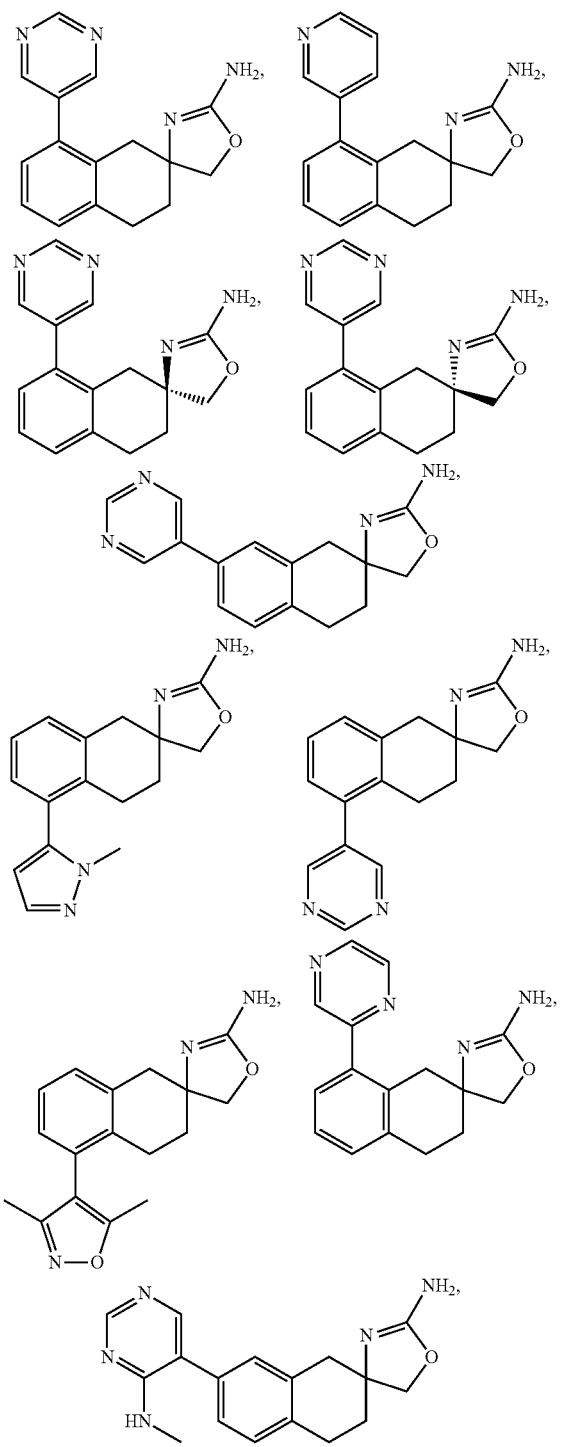

-continued
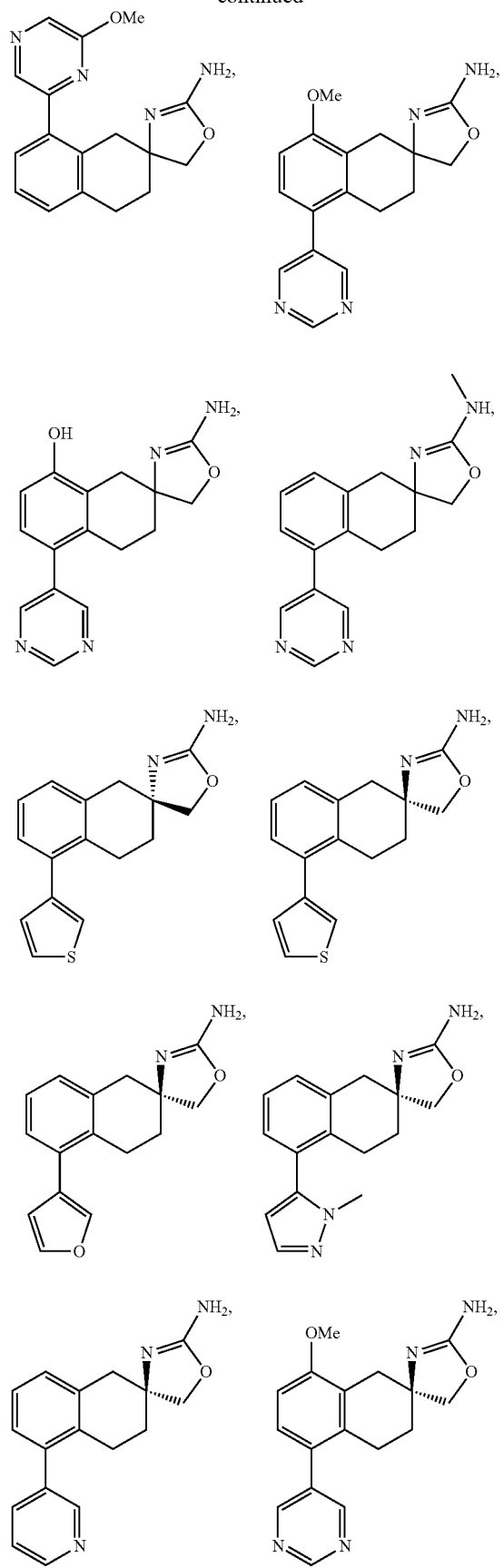
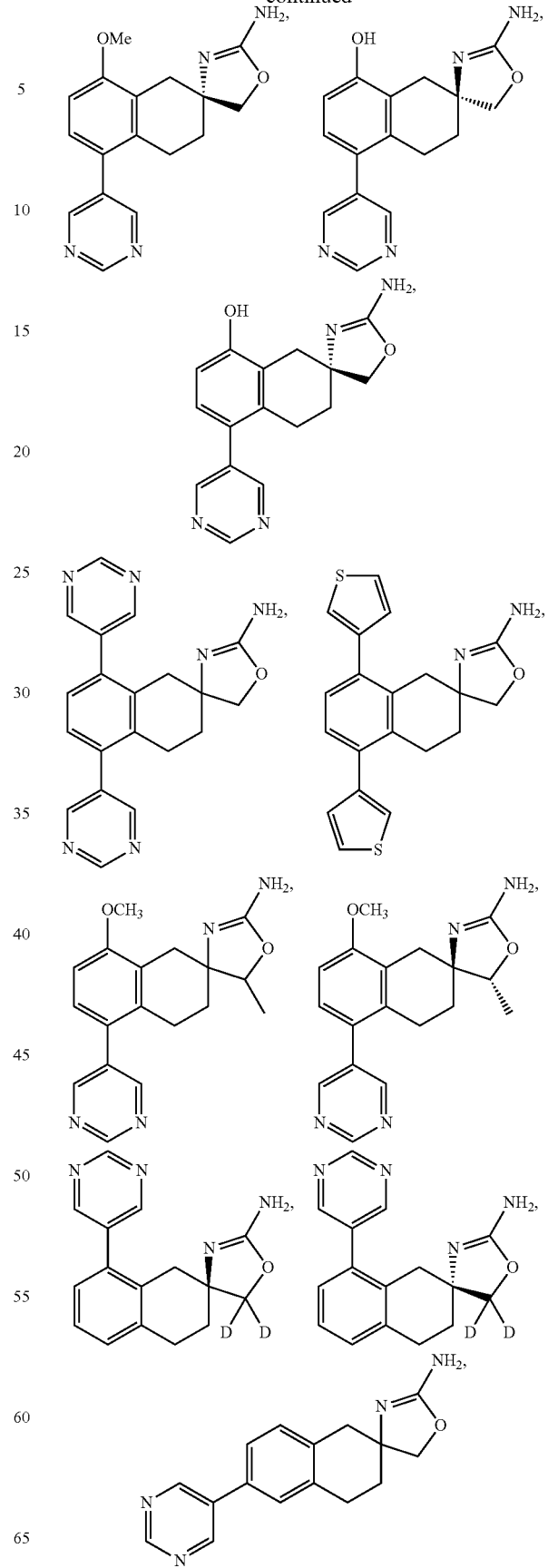

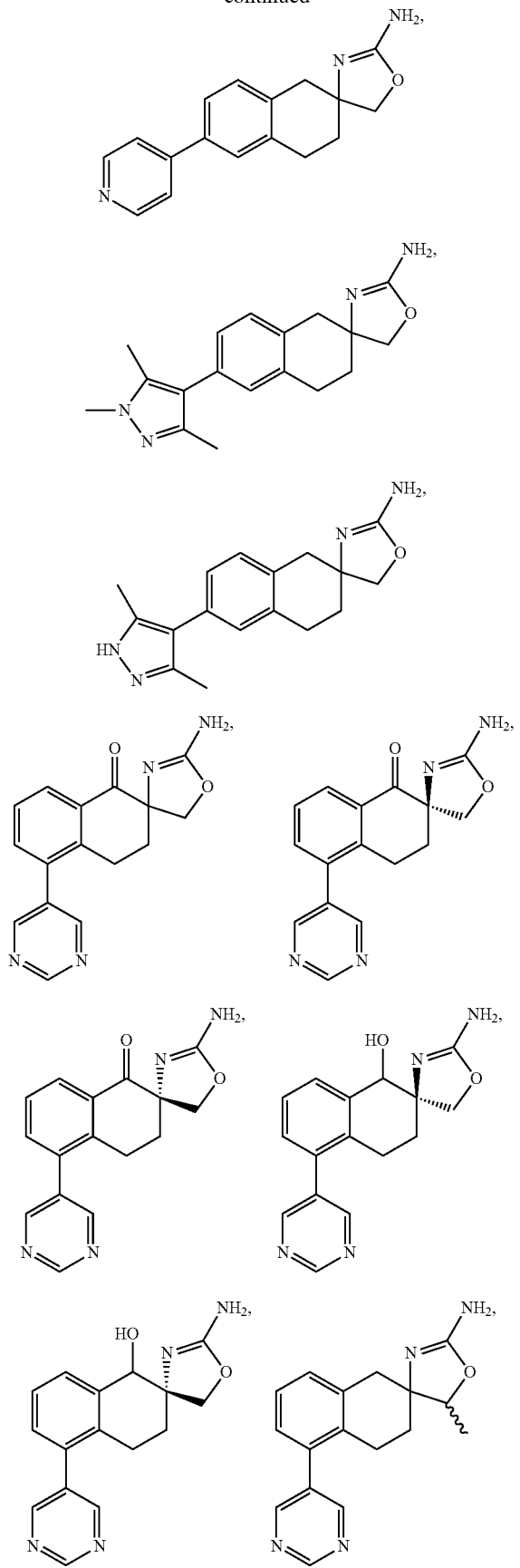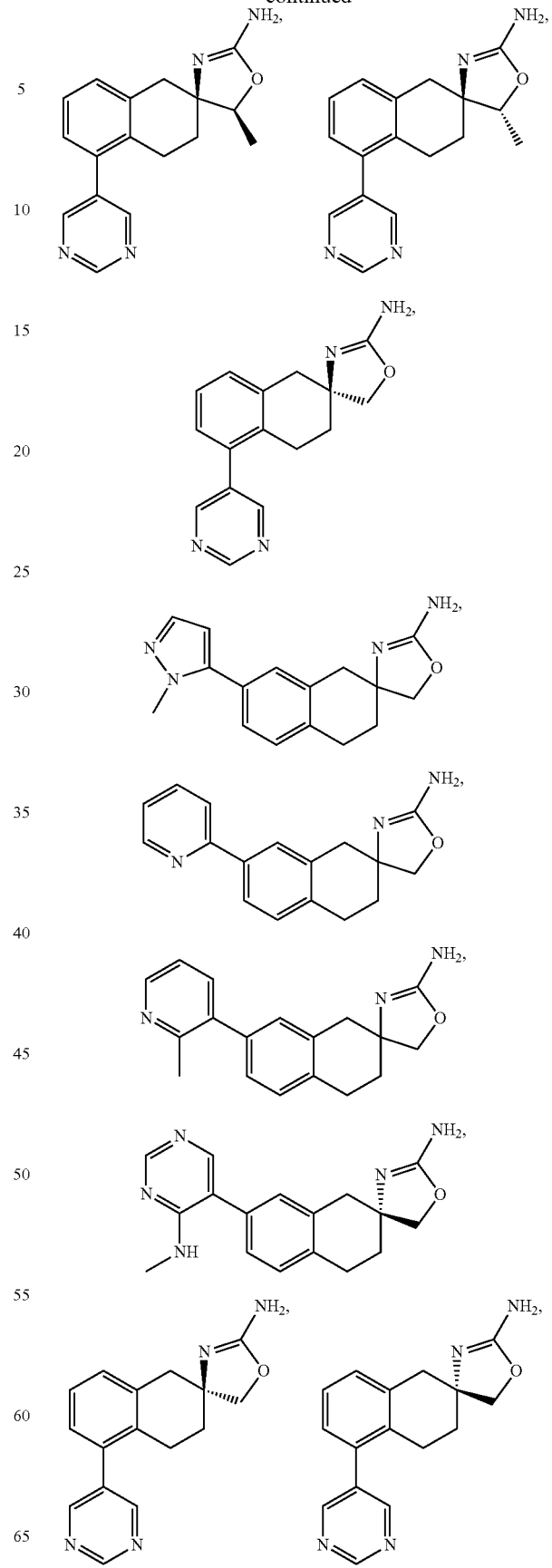

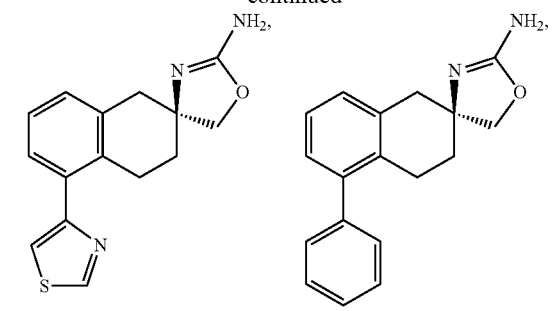
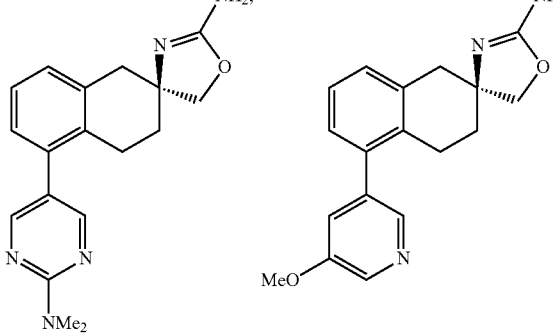
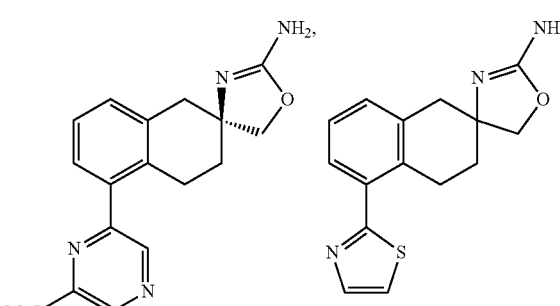
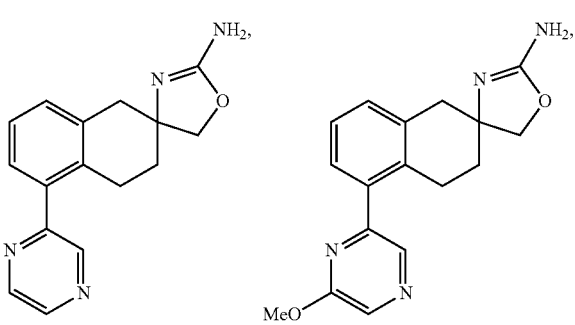
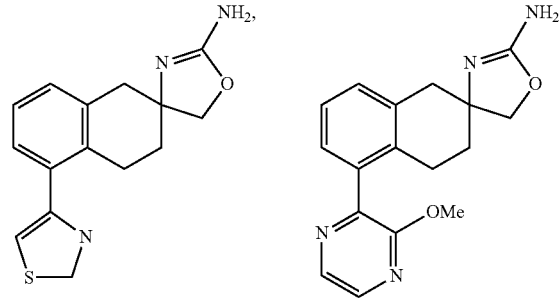
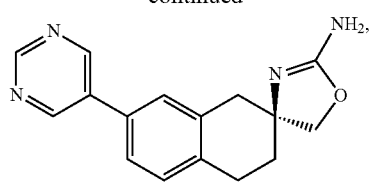
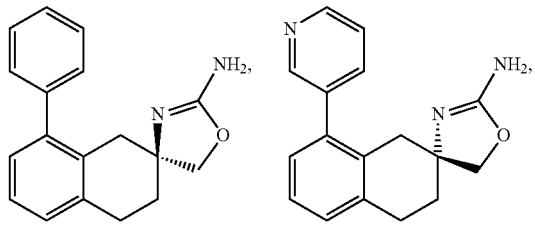
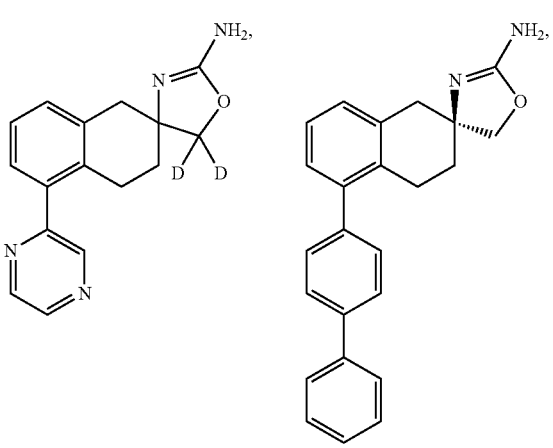
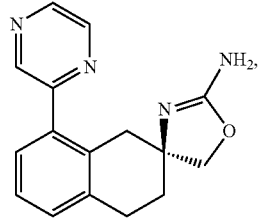
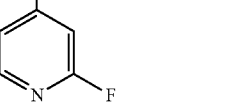
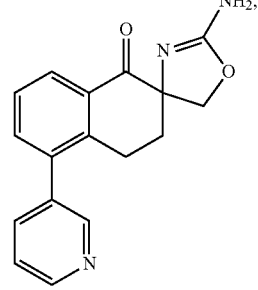

-continued
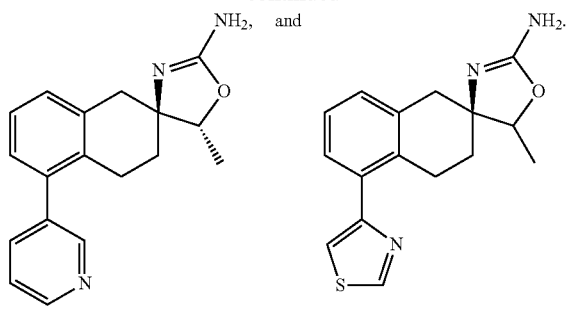
or a pharmaceutically acceptable salt thereof.
8. The following compounds or a pharmaceutically acceptable salt thereof:
-continued
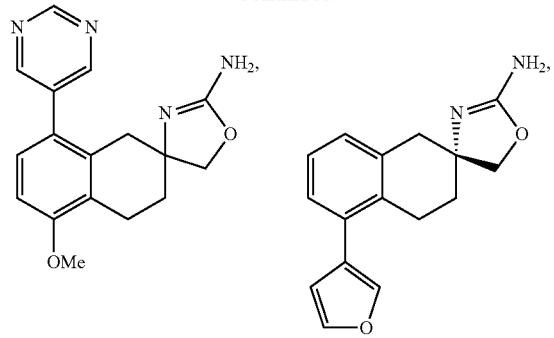
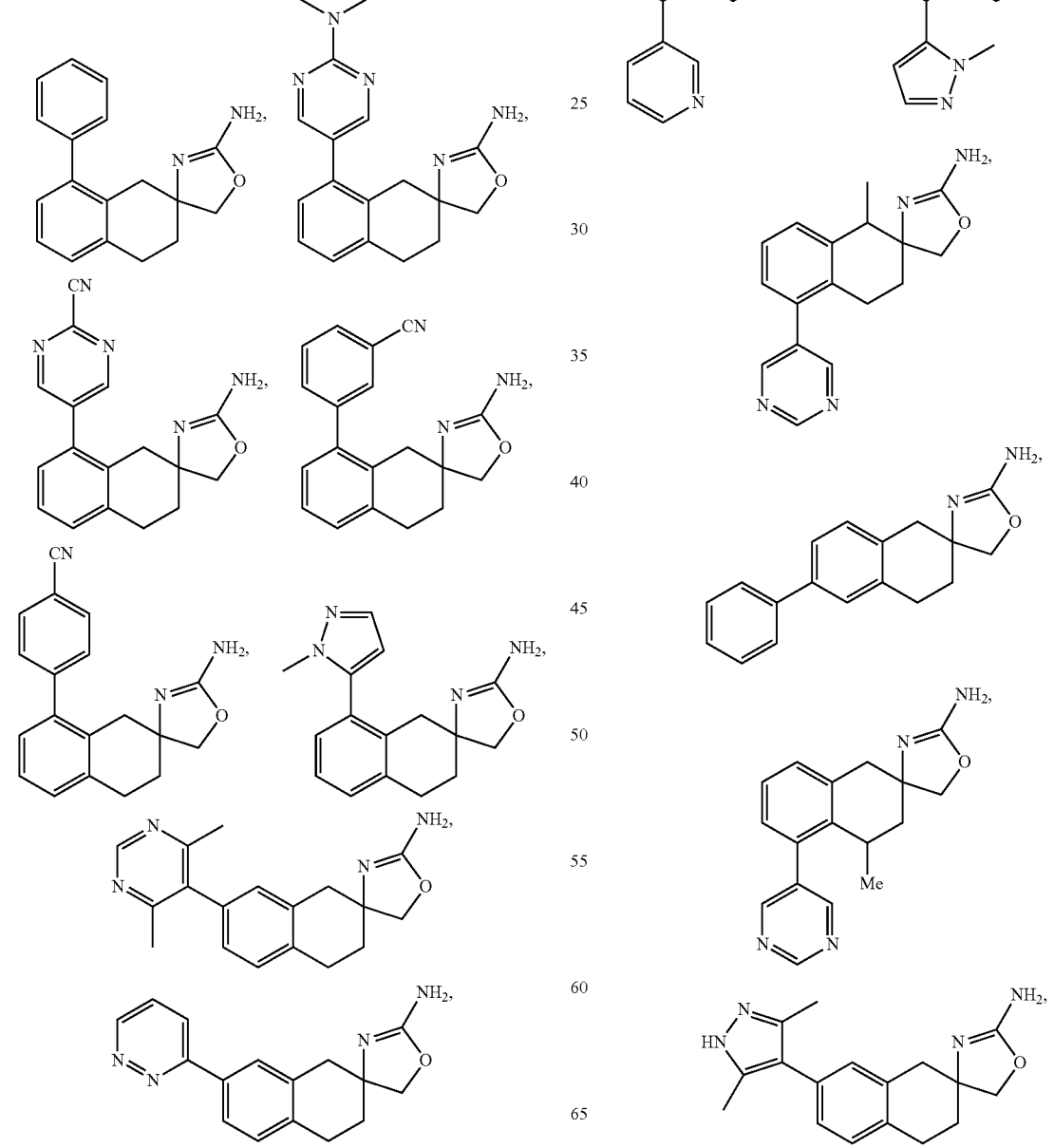

-continued

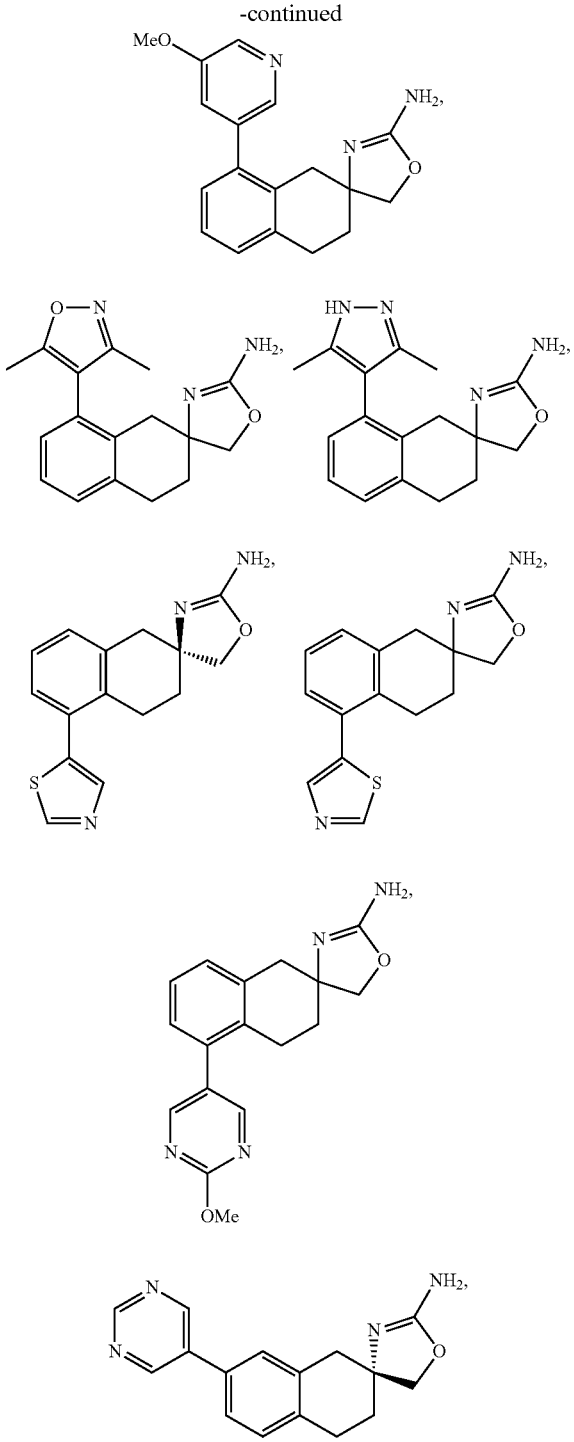

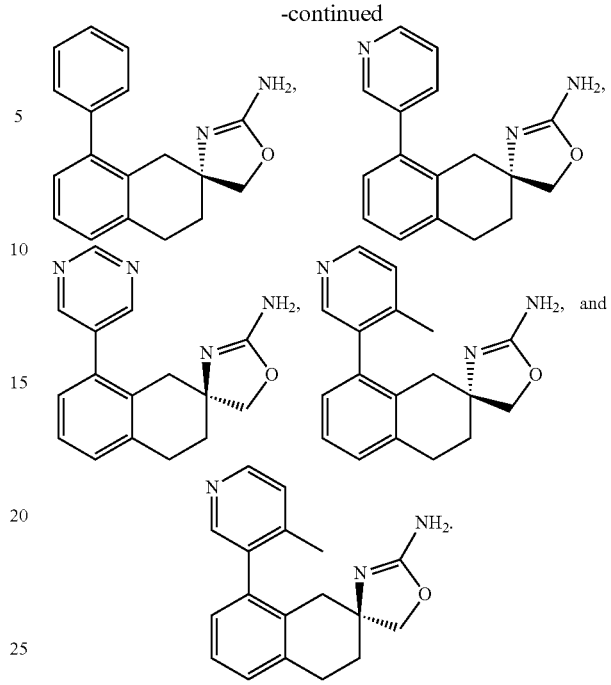

9. A pharmaceutical composition comprising at least one compound of claim 1, or a pharmaceutically acceptable salt, ester, solvate or prodrug thereof and at least one pharmaceutically acceptable carrier, adjuvant or vehicle, provided that when the composition is a liquid, aqueous composition one or more solubility enhancing components are excluded with the exception of cyclodextrin.

10. The pharmaceutical composition of claim 9, further comprising one or more additional therapeutic agents.

11. The pharmaceutical composition of claim 10, further comprising one or more additional therapeutic agents, wherein said additional therapeutic agents are selected from the group consisting of steroids, glucocorticosteroids, PDE-4 inhibitors, anti-muscarinic agents, muscle relaxants, cromolyn sodium, $H_1$ receptor antagonists, $5-HT_1$ agonists, NSAIDs, angiotensin-converting enzyme inhibitors, angiotensin II receptor agonists, β-blockers, long and short acting β-agonists, leukotriene antagonists, diuretics, aldosterone antagonists, ionotropic agents, natriuretic peptides, pain management/analgesic agents, anti-anxiety agents, anti-migraine agents, sedatives, NMDA receptor antagonists, alpha-adrenergics not including alpha-1 receptor antagonists, anti-convulsants, tachykinin (NK) antagonists, COX-2 inhibitors, neuroleptics, vanilloid receptor agonists or antagonists, beta-adrenergics, local anaesthetic, corticosteroids, serotonin receptor agonists or antagonists, PDEV inhibitors, alpha-2-delta ligands, canabinoids and therapeutic agents suitable for treating heart conditions, psychotic disorders, or glaucoma.

* * * * *